United States Patent [19]
Thornton

[11] Patent Number: 5,658,749
[45] Date of Patent: Aug. 19, 1997

[54] METHOD FOR PROCESSING MYCOBACTERIA

[75] Inventor: Charles G. Thornton, Gaithersburg, Md.

[73] Assignee: Corning Clinical Laboratories, Inc., Baltimore, Md.

[21] Appl. No.: 393,564

[22] Filed: Feb. 23, 1995

Related U.S. Application Data

[63] Continuation-in-part of Ser. No. 322,864, Oct. 11, 1994, abandoned, which is a continuation-in-part of Ser. No. 224,592, Apr. 7, 1994, abandoned, which is a continuation-in-part of Ser. No. 222,731, Apr. 5, 1994, abandoned.

[51] Int. Cl.$^6$ .............. C12Q 1/02; C12Q 1/18; C12N 1/00
[52] U.S. Cl. .............. 435/29; 435/4; 435/32; 435/863; 435/864; 435/865; 435/866; 424/248.1; 514/693; 514/702; 514/706; 514/727; 514/863; 514/864; 514/852
[58] Field of Search .............. 435/29, 4, 32, 435/863, 864, 865, 866; 424/248.1; 514/693, 702, 706, 727, 863, 852, 864

[56] References Cited

U.S. PATENT DOCUMENTS

| | | | |
|---|---|---|---|
| 3,852,210 | 12/1974 | Krezanoski | 435/29 |
| 4,062,976 | 12/1977 | Michaels | 435/29 |
| 4,247,538 | 1/1981 | Barker | 435/29 |
| 4,758,376 | 7/1988 | Hirota et al. | 435/29 |
| 5,099,065 | 3/1992 | Kubo et al. | 435/29 |

FOREIGN PATENT DOCUMENTS

| | | |
|---|---|---|
| WO 86/00139 | 1/1986 | WIPO. |
| PCT/NL93/00270 | 6/1994 | WIPO. |

OTHER PUBLICATIONS

Clarridge III, J.E., et al. "Large-Scale Use of Polymerse Chain Reaction for Detection of *Mycobacterium tuberculosis* in a Routine Mycobacteriology Laboratory," *Journal of Clinical Microbiology* 31:2049–2056, Aug. 1993.

Iralu, J.V., et al., "Diagnosis of *Mycobacterium avium* Bacteremia by Polymerase Chain Reaction," *Journal of Clinical Microbiology* 31:1811–1814, Jul. 1993.

Shawar, R.M., et al., "Detection of *Mycobacterium tuberculosis* in Clinical Samples by Two–Step Polymerase Chain Reaction and Nonisotopic Hybridization Methods," *Journal of Clinical Microbiology* 31:61–65, Jan. 1993.

Cousins, D. et al., "Use of Polymerase Chain Reaction for Rapid Diagnosis of Tuberculosis," *J. Clin. Microbiol.* 30(1):255–258 (1992).

Fiss, E.H. et al., "DNA Amplification and Reverse Dot Blot Hybridization for detection and Identification of Mycobacteria to the Species Level in the Clinical Laboratory," *J. Clin. Microbiol.* 30(5):1220–1224 (1992).

Fries, J.W.U. et al., "Detection of Untreated Mycobacteria by Using Polymerase Chain Reaction and Specific DNA Probes," *J. Clin. Microbiol.* 29(8):1744–1747 (1991).

Gonenne, A. and Ernst, R., "Solubilization of Membrane Proteins by Sulfobetaines, Novel Zwitterionic Surfactants," *Analytical Biochem.* 87:28–38 (1978).

Hassler, S., "TB is Back, But the Pipeline is Empty," *Bio/Tech.* 12:327 (1994).

Patel, R.J. et al., "Sequence Analysis and Amplification by Polymerase Chain reaction of a Cloned DNA Fragment for Identification of *Mycobacterium tuberculosis*," *J. Clin. Microbiol.* 28(3):513–518 (1990).

(List continued on next page.)

*Primary Examiner*—John Kight
*Assistant Examiner*—Louise Leary
*Attorney, Agent, or Firm*—Sterne, Kessler, Goldstein & Fox p.l.l.c.

[57] ABSTRACT

A method for the preparation of Mycobacteria from any liquid, semi-solid or exotic source is described. The extracted Mycobacterial sample is suitable for detection by culture and amplification.

72 Claims, 26 Drawing Sheets

OTHER PUBLICATIONS

Robinson, L. and Stovall, W.D., "Factors Influencing the Demonstration of Tubercule Bacilli by Concentration Methods," *J. Lab. Clin. Med.* 27:84–91 (1944).

Schaefer, W.B. and Lewis, Jr., C.W., "Effect of Oleic Acid on Growth and Cell Structure of Mycobacteria," *J. Bacteriol.* 90(5):1438–1447 (1965).

Dubos, R.J., "Rapid and Submerged Growth of Mycobacteria in Liquid Media," *Proc. Sco. Exp. Biol. Med.* 58:361–362 (1945).

Dubos, R.J. and Davis, B.D., "Factors Affecting the Growth of Tubercle Bacilli in Liquid Media," *J. Exp. Med.* 83:409–423 (1946).

Inderlied, C.B. et al., "The *Mycobacterium avium* Complex," *Clin. Microbiol. Rev.* 6(3):266–310 (1993).

Joklik, W.K., in: Zinsser Microbiology, 20th Edition, Appleton & Lange, pp. 81 and 499 (1992).

Kent, P.T. et al., "Public Health Mycobacteriology," in: A Guide for the Level III Laboratory, U.S. Dept. of Health and Human Services, Centers for Disease Control, pp. 47–56, (1985).

Ratnam, S. and March, S.B., "Effect of Relative Centrifugal Force and Centrifugation Time on Sedimentation of Mycobacteria in Clinical Specimens," *J. Clin. Microbiol.* 23(3):582–585 (1986).

Silverstolpe, L., "Förbättrad metod för påvisande av tuberkelbakterier," *Nord. Med.* 40/48:2220–2222 (1948).

Silverstolpe, L., "Improved Method for Detecting Tubercular Bacteria," *Nord. Med.* 40/48:2220–2222 (1948) English Translation.

Stinson, M.W. and Solotorovsky, J., "Interaction of Tween 80 Detergent with Mycobacteria in Synthetic Medium," *Amer. Rev. Resp. Dis.* 104:717–727 (1971).

Walsby, A.E., "Structure and Function of Gas Vacuoles," *Bacteriological Rev.* 36(1):1–32 (1972).

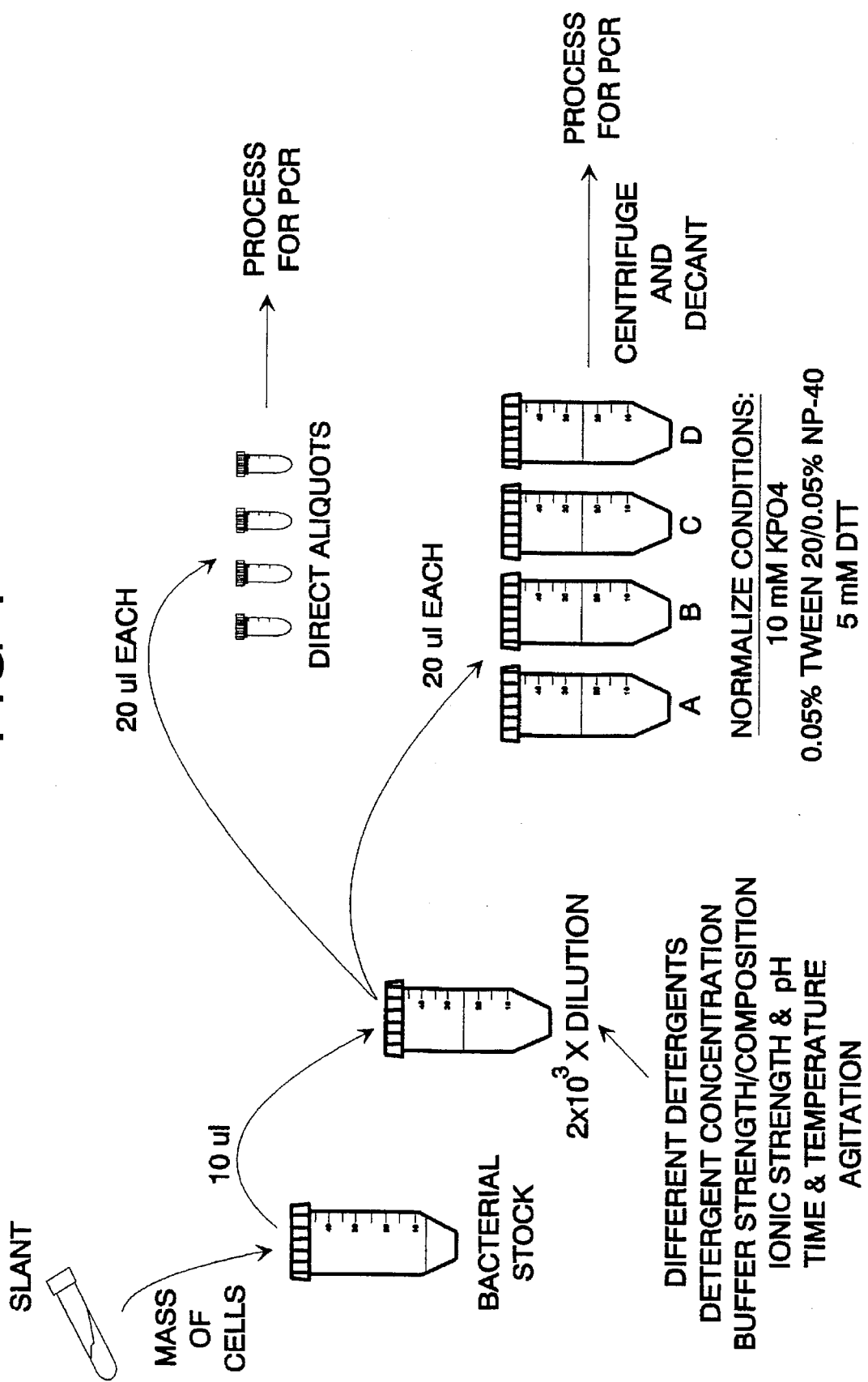

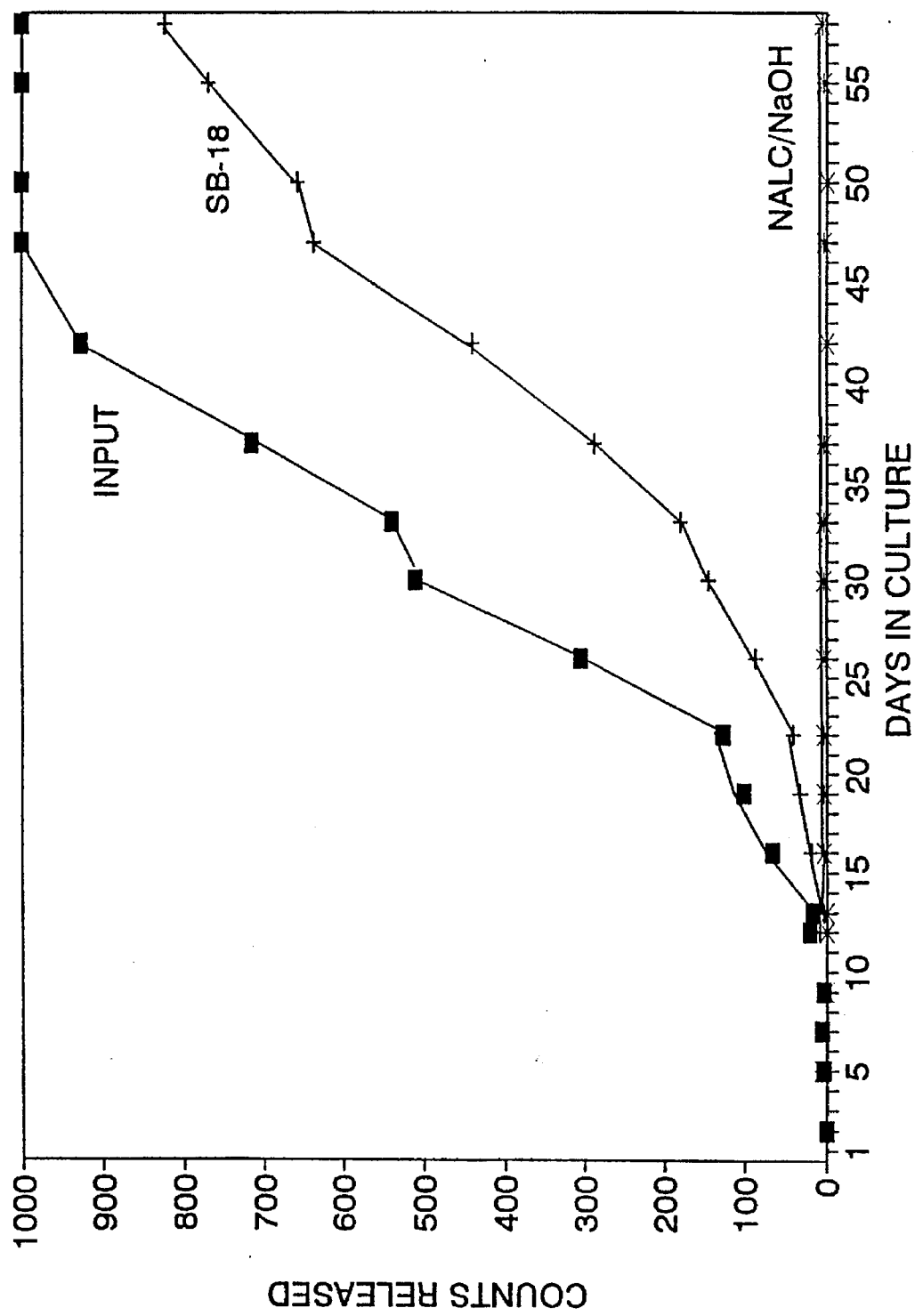

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 25 base pairs
      ( B ) TYPE: nucleic acid
      ( C ) STRANDEDNESS: both
      ( D ) TOPOLOGY: linear ( x i ) SEQUENCE DESCRIPTION: SEQ ID NO:1:

AAACTGGGTC TAATACCGGA TAGGA                                   25

( 2 ) INFORMATION FOR SEQ ID NO:2:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

CCACCTACCG TCAATCCGAG A                                       21

( 2 ) INFORMATION FOR SEQ ID NO:3:

( i ) SEQUENCE CHARACTERISTICS:
      ( A ) LENGTH: 20 base pairs
      ( B ) TYPE: nucleic acid
      ( C ) STRANDEDNESS: both
      ( D ) TOPOLOGY: linear ( i x ) FEATURE:
      ( A ) NAME/KEY: modified base
      ( B ) LOCATION: 7
      ( D ) OTHER INFORMATION: /label=modified base
            / note="The nucleotide at position 7 is inosine."

( x i ) SEQUENCE DESCRIPTION: SEQ ID NO:3:

GCGGGCNCAT CCCACACCGC                                         20

( 2 ) INFORMATION FOR SEQ ID NO:4:

( i ) SEQUENCE CHARACTERISTICS:
      ( A ) LENGTH: 23 base pairs
      ( B ) TYPE: nucleic acid
      ( C ) STRANDEDNESS: both
      ( D ) TOPOLOGY: linear ( x i ) SEQUENCE DESCRIPTION: SEQ ID NO:4:

GACCACGGGA TGCATGTCTT GTG                                     23

METHOD FOR PROCESSING MYCOBACTERIA

CROSS REFERENCE TO RELATED APPLICATIONS

This application is a continuation-in-part of U.S. application Ser. No. 08/322,864, filed Oct. 11, 1994 now abandoned, which is a continuation-in-part of U.S. application Ser. No. 08/224,592, filed Apr. 7, 1994 now abandoned, which is a continuation-in-part of U.S. application Ser. No. 08/222,731, filed Apr. 5, 1994 now abandoned.

BACKGROUND OF THE INVENTION

A. Mycobacteria and Disease

Mycobacterium tuberculosis (MTB) is the causative agent of the most common infectious disease in the world today, tuberculosis (TB). The World Health Organization (WHO) reported that 1.7 billion people (or approximately one-third of the world's population) are currently, or have been, infected by tuberculosis (Kochi, A. *Tubercle* 72:1–6 (1991)). The incidence of MTB infection is occurring at an increasing rate with 8 million new cases worldwide in 1991 (Sudre, P. et al., *Bull. W.H.O.* 70:149–159 (1992)), and the WHO estimates that 88.2 million people will contract TB during the 1990's and approximately 3 million people will die annually during this time period (Morbidity and Mortality Weekly Report 42 (No. 49):961–964 (1993)). In the United States the Centers for Disease Control and Prevention (CDC) recorded 26,673 cases in 1992 (Morbidity and Mortality Weekly Report 42:696–703 (1993)), and it is estimated that 10 to 15 million people in the U.S. have latent infections (Morbidity and Mortality Weekly Report 39(RR-8):9–12 (1990)).

The importance of Mycobacteria of the MAC complex, (primarily *M. avium* and *M. intracellulare*), as human pathogens was recently reviewed by Inderlied, C. B. et al., *Clin. Microbiol. Rev.* 6:266–310 (1993). MAC complex infections have been on the rise owing to their occurrence as opportunistic pathogens in AIDS patients. Approximately 43% of AIDS patients, with advanced stages of the disease, present with disseminated MAC infections (Nightingale et al., *Jour. Infect. Dis.* 165:1082–1085 (1992)). The WHO estimates that today approximately 3 million people have developed AIDS, approximately 15 million have been infected with the human immunodeficiency virus (HIV), and by the year 2000 the number infected could climb to approximately 40 million (World Health Organization (document WHO/GPA/CNP/EVA/93.1) *Global Programme on AIDS* (1993)). In addition to AIDS related infections, *M. paratuberculosis*, a subspecies of *M. avium* (Thorel, M. F. et al., *Int. J. Syst. Bacteriol.* 40:254–260 (1990)), is thought to be associated with Crohn's disease, an inflammatory disease of the bowel (Chiodini, R. J. *Clin. Micro. Rev.* 2:90–117 (1989)).

Mycobacterial infections are also a problem in animals. *M. paratuberculosis* also causes bowel inflammations in ruminants (Thoen, C. O. et al., *Rev. Infect. Dis.* 3:960–972 (1981)). This is more commonly known as Johne's disease. Cattle that test positive for Johne's are culled and destroyed. In the state of Wisconsin, where approximately one-third of the herds are infected (Collins, M. T., *Hoard's Dairyman Feb* 10:113 (1991)), the financial impact was estimated at $52 million in 1983 (Arnoldi, J. M. et al., *Proceedings, 3rd Int. Symp. World Assoc. Vet. Lab. Diag.* 2:493–494 (1983)). The incidence amongst herds nationwide typically ranges between 3% and 18% (Merkal, R. S. et al., *J. Am. Vet. Med. Assoc.* 190:676–680 (1987)). The financial impact of this one disease on the dairy industry exceeds $1.5 billion annually (Whitlock, R. *Proceedings of the Third International Colloquium on Paratuberculosis*, pp.514–522 (1991); Whitlock, R. et al., *Proceedings of the 89th Annual Meeting of the United States Animal Health Association*, pp.484–490 (1985)).

In addition to the organisms discussed above, a wide variety of Mycobacteria are also considered human pathogens, including *Mycobacterium leprae*, *Mycobacterium kansasii*, *Mycobacterium marinum*, *Mycobacterium fortuitum* complex, and many others. Wayne, L. G. et al., *Clin. Micro. Rev.* 5:1–25 (1992) review the diversity of infections associated with this genus of microorganism. However, the magnitude and impact of these infections is not on the same scale as MTB complex and MAC infections. For example, leprosy is probably the most common within this category: them are an estimated 5.5 million cases of *Mycobacterium leprae* worldwide (Nordeen, S. K. et al., *Int. J. Lepr.* 63:282–287 (1993)). Taken as a whole, this group of organisms exacts a tremendous social cost.

B. Culture and Detection of Mycobacteria

The contemporary protocol(s) for the laboratory diagnosis of Mycobacterial infections are relatively slow. Extended incubations are required owing to the innate slow growth rate of these bacteria. Owing to this lengthy time to diagnosis, individuals suspected of infection are quarantined, or else pose significant risk to society in general.

In addition, laboratory confirmation of the diagnosis of Mycobacterial infections requires several cultures per patient sample. Each sample must be incubated up to eight weeks (sixteen weeks for *M. paratuberculosis*) before the sample can be reported negative. The need for multiple cultures of each suspected sample is due in part to the intermittent shedding of detectable numbers of Mycobacteria, and the loss of infectious organisms due to the harsh chemical decontamination used to inactivate saprophytic microorganisms. These procedures are inefficient and often kill the Mycobacteria they are attempting to extract. For example, processing by the recommended N-acetyl-L-cysteine-NaOH (NALC/NaOH) procedure (Kent, P. T. et al., "Public Health Mycobacteriology," in *A Guide for the Level III Laboratory*, U.S. Department of Health and Human Service, Centers for Disease Control, (1985) pp. 31–46) is known to kill 28%–33% of the existing Mycobacteria (Krasnow, I. et al., *Am. J. Clin. Path.* 45:352–355 (1966); Kubica, G. P. W. et al., *Am. Rev. Resir. Dis.* 87:775–779 (1963)). The advent of contemporary probe assays (Gonzalez, R. et al., *Diag. Microbiol. Infect. Dis.* 8:69–78 (1987)) that complement culture techniques has improved the time to diagnosis; however, there still exists room for significant improvement.

The combination of social importance and reliance on culture methods reveals a critical need for a Mycobacterial testing protocol that reduces turn around time and increases sensitivity. The isothermal scheme being commercialized by Gen-Probe, Inc. (San Diego, Calif.: Jonas, V. et al., *J. Clin. Micro.* 31:2410–2416 (1993)) and the polymerase chain reaction (PCR) both have the potential for single molecule detection (Higuchi et al., *Nature* (London) 332:543–546 (1988)). Furthermore, amplification and detection can be performed in approximately eight hours and the reagents do not add a significant cost. If available, an amplification assay could greatly enhance the speed and sensitivity of detection, and reduce the cost of Mycobacterial diagnosis (De Cresce, R. P. et al., *Med. Laboratory Obs.* 25:28–33 (1993)). The rapidity with which these technologies could potentially diagnose Mycobacterial infections would have a tremendous financial impact on society.

However, as described herein, researchers have encountered a plethora of problems in an effort to adapt these technologies, such as PCR amplification, to the detection of Mycobacteria. Especially it has not been possible to develop a protocol for the preparation of a sample for analysis in a manner that will (a) ensure amplification assay detection of a true positive result and also (b) not give false negative results. The variability encountered by researchers is exemplified by the study of Noordhoek, G. T. et al., *J. Clin. Micro.* 32:277–284 (1994). These authors describe a blind study in which seven laboratories participated. All laboratories used the same amplification system, but different processing and detection methodologies. The original summary of these results (Noordhoek, G. T. et al., *N. Eng. J. Med.* 329:2036 (1993) concisely shows that at low copy numbers (1000 copies), the correlation varied from 2% to 90%, with the average being 54%. As a result of these problems, there is still no available FDA approved TB-amplification kit.

C. Methods of Processing Mycobacterium Samples

A review of the scientific literature on Mycobacteria-nucleic acids amplification references relating to system design, sample processing techniques and clinical studies reveals the highly variable results that have precluded FDA approval of a TB-amplification kit.

Two different amplification schemes have been used; there are numerous PCR system designs and many clinical studies that focus on Mycobacterial infections, the vast majority on MTB. Typically, samples are processed for culture first and then subjected to amplification. Therefore, sample preparation for amplification can be viewed, in most cases, as an extension of the culture processing protocol.

There are several reasons the field has evolved in this manner. First, obtaining clinical specimens is difficult. Individuals diagnosed with MTB are invariably started on drug therapy upon diagnosis. Second, processing MTB specimens requires specialized containment facilities and appropriately trained technicians. Third, it is the easiest way to obtain "culture correlation" results; that is, a correlation of amplification positive and negative results with those that were positive or negative in culture. Consequently, researchers have typically processed the sample for culture and then used protocols that "further" process the sediment for amplification. In this way, actual clinical specimens can be used, containment is not breached, work flow is not interrupted, patient care is not compromised and correlation to contemporary protocols is feasible. This "further" processing referred to above has involved a wide variety of sample preparation and cell lysis techniques.

Table 1 summarizes 35 publications, using samples derived from 17 different countries, evaluating the performance of amplification technologies in the clinical laboratory. The works in Table 1 are presented chronologically. Every effort has been made to accurately represent the original publication. There were, however, ambiguities in interpretation in some instances, and distinctive features of several papers. Clarifications are highlighted in the footnotes that follow.

Correlation of nucleic acid amplification results with culture results was chosen as the basis to compare the studies shown in Table 1. Using this perspective, this analysis reveals a conundrum: according to the methodologies outlined in Table 1, the sample subjected to amplification is derived, in the vast majority of instances, from the "button" used to seed the culture. Given the sensitivity of amplification relative to culture, a culture positive/amplification negative (e.g., false negative amplification) does not make intuitive sense. Several authors present "corrected correlations" (see Footnote C in Table 1). For example, if several false negatives were obtained, and the result could be resolved by further purification of the target DNA, dilution of inhibitors, multiple amplifications of the same sample, multiple amplifications of different samples from the same patient, or reamplification of the amplified specimen; the corrected results were presented.

This introduces an interesting dilemma. Jackson, J. B. et al., *J. Clin. Micro.* 31:3123–3128 (1993)) have successfully implemented an HIV-PCR quality assurance panel involving 11 laboratories. The reported sensitivity suggests that all laboratories have the routine capability of identifying 2 copies of the HIV genome in a background of $10^6$ human cells. The studies in Table 1 that are reviewed herein strongly suggest that the sensitivity of TB-amplification technologies is similar. What is apparent from the discussion of the studies in Table 1 is that, while the sensitivity of these amplification technologies for detection of Mycobacteria is expected to be orders of magnitude greater than that of either culture or smear, there are consistent aberrations to this expectation. While some of the anomalies are due to inhibition, and are, therefore, easily explained, many of the irregularities are "unexplained." What will become apparent is that, even if an internal control is used to detect inhibitors, these unexplained aberrations are reasonably common, and as such pose a significant obstacle to validation of amplification technologies for the detection of Mycobacteria in the clinical laboratory. For example, while positives, or suspected positives, may be rechecked, typically negatives are not. Since false negatives will occur with regularity, the laboratory will have no way of knowing which samples are truly false negative and which need to be "resolved." Consequently, patient care will be compromised as the diagnosis will incorrectly appear negative. Therefore, for the purpose of discussion of the published art herein, the art's uncorrected data was used. These aberrations—the false negatives—are the focus of the remaining discussion.

TABLE 1

Art Reported Correlation of Culture Results with Nucleic Acids Amplification Results.
For each study in Table 1 the processing protocol is abbreviated (see Footnote A), the number of clinical specimens evaluated is stated with the corresponding number of culture and amplification positive samples (see Footnote B), and then the "uncorrected" correlation to culture shown (see Footnote C). These 35 were chosen because a clear comparison between the amplification results and the culture results was presented. The studies of Shankar, P. et al., Lancet 337:5–7(1991); deWit, D. et al., Tubercle and Lung Dis. 73:262–267 (1992); and Kaneko, K. et al., Neurology 40:1617–1618 (1990) were omitted because no clear comparison on this basis could be made.

| Author(s) | [A]Processing Protocol | [B]Total: Cult⊕/Amp⊕ | [C]Correl. |
|---|---|---|---|
| Brisson-Noël et al., Lancet ii: 1069–1071 (1989) | SDS$_P$ ⇒ NaOH/SDS/95°/15' ⇒ Org/ppt | 35: 13/15 | 100% |
| Shankar et al., Lancet 335:423 (1990) | NALC ⇒ NaOH/NaCl/SDS/95°/15' ⇒ Org/ppt | [D]23: 8/10 | 100% |
| Hermans et al., J. Clin. Micro. 28:1204–1213 (1990) | ⇒ (NaOH/NaHPO$_4$)$_P$ ⇒ (TE)$_W$ ⇒ Lz/SDS/PrK ⇒ Org/ppt | [B]17: 7/11 | 100% |
| Pao et al., J. Clin. Micro. 28:1877–1880 (1990) | OxAc ⇒ NaCl/EDTA ⇒ Lz ⇒ Phenol/SDS ⇒ ppt | 284: 49/118 | (100%)[F] |
| ‡Sjöbring et al., J. Clin. Micro. 28:2200–2204 (1990) | DTT ⇒ TE/95° ⇒Sonic | [G]7: 4/3 | 75% |
| DEWit et al., J. Clin. Micro. 28:2437–2441 (1990) | ⇒ PEG ⇒ 70°/30' ⇒ Phenol/SDS ⇒ Org/PEG-ppt | [H]26: 14/14 | 100% |

TABLE 1-continued

Art Reported Correlation of Culture Results with Nucleic Acids Amplification Results.
For each study in Table 1 the processing protocol is abbreviated (see Footnote A), the number of clinical specimens evaluated is stated with the corresponding number of culture and amplification positive samples (see Footnote B), and then the "uncorrected" correlation to culture shown (see Footnote C). These 35 were chosen because a clear comparison between the amplification results and the culture results was presented. The studies of Shankar, P. et al., Lancet 337:5–7(1991); deWit, D. et al., Tubercle and Lung Dis. 73:262–267 (1992); and Kaneko, K. et al., Neurology 40:1617–1618 (1990) were omitted because no clear comparison on this basis could be made.

| Author(s) | [A]Processing Protocol | [B]Total: Cult⊕/Amp⊕ | [C]Correl. |
|---|---|---|---|
| Thierry et al., J. Clin. Micro. 28:2668–2673 (1990) | (→) NaOH/SDS/95°/15' ⇒ Org/ppt | [I]75: 30/35 | 100% |
| [††]Pierre et al., J. Clin. Micro. 29:712–717 (1991) | (a) SDS$_P$ → NaOH/SDS/95°/15' → Org/ppt | [J]82: 24/23 | (79.2%)[K] |
| | (b) SDS$_P$ → (PBS)$_W$ → PCR$_{Buf}$/PrK/NonI → 95° C./10' | | |
| Del Portillo et al., J. Clin. Micro. 29:2163–2168 (1991) | ⇒ (Water/95°/10')$_P$ ⇒ Lz ⇒ SDS/PrK → Org/ppt | [L]30: 11/18 | 100% |
| [†‡]Brisson-Noël et al., Lancet 338:364–366 (1991) | SDS$_P$ → NaOH/SDS/95°/15' → Org/ppt | [M]446: 141/110 | (89.4%)[N] |
| [‡]Sritharan et al., Mol. Cell. Probes 5:385–395 (1991) | NALC$_P$ → (TEX)$_W$ → TEX/95°/30' | [O]96: 74/88 | (95.9%)[P] |
| Eisenach et al., Am. Rev. Resp. Dis. 144:1160–1162 (1991) | NALC$_P$ → Lz → NaOH/SDS/95°/5' → GuSCN/Si | 162: 48/53 | 97.7% |
| Manjunath et al., Tubercle 72:21–27 (1991) | NALC ⇒ NaOH/SDS/95°/15' ⇒ Org/ppt | 117: 17/31 | 100% |
| ¶Cousins et al., J. Clin. Micro. 30:255–258 (1992) | NALC$_P$ → (Water)$_W$ → Lz → SDS/PrK → TMA/Org/ppt | 177: 64/92 | 98.4% |
| [†]VAN DER Giessen et al., J. Clin. Micro. 30:1216–1219 (1992) | (a) NaOH$_S$ → Phenol/CHCl$_3$ → Silica → H$_2$O | [Q]87: 30/5 & 1 | 16%, 3% |
| | (b) NaOH$_S$ ⇒ Phenol/CHCl$_3$ ⇒ Silica ⇒ H$_2$O | 87: 30/7 & 1 | 23%, 3% |
| | (c) IDEXX$_{BUF}$ ⇒ Column ⇒ Pellet ⇒ NaOH → 120°/10' | 87: 30/4 & 4 | 13%, 13% |
| [†¶]Buck et al., J. Clin. Micro. 30:1331–1334 (1992) | NALC$_P$ → 2x(Water)$_W$ → Sonic → 95°/10' | [R]43; 25/24 | 92.0% |
| [†‡]Victor et al., J. Clin. Micro. 30:1514–1517 (1992) | (a) NALC → PCR$_{Buf}$ → 95°/10' | [S]155: 131/100 | 76.3% |
| | (b) NALC ⇒ Sucrose → (PBS)$_W$ → PBS | 155: 131/131 | 98.5% |
| [†]Soini et al., J. Clin. Micro. 30:2025–2028 (1992) | NaOH/SDS$_P$ ⇒ NaOH/SDS/95°/15' ⇒ Org/ppt | 127: 34/25 | 55.9% |
| Altamirano et al., J. Clin. Micro. 30:2173–2176 (1992) | NALC$_P$ → Lz/SDS → perCl → Org/ppt | 200: 44/43 | 97.7% |
| [†]Fauville-Dufaux et al., Eur. J. Micro. Inf. Dis. 11:797–803 (1992) | SDS or TriPO$_4$ → NaOH/SDS/95°/15' → Org/ppt | [T]206: 92/84 | (91.3%)[U] |
| [†‡]Kolk et al., J. Clin. Micro. 30:2567–2575 (1992) | NALC$_P$ → (TX)$_W$ → TX/PrK/60°/18 hrs → 95°/15' | 227: 45/81 | 95.6% |
| [†‡¶]Shawar et al., J. Clin. Micro. 31:61–65 (1993) | NALC$_P$ → (TEX)$_W$ → TEX/95°/30' | 384: 71/75 | 78.9% |
| ¶Wilson et al., J. Clin. Micro. 31:776–782 (1993) | (a) NaOH → (PBS)$_W$ → PBS/80°/20' → GuSCN/Si | [V]171: 27/19 | (66.7%)[W] |
| | (b) NaOH ⇒ (PBS)$_W$ ⇒ PBS/80°/20' ⇒ CHCl$_3$ | 171: 27/26 | (89.9%) |
| [†]Folgueira et al., J. Clin. Micro. 31:1019–1021 (1993) | NALC$_P$ → PCR$_{Buf}$/PrK/NonI → 95°/10' | [X]75: 71/75 | (90.7%)[Y] |
| Kocagöz et al., J. Clin. Micro. 31:1435–1438 (1993) | NALC$_P$ → 3x(TE)$_W$ → TE/95°/10' | [Z]78: 29/36 | (100%)[α] |
| [†‡]Forbes et al., J. Clin. Micro. 31:1688–1694 (1993) | NaOH ⇒ PBS/NonI → 95°/10' ⇒ Sonic | [β]173: 31/25 | (80.6%)[γ] |
| | | 727: 80/75 | (83.8%) |
| ¶Nolte et al., J. Clin. Micro. 31:1777–1782 (1993) | NALC$_P$ → TEX → 95°/30' | 313: 123/113 | 91.1% |
| [††]Irula et al., J. Clin. Micro. 31:1811–1814 (1993) | → Fic/Hyp/PBMC → (TEX)$_W$ → ChX/56°/30' → 95°/30' | [δ]243: 15/44 | 80.0% |
| [†‡¶]Clarridge et al., J. Clin. Micro. 31:2049–2056 (1993) | NALC$_P$ ⇒ (TEX)$_W$ ⇒ TEX/95°/30' | 1,166: 218/192 | (83.0%)[ε] |
| Miyazaki et al., J. Clin. Micro. 31:2228–2232 (1993) | DTT → Lz → PrK/SDS → Org/ppt | 417: 56/92 | (96.4%)[ζ] |
| [†‡]Jonas et al., J. Clin. Micro. 31:2410–2416 (1993) | NALC → HCl → Gen$_{Buf}$ → Sonic → 95°/15' | [η]758: 119/116 | (79.8%)[θ] |
| [‡¶]Abe et al., J. Clin. Micro. 31:3270–3274 (1993) | (a) Gen: NALC → PBS/HCl ⇒ Gen$_{Buf}$ → Sonic → 95°/15' | [ι]135: 32/34 | (90.6%)[κ] |
| | (b) PCR: NALC → TEX/GuSCN/Si | 135: 32/32 | (81.2%) |
| [†‡¶]Miller et al., J. Clin. Micro. 32:393–397 (1994) | (a) Gen: NALC → HCl → Gen$_{Buf}$ → Sonic → 95°/15' | [λ]750: 142/131 | (83.9%)[μ] |
| | (b) PCR: (NALC)$_P$ ⇒ PCR$_{Buf}$ → Sonic → 95°/15' | 156: 142/122 | (78.2%) |
| [†¶]Pfyffer et al., J. Clin. Micro. 32:918–923 (1994) | (a) NALC → HCl → Gen$_{Buf}$ → Sonic → 95°/15' | [ν]515: 42/57 | (92.9%)[ζ] |
| | (b) SDS → HCl → Gen$_{Buf}$ → Sonic → 95°/15' | 423: 36/50 | (97.2%) |
| [‡]Bodmer et al., J. Clin. Micro. 32:1483–1487 (1994) | SDS → HCl → Gen$_{Buf}$ → Sonic → 95°/15' | [π]617: 21/21 | 71.4% |

(A) All studies, with the exception of Hermans, P.W.M. et al., J. Clin. Micro. 28:1204–1213 (1990), DEWit, D. et al., J. Clin. Micro. 28:2437–2441 (1990), Del Portillo, P. et al., J. Clin. Micro. 29:2163–2168 (1991), Irula, J.V. et al., J. Clin. Micro. 31:1811–1814 (1993), and possibly Thierry, D. et al., J. Clin. Micro. 28:2668–2673 (1990), process the specimens for culture first. In general, all specimen processing techniques utilized are summarized in Kent, P.T. et al., "Public Health Mycobacteriology" in A Guide for the Level III Laboratory, U.S. Department of Health and Human Services, Centers for Disease Control, 1985, pp. 31–46. The symbology used to describe the processing of clinical specimens is as follows: "NALC" refers to the N-Acetyl-L-Cysteine/sodium hydroxide liquification/decontamination protocol described by Kubica, G.P.W. et al., Am. Rev. Resir. Dis. 87-775-779 (1963). "DTT" refers to utilization of dithiothreitol (also known as Sputolysin ™) for the processing of Mycobacteria according to the protocol of Hirsch, S.R. et al., J. Lab. Clin. Med. 74:346–353 (1969). "SDS" (sodium dodecylsulfate) refers to the protocol of Engbaek, H.C. et al., Scand. J. Respir. Dis. 48:268–284 (1967). "Fic/Hyp" refers to the Ficoll/Hypaque gradient protocol for the purification of peripheral blood mononuclear cells (PBMC) after the method of Boyum (Boyum, A.J. Clin. Lab. Invest. 21(Suppl. 97):77–109 (1968)). "NaOH" refers to sodium hydroxide decontamination protocols specific to the authors, or is a direct quote from the author where the specifics of the decontamination protocol are not clearly stated. "OxAc" refers to the use of oxalic acid (Corper, H.J. et al., J. Lab. Clin. Med. 15:348–369 (1930). "PEG" refers to the use of polyethylene glycol precipitation specific to the authors. "TriPO$_4$" refers to the triphosphate procedure of Collins et al., Organization and Practice in Tuberculosis Bacteriology, Buttersworth, London, 1985. Invariably, the processed specimen is centrifuged to produce

TABLE 1-continued

Art Reported Correlation of Culture Results with Nucleic Acids Amplification Results.
For each study in Table 1 the processing protocol is abbreviated (see Footnote A), the number of clinical specimens evaluated is stated with the corresponding number of culture and amplification positive samples (see Footnote B), and then the "uncorrected" correlation to culture shown (see Footnote C). These 35 were chosen because a clear comparison between the amplification results and the culture results was presented. The studies of Shankar, P. et al., Lancet 337:5–7(1991); deWit, D. et al., Tubercle and Lung Dis. 73:262–267 (1992); and Kaneko, K. et al., Neurology 40:1617–1618 (1990) were omitted because no clear comparison on this basis could be made.

| Author(s) | [A]Processing Protocol | [B]Total: Cult⊕/Amp⊕ | [C]Correl. |
|---|---|---|---| a "button" (sediment). The button is resuspended in either water or phosphate buffered saline (PBS) and aliquots removed for culture and smear. The remaining sediment is then further processed for amplification. A subscript "P" attached to the processing designation refers to the fact that the resuspended sediment was again centrifuged prior to further processing for amplification, and it is the pelleted sediment that was used in the study. A subscript "S" attached to the processing designation refers to the fact that the supernatant clarified by centrifugation, and it was the supernatant that was used in the study. Following processing for culture, several authors compare different protocols for preparation of the sample for amplification: only the protocol used to prepare specimens for the actual study are included. Those studies that compare sample preparation methodologies are identified in the text and the results of these findings discussed as well. The following buffer abbreviations apply: "TE" = Tris/EDTA, "TX" = Tris/Triton-X100, "TEX" = Tris/EDTA/Triton-X100, and "NonI" = Tris/Tween20 & NP-40. A subscript "W" refers to a wash step using the parenthetic buffer. "Gen$_{Buf}$," "IDEXX$_{Buf}$," and "PCR$_{Buf}$" refer to suspension/resuspension of the sample in Gen-Probe buffer or IDEXX buffer (the compositions of which are unknown) or PCR buffer (20 mM Tris-HCl pH8.3, 50 mM KCl, 2.5 mM MgCl$_2$, 0.45% Tween20, 0.45% NP-40), respectively. "CHCl$_3$," "HCl," and "perCl" refer to inclusion of chloroform, hydrochloric acid and perchloric acid, respectively, in the processing steps. "PrK" and "Lz" refer to enzymatic digestion of the sample with proteinase K and/or lysozyme. Any step involving boiling or treatment at extreme temperature is simplified as 95° for the prescribed length of time. "Org/ppt" refers to any extraction methodology involving organic compounds, or combinations thereof, including phenol, chloroform, and/or isoamyl alcohol, followed by precipitation of the nucleic acid with either ethanol or isopropanol. There are numerous variations on this theme, but all methodologies are similar to that found in Maniatis, T. et al., "Molecular Cloning A Laboratory Manual," Cold Spring Harbor Laboratory, New York, 1982, pp. 458–463). "TMA" refers to the utilization of quaternary amines to precipitate DNA or polysaccharides similar to the methodology of Baess, I. Acta Path. Microbial. Scand. Sect. B, 82:780–784 (1974). "GuSCN/Si" refers to purification of DNA from the sample using guanidinium isothiocyanate in the presence of silica, as described, for example, by Boom, R. et al., J. Clin. Microbial. 28:495–503 (1990). "Sonic" refers to release of the DNA by sonication of the sample (in the presence or absence of glass beads).

(B) The total number of clinical samples used in a given study is followed first by the number of culture positives and then by the number of amplification positives. Additional footnotes referred to in this column describe pertinent characteristics of the study.

(C) Shown is the uncorrected correlation between the amplification result and the culture result (e.g., the number of amplification positive specimens that were also culture positive, divided by the total number of culture positives). Several authors have further examined discrepant results (e.g., "false negatives" or "false positives"), or incorporated patient information into the analysis and published corrected results. The correlation listed in this column refers to uncorrected results. If a discrepancy between the published result and the result listed in this column exists, the number is in parentheses with an appropriate footnote explaining the difference.

(D) Shanker, P. et al., Lancet 335:423 (1990) do not explicitly state the protocol used to process samples for either culture or PCR. However, Manjunath, N. et al., Tubercle 72:21–27 (1991) state that their publication is the final version of preliminary work presented in the Shanker, P. et al., Lancet 335:423 (1990) study. Therefore, it is assumed, for the purpose of discussion, that the processing conditions are identical to those of Manjunath, N. et al., Tubercle 72:21–27 (1991).

(E) The study of Hermans, P.W.M. et al., J. Clin. Micro. 28:1204–1213 (1990)) process crude specimens directly for amplification (e.g., the specimen was not processed for culture and the sediment split for analysis by both culture and PCR).

(F) Pao, C.C. et al., J. Clin. Micro. 28:1877–1880 (1990) do not give uncorrected results for PCR. They do, however, state that: "If the initial result was negative, a portion (usually one-fifth) of the first amplified reaction mixture was amplified for another 32 cycles . . ." Therefore, there may originally have been false negatives.

(G) The slant corresponding to this false negative PCR result in the Sjöbring et al., J. Clin. Micro. 28:2200–2204 (1990) study produced a single colony. The remaining three culture/PCR positive specimens were processed directly for amplification.

(H) The study of DEWit, D. et al., Tubercle and Lung Dis. 73:262–267 (1992) uses pleural fluid aspirates exclusively. The crude specimens were precipitated by PEG directly and subjected to amplification.

(I) Thierry, D. et al., J. Clin. Micro. 28:2668–2673 (1990) state: "DNA was extracted from 0.2 to 1 ml of crude or sodium hydroxide decontaminated clinical specimens . . ." Therefore, for the purpose of discussion, it is assumed that the specimens may have been used directly for amplification.

(J) Pierre, C. et al., J. Clin. Micro. 29:712–717 (1991) discuss two methodologies for processing of clinical specimens. They do not explicitly state which is used for the study. They do, however, suggest that "In some cases, a portion of the sample . . ." was processed using the second, nonionic lysis methodology. They also state that more inhibitors were found in these samples. Therefore, it is assumed, for the purpose of discussion, that organic extraction was the primary protocol used in this study.

(K) Pierre, C. et al., J. Clin. Micro. 29:712–717 (1991) utilize a "reamplification" protocol in which the tubes are opened, a portion is transferred to a fresh PCR mix and re-amplified. Their results were 79.2% using the initial amplification and 100% upon reamplification.

TABLE 1-continued

Art Reported Correlation of Culture Results with Nucleic Acids Amplification Results.
For each study in Table 1 the processing protocol is abbreviated (see Footnote A), the number of clinical specimens
evaluated is stated with the corresponding number of culture and amplification positive samples (see Footnote B),
and then the "uncorrected" correlation to culture shown (see Footnote C). These 35 were chosen because a
clear comparison between the amplification results and the culture results was presented. The studies of Shankar,
P. et al., Lancet 337:5–7(1991); deWit, D. et al., Tubercle and Lung Dis. 73:262–267 (1992); and Kaneko,
K. et al., Neurology 40:1617–1618 (1990) were omitted because no clear comparison on this basis could be made.

| Author(s) | [A]Processing Protocol | [B]Total: Cult⊕/Amp⊕ | [C]Correl. |
|---|---|---|---|

(L) The study of Del Portillo, P. et al., J. Clin. Micro. 29:2163–2168 (1991) processed the sputum directly for amplification.
(M) Brisson-Noël, A. et al., Lancet 338:364–366 (1991) test 514 specimens but only 446 were processed for both PCR and culture.
(N) The system used by Brisson-Noël, A. et al., Lancet 338:364–366 (1991) is designed against the 65Kd protein and amplifies most Mycobacteria. Of 141 culture positive specimens, 130 were MTB and 11 were MOTT (Mycobacteria other than tuberculosis). Of the 141, 126 were positive by PCR, 6 were false negatives and 9 contained inhibitors. Therefore, the correlation to culture was 89.4% (126 ÷ 141 = 0.894). The correlation reported is 97.4% and includes both elimination of samples with inhibitors and analysis of patient data (e.g., high clinical suspicion of samples that were PCR positive/culture negative).
(O) Sritharan, V. et al., Mol. Cell. Probes 5:385–395 (1991) actually compare 8 different methodologies for the release of DNA for PCR. The boiling method was that chosen for the study.
(P) The correlation stated by Sritharan, V. et al., Mol. Cell. Probes 5:385–395 (1991) is 100%, and represents reamplification of 3 samples that were false negative on the first PCR. The uncorrected correlation is 96.0%.
(Q) van der Giessen, J.W.B. et al., J. Clin. Microbiol 30:1216–1219 (1992) compared three PCR based systems (McFadden, J.J. et al., Mol. Microbial. 1:283–291 (1987); van der Giessen, J.W.B. et al., J. Med. Microbiol. 36:255–263 (1992); Vary, P.H. et al., J. Clin. Microbial. 28:933–937 (1990)) designed to detect *M. paratuberculosis* in bovine feces. One of these is the commercially available kit from IDEXX (Vary, P.H. et al., J. Clin. Microbial. 28:933–937 (1990)). In this study they tested 87 samples by all three methods in two separate runs. The cultures were run only once (culure⊕ = 30), whereas each PCR was run twice, hence the two numbers.
(R) Buck, G.E. et al., J. Clin. Micro. 30:1331–1334 (1992) actually compare 4 different methodologies for the release of DNA for PCR. The sonication method shown was that chosen for the study. In addition, all samples in the study were known TB-positives, and all were smear positive.
(S) Victor et al., J. Clin. Micro. 30:1514–1517 (1992) split all sediments and either amplified directly, or further purified the sample by sucrose gradient fractionation. The results from both methodologies were available for discussion.
(T) Fauville-Dufaux et al., Eur. J. Micro. Inf. Dis. 11:797–803 (1992) state that specimens were processed by " . . . either . . . " SDS or triphosphate. They do not differentiate further which samples were processed by which method.
(U) The primer pair used by Fauville-Dufaux et al., Eur. J. Micro. Inf. Dis. 11:797–803 (1992) was designed against the antigen 85 sequence. Consequently, their system was able to amplify most Mycobacterial species. Of the 206 samples processed, 92 were culture positive. Of these 92, 84 were initially positive by PCR (91.3%). Of the 92, 82 were identified as MTB. Of these, 82, only 74 were initially positive by PCR (90.2%). Whereas all 8 missed were seen to contain inhibitors, 3 could be diluted to the point where a positive signal was observed. Therefore, upon resolution, the authors state that 77 of the 82 (93.9%) were correctly identified by PCR. The authors report their correlation as 93.9%.
(V) Wilson, S.M. et al., J. Clin. Micro. 31:776–782 (1993) compare 2 different methodologies for the release of DNA for PCR. Both methods were used on all samples in this study, hence the two correlations. In addition, Wilson, S.M. et al., J. Clin. Micro. 31:776–782 (1993) use a "one-tube" nested protocol.
(W) Wilson. S.M. et al., J. Clin. Micro. 31:776–782 (1993) state the correlation as 75% for the GuSCN/Si procedure and 92% for the chloroform procedure. This represents "patient results." The stated correlations in this column represent the published correlations of "individual specimen" results. In addition, all samples in this study were run in duplicate and discrepants resolved.
(X) Folgueira, L. et al., J. Clin. Micro. 31:1019–1021 (1993) compare 2 different methodologies for the release of DNA for PCR. The boiling method shown was that chosen for the study. All specimens in this study were known TB-positives.
(Y) The correlation between culture and PCR stated by Folgueira, L. et al., J. Clin. Micro. 31:1019–1021 (1993) is 100%, and represents inclusion of seven samples that required dilution of inhibitors. The uncorrected correlation is 90.7%.
(Z) Kocagöz, T. et al., J. Clin. Micro. 31:1435-1438 (1993) compare two different methodologies for preparing the sediment for PCR. The boiling method shown was that chosen for the study.
($\alpha$) The "gold standard" used by Kocagöz, T. et al., J. Clin. Micro. 31:1435–1438 (1993) is "high clinical suspicion." While the stated correlation to this criterion is given as 87%, the correlation to culture is 100%.
($\beta$) Forbes, B.A. et al., J. Clin. Micro. 31:1688–1694 (1993) initially test 173 samples to optimize PCR. They then tested 727 samples. Information on both studies was available for discussion.
($\gamma$) Forbes, B.A. et al., J. Clin. Micro. 31:1688–1694 (1993) state the correlation for the 727 samples examined as 87.2%. This sensitivity includes incorporation of patient data in analyzing PCR positive/culture negative samples. Table 2 of this work shows that of 80 MTB culture positives, 67 were picked up by PCR. Therefore, the uncorrected sensitivity would be 83.8%.
($\delta$) The study of Irula, J.V. et al., J. Clin. Micro. 31:1811–1814 (1993) uses blood samples exclusively. In addition, the aim of this study is the identification of *M. avium*, as opposed to MTB.

TABLE 1-continued

Art Reported Correlation of Culture Results with Nucleic Acids Amplification Results.
For each study in Table 1 the processing protocol is abbreviated (see Footnote A), the number of clinical specimens evaluated is stated with the corresponding number of culture and amplification positive samples (see Footnote B), and then the "uncorrected" correlation to culture shown (see Footnote C). These 35 were chosen because a clear comparison between the amplification results and the culture results was presented. The studies of Shankar, P. et al., Lancet 337:5–7(1991); deWit, D. et al., Tubercle and Lung Dis. 73:262–267 (1992); and Kaneko, K. et al., Neurology 40:1617–1618 (1990) were omitted because no clear comparison on this basis could be made.

| Author(s) | $^A$Processing Protocol | $^B$Total: Cult⊕/Amp⊕ | $^C$Correl. |
|---|---|---|---|

(ε) Clarridge, J.E. et al., J. Clin. Micro. 31:2049–2056 (1993) state several numbers for culture correlation. The actual number of culture positive MTB specimens is stated as 218, and the number of PCR positives within this group is stated as 181 (see Table 2 of this reference). Therefore, the uncorrected correlation recorded for discussion is 83.0%.

(ζ) Miyazaki, Y. et al., J. Clin. Micro. 31:2228–2232 (1993) use a nested PCR system (e.g., sample from the first reaction was actually transferred to fresh PCR mix and reamplified) and identify 54 of the 56 that were culture positive (96.4% correlation). However, there were 10 samples that were culture negative/smear positive/PCR positive. The authors include these 10 and state the correlation as 97.0% (64 ÷ 66 = 0.970).

(η) The study of Jonas, V. et al., J. Clin. Micro. 31:2410–2416 (1993) utilized the proprietary amplification scheme commercialized by Gen-Probe, exclusively.

(θ) In the study of Jonas, V. et al., J. Clin. Micro. 31:2410–2416 (1993), of 119 culture positive specimens, only 95 were picked up by amplification (79.8%). There were 21 specimens that were culture negative/amplification positive. The authors concluded that only 17 of these 21 were true positives. Inclusion of these 17 suggests that amplification identified 112 of 136 true positives. This increases the sensitivity to that reported: 82.4%.

(ι) In the study of Abe, C. et al., J. Clin. Micro. 31:3270–3274 (1993) all specimens were split such that the results derived from the Gen-Probe method (Gen), could be compared with the results derived from the PCR system described by Kolk, A.H.J. et al., J. Clin. Micro. 30:2567–2575 (1992).

(κ) Abe, C. et al., J. Clin. Micro. 31:3270–3274 (1993) resolve several discrepant results and state that the correlation of the Gen-Probe method is 91.9%, and 84.2% by PCR. Disregarding resolution of the discrepants gives 90.6% and 81.3%, respectively. The sensitivity of Gen-Probe amplification appears better than that obtained by PCR.

(λ) The principle amplification scheme used by Miller et al., J. Clin. Micro. 32:393–397 (1994) is that being commercialized by Gen-Probe. They do, however, compare these results with the results obtained by the PCR system of Eisenach et al., J. Clin. Micro. 26:2240–2245 (1988). Whereas all 750 samples were amplified by the Gen-Probe methodology, only those specimens considered positive (156) were amplified by PCR.

(μ) 156 specimens in the Miller et al., J. Clin. Micro. 32:393–397 (1994) study were "... culture-proven and/or clinically diagnosed [with] tuberculosis." Of these 156, only 142 were actually culture positive. Using the Gen-Probe scheme, 131 of the 156 (83.9%) were positive. Subsequently, "[r]epeat testing of specimens with a different aliquot from the same processed sediment increased detection to 142 of 156 (91.0%)." The actual data is presented in a way that makes it all but impossible to determine if this number represents the correlation to culture. Amplification of the 156 positives by PCR initially identified 122 (78.2%) specimens. 143 (92.3%) were identified upon repeated PCR testing (the sensitivity of PCR appears only marginally better than that of the Gen-Probe method). There were a number of smear positive specimens that were missed on initial examination by both methodologies. All smear positives were identified on repeat testing.

(ν) Pfyffer et al., J. Clin. Micro. 32:918–923 (1994) produced sediments by two different methods, NALC and SDS, and amplified all sediments using the Gen-Probe methodology. Specimens were unique for each category (e.g., the same specimen was processed by one or the other of the methods, not both).

(ξ) In the Pfyffer et al., J. Clin. Micro. 32:918–923 (1994) study, 42 NALC specimens were culture positive, and 39 (92.9%) were identified by amplification. Thirty-six SDS specimens were culture positive and 35 (97.2%) were identified by amplification. However, the authors resolve amplification positive/culture negative results and conclude that amplification of NALC sediments correctly identified 46 of 49 "true positives" (93.9%), and amplification of SDS sediments correctly identified 38 of 39 "true positives" (97.4%).

(π) Bodmer et al., J. Clin. Micro. 32:1483–1487 (1994) used the Gen-Probe amplification scheme.

(†) Indicates those studies in which the authors discuss inhibition or inhibitors as a contributing factor to false negatives.

(‡) Indicates those studies in which the authors discuss low copy numbers as a contributing factor to false negatives.

(§) Indicates those studies in which the authors discuss the phenomenon of statistical dropouts, or a phenomenon that is consistent with statistical dropouts (this would include "unexplained" results), or discuss the possibility of aberrant being exacerbated by clumping.

(¶) Indicates those studies in which examples of culture positive/smear positive/amplification negative specimens were observed.

D. The Studies of Table 1

Examination of the data reported in the publications of Table 1 suggests that, regardless of system design or sample processing technique, there was a wide variation in results. These studies include literally all possible sources of specimen; including sputum, bronchial washes, pleural fluid, gastric aspirates, cerebrospinal fluid (CSF), urine, tissue biopsy, bone marrow, abscess and exudates, blood, serum, peritoneal fluid and feces. Two different amplification schemes were used: 30 studies used PCR exclusively, three studies used the isothermal, retroviral type, proprietary amplification scheme being commercialized by Gen-Probe (Jonas, V. et al., *J. Clin. Micro.* 31:2410–2416 (1993); Pfyffer et al., *J. Clin. Micro.* 32:918–923 (1994); Bodmer et al., *J. Clin. Micro.* 32:1483–1487 (1994)), and two studies compared the two amplification technologies (Abe, C. et al., *J. Clin. Micro.* 31:3270–3274 (1993); Miller et al., *J. Clin. Micro.* 32:393–397 (1994)). Thirty-three studies focussed on detection of MTB, one study focussed on *M. avium* diagnosis (Irula, J. V. et al., *J. Clin. Micro.* 31:1811–1814 (1993)), and one study pursued *M. paratuberculosis* detection (van der Giessen, J. W. B. et al., *J. Clin. Microbiol.* 30:1216–1219 (1992)). False negative results could be found in most specimen categories, regardless of target, processing technique or amplification technology.

The studies reported in Table 1 range in sample size from 7 to 1,166 specimens. Correlations with culture ranged from 3% to 100%. Nine of the 35 studies (26%) claim correlations of 100%. However, the majority, 7 of 9 (78%), involve sample sizes of less than 100 (n<100). Only two studies (Manjunath, N. et al., *Tubercle* 72:21–27 (1991); Pao, C. C. et al., *J. Clin. Micro.* 28:1877–1880 (1990)) used more than 100 specimens (however, Pao, C. C. et al., *J. Clin. Micro.* 28:1877–1880 (1990) may have reamplified in an effort to confirm negative samples: see footnote F in Table 1). Alternatively, 26 of the 35 studies (74%) show correlations of less than 100%. In this group, 20 of the 26 (77%) utilize sample sizes greater than 100 (n>100). It appears that there is an inverse relationship between the amplification-culture correlation and sample size: in general, the more samples included in a study, the lower the correlation.

In Table 1, 32 of the 35 studies (91%) show that amplification was able to detect the presence of Mycobacterial DNA in culture negative specimens (two of the three remaining studies used known positive specimens only). Two of these 32 more than double the number of culture positives (Irula, J. V. et al., *J. Clin. Micro.* 31:1811–1814 (1993); Pao, C. C. et al., *J. Clin. Micro.* 28:1877–1880 (1990)), and three very nearly double this number (Kolk, A. H. J. et al., *J. Clin. Micro.* 30:2567–2575 (1992); Manjunath, N. et al., *Tubercle* 72:21–27 (1991); Miyazaki, Y. et al., *J. Clin. Micro.* 31:2228–2232 (1993)). Thirty-one authors state directly, or reference the fact, that under ideal in vitro conditions their systems have the ability to detect the presence of 10 copies or less. The sensitivity of the remaining 4 range from 15 to 40 copies (Altamirano, M. et al., *J. Clin. Micro.* 30:2173–2176 (1992); Hermans, P. W. M. et al., *J. Clin. Micro.* 28:1204–1213 (1990); Pao, C. C. et al., *J. Clin. Micro.* 28:1877–1880 (1990); Soini, H. et al., *J. Clin. Micro.* 30:2025–2028 (1992)). Culture negative samples, that are positive by amplification, are more easily explained than culture positive-amplification negative samples: contrary to culture, PCR does not require viable organisms. For example, processing is known to kill the organisms, drug therapy may have already compromised viability, or low copy number combined with reduced viability might all contribute to the former class of samples. Regardless of system parameters, amplification should have superior sensitivity relative to either culture or smear.

Among the 35 studies, 8 different methods are used to process the raw specimens. Seventeen studies processed samples for both culture and amplification by treatment with N-acetyl-L-cysteine/NaOH (NALC), 6 studies used sodium dodecyl sulfate (SDS), 3 studies used sodium hydroxide (NaOH), 2 studies used dithiothreitol (DTT); and oxalic acid (OxAc), polyethylene glycol (PEG), and the ficoll-hypaque (Fic/Hyp) gradient method were each used once. One study actually compared processing by NALC with that of SDS (Pfyffer et al., *J. Clin. Micro.* 32:918–923 (1994)). Three studies avoided using the culture sediment and directly processed samples for amplification. Of the nine studies that obtained correlations of 100%, three used NALC, three processed specimens for amplification directly, one study used SDS, one used OxAc, and one used PEG. Keeping in mind that 7 of these studies utilized sample sizes of less than 100 (n<100), no conclusions can be drawn between how the raw specimens were processed, and perfect correlation. The study of Pfyffer et al., *J. Clin. Micro.* 32:918–923 (1994) compared NALC and SDS processing and concluded that neither method was superior.

Preparation of the processed sediment (or samples directly) for amplification falls into seven basic categories: (i) sixteen examples use variations on organic extraction and alcohol precipitation methodologies (org/ppt) as described by Maniatis, T. et al. ("Molecular Cloning A Laboratory Manual," Cold Spring Harbor Laboratory, New York (1982), pp. 458–463); (ii) two examples use an enzymatic lysis and boiling protocol (Lz/Prk→95°/15') as described by Higuchi, R. *Amplifications* 2:1–3 (1989), and six examples simply boil the specimen; (iii) ten examples use sonication (sonic); (iv) three use chaotropic agents and glass beads (GuSCN/Si) as described by Boom, R. et al., *J. Clin. Microbiol.* 28:495–503 (1990), and two use a similar protocol of binding the DNA to silica; (v) one example used sucrose gradient fractionation (Victor, T. et al., *J. Clin. Micro.* 30:1514–1517 (1992)); (vi) one example used Chelex-100 as described by de Lamballerie, X. et al., *Res. Microbiol.* 143:785–790 (1992); and (vii) one example (van der Giessen, J. W. B. et al., *J. Clin. Microbiol.* 30:1216–1219 (1992)) used the column chromatography procedure suggested by the manufacturer (Vary, P. H. et al., *J. Clin. Microbiol.* 28:933–937 (1990)). The sum is greater than 35 because the studies of van der Giessen, J. W. B. et al., *J. Clin. Microbiol.* 30:1216–1219 (1992), Victor, T. et al., *J. Clin. Micro.* 30:1514–1517 (1992), Wilson, S. M. et al., *J. Clin. Micro.* 31:776–782 (1993) and Abe, C. et al., *J. Clin. Micro.* 31:3270–3274 (1993), Miller et al., *J. Clin. Micro.* 32:393–397 (1994) and Pfyffer et al., *J. Clin. Micro.* 32:918–923 (1994) process all specimens by more than one protocol and present analyses for each method. Eight of the nine studies that claim 100% correlation isolate the DNA by organic extraction/alcohol precipitation methodologies. However, eight studies that also use organic extraction methodologies had correlations ranging from 55.9% to 98.4%. One study that claimed 100% correlation was processed by boiling (Kocagoz, T. et al., *J. Clin. Micro.* 31:1435–1438 (1993)). Alternatively, six studies using this same protocol reported correlations between 78.9% and 95.9%. Seven studies actually compare methods to prepare the culture sediment for amplification. Their conclusions differ as follows: Pierre, C. et al., J. Clin. Micro. 29:712–717 (1991)) selected organic extraction/alcohol precipitation; Wilson, S. M. et al., *J. Clin. Micro.* 31:776–782 (1993)) simply treated with chloroform; Folgueira, L. et al., *J. Clin. Micro.* 31:1019–1021 (1993) preferred the enzymatic lysis/boiling method; Kocagöz, T. et al., *J. Clin. Micro.* 31:1435–1438 (1993) and Sritharan, V. et al., *Mol. Cell. Probes* 5:385–395 (1991) chose the simple boiling method; and Forbes, B. A. et al., *J. Clin. Micro.* 31:1688–1694 (1993) and Buck, G. E. et al., *J. Clin. Micro.* 30:1331–1334 (1992) identified sonication as the optimal method (only the study of Kocagöz, T. et al., *J. Clin. Micro.* 31:1435–1438 (1993) achieved 100% correlation). It would appear that the occurrence of false negatives is not only independent of the protocol employed to prepare the sample for amplification, but there is controversy surrounding this issue as well.

Two studies actually compare amplification methods: Abe, C. et al., *J. Clin. Micro.* 31:3270–3274 (1993) show that the Gen-Probe method was marginally better than PCR (see footnote κ in Table 1), while Miller et al., *J. Clin. Micro.* 32:393–397 (1994) determine the opposite (see footnote μ in Table 1). Apparently, neither amplification technique confers a significant advantage for clinical diagnosis of TB infections.

E. PCR Inhibitors

Of the papers reporting correlations less than 100%, 17 studies refer to amplification "inhibitors" as a contributing factor to false negatives (see those authors with a superscript † in Table 1). Blood (Panaccio, M. et al., *Nucl. Acids Res.* 19:1151 (1991)), feces (Allard, A. et al., *J. Clin. Microbiol.* 28:2659–2667 (1990)), sputum (Hermans, P. W. M. et al., *J. Clin. Micro.* 28:1204–1213 (1990); Shawar, R. M. et al., *J. Clin. Micro.* 31:61–65 (1993)) and urine (Khan, G. et al., *J. Clin. Pathol.* 44:360–365 (1991)) all contain PCR inhibitors. In addition, with respect to sputum, bronchial washes and tracheal aspirates, there is a direct correlation between the viscosity of the specimen (mucous content) and disease state: patients with advanced stages of tuberculosis have the most viscous sputum and these specimens have the highest probability of retaining amplification inhibitors. Hermans, P. W. M. et al., *J. Clin. Micro.* 28:1204–1213 (1990)) and Shawar, R. M. et al., *J. Clin. Micro.* 31:61–65 (1993)) show reductions in sensitivity of 5–20 fold, and 5 fold, respectively, in the presence of sputum.

Of the 42 methodologies presented for processing in Table 1 only twelve do not incorporate some form of buffer exchange. For example, organic extraction/precipitation, washing of the pellet, or protocols using chaotropic agents (GuSCN/Si), all require a buffer exchange at some point. Sonication of the sediment, however, does not require a buffer exchange. None of these twelve studies achieves 100% correlation, and nine within this group refer to inhibitors as a contributing factor to false negatives. Inhibitors appear to be derived from both the specimen and solutions used for processing, and both sources pose significant challenges to clinical implementation of amplification technologies.

F. Low Copy Numbers, Statistical Dropouts and "Unexplained" Results

Statistical dropouts, also referred to as "sample bias," are due to low copy number; in a sample with extremely low copy numbers, from which aliquots must be taken, there exists the possibility that some aliquots will contain no target. For example, if there are ten copies of the target in a milliliter, and ten 100 μl aliquots are taken, target will be absent from some fractions. These aliquots, while being interpreted as false negatives, are "true amplification negatives." Eight studies in Table 1 describe a phenomenon that could be explained by this type of sample bias (see those authors' names with a superscript § in Table 1). As discussed below, this phenomenon is greatly exacerbated by aggregation.

Of the papers reporting correlations less than 100%, 15 refer to "low copy number" directly as a contributing factor to false negative results (see those authors with a superscript ‡ in Table 1). However, 6 of these 15, plus 3 others, present examples where negative amplification specimens were both culture positive and smear positive (see those authors' names with a superscript ¶ in Table 1). The limit of detection of acid fast staining has been reported as 7,800 to 9,500 organisms per milliliter of sputum (Hobby, G. L. et al., *Antimicrob. Ag. Chemother.* 4:94–104 (1973); Yeager, H. et al., *Amer. Rev. Resp. Dis.* 95:998–1004 (1967)). Clarridge, J. E. et al., *J. Clin. Micro.* 31:2049–2056 (1993) present an extensive analysis of false negatives (see Table 7 of this reference). Of 37 false negative specimens analyzed in detail, 26 showed dropouts, while 11 were "true" PCR negatives. Nine of these 37 were smear positive: 4 of these 9 contained inhibitors, 3 were not tested for inhibitors, and 2 were found to be free of inhibitors. Of these last two, one was a true PCR negative. Shawar, R. M. et al., *J. Clin. Micro.* 31:61–65 (1993) also reported culture positive-smear positive-PCR negative specimens that were seen to be free of inhibitors. If the sample does not contain inhibitors, and is smear/culture positive, "low copy number" cannot be a realistic possibility. Shawar, R. M. et al., *J. Clin. Micro.* 31:61–65 (1993) refer to this class of false negatives as "unexplained."

G. Partitioning of Mycobacteria During Centrifugation

The buoyant nature of Mycobacterium was evident as early as 1924 (Andros, P. M. et al., *Am. Rev. Tuberc.* 9:99 (1924)). Since then, several studies have highlighted the difficulty of sedimenting Mycobacteria (Hanks, J. H. et al., *J. Lab. Clin. Med.* 23:736–746 (1938); Hata, Jr., D. et al., *Dis. Chest* 18:352–362 (1950); Klein, G. C. et al., *Am. J. Clin. Pathol.* 22:581–585 (1952); Ratman, S. et al., *J. Clin. Microbiol.* 23:582–585 (1986); Rickman, T. W. et al., *J. Clin. Microbiol.* 11:618–620 (1980); and Robinson, L. et al., *J. Lab. Clin. Med.* 27:84–91 (1941)), and, in several instances, culturing the supernatant is advocated as standard practice.

While several studies report that the supernatant fractions contained smear positive material (Hanks, J. H. et al., *J. Lab. Clin. Med.* 23:736–746 (1938); Rickman, T. W. et al., *J. Clin. Microbiol.* 11:618–620 (1980)), another study showed that in 88.8% and 82.4% of all specimens centrifuged at 2,000 rpm and 3,000 rpm, respectively, the supernatant was culture positive (Klein, G. C. et al., *Am. J. Clin. Pathol.* 22:581–585 (1952)). In fact, this same study showed that in 2.2% and 2.7% of all specimens centrifuged at 2,000 rpm and 3,000 rpm, respectively, the sediment was culture negative while the supernatant was culture positive. Analyzing the supernatant fraction is still discussed in contemporary laboratory manuals (Kent, P. T. et al., "Public Health Mycobacteriology" in *A Guide for the Level III Laboratory*, U.S. Department of Health and Human Service, Centers for Disease Control, (1985) pp. 31–46; Sommers, H. M. et al., "Mycobacterium," in: *Manual of Clinical Microbiology*, E. H. Lennette et al., eds., 4th ed., Am. Soc. Microbiol., Washington, D.C. (1985), pp. 216–248).

The inverse relationship between sample size and correlation could potentially be explained by the buoyancy phenomenon. Larger sample sizes require batch processing. During batch processing the time it takes between work-up of the first and last specimens increases. As this time increases, buoyancy has a greater amount of time to exert an effect. It has been suggested that the source of this buoyancy is the high lipid content of these organisms (Silverstolpe, L. *Nord. Med.* 40/48:2220–2222 (1948)).

H. Influence of the Cell Wall and Surface Tension on Recovery of Mycobacteria

The nature of the cell wall of the Mycobacteria is responsible for their survival tenacity. Micrographs reveal a very complex structure 30–40 nm thick (Rastogi, N. et al., *Antimicrob. Agents Chermother.* 20:666–677 (1981)). As much as 60% of the dry weight of the cell wall is lipid (Joklik, W. K. et al., *Zinsser Microbiology* 20th edition, Appleton & Lange, Norwalk, Conn. (1992), pp. 499).

The cell wall of the Mycobacterium has three distinct layers: (i) the peptidoglycan, (ii) the arabinogalactan, and (iii) glycolipids (for a comprehensive review of cell wall structure see McNeil, M. R. et al., *Res. Microbiol.*

142:451–463 (1991)). Mycolic acids, which are extremely hydrophobic and consist primarily of hydrocarbon chains ($\Sigma=C_{76}-C_{80}$), are used extensively in the construction of both the arabinogalactan and the glycolipid layers. The structure and species distribution of mycolic acids is reviewed in Takayama, K. et al., "Structure and Synthesis of Lipids," in: *The Mycobacteria*: a Source Book, Part A, G. P. Kubica et al., eds., Marcel Dekker, Inc., New York, N.Y. (1984), pp. 315–344. The Mycobacteria are essentially encased in wax.

*M. tuberculosis* form "cords" during growth (cords are clumps or aggregates of large numbers of organisms), and there is a direct relationship between MTB virulence and cord formation (Joklik, W. K. et al., *Zinsser Microbiology* 20th ed., Appleton & Lange, Norwalk, Conn. (1992), pp. 503). Organisms of the MAC complex have additional glycolipid (C-mycoside) components in their cell wall (the differences among the serovars is summarized in Brennan, P. J. *Rev. Infect. Dis.* 11 (Supp. 2): s420–s430 (1989)). In culture, while MTB complex organisms are seen to form dense clumps, *M. avium* grows in a more diffuse, single cell fashion (Dubos, R. J. et al., *J. Exp. Med.* 83:409–423 (1946)).

Dubos, R. J. *Proc. Soc. Exp. Biol. Med.* 58:361–362 (1945) observed that the hallmark pellicle growth of cultured MTB could be modified by the addition of the polyoxyalkylene derivative of sorbitan monostearate (Tween 60; CAS®No. 9005-67-8). This observation was later extended to show that other similar derivatives could cause MTB to exhibit "rapid," "diffuse" and "submerged" growth characteristics (Dubos, R. J. et al., *J. Exp. Med.* 83:409–423 (1946)). Tween 80 (CAS®No. 9005-65-6) was found to be the most active in that regard. These authors concluded that submerged growth was due to "wetting" of the cell surface. The term "wetting" is used exclusively in the context of surface tension. The implication of these studies was that pellicle growth resulted from surface tension between the waxy coat and the aqueous media, and that the addition of Tween 80 alleviated this physical interaction.

If surface tension confined the organisms to the surface, this, in combination with cording, could explain aberrant results: very sick patients are infected by organisms that have a propensity for cord formation. In addition, large cords produce smear positive results and cultures that turn positive fairly quickly. Large cords would also exacerbate sample bias because a large cord would distribute as a single copy, but have the potency of thousands of copies. Consequently, as suggested by Klein, G. C. et al., *Am. J. Clin. Pathol.* 22:581–585 (1952), the microorganisms would easily be poured off with supernatant fraction, thereby facilitating the sample bias phenomenon. In addition, cording would cause the bacteria to partition such that smear/culture positive and amplification negative results would occur.

If surface tension and aggregation were responsible for the anomalous results, and surface tension and aggregation could be overcome by the addition of nonionic detergents, then it seems logical that these reagents should improve correlation to culture: five studies in Table 1 use nonionic detergents to wash sediments prior to amplification (Clarridge, J. E. et al., *J. Clin. Micro.* 31:2049–2056 (1993); Irula, J. V. et al., *J. Clin. Micro.* 31:1811–1814 (1993); Kolk, A. H. J. et al., *J. Clin. Micro.* 30:2567–2575 (1992); Shawar, R. M. et al., *J. Clin. Micro.* 31:61–65 (1993); and Sritharan, V. et al., *Mol. Cell. Probes* 5:385–395 (1991)). The correlations to culture range from 78.9% to 95.5% in this subset. As early as 1941 it was recognized that agents that alleviated surface tension were impotent in enhancing recovery by centrifugation (Robinson, L. et al., *J. Lab. Clin. Med.* 27:84–91 (1941)). Therefore, the art teaches there clearly is no additional advantage to inclusion of these detergents in the wash buffer.

I. Problems Unique to MAC Complex Organisms

Of the 35 studies in Table 1, 27 use MTB specific sequences for amplification and/or detection. Six studies use genus specific primers, but the designs preferentially favor amplification of TB complex organisms. Only the study of Irula, I. V. et al., *J. Clin. Micro.* 31:1811–1814 (1993) focussed on *M. avium*, and only the study of van der Giessen, J. W. B. et al., *J. Clin. Microbiol.* 30:1216–1219 (1992) focussed on *M. paratuberculosis.* Irula used a different isolation technique, making comparisons difficult. However, while PBMC were isolated, they were in fact subjected to a wash step in Tris/EDTA/Triton X-100: if the PBMC had lysed during washing, the bacteria may have been discarded with the supernatant. Regardless, it might be expected that PBMC isolation would be an extremely effective means of capturing the organisms. The study of van der Giessen compared three PCR based systems (McFadden, J. J. et al., *Mol. Microbiol.* 1:283–291 (1987); van der Giessen, J. W. B. et al., *J. Med. Microbiol.* 36:255–263 (1992); Vary, P. H. et al., *J. Clin. Microbiol.* 28:933–937 (1990)) designed to detect *M. paratuberculosis* in bovine feces (one of these is a commercially available kit from IDEXX (Vary, P. H. et al., *J. Clin. Micobiol.* 28:933–937 (1990))). Their results were far worse than anything else presented in Table 1 and appear to be artificially low. These results indicate that MAC complex organisms, with their additional lipophilic components, present a further undefined complication to processing for amplification.

J. The Innate Character of the Mycobacteria has Thwarted Exploitation of Amplification Technologies Clearly, there are two primary sources of false negative results. First, inhibitors are abundant in a variety of specimen types and the preparatory solutions also play a role in modifying the efficiency of the amplification reaction. The second category is due to the innate character of the Mycobacteria. While the source of these characteristics appears obvious, the influence of these idiosyncrasies on sensitivity is so prevalent that Noordhoek et al., *J. Clin. Micro.* 32:277–284 (1994) conclude: "... we will not speculate on the possible factors that might explain the extreme differences in sensitivity of PCR among the seven laboratories ..."

The cording, buoyant nature of these organisms causes them to partition in an inefficacious manner, and be poured off with the supernatant. An extreme example of this situation causes "unexplained" results: a sample that is culture positive and smear positive, but appears to be a true negative in the face of multiple amplifications, and does not contain inhibitors. Clearly, the source and nature of these characteristics remains to be fully explained. However, it is these phenomena, the basis of which resides in the innate qualities of these organisms, that the methods described herein solve.

SUMMARY OF THE INVENTION

Recognizing the problems involved in current methods for the preparation of Mycobacteria for subsequent analysis and culture, and cognizant of the need for a fast, inexpensive but accurate method for preparing biological and inorganic samples for the detection of Mycobacteria, the inventor investigated sample extraction methods for the preparation of such Mycobacteria.

These studies culminated in methods for the processing of Mycobacteria for detection, including detection by culture, especially detection by methods, such as, amplification, and most especially nucleic acid amplification, that, for the first time, effectively overcome art-recognized problems, such as aggregation and buoyancy, that are responsible for false-negatives and statistical drop-outs. The inventor found that certain zwitterionic detergents herein termed "SB-18-like detergents" surprisingly and unexpectedly disperse Mycobacteria, and all SB-18-like detergents apparently compromise the buoyant nature of these organisms. For Mycobacteria of the MTB complex, where aggregation is dramatic, dispersion appears to be the primary driving force in improving the efficacy of recovery. For other Mycobacteria that grow as single cells, the MAC complex organisms for example, the driving force in improving recovery appears to be the counteracting of buoyancy by accumulation of detergent. For those Mycobacteria in neither the MTB or MAC complex, inclusion of such detergents in the sample preparation protocol obviates similar problems in the art that led to false negative amplifications.

The inventor has also found that when the Mycobacteria are degassed, additional detergents, which previously showed no proficiency in compensating buoyancy, become germane in improving recovery. Presumably, degassing eliminates buoyancy to the point where surface tension is the only remaining factor restricting the organisms to the surface of the media. Given the appropriate conditions, the vast majority of detergents have the capacity to overcome surface tension. While these detergents do not eliminate aggregation in MTB complex organisms and, therefore, do not obliterate the sample bias phenomenon, they do, nonetheless, improve efficacy of collection by centrifugation. The inventor shows that, for MAC complex organisms, and other Mycobacteria that grow primarily as single cells, there is a particular class of detergents that, when combined with limited degassing, improve recovery with enhanced proficiency.

The methods of the invention are generally applicable to any microorganism, especially those that contain mycolic acid or mycolic acid-like lipids in their cell walls, including, for example, Corynebacteria (having lipids containing corynomycolic acid) and Nocardia (having lipids containing nocardomycolic acid). The methods of the invention are also generally applicable for the processing of biological samples for detection of any microorganisms.

BRIEF DESCRIPTION OF THE DRAWINGS

FIG. 4 is a schematic describing the "aggregation assay": a protocol designed to assess the ability of detergents to disperse Mycobacterium tuberculosis.

FIG. 16A presents the growth curves of Mycobacterium tuberculosis when the protocol of FIG. 16 is followed.

DETAILED DESCRIPTION OF THE PREFERRED EMBODIMENTS

Figure 1:
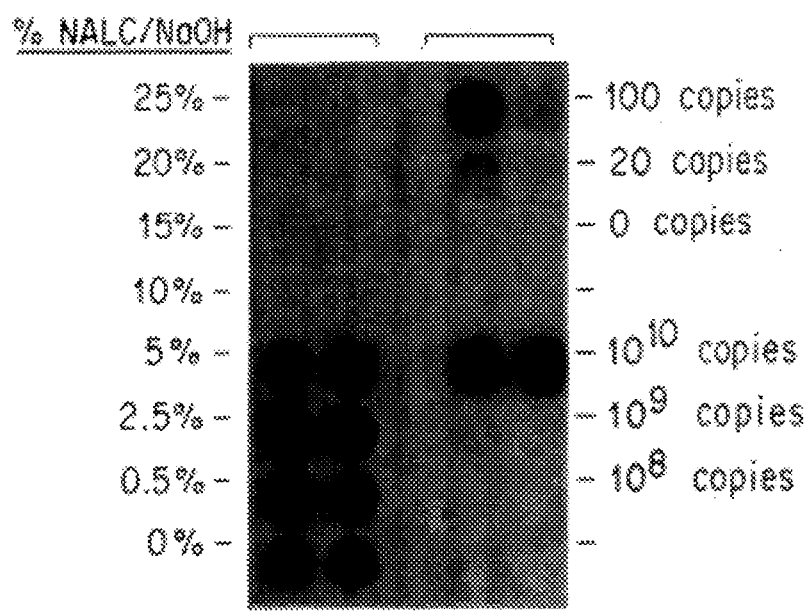
FIG. 1 is a dot-blot assay that shows the inhibition of the PCR by the NALC/NaOH sample extraction solution.

The present invention provides a method for the preparation of specimens for the detection or culture of microorganisms that are characterized in that they float (are "buoyant") in liquid media, and/or form cords or clump during growth.

By "specimen" is meant any material to be assayed or cultured for the presence of a microbacterium, especially a Mycobacterium, including, but not limited to, biological samples and inorganic samples.

By "biological sample" is meant a specimen taken from an animal (including human) or plant source. Biological samples from animal sources of special interest include those from ruminant animals (such as bovine or ovine animals), and fish and avian animals. The term biological sample is also intended to include a specimen from a processed or an unprocessed food (including, for example, eggs, cheese, milk and other dairy products), plant, or cell culture source (such as monocyte or fibroblast cultures).

By "inorganic sample" is meant a sample from a non-biological source, such as, for example, an environmental source such as soil, water, sawdust and air.

By "sediment" is meant a specimen that has been handled and/or clarified in a manner that concentrates the Mycobacteria, thus permitting the taking of a sample for subsequent detection processing.

By a "wash" is meant that the desired sample is placed in contact with the solution, generally an approximately-octadecyl or SB-18-like detergent-containing solution.

By "mycolic acid structures" is meant β-hydroxy acids substituted at the α-position with a moderately long alphatic chain, as understood in the art (Goren, M. B. *Bact. Rev.* 36:33–64 (1966), incorporated herein by reference).

By "SB-18-like detergent" is meant a betaine having the ability to facilitate physical collection of microbacteria containing mycolic acid structures in a qualitative manner for subsequent detection. The term "SB-18-like" is synonymous with "betaine-like." The SB-18-like detergents of the invention have the ability to disperse cords (and clumps) of Mycobacteria and/or compensate buoyancy of the Mycobacteria. Dispersion facilitates detection by increasing the probability that aliquots taken for detection will include microorganisms. SB-18-like detergents that disperse cords have alkyl chain length greater than 16 carbon atoms, and alkyl chains with 18–20 carbon are most preferred. The SB-18-like detergents of the invention also have the ability to facilitate collection of Mycobacteria, such as, for example, MAC organisms, that do not grow in clumps, by compensating the natural buoyancy to some degree, preferably by facilitating movement of the detergent into bacterial cells. SB-18-like detergents that compensate buoyancy preferably have an alkyl chain length greater than 12 carbon atoms, and most preferably 16–20 carbon atoms.

By "SB-18-like activity" is meant the ability to either facilitate cord disruption (and thus evenly distribute the microorganism in solution), or the ability to compensate buoyancy and thus facilitate essentially quantitative collection of such microorganisms by centrifugation, or both. For example, in the case of microorganisms that clump during growth, MTB organisms for example, treatment with an SB-18-like detergent facilitates detection by both compensating buoyancy, and also by dispersing the organisms more evenly throughout the processing solution. This duality of function is the "SB-18-like activity" of the detergent. Examples of SB-18-like detergents with these properties include the any of the betaines described herein that possess these properties, either by exemplification or by analogy to the structures of the exemplified betaines, including the CB-like, SB-like, HSB-like, PB-like, StB-like, PhB-like, So-like, Rev-B-like, AO-like, cAB-like and ImB-like detergents having structures as shown in Tables 2 and 3 and/or described herein.

By "degassing" is meant placing the specimen or sediment under vacuum for a time and at a temperature necessary to offset the natural buoyancy of microorganisms containing mycolic acid structures, such as mycolic acids, nocardomycolic acids or corynomycolic acids, for example. Without intending on being held to the following explanation, it is believed that the degassing removes $CO_2$ trapped in the cell wall, thereby removing some of the natural buoyancy of these organisms. Placing the sample under 600 mm Hg for 60 minutes at 40° C.–42° C. is preferred, and facilitates the collection of microorganisms when SB-18-like detergents are used; however, degassing for extended periods of time under the same vacuum and at the same temperature will allow any detergent to facilitate detection.

Hence, according to the methods of the invention buoyancy can be offset in three different ways: either by accumulation of the detergent inside the cell, by degassing, or both. There are certain detergents, that were not betaines, that facilitated detection in the presence or absence of degassing. For example, the nonionic linear detergents such as Brij 96 (polyoxyethylene 10 oleylether ($C_{18:1}E_{10}$) (CAS®No-9004-98-2)) has a headgroup diameter similar to that of a betaine. These "rod-like" detergents are not as sterically hindered from entering the cell (in comparison to Tween 80), and as such can be rapidly sequestered inside the cell, thereby compensating buoyancy. Therefore, "rod-like," as used herein, refers to a nonionic detergent that displays SB-18-like activity, in the absence of degassing, in the methods of the invention. Other nonionic rod-like detergents would be expected to compensate buoyancy in this manner. Other detergents, such as the octadecyl cationic detergents oetadecyltrimethylammonium bromide (TMA-18: CAS®No. 1120-02-1) or benzyldimethyloctadecylammonium chloride (BenzDMA-18) were seen to facilitate detection to a greater degree than their short chain homologues, but only in the context of degassing. Without intending on being held to the following explanation, it is believed that certain detergents, due to their "approximately-octadecyl" structure, more readily accumulate in the cell.

"Rod-like," as used herein, refers to a detergent molecule with an "axial ratio" similar to that of a betaine, wherein axial ratio is defined as: "The ratio of the major axis to the minor axis...." (McGraw-Hill Dictionary of Scientific and Technical Terms, 5th ed., Parker, S. P. ed. McGraw-Hill, Washington, D.C. (1994), p. 168). The major axis is taken as the extended alkyl chain (e.g., the hydrophobic domain: $R_1$ as defined in Table 2), and the minor axis as the diameter of the headgroup. The major and minor axes would, by definition, be perpendicular to each other.

By "approximately-octadecyl" is meant a detergent molecule possessing an octadecyl-like moiety, preferably 12–20 carbon atoms, and most preferably 18–20 carbon atoms, similar to the SB-18-like octadecyl moiety, that can be used in the methods of the invention such that SB-18-like activity is observed, but does not require the presence of the zwitterion function to be effective. This would include, but is not limited to, the rod-like detergents that do not require degassing, or the cationic detergents that do require degassing, to display SB-18-like activity. Approximately-octadecyl detergents are useful in the methods of the invention when applied to the MAC complex organisms; approximately-octadecyl detergents include SB-18-like detergents. Not all approximately-octadecyl detergents are SB-18-like detergents, but all SB-18-like detergents are approximately-octadecyl detergents.

By "CAS®Number" or "CAS®No." is meant the Chemical Abstracts Service Registry Number, 2540 Olentangy River Road, PO Box 3012, Columbus, Ohio. A listing of all CAS® numbers and structures referred to in this application is found in Table 13.

Processing Specimens for Detection

As exemplified herein, and in the most preferred embodiment, the microorganism is a Mycobacterium. As further exemplified herein, the methods of the invention for processing a specimen for subsequent detection of a clumping microorganism that contains mycolic acid structures in the outer cell wall are exemplified by the processing and detection of the MTB complex of Mycobacteria. As further exemplified herein, the methods of the invention for processing of a specimen for subsequent detection of a microorganism group that contains mycolic acid structures in the outer cell wall and that floats are exemplified by detection of the MAC complex of Mycobacteria. Although members of the Mycobacteria are specifically exemplified herein, it is to be understood that the teaching herein and the methods of the invention are useful for the sample preparation of any organism that is similarly characterized in that it floats, and/or clumps and/or contains mycolic acid structures in the cell wall.

According to a first embodiment of the invention, the sample, (or, if prepared, the sediment sample) is processed by exposing the sample or sediment to a medium containing a buffered SB-18-like detergent, or an approximately-octadecyl detergent that possesses SB-18-like activity in the absence of degassing, a rod-like detergent, for example. In the case of microorganisms that do not grow as clumps, MAC organisms, for example, this step facilitates collection by compensating the natural buoyancy to some degree. In the case of microorganisms that do clump during growth, MTB organisms, for example, this step both facilitates collection by compensating buoyancy, and by dispersing the organisms more evenly throughout the processing solution. In the first embodiment of the methods of the invention, there is no degassing step, and an SB-18-like detergent is used to disaggregate clumping microorganisms, especially the Mycobacteria, and MTB complex organisms in particular.

According to a second embodiment of the invention, the sample, (or, if prepared, the sediment sample) is processed by exposing the sample or sediment to a degassing step, such as a vacuum. In the second embodiment of the invention, the Mycobacteria, such as those of the MAC complex, are simply degassed, and then assayed. The composition of the wash solution in the second embodiment might be, but is by no means limited to, water or an aqueous buffer, as further described below.

According to a third embodiment of the invention, the sample (or, if prepared, the sediment sample) is subjected to both a degassing step and a detergent-containing wash step. In the third embodiment, any detergent, but especially those detergents that are approximately-octadecyl, and most preferably an SB-18-like detergent, can be used in combination with the vacuum step; additionally, any detergent, but especially those detergents that are approximately-octadecyl, and most preferably SB-18-like, can be used in the wash step that can precede, follow or be concurrent with the degassing step, depending on the desired use. The third embodiment is especially useful for samples wherein the species of Mycobacteria is unknown, or that is suspected of containing at least one species of the MTB and the MAC complex.

Liquid medium that is placed in contact with the specimen or sediment, such as the wash buffer, in addition, if necessary, to the desired detergent, can contain components, such as, dithiothreitol (DTT) and enzymes, such as, glycosidases and DNase, to help solubilize certain biological matter, such as, sputum, or otherwise to assist in the disposition of undesired characteristics of the sample. DTT and enzymes such as glycosidases and DNase are useful agents to reduce the viscosity of biological fluids.

More than one wash step may be performed, as desired, and such multiple wash steps may occur tandemly (one after the other) or be separated by other manipulative steps. Such multiple wash steps can contain additional reagents. To the extent that additional processing steps require the inclusion of additional reagents, such as, for example, reagents to further decontaminate the specimen, such steps can be used. Such multiple wash steps can contain different detergents or can all contain the same detergent. Combining different non-SB-18-like detergents in the same wash step has generally led to decreased efficacy of the individual detergents. However, to the extent that a certain combination of these detergents, with SB-18-like or with approximately-octadecyl detergents, retains efficacy in the methods of the invention, such combinations can be used.

In any of the embodiments of the invention, a sample to be assayed for the presence of Mycobacteria can be first extracted through any standard biological procedure that is desired as a first processing step, for example, one of the procedures recommended by Kent (Kent, P. T. et al., "Public Health Mycobacteriology" in *A Guide for the Level III Laboratory*, U.S. Department of Health and Human Service, Centers for Disease Control (1985), pp. 31–46), and especially, the NALC/NaOH Isolation Procedure as shown in Examples 2, 4 and 6. A portion of the sediment is first removed for culture and smear. The remaining sediment is then further processed by any of the embodiments for subsequent detection by amplification (nucleic acid or signal) or immunodetection or any method capable of distinguishing the presence of the desired Mycobacterium in the sample. However, as discussed below and in the Examples, such processing by standard techniques currently used in the art is highly likely to compromise collection and/or detection of the Mycobacteria that are in the sample, especially when such Mycobaeteria are present in very low numbers. Thus, while the methods of the invention when used by themselves are essentially quantitative for even low numbers of Mycobacteria that are in the sample, when used in combination with current protocols that do not provide the detergent or degassing of the invention, recovery of the Mycobacteria may have already been compromised. It is also possible to modify the contemporary protocols of Kent, P. T. et al. [supra] in such a manner as to avoid inefficient recovery by, for example, neutralizing sodium hydroxide or oxalic acid, or any of the decontaminants described by Kent, P. T. et al., [supra] with the appropriate reagent and then adding the SB-18-like or approximately-octadecyl detergent for processing prior to centrifugation; or by adding an appropriately buffered SB-18-like or approximately-octadeeyl detergent such that it acts as the neutralization buffer for further processing by the methods of the invention prior to centrifugation; or by simply degassing the neutralized specimen prior to centrifugation. Such modified protocols would allow SB-18-like activity and/or degassing to improve the efficiency of recovery by centrifugation while still utilizing contemporary methodologies.

Therefore, in a highly preferred embodiment as exemplified in Example 13, a sample to be assayed for the presence of Mycobacteria is utilized in the method of the invention for the immediate isolation of Mycobacteria for detection by amplification directly and/or for culture, without first having been processed by any standard preliminary protocol. Rather, the sample is either used directly, or clarified or otherwise purified of solids and/or inhibitors, if necessary, using routine separation techniques known in the art, such as, centrifugation, filtration, gel exclusion chromatography or ion exchange chromatography. The sample is subjected directly to either a wash with an SB-18-like detergent, a vacuum treatment to obviate buoyancy, or both, as described herein. The processed cells are efficiently collected and the sediment used for the detection of the desired microorganism.

In the first embodiment described above, the desired amount of the sediment or sample is processed in a sufficiently sized container with a wash buffer that contains an SB-18-like detergent, for a time and at a temperature and agitation level sufficient to disaggregate the Mycobacteria uniformly throughout the solution and compensate buoyancy. Such agitation may be achieved by, for example, vortexing or generally keeping the container holding the sample in motion in order to resuspend the pellet (or to suspend the specimen) hard enough to allow the detergent to efficiently break up the microorganisms and disperse them into the fluid, just prior to the next step. Slightly elevated temperatures, such as, 37° C., facilitate disaggregation without compromising subsequent detection methods, and may be necessary to keep the SB-18-like detergent from precipitating. After uniform dispersion of the microorganisms, and especially of the Mycobacteria, they may be collected in a mass using techniques known in the art, such as centrifugation, and detected or otherwise assayed and analyzed as described below.

In the second embodiment, the sample, or the remaining sediment, is simply resuspended in water or other desired medium, not necessarily a medium with a detergent, and is degassed at a desired pressure and temperature, for a time sufficient to obviate the natural buoyant tendency of the microbacteria, especially the MAC complex organism, in the solution. The microorganisms can then be collected and detected as described below.

In third embodiment described above, the first two embodiments are essentially combined, except that prior to, during or following degassing almost any detergent, but especially those that are approximately-octadecyl, and most especially, those that are SB-18-like, can be used in the medium to achieve dispersion and additionally compensate buoyancy. The degassing step can precede, follow the detergent wash step, or the detergent step can be simultaneous with the degassing step. Those practicing this art should be aware that, given the current state of the technology, simultaneously washing and degassing specimens can pose a significant safety risk.

The third embodiment is further described in Example 10. As shown in Example 10, when the vacuum treatment is used in conjunction with the detergent wash, then approximately-octadecyl detergents can be used, preferably SB-18-like detergents, and most preferably SB-18. As further shown in Example 10, under conditions where the sample is extensively degassed to eliminate most natural buoyancy, any detergent can be used. In this embodiment, the sample may or may not require clarification or purification; these steps can take place either before, in between, or after the desired vacuum-detergent treatment steps. As described above, the microorganisms can then be collected and detected.

Thus, for quantitative recovery of Mycobacteria, the standard sample processing methods such as the N-acetyl-L-cysteine/NaOH (NALC) procedure described within Kent, P. T. et al., "Public Health Mycobacteriology" in *A Guide for the Level III Laboratory*, U.S. Department of Health and Human Service, Centers for Disease Control (1985), pp. 31–46, are preferably abandoned, or modified as described above, and the specimen, or decontaminated specimen, is directly subjected to (i) a wash with an SB-18-like detergent, preferably SB-18, (ii) simple degassing, or (iii) a combination of both a detergent wash and a vacuum treatment, depending upon the Mycobacteria it is desired to assay.

However, if desired, for the practice of the methods of the invention from biological fluids including, for example, sputum, cerebrospinal fluid and urine, the sample can be processed in a first step to provide a sediment. For example, the sample can be first processed by any of the methods described within Kent, P. T. et al., "Public Health Mycobacteriology" in *A Guide for the Level III Laboratory*, U.S. Department of Health and Human Service, Centers for Disease Control (1985), pp. 31–46, incorporated herein by reference, including the N-acetyl-L-cysteine/NaOH (NALC) procedure, as highlighted in Example 12, below, and as described above.

The sediment can be subjected to a secondary wash step by mixing with a liquid, such as, water, or other buffer containing a desired SB-18-like detergent, in a sufficiently sized container to permit vigorous mixing, such as by vortexing, and further purified if necessary, using methods known in the art, such as, for example, gel chromatography, ion exchange chromatography, or filtration methodologies, prior to, during, or after the secondary wash step. The bacterial pellets (the sediment) obtained from such processing can be used as a source of Microbacteria for detection, including detection by culturing.

In a preferred embodiment, the sample is directly processed with a solution that provides the desired detergent, such as SB-18 as exemplified in Example 13, below, in a sufficiently sized container to permit vigorous mixing, such as by vortexing, and further purified if necessary, using methods known in the art, such as, for example, gel chromatography, ion exchange chromatography, or filtration methodology, prior to, during, or after direct processing. The bacterial pellets (the sediment) obtained from such initial processing can be used as a source of Microbacteria for detection, including detection by culturing.

Additional primary or secondary clarification or purification steps known in the art can be included at appropriate steps in the process, if they incorporate an appropriate detergent, if necessary, such as an SB-18-like or approximately-octadecyl detergent, into the medium. As further indicated above, when both exposure to detergent and degassing are employed, that is, when an exposure to an appropriate detergent as described herein either precedes, is simultaneous with, or follows the degassing step, it is not necessary to use only SB-18-like detergents and any detergent can be used, especially those that are approximately-octadecyl as herein defined and exemplified.

Of course, if the specimen is initially processed by a standard method (such as the NALC/NaOH method), such as shown in Example 12 and then either subjected to (i) a wash with an SB-18-like detergent, preferably SB-18, (ii) simple degassing, or (iii) a combination of both a detergent wash and a vacuum treatment to obviate buoyancy, recovery of the remaining organisms will be enhanced, but not necessarily quantitative insofar as losses that result from processing by any of the standard methods will have already compromised the sample.

In any of the combinations described herein, including the combination of the methods of the invention with the standard NALC/NaOH method, the processed cells are more efficiently collected and the sediment can now be used for the detection of the desired microorganisms therein.

The practice of the invention results in the quantitative extraction of Mycobacteria from a specimen in a manner that virtually eliminates false negatives that result from clumping or buoyancy. The methods of the invention, for the first time, permit reliance upon the results of detection techniques, for example, nucleic acid amplification results, and provide such Mycobacteria in a manner that allows the culture or lysis of such Mycobacteria by other methods, for example, boiling.

The methods of the invention are useful for the detection of Mycobacteria in specimens taken from any host. Examples of animals other than human that are known to be susceptible to Mycobacterial infections include cattle, hogs, poultry, sheep, goats, deer, monkeys, elephants, horses, dogs, cats, mink, and various zoo and aquarium animals. A tissue sample that is submitted for use in the method of the invention is usually taken from a granulomatous lesion, generally nodular and having a caseocalcareous center surrounded by a fibrous capsule. If there is no gross lesion, it is preferred to analyze lymph nodes. If the infection is intestinal, a thickened portion of the intestine is generally sampled.

Specimens can be in the form of a biological fluid including, for example, sputum, cerebrospinal fluid, urine, bronchial washes, pleural fluid, gastric aspirates, blood, serum, peritoneal fluid, abscesses and exudates or other biological fluid and may be obtained from public or private culture collections and the like, or especially from clinical or veterinary sources. Liquid cultures, frozen suspensions or colonies grown on solid medium can be utilized. Some specimens may be semi-solid material and/or require clarification, such as feces and whole or cultured blood. The methods of the invention are also useful with specimens from exotic sources, such as, for example, fish or reptile scales, and from tissue samples.

It is not necessary that a sample of the specimen be taken for culture. Indeed, it is an advantage of the invention that direct detection of the desired microorganism by nucleic acid or signal amplification can be performed on a sample taken directly from the sediment. It is shown herein that the Mycobacteria are still viable (e.g., not lysed) after the processing method of the invention, and therefore, culture can be performed if desired. For example, all specimens can first be processed by the methods of the invention to provide maximum efficiency of recovery of the microorganisms for detection by amplification techniques, and an answer concerning the diagnosis in the shortest possible time. Positive specimens can then be further processed for culture. Such a format dramatically decreases the time to diagnosis and provides microbactria, especially Mycobacteria, that are in the specimen, in a form that is suitable for cultivation. The increased incidence of drug resistance among MTB strains necessitates that all MTB positive specimens be cultured for drug susceptibilities. In that the efficiency of recovery of the Mycobacteria, in a viable form, is optimal, the methods of the invention facilitate diagnosis and susceptibility determination.

The methods of the invention, for the first time, essentially eliminate false negatives due to the "clumping" of microorganisms, such as Mycobaeteria of the MTB complex. Clumping substantially exacerbates inefficient partitioning of clumping organisms during sample processing. In fact, the methods of the invention facilitate the homogeneous distribution of clumping organisms in a desired solution, and thus promotes their detection, using detection techniques known in the art, for example, culture and nucleic acid (DNA or RNA) amplification, by increasing the probability that all aliquots from a given sample will contain the organism.

Additionally, the methods of the present invention overcome the natural buoyancy of these organisms in aqueous liquids, thereby facilitating collection of these organisms using collection techniques known in the art, for example, centrifugation. The natural buoyancy substantially reduces the ability to efficiently collect these organisms by centrifugation.

In that the methods of the present invention substantially improve the efficiency of recovery of these microorganisms from specimens, the need for long term culture results is eliminated insofar as more technologically advanced methods can supplant diagnosis; nucleic acid based amplification technology is one example of such a more advanced method. The methods of the invention, however, do not lyse the microorganisms but instead produce viable organisms such that culture techniques are not precluded as a method for detection.

The methods of the invention are directed to the manner in which a specimen is prepared for testing for the presence of a microorganism such as a Mycobacterium. Therefore, the microbacterium that is ultimately detected will depend upon the detection procedure that is used in conjunction with the methods of the invention. Such detection procedure can be designed to detect any desired microorganism, and especially, any desired Mycobacterium group or complex or Mycobacterium species, and most preferred, a Mycobacterium complex such as M. tuberculosis (MTB) complex, M. avium (MAC) complex, MAIS complex and M. fortuitum complex, as well as fast growing and slow growing Mycobacteria including specified and unspecified photochromogens, nonphotochromogens, scotochromogens, and especially M. africanum, M. asiaticum, M. avium, M. bovis, M. bovis (BCG), M. butyricum, M. chelonae, M. duvalii, M. flavescens, M. fortuitum, M. gastri, M. gordonae, M. haemophilum, M. intracellularae, M. kansasii, M. leprae, M. lepraemurium, M. linda, M. lufu, M. marinum, M. malmoense, M. microti, M. mucoscum, M. nonchromogenicum, M. paratuberculosis, M. peregrinum, M. phlei, M. rhodochrous, M. scrofulaceum, M. shimoidei, M. simiae, M. smegmatis, M. szulgai, M. terrae, M. thermoresistable, M. triviale, M. tuberculosis, M. ulcerans, M. vaccae, M. xenopi, and serovats thereof.

M. kansasii, M. marinum, M. simiae and M. asiaticum are examples of photochromogens. M. scrofulaceum, M. szulgai, M. xenopi, M. gordonae and M. flavescens are examples of scotochromogens. M. avium, M. intracellulare, M. gastri, M. malmoense, M. terrae and M. triviale are all examples of nonphotochromogens.

M. africanum, M. avium, M. bovis, M. haemophilum, M. intracellulare, M. kansasii, M. malmoense, M. marinum, M. microti, M. paratuberculosis, M. scrofulaceum, M. simiae, M. szulgai, M. tuberculosis, and M. xenopi are all examples of slow-growing (requiring more than seven days) Mycobacterial species. M. chelonei, M. flavescens, M. fortuitum, M. gordonae, M. leprae, M. phlei, M. smegmatis, M. terrae, M. ulcerans are all examples of rapid-growing (requiring less than seven days) Mycobacterial species.

M. tuberculosis, M. africanum, M. bovis, M. bovis (BCG), and M. microti are the members of the MTB complex. M.

*avium* and *M. intracellulare* are the members of the MAC complex; there are at least three distinct serologic groups of *M. avium*, and more than 25 serovars of *M. intracellulare*.

The present invention is especially useful for microorganisms that are lipophilic, or encased in a wax-like capsule characterized by having lipids that are mycolic acid-like molecules in their outer cell wall (such as, for example, corynomycolic acid, nocardomycolic acid and mycolic acid, among others. These are all characterized as "mycolic acid structures," that is, β-hydroxy acids substituted at the α-position with a moderately long alphatic chain, as understood in the art (Goren, M. B. *Bact. Rev.* 36:33–64 (1966), incorporated herein by reference). An example of an organism having corynomycolic acid is *Corynebacterium diptheria*; an example of an organism having nocardomycolic acid is *Nocardia asteroides*; and an example of an organism having mycolic acid is *Mycobacterium tuberculosis*. Such mycolic acid-like molecules are herein collectively termed "mycolic components." Additional tables of representative mycolic acid structures, including some that are unsaturated, cyclopropanoid, methoxylated and ketonic acids, may also be found, for example, in Lederer, E. *Chem. Phys, Lipids* 1:294–315 (1967); Lederer, E. *Pure Appl. Chem.* 25:135–165 (1971), both incorporated herein by reference. "Mycolic acid structures" are acid-stable molecules.

Examples of the diseases and conditions in which the various Mycobacterial species are of heightened importance in detection include especially the causative agents of tuberculosis (*M. tuberculosis* complex) and leprosy (*M. leprae* (human leprosy) and *M. lepraemurium* (rodent leprosy)). *Mycobacterium avium* Complex is an important bird disease. *M. avium* has also been isolated from AIDS patients who are afflicted with a mycobacterial superinfection. *M. bovis* is of importance in veterinary medicine. *M. fortuitum* is a soil bacterium that has been isolated from lesions in animals and humans. *M. intracellulare* is oppormnistic and is especially seen in patients infected with the AIDS virus. *M. paratuberculosis* is of interest in the diagnosis of Crohn's disease (regional ileitis) in humans. *Mycobacterium kansasii* is a rare but devastating agent, generally associated with pulmonary disease. *Mycobacterium marinum* infects cold-blooded animals and fish; it has also been isolated form superficial granulomas on the extremities of humans. *Mycobacterium paratuberculosis* is the causative agent of Johne's disease in cattle; it is very slow growing and cultures must be held for 16 weeks before it can be assured that they are negative. *M. ulcerans* is also of interest in human medicine. Many of the above and others have been discussed by Wayne, L. G. et al., *Clin. Micro. Rev.* 5:1–25 (1992), and are incorporated herein by reference.

The detection step can utilize any method known to detect the desired microorganism, especially a desired Mycobacteria, including, but not limited to nucleic acid amplification, signal amplification, hybridization, culture and immunoassay. In the preferred embodiment, the detection method is nucleic acid amplification and/or culture. In the most preferred embodiment amplification, polymerase chain reaction (PCR) amplification, is used. Indeed, it is an advantage of the method of the invention that the SB-18-like detergents are not inhibitory to the PCR, and that the organisms are still viable and can be cultured. In contrast to the standard art, the NALC/NaOH solution is extremely inhibitory to the PCR. In addition, it is well established that, while the organisms are still viable following treatment with NALC/NaOH, 28%–33% of the Mycobacteria are known to have been killed (Krasnow, I. et al., *Am. J. Clin. Path.* 45:352–355 (1966); Kubica, G. P. W. et al., *Am. Rev. Resir.*

*Dis.* 87:775–779 (1963)). In contrast, while SB-18-like detergents may have bacteriocidal and some degree of bacteriostatic activity, when used at the desired concentrations in the methods of the invention, the Mycobacteria are not lysed and are still viable.

The means for identification of the presence of Mycobacterium may employ labels, such as those commonly used with nucleic acid detection and/or immunodetection of Mycobacterium antigens, including, but not limited to radio-labeled markers (for example, $^{32}P$, $^{33}P$, $^{35}S$, $^{14}C$, and $^{3}H$), fluorescent markers (for example, fluorescein, auramine, rhodamine, Texas Red, etc.), chemiluminescent markers (for example, acridinium-ester labelled probes, LUMI-PHOS 530™, Schaap Reagent (4-methoxy-4-(3-phosphatephenyl)-spirol-[1,2-dioxetane-3,2'-adamantane), CSPD®(U.S. Pat. No. 5,112,960), etc.), colorimetric detection (for example 3,3',5,5'-tetramethylbenzidine (TMB), etc.), electrochemiluminescent (for example tris(2,2'-bipyridine)ruthenium (II) chelate (TBR)), and protein or enzymatic markers (for example, antibodies, alkaline phosphatase, horseradish peroxidase, etc.) that can be used in conjunction with any of the reagent categories above.

The methods of the invention are most conveniently practiced by providing the agents used in such method in the form of a kit. Such a kit preferably contains appropriate buffers, salts, SB-18-like detergent (or an equivalent thereof, such as a detergent useful in combination with degassing) and if desired, water of the appropriate purity. At least one type of identifying agent may also be included, the type of identifying agent being dependent upon the type of detection assay being used (for example, whether an amplification, immunodetection, etc. is ultimately used); and a "positive" standard providing either nucleic acid (DNA or RNA) useful in the detection of the microorganism, or a desired specific antigen (protein or otherwise) or other characteristic substance, such as components for identification by the microorganism's lipid profile, especially by gas-liquid chromatography. Specific kits may contain, inter alia, particular Mycobacterium identifying means such as particular nucleic acid probes, antibodies or smear or culture materials. The means by which the identifying agent is detected may be specific for the kit, such that the kit provides for, for example, an enzymatic, fluorescent, radioactive or chemiluminescent detection, or any other appropriate detection as known in the art. In such a kit, such detection means are generally in close proximity to the detergent reagent(s), even if confined in separate containers or packages.

If nucleic acid amplification is utilized as the detection method, many types of such amplification are known and all would be useful in the methods of the invention. For example, types of nucleic acid amplification systems include the polymerase chain reaction (PCR), ligase chain reaction (LCR), Qβ replicase amplification, strand displacement amplification (SDA), and single primer amplification (SPA), or transcription based amplification systems such as NASBA (nucleic acid sequence based amplification), SSSR (self sustained sequence replication), or LAT (ligation activated transcription) amplification. Signal amplification systems, such as that of branched-DNA (bDNA), are also useful.

The development of Mycobacterial genus-specific and sequence-specific probes has been described (Fries, J. W. U. et al., *Molec. Cell. Probes* 4:87–105 (1990)). Certain genetic sequences appear in more than one Mycobacterium species and can be advantageously used to detect the presence of any of a family of Mycobacterium species. For example, Crawford et al., U.S. Pat. No. 5,183,737 describe a repetitive DNA sequence that is specific for members of the *M.*

*tuberculosis* (MTB) complex. Detection may be performed by direct hybridization analysis (for example, Southern analysis) or by using a fragment of the conserved sequence as primers in an amplification assay. In a novel amplification assay described herein, MTB Complex, *Mycobacterium avium* Complex, *Mycobacterium intracellulare, Mycobacterium paratuberculosis, Mycobacterium kansasii, Mycobacterium marinum, Mycobacterium szulgai,* and *Mycobacterium gastri* may also be amplified using one set of probes as described herein using sequences based on the 16S rRNA gene sequences as published by Rogall, T. et al., *Int. J. Sys. Bacteriol.* 40:323–330 (1990). The primers were designed such that they had the ability to provide optimal amplification of the following groups/species of Mycobacteria: *M. tuberculosis* (TB complex: [MTB]), *M. avium-M. intracellulare* and *M. paratuberculosis* (MAC complex), *M. kansasii* and *M. marinum*. The forward primer was designed against nucleotides 119–144 (according to the nomenclature of Rogall, T. et al., *Int. J. Sys. Bacteriol.* 40:323–330 (1990)) of the second variable (V2) region of the 16S rRNA gene sequence of these Mycobacteria. The sequence of the forward primer (TBv2-119) is: 5'-AAA CTG GGT CTA ATA CCG GAT AGG A-3'[SEQ ID No. :1:]. The reverse primer was designed against nucleotides 431–453 of the third variable (V3) region. The sequence of the reverse primer (TBv3-453) is: 5'-CCA CCT ACC GTC AAT CCG AGA-3'[SEQ ID No. :2:]. The amplification product was approximately 335 base pairs (depending on the species amplified). The genus specific probe was designed against a central portion of the amplification product and is common to all Mycobacteria. Its sequence is: 5'-GCG GGC iCA TCC CAC ACC GC-3'[SEQ ID No. :3:]. The MTB-species specific probe was designed against a distinct portion of the amplification product and is specific to organisms of the TB complex. Its sequence is: 5'-GAC CAC GGG ATG CAT GTC TTG TG-3'[SEQ ID No. :4:].

On the other hand, species-specific probes are known. For example, McFadden et al., U.S. Pat. No. 5,225,324 describe a family of DNA insertion sequences that can be used as probes for the identification of mycobacteria and for the differentiation between closely related species. U.S. Pat. No. 5,216,143 describes probes specific for *M. gordonae*. Probes for *M. paratuberculosis* are also known: the IS900 insertion element is specific for that species (McFadden et al., *Mol. Microbiol.* 1:283–291 (1987).

SB-18-Like Activity

In the most preferred embodiment the detergent preferred in the medium, and especially, in the secondary wash step, is an SB-18-like detergent that is capable of disrupting cord formation, and most especially, SB-18 (CAS®Number 13 177-41-8), in an amount sufficient to disrupt cord formation and to allow for the even dispersal of the Mycobacterium. SB-18 is preferred owing to its economical availability in a purified form. $C_{18}$-carboxypropylbetaine (CAS®No. 78195-27-4) is highly preferred because it provides the ideal combination of solubility, chain length and bridge structure for use in the methods of the invention.

SB-18 (CAS®Number 13177-41-8) has the chemical composition $C_{23}H_{49}NO_3S$ and the chemical formula $CH_3(CH_2)_{17}N(CH_3)_2(CH_2)_3SO_3$. The chemical names of SB-18 include dimethyloctadecyl (3-sulfopropyl)ammonium hydroxide inner salt (Aldrich No. 36,712-5), and N-octadecyl-N,N-dimethyl-3-ammonio-1-propane sulfonate (Sigma No. 08004), and 3-(N,N-dimethylstearylammonio) propanesulfonate and 3-(stearyl-dimethylammonio) propanesulfonate (Fluka No. 41570)). Most preferably, SB-18 from Sigma is used in the methods of the invention.

Only one other detergent in the SB series was useful in disrupting cord formation: SB-16 (CAS®Number 2281-11-0; N-hexadecyl-N,N-dimethyl-3-ammonio-1-propane-sulfonate; palmityl sulfobetaine; Sigma H 6883), however, it was not as effective as SB-18 at the same concentrations. The data presented herein show that most octadecyl betaines, that is betaines wherein $R_1$ as defined below is greater than 16 carbon atoms, have the ability to disrupt clumps of *M. tuberculosis*.

Certain detergents do not possess the ability to disrupt cord formation and disperse the MTB complex organisms to a satisfactory degree. Detergents and other compounds that were tested and found not to have this ability to disaggregate the MTB complex included: SB-10 (CAS®No. 15163-36-7), SB-12 (CAS®No. 14933-08-5), SB-14 (CAS®No. 14933-09-6), decanoic acid (CAS®No. 334-48-5), dodecanoic acid (CAS®No. 143-07-7), sodium dodecyl sulfate (SDS: CAS®No. 151-21-3), benzalkonium chloride (BenzAlk: CAS®No. 8001-54-5), mixed alkyltrimethyl ammonium bromide (mTMA), dodecyltrimethylammonium bromide (TMA-12: CAS®No. 1119-94-4), myristyltrimethylammonium bromide (TMA-14: CAS®No. 1119-97-7), octadecyltrimethylammonium bromide (TMA-18: CAS®No. 1120-02-1), deoxycholic acid (CAS®No. 302-95-4), benzyldimethyldodecylammonium bromide (BenzDMA-12: CAS®No. 7281-04-1), benzyldimethyltetradecylammonium chloride (BenzDMA-14: CAS®No. 139-08-2), benzyldimethyloctadecylammonium chloride (BenzDMA-18), Tween 20 (CAS®No. 9005-64-5), Tween 60 (CAS®No. 9005-67-8), Tween 80 (CAS®No. 9005-65-6), Triton X-100 (CAS®No. 9002-93-1), NP-40 (CAS®No. 127087-87-0), Brij 35 (CAS®No. 9002-92-0), Brij 99 (CAS®No. 9004-98-2), Span 20 (CAS®No. 1338-39-2), Span 60 (CAS®No. 1338-41-6), Span 80 (CAS®No. 1338-43-8), Synperonic F/68, polyethyleneglycol 1450 (CAS®No. 25322-68-3), Ficoll 400,000 (CAS®No. 26873-85-8), polyvinylpyrrolidone 360,000 (CAS®No. 9003-39-8), formamide (CAS®No. 75-12-7), and dimethyl formamide (CAS®No. 68-12-2).

Some detergents, while being unable to disrupt cord formation, were seen to facilitate collection. For example, it is shown herein that all SB-series detergents, especially SB-12, SB-14, SB-16 and SB-18, and most especially SB-18, can be used with equal efficiency with organisms that did not clump. *M. avium* for example. Therefore, in addition to SB-18 (CAS®No. 13177-41-8), other detergents in the SB-series that offset buoyancy, thus facilitating collection by gravitational force methods, include: SB-16 (CAS®Number. 2281-11-0; N-hexadecyl-N,N-dimethyl-3-ammonio-1-propane-sulfonate; palmityl sulfobetaine; Sigma H 6883); SB-14 (CAS®Number 14933-09-6; N-tetradecyl-N,N-dimethyl- 3-ammonio-1-propane-sulfonate; myristyl sulfobetaine; Sigma T 7763); and SB-12 (CAS®Number 14933-08-5; N-dodecyl-N,N-dimethyl-3-ammonio-1-propane-sulfonate; lauryl sulfobetaine; Sigma D 4516).

The zwitterionic SB-series detergents possess both a quarternary nitrogen and a sulfonate group separated by a propyl function, and each has a long chain alkyl moiety; dodecyl, tetradecyl, hexadecyl or octadecyl for SB-12, SB-14, SB-16 and SB-18, respectively, bonded to the quarternary nitrogen. It is shown herein that, whereas SB-18 was the most efficient at disrupting cord formation, the entire SB-series of detergents showed some degree of efficacy in facilitating collection of *M. tuberculosis* by centrifugation. In addition, the SB-series detergents showed equal efficiency in facilitating collection of those organisms that do not cord, for example *M. avium*. As described below, and without intending on being held to this explanation, these zwitterionic detergents are believed to possess characteristics that facilitate movement of the detergents into bacterial cells. The net effect of this accumulation is to compensate the natural buoyancy of the organisms, to a degree sufficient to allow for their collection by centrifugation.

According to the invention, and in those embodiments that utilize detergents, the end result is the same whether an SB-18-like detergent is used that facilitates dispersion of cords or whether an SB-18-like detergent is used that facilitates collection of the bacteria by centrifugation: according to the invention, the Mycobacteria are placed in an environment that facilitates their subsequent detection, either by evenly dispersing them throughout the sample, and/or by facilitating their collection and concentration by centrifugation.

This duality of function is herein termed "B-18-like activity." Therefore, SB-18-like activity, as used herein, shall refer to either the ability of an SB-18-like detergent to facilitate cord disruption when processing an organisms that grows in clumps (and thus evenly distribute the microorganism in solution), or the ability of an SB-18-like detergent or approximately-octadecyl detergent, to facilitate essentially quantitative collection of such microorganisms by centrifugation due to offsetting buoyancy, or the ability of an SB-18-like detergent to do both.

Betaine-Like Detergents

It is shown herein that compounds similar to SB-18 that possess (a) only a quarternary amine (the octadecyl, cationic detergents trimethyloctadecylammonium bromide (TMA-18: CAS®No. 1120-02-1)) and benzyldimethyloctadecylammonium chloride (BenzDMA- 18), for example); (b) only the sulfate moiety (the octadecyl, anionic detergent sodium octadecyl sulfate (SOS): CAS®No. 1120-04-3); and (c) only the zwitterionic functionality (3-[(3-cholamidopropyl)-dimethylammonio]-1-propane-sulfonate (CHAPS): CAS®No. 75621-03-3), were all impotent in enhancing recovery in the absence of degassing. This suggests that the relationship between the alkyl moiety and the zwitterion functionality facilitates SB-18-like activity.

The SB-series detergents, also known as the sulfobetaines, are a subset of a broad class of zwitterionic detergents known as the betaines. The betaines are zwitterionic molecules containing, inter alia, a center of positive charge, separated from a center of negative charge. Table 2 gives the generic structure of the most common class of betaines (n-alkyl betaines), and Table 3 describes several common structural variations on this theme. Without intending on being held to any theory, it is believed that the zwitterion functionality produces a dipole moment that apparently confers SB-18-like activity on this entire class of molecules. Regardless, it is shown herein that variations in betaine structure produce predictable results with respect to utilization of the betaine in the methods of the invention.

A generic description of the n-alkyl betaines is described in Table 2. As used throughout this description, "$R_1$" represents the hydrophobic portion of the detergent. This is typically an alkyl moiety and can be a short aliphatic chain with as few as 8 carbon atoms, to a long chain exceeding 22 carbon atoms. Preferably, the alkyl moiety contains from 12 to 20 carbon atoms, more preferably 16–18 carbon atoms. The alkyl chain can have alkylenic unsaturation, be branched, and/or be substituted with, for example, hydroxyl, ester, ether, carbonyl functions, as well as other groups.

The "$\alpha$" may or may not be present, depending upon whether "n" equals 0 or 1. If n=0, $\alpha$ is not present; if n=1, $\alpha$ is present. Where $\alpha$ is present, it links $R_1$ to the center of positive charge. This linkage may be a methylene group. One of the more common such linkages is an amidopropyl group (—(CO)—NH—CH$_2$CH$_2$CH$_2$—). Others, such as, ether linkages (—O—), carbonyl linkages (—CO—) or hydroxymethyl (—CH(OH)—) linkages are known as well. However, other groups are certainly possible, amines for example.

"$R_2$" and "$R_3$" are independently selected from the group consisting of hydrogen and alkyl, preferably lower alkyl of 1–4 carbon atoms, e.g., methyl, ethyl, propyl, butyl, or isomers thereof and most preferably methyl; however, increasing the bulk of these alkyl groups, as by lengthening or branching them, while possible, compromises function, as discussed in Examples 9 and 10.

"$\beta$" represents the center of positive charge. In the vast majority of cases $\beta$ is a quaternary nitrogen (—N⊕—), however, phosphonium (—P⊕—), sulfonium (—S⊕—) and other moieties are possible. It should be noted that in most instances $\beta$ is a quaternary nitrogen, and as such $R_2$ and $R_3$ would be required. However, for other cations $R_2$ and $R_3$ may not need to be present.

"$R_4$" is a bridge separating the charged species. This bridge can be an alkylene group (e.g., m≥1), for example, methylene, ethylene, propylene, butylene, pentylene, and hexylene bridges are known. The composition and structure of $R_4$ are not limited to that of an alkylene group: examples incorporating hydroxyl groups, or in which $R_4$ is branched, or a benzyl group are also common. Other modifications to $R_4$, incorporating amines, for example, are possible as well, and would be expected to function similarly.

The center of negative charge, "$\gamma$," has been derived from a wide variety of groups, including sulfonate (—SO$_3^\ominus$), sulfate (—OSO$_3^\ominus$), carboxylate (—COO$^\ominus$) and phosphate (—OPO$_3^\ominus$) moieties. Combinations incorporating these groups have been studied extensively in the literature. Other possibilities would include, but are not limited to, phosphonate (—POs$_3^\ominus$) and phosphinate (—PO$_2^\ominus$) groups. There are also examples in which organic groups (e.g., —CH$_2$CH$_3$) are attached to $\gamma$. While the betaines as a class of detergents have unusual characteristics, as might be expected, interchanging the various moieties produces interesting and predictable changes in chemical and physical properties and their use are contemplated in the methods of the invention.

TABLE 2

The Structure of n-Alkyl Betaines
The general structure of n-alkyl betaities is shown.
$R_1$ is the hydrophobic alkyl chain, and $\alpha$ is the "linkage" connecting $R_1$ to the cation, $\beta$. $R_2$ and $R_3$ modify the cation, when required. $R_4$ is the "bridge" that connects the cation to the anion, $\gamma$.

$$R_1-[\alpha]_n-\overset{R_2}{\underset{R_3}{\beta^\oplus}}-R_4-[\gamma]^\ominus$$

| | |
|---|---|
| $R_1$ | $C_8$–$C_{22}$ |
| $\alpha$ | —CH$_2$—, —CH(OH)—, —(CO)—NH—CH$_2$CH$_2$CH$_2$—, —O—, —(CO)— |
| n | 0 or 1 |
| $\beta$ | —N$^\ominus$—, —P$^\ominus$—, —S$^\ominus$— |
| $R_2$ | —H, —CH$_3$, —C$_2$H$_5$, —C$_3$H$_7$, —C$_4$H$_9$ |
| $R_3$ | —H, —CH$_3$, —C$_2$H$_5$, —C$_3$H$_7$, —C$_4$H$_9$ |
| $R_4$ | —CH$_2$—, —C$_2$H$_4$—, —C$_3$H$_6$—, —C$_4$H$_8$—, —C$_5$H$_{10}$—, —C$_6$H$_{12}$—, —CH$_2$—C$_6$H$_4$—, —C$_m$H$_{2m}$—, —CH(OH)CH$_2$CH$_2$—, —CH$_2$CH(OH)CH$_2$—, —C$_m$H$_{2m-1}$(OH)—, where m≥1 |
| $\gamma$ | —SO$_3^\ominus$, —OSO$_3^\ominus$, —COO$^\ominus$, —OPO$_3^\ominus$, —PO$_3^\ominus$, —PO$_2^\ominus$— |

The sulfopropylbetaines are available from a variety of sources (e.g., CalBiochem, La Jolla, Calif.; Sigma, St. Louis, Mo.; Fluka, Ronkonkoma, N.Y.; and Aldrich, Milwaukee, Wis.). Several have been tested successfully in the methods of the invention and show SB-18-like activity. These include: $C_{12}$-sulfopropylbetaine (SB-12: CAS®No. 14933-08-5), $C_{14}$-sulfopropylbemine (SB-14: CAS®No. 14933-09-6), $C_{16}$-sulfopropylbetaine (SB-16: CAS®No. 2281-11-0), and $C_{18}$-sulfopropylbetaine (SB-18: CAS®No. 13177-41-8). Several other sulfobetaines used successfully have either been custom synthesized, or were obtained as samples as described herein. These include: $C_{18}$-sulfobutylbetaine (CAS®No. 223 13-73-1), $C_{16}$-hydroxypropylsulfobetaine (CAS®No. 7425-12-9), and 3-butoxy-2-hydroxy hydroxypropylsulfobetaine (CAS®No. 108797-84-8). Several sulfobetaines whose alkyl chains were derived from natural oils have also been tested. These include: cocoamidopropyl hydroxypropylsulfobetaine (CAS®No. 68139-30-0), tallowamidopropyl hydroxypropylsulfobetaine and erucamidopropyl hydroxypropylsulfobetaine.

Owing to their high solubilities, the most widely studied are the carboxybetaines ($\gamma=COO^{\ominus}$). Several carboxybetaines have been tested and show SB-18-like activity in the methods of the invention. These include: $C_{16}$-carboxymethylbetaine (CAS®No. 693-33-4), $C_{18}$-carboxyethylbetaine (CAS®No. 30612-73-8), $C_{18:1}$-carboxymethylbetaine (CAS®No. 871-37-4), and $C_{18}$-amidopropyl carboxymethylbetaine (CAS®No. 6179-44-8). Several carboxybetaines whose alkyl chains were derived from natural oils have also been tested. These include: cocoamidopropyl carboxymethylbetaine (CAS®No. 61789-37-9 and CAS®No. 61789-40-0), cococarboxymethylbetaine (CAS®No. 68424-94-2), ricinamidopropyl carboxymethylbetaine (CAS®No. 71850-81-2), and Tallow bishydroxyethyl glycinate (CAS®No. 70750-46-8). There are also several carboxybetaines that have been tested for which no CAS®Number has been given. These include: behenyl carboxymethylbetaine, which is thought to be a $C_{22}$-chain, wheat germ oil-amidopropyl carboxymethylbetaine (Schercotaine WOAB: Scher Chemicals, Inc., Clifton, N.J.), babassuamidopropyl carboxymethylbetaine (Croda, Inc., Parsippany, N.J.), soyamidopropyl carboxymethylbetaine (Chembetaine S: Chemron Corp., Paso Robles, Calif.), and canolamidopropyl betaine (Hetaine CLA: Heterene, Inc., Patterson, N.J.).

Given the diverse nature of the betaines, there were several that would operate only under specialized conditions: behenyl carboxymethylbetaine is a $C_{22}$-chain and would only function when salt concentrations were minimized, and $C_{16}$-hydroxypropyl sulfobetaine required the presence of potassium iodide.

Two additional betaines were custom synthesized that were representative of two other classes of betaines. These were also used successfully and include: $C_{16}$-amidopropyl sulfatobetaine (CAS®No. 58930-11-3), and $C_{18}$-phosphoethylbetaine (CAS®No. 126712-89-8), representing the use of sulfate and phosphate anions, respectively.

Hence, 25 betaines, representing a wide structural selection of these molecules, have been tested for efficacy in enhancing the collection of the Mycobacteria, for example, by centrifugation. Those with chain lengths less than 16 carbon atoms were seen to function primarily by offsetting buoyancy without disrupting clumping, whereas those with chain lengths of 18 carbon atoms or greater were seen, for the most part, to operate by disrupting cording as well as countering buoyancy. All have been shown to be useful in the methods of the invention. The combination of the zwitterion and hydrophobic alkyl chain impart characteristics that make the betaines unique. Therefore, any molecule with a "betaine-like" structure can be expected to display SB-18-like activity.

Synthetic routes for many of the structural combinations above are known to exist. The SB-18-like detergent species that are useful in the methods of the invention are not meant to be limited to the exemplified species since behavior of this class in the methods is predicable.

Additional guidance is provided by the list below, which cites examples of betaines that are commercially available or for which there are known synthetic routes, and which would be useful in the methods of the invention.

Most examples of betaines utilize a quaternary nitrogen as the cation ($\beta$). Members of this large family of detergents are most easily listed by assuming the cation is a quaternary N,N-dimethylammonio and then grouping subsets based first on the anion ($\gamma$) used. Each subset can then be further subdivided first on the bridge structure ($R_4$), then on linkage ($\alpha$), and then on alkyl chain length ($R_1$). Additional combinations that do not fall into these discrete categories are then be easily listed. Again, all would be reasonably expected to function in the methods of the invention.

Examples of carboxybetaines that utilize a methylene bridge ("carboxymethylbetaines": $R_4$=—$CH_2$—), a methylene linkage ($\alpha$=—$CH_2$—), and vary solely based on alkyl chain length are: $C_{10}$ (CAS®No. 2644-45-3), $C_{11}$ (CAS®No. 2956-38-9), $C_{12}$ (CAS®No. 683-10-3), $C_{13}$ (CAS®No. 23609-76-9), $C_{14}$ (CAS®No. 2601-33-4), $C_{15}$ (CAS®No. 23609-77-0), $C_{16}$ (CAS®No. 693-33-4), and $C_{18}$ (CAS®No. 820-66-6). There is a $C_{12}$-carboxymethylbetaine (CAS®No. 6232-16-2) example that is N,N diethyl ($R_3$=$R_4$=—$CH_2CH_3$); and an example in which the alkyl has a double bond: $C_{18:1}$ (CAS®No. 871-37-4). There are several carboxymethylbetaine examples in this subset in which $\alpha$ is an amidopropyl group. They include: $C_{12}$-amido (CAS®No. 4292-10-8), $C_{14}$-amido (CAS®No. 59272-84-3), $C_{16}$-amido (CAS®No. 32954-43-1), and $C_{18}$-amido (CAS®No. 6179-44-8). The $C_{18}$-amido (CAS®No. 6179-44-8) is of undefined structure because the alkyl is the "iso" form, which suggests that it branches in some undefined manner. There are several amidopropyl carboxymethylbetaines in which the alkyl chain is derived from coconut oil, and differences are due to the method of preparation. Two examples in this category include CAS®Numbers 61789-39-7 and 61789-40-0. An example of cococarboxymethylbetaine would be CAS®No. 68424-94-2. Other natural oil carboxymethyl derivatives include: ricinamidopropyl carboxymethylbetaine (CAS®No. 71850-81-2), and Tallow bishydroxyethyl glycinate (CAS®No. 70750-46-8). There are also several carboxymethylbetaines that have been tested for which no CAS®Number has been given. These include: wheat germ oil-amidopropyl carboxymethylbetaine (Schercotaine WOAB: Scher Chemicals, Inc., Clifton, N.J.), babassuamidopropyl carboxymethylbetaine (Croda, Inc., Parsippany, N.J.), soyamidopropyl carboxymethylbetaine (Chembetaine S: Chemron Corp., Paso Robles, Calif.), and canloamidopropyl betaine (Hetaine CLA: Heterene, Inc., Patterson, N.J.). There are several examples in which the nitrogen in the amide linkage is the quaternary nitrogen (e.g., the linkage ($\alpha$) is a carbonyl). These include: $C_{11}$ (CAS®No. 66451-67-0), $C_{15}$ (CAS®No. 66516-99-2), and $C_{17}$ (CAS®No-66451-68-1). Examples of carboxybetaines that utilize an ethyl bridge ("carboxyethylbetaine": $R_4$=—$CH_2CH_2$—), a methylene linkage ($\alpha$=—$CH_2$—), and vary solely based on alkyl chain length include: $C_{12}$ (CAS®No. 16527-85-8), $C_{13}$ (CAS®No. 132621-79-5), $C_{14}$ (CAS®No. 69725-38-3), $C_{16}$ (CAS®No. 42416-43-3), and $C_{18}$ (CAS®No. 30612-73-8). An example of a carboxyethylbetaine in which $R_2$ and $R_3$ are hydrogen atoms, under the appropriate conditions, would be CAS®No. 1462-54-0 ($C_{12}$-beta alanine). Examples of carboxy betaines that utilize a propyl bridge ("carboxypropylbetaine": $R_4$=—$CH_2CH_2CH_2$—), a methylene linkage ($\alpha$=—$CH_2$—), and vary solely based on alkyl chain length include: $C_{11}$ (CAS®No. 150147-53-8), $C_{12}$ (CAS®No. 15163-30-1), $C_{14}$ (CAS®No. 146959-90-2), $C_{15}$ (CAS®No. 146959-91-3), $C_{16}$ (CAS®No. 71695-32-4), and $C_{18}$ (CAS®No. 78195-27-4). An example of a carboxy betaine that utilizes a butyl bridge ("carboxybutylbetaine": $R_4$=—$CH_2CH_2CH_2CH_2$—), and a methylene linkage ($\alpha$=—$CH_2$—), would be: $C_{12}$ (CAS®No. 120139-51-7). Two examples of carboxy betaines that utilize a pentyl bridge ("carboxypentylbetaine": $R_4$=—$CH_2CH_2CH_2CH_2CH_2$—), and a methylene linkage ($\alpha$=—$CH_2$—), would be: $C_{12}$ (CAS®No. 76392-97-7), and $C_{16}$ (CAS®No. 73565-98-7). An example of a carboxy betaine that utilizes a hexyl bridge ("carboxyhexylbetaine": $R_4$=—$CH_2CH_2CH_2CH_2CH_2CH_2$—), and a methylene linkage ($\alpha$=—$CH_2$—), would be: $C_{12}$ (CAS®No. 132621-80-8). There are several carboxybetaine examples in which a benzyl group is used as the bridge function ($R_4$=$CH_2$—$C_6H_4$—). There are two $C_{12}$ examples, one in which the carboxy function is in the 4, or para, position (CAS®No. 71695-31-3), and one in which the carboxy function is in the 2, or ortho, position (CAS®No. 71695-34-6). There are two $C_{16}$ examples, one in which the carboxy function is in the 4, or para, position (CAS®No. 71695-33-5), and one in which the carboxy function is in the 2, or ortho, position (CAS®No. 71695-35-7). Therefore, "carboxybetaine-like" ("CB-like") shall include those SB-18-like betaine structures that utilize a carboxyl group as the anion ($\gamma$=—$COO^{\ominus}$), as shown in Table 2, and shall include all possible combinations of $R_1$, $\alpha$, $R_2$, $R_3$, $\beta$, and $R_4$, as hereinbefore defined.

A second major subset of betaines are the sulfobetaines ($\gamma$=$SO_3^{\ominus}$). Examples of sulfobetaines that utilize a methyl bridge ("sulfomethylbetaine": $R_4$=—$CH_2$—), a methylene linkage ($\alpha$=—$CH_2$—), and vary solely based on alkyl chain length include: $C_{12}$ (CAS®No. 52667-78-4), $C_{16}$ (CAS®No. 69775-75-3), and $C_{18}$ (CAS®No. 36051-36-2). Examples of sulfobetaines that utilize an ethyl bridge ("sulfoethylbetaine": $R_4$=—$CH_2CH_2$—), a methylene linkage ($\alpha$=—$CH_2$—), and vary solely based on alkyl chain length include: $C_{12}$ (CAS®No. 24020-67-5), $C_{14}$ (CAS®No. 58930-04-4), and $C_{16}$ (CAS®No. 58930-05-5). $C_{16}$-amido (CAS®No. 58930-06-6) is an example of a sulfoethylbetaine that utilizes the amidopropyl function to link the alkyl chain to the quaternary nitrogen. Examples of sulfobetaines that utilize a propyl bridge ("sulfopropylbetaine": $R_4$=—$CH_2CH_2CH_2$—), a methylene linkage ($\alpha$=—$CH_2$—), and vary solely based on alkyl chain length include: $C_8$ (CAS®No. 15178-76-4), $C_{10}$ (CAS®No. 15163-36-7), $C_{12}$ (CAS®No. 14933-08-5), $C_{14}$ (CAS®No. 14933-09-6), $C_{15}$ (CAS®No. 67030-70-0), $C_{16}$ (CAS®No. 2281-11-0), and $C_{18}$ (CAS®No. 13177-41-8). There is a $C_{12}$ (CAS®No. 15163-34-5) example that is N,N dipropyl ($R_3$=$R_4$=—$CH_2CH_2CH_3$); and there are at least two examples of $C_n$-sulfopropylbetaines in which $\alpha$ is the amidopropyl group. These include $C_{12}$-amido (CAS®No. 52562-28-4), and $C_{16}$-amido (CAS®No. 52562-29-5). There are several sulfopropylbetaine examples in which the bridge is an isopropyl (—$C_3H_6$—) of undefined structure. These include $C_{12}$ (CAS®No. 59942-40-4), $C_{14}$ (CAS®No. 59942-41-5), and $C_{16}$ (CAS®No. 59942-42-6). There is also a $C_{16}$-amido (CAS®No. 63663-13-8) example that utilizes an isopropyl bridge and an amidopropyl linkage. Examples of sulfobetaines that utilize a butyl bridge ("sulfobutylbetaine": $R_4$=—$CH_2CH_2CH_2CH_2$—), a methylene linkage ($\alpha$=—$CH_2$—), and vary solely based on alkyl chain length include: $C_{12}$ (CAS®No. 64463-49-6), $C_{16}$ (CAS®No. 58930-07-7), and $C_{18}$ (CAS®No. 22313-73-1). There is a $C_{12}$ (CAS®No. 35489-44-2) example that is 1,3-dimethyl-3-sulfobutyl; and there is a sulfobutylbetaine example in which $\alpha$ is the amidopropyl group: $C_{16}$-amido (CAS®No. 58930-08-8). There is an example of a "sulfohexylbetaine" ($R_4$=—$CH_2CH_2CH_2CH_2CH_2CH_2$—): $C_{16}$ (CAS®No. 132621-81-9). There are several examples in which a benzyl group is used as the bridge function ($R_4$=—$CH_2$—$C_6H_4$—). These include $C_{12}$ (CAS®No. 65180-40-7), $C_{14}$ (CAS®No. 65180-41-8), $C_{16}$ (CAS®No. 65180-42-9), and $C_{18}$ (CAS®No. 65180-43-0), in which the sulfonate is in the 4, or ortho position. There are also several examples in which these last four link the alkyl chain to the quaternary nitrogen by an amidopropyl group: $C_{12}$ (CAS®No. 65180-44-1), $C_{14}$ (CAS®No. 65180-45-2), $C_{16}$ (CAS®No. 65180-46-3), and $C_{18}$ (CAS®No. 65180-47-4). Therefore, "sulfobetaine-like" ("SB-like") shall include those SB-18-like betaine structures that utilize a sulfonate as the anion ($\gamma$=—$SO_3^{\ominus}$), as shown in Table 2, and shall include all possible combinations of $R_1$, $\alpha$, $R_2$, $R_3$, $\beta$, and $R_4$ as hereinbefore defined.

A large subset of the sulfobetaines, which are typically treated separately owing to their dramatically different characteristics, and which are all reasonably expected to show SB-18-like activity, are the hydroxypropyl sulfobetaines (HSB). These detergents have not been studied as intensively owing to their lower solubilities. The majority of these sulfobetaines utilize a 2-hydroxypropyl bridge ($R_4$=—$CH_2CH(OH)CH_2$—). These include the straight chain alkyl's: $C_{10}$ (CAS®No. 34135-76-7), $C_{12}$ (CAS®No. 13197-76-7), $C_{14}$ (CAS®No. 13 177-42-9), $C_{15}$ (CAS®No. 71502-45-9), $C_{16}$ (CAS®No. 7425-12-9), and $C_{18}$ (CAS®No. 19223-56-4); as well as those that use an amidopropyl linkage: $C_{12}$-amido (CAS®No. 19223-55-3), $C_{14}$-amido (CAS®No. 63663-10-5), $C_{16}$-amido (CAS®No. 63663-11-6), and $C_{18}$-amido (CAS®No. 63663-12-7). There are also several $C_{14}$ examples in which the alkyl is not a simple straight chain: (CAS®No. 56505-82-9) and (CAS®No. 71497-51-3). Therefore, "hydroxysulfobetaine-like" ("HSB-like") shall include those SB-18-like betaine structures that utilize a hydroxypropyl bridge ($R_4$=—$C_mH_{2m-1}(OH)$—), with sulfonate as the anion ($\gamma$=—$SO_3^{\ominus}$) as shown in Table 2, and shall include all possible combinations of $R_1$, $\alpha$, $R_2$, $R_3$, and $\beta$, as hereinbefore defined.

The third subset of this family of detergents, and also very well characterized, are the phosphobetaines. Examples of phosphobetaines ($\gamma$=—$OPO_3^{\ominus}$) that utilize an ethyl bridge ("phosphoethylbetaine": $R_4$=—$CH_2CH_2$—), a methylene linkage ($\alpha$=—$CH_2$—), and vary solely based on alkyl chain length include: $C_{10}$ (CAS®No. 134842-83-4), $C_{11}$ (CAS®No. 134842-84-5), $C_{12}$ (CAS®No. 126712-86-5), $C_{14}$ (CAS®No. 126712-87-6), $C_{16}$ (CAS®No. 126712-88-7), $C_{17}$ (CAS®No. 145578-49-0), and $C_{18}$ (CAS®No. 126712-89-8). There are two phosphoethylbetaine examples in which the alkyl has a double bond: $C_{18:1}$ (CAS®No. 134590-60-6 and CAS®No. 148716-30-7). There are several examples of $C_{16}$-phosphoethylbetaines where the $R_3$ and $R_4$ moieties vary significantly. These include: N,N-diethyl (CAS®No. 126712-90-1); N,N-dipropyl (CAS®No. 126712-91-2); N,N-dibutyl (CAS®No. 126712-92-3); N-ethyl-N-propyl (CAS®No. 126712-93-4); N-methyl-N-ethyl (CAS®No. 134842-85-6); and N-ethyl-N-butyl (CAS®No. 126712-94-5). An example of a phosphobetaine that utilizes a propyl bridge ("phosphopropylbetaine": $R_4$=—$CH_2CH_2CH_2$—) would be: $C_{16}$-phosphopropylbetaine (CAS®No. 89367-17-9). An example of a phosphobetaine that utilizes a butyl bridge ("phosphobutylbetaine": $R_4$=—$CH_2CH_2CH_2CH_2$—) would be: $C_{16}$-phosphobutylbetaine (CAS®No. 134842-86-7), and an example of phosphobetaine that utilizes a hexyl bridge ("phosphohexylbetaine": $R_4$=—

$CH_2CH_2CH_2CH_2CH_2CH_2$—) would be: $C_{16}$-phosphohexylbetaine (CAS®No. 134842-87-8). There are several examples of n-hydroxyalkyl phosphoethylbetaines (e.g., they utilize a hydroxyl linkage). These would include: $C_{12}$ (CAS®No. 124591-53-3), $C_{14}$ (CAS®No. 124591-54-4), and $C_{16}$ (CAS®No. 124591-57-7). Hydroxypropyl phosphobetaines that use an amidopropyl linkage include: $C_{12}$-amido (CAS®No. 73602-79-6) and $C_{18}$-amido (CAS®No. 144077-12-3). There are several examples of phosphoethylbetaines that utilize an hydroxypropyl group in combination with an ether function as the linkage: $C_{10}$ (CAS®No. 128506-41-2), $C_{12}$ (CAS®No. 128506-42-3), and $C_{14}$ (CAS®No. 128506-46-7). Gallot, B. et al., *J. Colloid Interface Sci.* 121:514–521 (1988) describe a series of phosphobetaines in which an ethyl group has been used to modify the anion (e.g., $-OPO_3^{\ominus}-(C_2H_5)$). These structures, as well as examples in which γ is a phosphonate or phosphinate, would also be reasonably expected to possess SB-18-like activity in the methods of the invention. Therefore, "phosphobetaine-like" ("PB-like") shall include those SB-18-like betaine structures of Table 2 that utilize a phosphate, phosphonate, or phosphinate as the anion (γ=—$OPO_x^{\ominus}$, where x=1, 2 or 3), and shall include all possible combinations of $R_1$, α, $R_2$, $R_3$, β, and $R_4$ as hereinbefore defined.

A fourth subset of betaines includes those that utilize sulfate ($-OSO_3^{\ominus}$) as the anion. As with the HSB-like examples, these molecules are even less soluble, and as such, have been studied with less enthusiasm. However, these, too, are reasonably expected to display SB-18-like activity. Examples that use an ethyl bridge ("sulfatoethylbetaine": $R_4$=—$CH_2CH_2$—), a methylene linkage (α=—$CH_2$—), and vary solely based on alkyl chain length include: $C_{10}$ (CAS®No. 92764-24-4), $C_{14}$ (CAS®No. 58930-09-9) and $C_{16}$ (CAS®No. 58930-10-2). Examples that use a propyl bridge ("sulfatopropylbetaine": $R_4$=—$CH_2CH_2CH_2$—), a methylene linkage (α=—$CH_2$—), and vary solely based on alkyl chain length include: $C_{10}$ (CAS®No. 92764-22-2), $C_{12}$ (CAS®No. 15163-35-6), $C_{14}$ (CAS®No. 58930-12-4), and $C_{16}$ (CAS®No. 34236-95-8). Examples that use a butyl bridge ("sulfatobutylbetaine": $R_4$=—$CH_2CH_2CH_2CH_2$—), a methylene linkage (α=—$CH_2$—), and vary solely based on alkyl chain length include: $C_{12}$ (CAS®No. 58930-14-6) and $C_{16}$ (CAS®No. 58930-15-7). There are several examples of sulfates that use the amidopropyl linkage: the $C_{16}$-amidopropyl-sulfatoethylbetaine (CAS®No. 58930-11-3), the $C_{16}$-amidopropyl-sulfatopropylbetaine (CAS®No. 58930-13-5), the $C_{13}$-amidopropyl-sulfatobutylbetaine (CAS®No. 144077-11-2), and the $C_{16}$-amidopropyl-sulfatobutylbetaine (CAS®No. 58930-16-8). Therefore, "sulfatobetaine-like" ("StB-like") shall include those SB-18-like betaine structures of Table 2 that utilize sulfate as the anion (γ=—$OSO_3^{\ominus}$), and shall include all possible combinations of $R_1$, α, $R_2$, $R_3$, β, and $R_4$ as hereinbefore defined.

Phosphonium-like betaines (β=—$P^{\oplus}$—) have been described by Gaertner, V. R. et al. (U.S. Pat. No. 2,828,332). Based on the data and hypotheses herein, "phosphoniumbetaine-like" ("PhB-like") includes all possible SB-18-like betaine combinations having the phosphonium cation as shown in Table 2, and all possible combinations of $R_1$, α, γ, $R_2$, $R_3$, and $R_4$, as hereinbefore defined.

As with the phosphoniumbetaines, "sulfoniumbetaine-like" ("SoB-like"), included within the meaning of SB-18-like, are those in which β=—$S^{\oplus}$— as shown in Table 2, including all possible combinations of $R_1$, α, γ, $R_2$, $R_3$, and $R_4$ as hereinbefore defined.

There are several other notable betaine-like structures listed in Table 3. These include "reverse betaines" (RevB), amine oxide-like (AOx) detergents, c-alkyl betaines (cAB), and the imidazolinium-betaine derivatives (ImB). These are easily described using the nomenclature in Table 2, and it is perhaps most convenient to think of the various structures from the perspective of the alkyl ($R_1$): the alkyl can be bound to either the cation (β), the anion (γ) or the bridge ($R_4$), all are considered betaine-like structures. For example, in the case of n-alkyl betaines the hydrophobic domain ($R_1$) is covalently linked to the cation, whereas in the case of the reverse betaines, the alkyl is bound to the anion (—$\gamma^{\ominus}$—), and in the case of c-alkyl betaines, the alkyl is bound to the bridge ($R_4$).

The reverse betaines are similar to the n-alkyl betaines in that the opposing charge (in this case the cation, —$[\beta]^{\oplus}$—) is connected to the anion by a bridge (—$R_4$—). Typically, the cation (—$[\beta]^{\oplus}$—) is a quaternary nitrogen, and as such the $R_2$ and $R_3$ groups are bound at this position instead.

The c-alkyl betaines are structurally distinct in that the alkyl is covalently bound to the bridge ($R_4$), as opposed to either the cation (—$[\beta]^{\oplus}$—) or the anion (—$\gamma^{\ominus}$—).

In the case of amine oxides the n-alkyl betaine structure is maintained; however, β is, by definition a quaternary nitrogen and γ is, by definition, an oxide. It is convenient to think of the bridge as being minimized: $R_4$ is simply a covalent N—O bond. There are other oxide-like structures, similar to the amine oxides, such as the phosphonium oxides, for example, which would also be reasonably expected to function in the methods of the invention.

The zwitterionic imidazolinium-type detergents are also marketed as amphoteric betaines. In this instance, the center of positive charge is not a radical, but instead a modified imidazoline in which the resonance structure produces the cation. The classic bridge structure is maintained, and the alkyl can be attached at any point on the ring.

TABLE 3

Additional Betaine-Like Structures
Alternative betaine structures are presented. The nomenclature used in Table 2 is maintained to describe these structures.

| Betaine Subgroup | Structure |
|---|---|
| Reverse Betaine | $R_1 - [\alpha]_n - \gamma^{\ominus} - R_4 - [\beta]^{\ominus} - (R_{2,3})_m$ |
| Amine Oxide-Like | $R_1 - [\alpha]_n - \overset{\underset{\mid}{R_2}}{\underset{\underset{\mid}{R_3}}{\beta^{\oplus}}} - O^{\ominus}$ |
| c-Alkyl Betaine | $Y^{\ominus} - R_4 - \beta^{\oplus} - (R_{2,3})_m$ with $[\alpha]_n$ and $R_1$ attached |
| Imidazolinium Betaines | $R_1 - [\alpha]_n$ attached to imidazolinium ring with $R_2$, $R_3$, $R_4 - [\gamma]^-$ |

While the structures of Table 3 have been studied to a limited degree, they have not received as much attention as the n-alkyl betaines (Table 2) and, therefore, represent only a small percentage of the structural diversity seen in betaines. Regardless, representatives from several of the classes above have been used in the methods of the invention. The reverse betaine representative used, alkyl 2-hydroxy-3-trimethylammoniopropyl phosphate ($C_{16}$-AHTMAP: CAS®No. 99485-86-6), was described by Kurosaki, T. et al., *Chem. Soc. Japan* 11:1297–1301 (1990) and was obtained as a gift from KAO Chemical (Japan). The amine oxide used, Ammonyx MO (myristyl dimethyl amine oxide: CAS®No. 3332-27-2), was obtained as a sample from Stepan Company, Northfield, Ill. The c-alkyl betaine used, Darvan NS (a mixture of c-decyl betaine (CAS®No. 96-55-9) and c-cetyl betaine (CAS®No. 95-56-0)), was obtained as a sample from R. T. Vanderbilt, Norwalk, Conn.

Several groups of reverse betaines have been studied. There are several alkyl 2-hydroxy-3-trimethylammoniopropyl phosphate ($C_n$-AHTMAP) examples originally described by Kurosaki, T. et al., *Chem. Soc. Japan* 11:1297–1301 (1990), all of which would be reasonably expected to function in the methods of the invention. These include: $C_{12}$ (CAS®No. 99485-91-3), $C_{14}$ (CAS®No. 132630-63-8), $C_{16}$ (CAS®No. 99485-86-6), $C_{18}$ (CAS®No. 99485-87-7). Zimmer, R. E. et al., (U.S. Pat. No. 3,560,393) has described the synthesis of several very interesting reverse betaines, all of which would be reasonably expected to function in the methods of the invention. These include examples that combine an ammonium cation ($\beta$=—$N^{\oplus}(CH_3)_3$) with a phosphinate anion ($\gamma$=—$PO^{\ominus}_2$—): $C_{12}$ (CAS ®No. 29557-49-1); an ammonium cation ($\beta$=—$N^{\oplus}(CH_3)_3$) with a phosphonate anion ($\gamma$=—$PO^{\ominus}_3$—): $C_{12}$ (CAS®No. 32020-41-0); a sulfonium cation ($\beta$=—$S^{\oplus}$—) with a phosphinate anion ($\gamma$=—$PO^{\ominus}_2$—): $C_{12}$ (CAS®No. 32020-40-9); a sulfonium cation ($\beta$=—$S^{\oplus}$—) with a phosphonate anion ($\gamma$=—$PO^{\ominus}_3$—): $C_{10}$ (CAS®No. 32020-42-1); and a sulfonium cation ($\beta$=—$S^{\oplus}$—) with a phosphate anion ($\gamma$=—$OPO^{\ominus}_3$—): $C_{10}$ (CAS®No. 32020-43-2). Therefore, "reverse betaine-like" ("RevB-like"), as shown in Table 3, shall include all possible combinations of $R_1$, $\alpha$, $\beta$, $R_2$, $R_3$, $\gamma$, and $R_4$ as shown in Table 2, and as hereinbefore defined.

Examples of N,N-dimethyl amine oxides that would reasonably be expected to function in the methods of the invention include: $C_{12}$ (CAS®No. 1643-20-5), $C_{14}$ (CAS®No. 3332-27-2), $C_{16}$ (CAS®No. 7128-91-8), $C_{18}$ (CAS®No. 2571-88-2), and $C_{22}$ (CAS®No. 26483-35-2). An example of an amine oxide that uses an amidopropyl linkage would be: $C_{18:1}$-amido (CAS®No. 14351-50-9). Those examples in which $R_1$ is derived from a natural oil include: cocamidopropyl (CAS®No. 68155-09-9), and Babassuamidopropyl (CAS®No. 124046-26-0). Therefore, "amine oxide-like" ("AO-like"), as shown in Table 3, would be defined as those structures in which $\gamma$=$O^{\ominus}$, and $R_4$ is a covalent $\beta$—O bond, and include all possible combinations of $R_1$, $\alpha$, $\beta$, $R_2$, and $R_3$ as shown in Table 2 and as hereinbefore defined.

Examples of c-alkyl betaines ($\gamma$=$COO^{\ominus}$, $\beta$=—$N^{\oplus}(CH_3)_3$, $R_4$=—CH—) that would be reasonably expected to function in the methods of the invention include: $C_{10}$ (CAS$\phi$No. 96-55-9), $C_{12}$ (CAS®No. 686-83-9), $C_{14}$ (CAS®No. 16545-85-0), $C_{16}$ (CAS®No. 95-56-0), and $C_{18}$ (CAS®No. 686-84-0). Therefore, "c-alkyl betaine-like" ("cAB-like"), as shown in Table 3, would be defined as those structures in which $R_1$ is attached to $R_4$, and include all possible combinations of $\alpha$, $\beta$, $\gamma$, $R_1$, $R_2$, $R_3$, and $R_4$ as shown in Table 2 and as hereinbefore defined.

An example of an imidazolinium betaine would be one in which $R_4$ is derived from coconut oil (CAS®No. 68334-21-4)). Therefore, all "imidazolinium betaine-like" ("ImB-like") structures would be reasonably expected to function in the methods of the invention, and would, therefore, be defined as those structures in which $\beta$ is, by definition, an imidazolinium functionality, and include all possible combinations of $\alpha$, $\gamma$, $R_1$, $R_2$, $R_3$, and $R_4$ as shown in Table 2 and as hereinbefore defined.

Therefore, "betaine-like," as used herein refers to those structures described in Tables 2 and 3, including, for example, CB-like, SB-like, HSB-like, PB-like, StB-like, PhB-like, SoB-like, RevB-like, AO-like, cAB-like, and ImB-like, that possess SB-18-like activity. It should be noted that, as with the example of Gallot, B. et al., *J. Colloid Interface Sci.* 121:514–521 (1988), modifications to $\gamma$ that do not alter SB-18-like activity would be included within this definition as well. Further, incorporation of multiple charges on the same molecule (e.g., two or more charges, where at least two of the charges are of the opposite sign) that would produce a dipole moment such that the behavior was consistent with that of a betaine as described herein, and that possessed SB-18-like activity, would also be considered betaine-like.

Use of Betaine-Like Detergents

Betaine-like character is dependent on alkyl chain length, charge combinations and bridge structure. Longer alkyl chains, such as, $C_{16}$–$C_{20}$, are preferred, owing to their ability to disrupt cord formation and their apparent ability to be more actively sequestered. However, limited solubility of these long chain alkyls may hinder effective utilization of these betaines in the methods of the invention. Either phosphobetaines, carboxybetaines or sulfobetaines are preferred owing to the enhanced solubility provided by these anions, however, carboxybetaines and sulfobetaines are more easily synthesized. Carboxybetaines possess characteristics more commonly associated with ionic detergents, whereas sulfobetaines exhibit behavioral traits more commonly associated with nonionic detergents. A straight chain bridge is preferred, and a propyl function is the most preferred bridge structure because it (a) permits "salting-in" of the detergent, and (b) is the least bacteriostatic structure. A methylene bridge is the least preferred because it displays salting out behavior. A methylene linkage is preferred; however, while amidopropyl linkages do not appear to interfere with overall SB-18-like activity, they do appear to enhance nonionic behavior. Therefore, the choice of which SB-18-like detergent to use in the methods of the invention may vary depending on the desired use or system used for detection or degree of bacteriostatic activity desired. For example, when the objective is the detection of organisms which do not clump, *M. paratuberculosis* for example, those characteristics associated with dispersion and ionic performance are not essential. Under these circumstances betaines with shorter chains and more nonionic character may be used. Alternatively, when the purpose is the detection of clumping organisms, *M. tuberculosis* for example, ionic behavior and longer chains are essential. Whereas alkyl chain length and bridge length appear to be important determinants in bacteriostatic activity, betaine-like structure may be altered to facilitate detection by amplification. For example, while the Examples herein use PCR as the preferred method for detection, as discussed above, the methods of the invention can facilitate detection by other amplification methodologies. It is to be expected that a betaine that works optimally for PCR might be useful, but not necessarily optimal, for other methodologies, ligase chain reaction (LCR), strand displacement amplification (SDA) or transcription amplification (NASBA, 3SR or LAT), for example. The guidance hereafter, in regard to understanding aspects of betaine-like structure and function, is included to instruct the artisan with respect to modifications of SB-18-like detergents that may yield an optimal betaine for a given application. Given the above constraints, $C_{18}$-carboxypropylbetaine (CAS®No. 78195-27-4) is expected to provide the ideal combination of solubility, chain length and bridge structure for a wide variety of applications in conjunction with PCR, and thus methods of the invention utilizing this compound are a very highly preferred embodiment. CAS®No. 78195-27-4 can be synthesized using common techniques, for example, as described in JP Appl. No. 79100920 [54-100920]; and JP 81251394.

Concentrations of SB-18 below 2 µM seemed impotent in dispersion; concentrations between 2 µM and 2 mM were most useful, presumably due to the critical micellar concentration (CMC); and SB-18 concentrations much greater than 2 mM were difficult to keep in solution due to insolubility. As understood by the artisan, these considerations will vary depending on which SB-18-like detergent is used. For example, shorter chains will require higher concentrations to be above the CMC, but Krafft temperatures will be of less concern. Regardless, concentrations 10 to 1,000 fold above the CMC of the desired detergent should be used, and the relationship of assay temperature and SB-18-like detergent Krafft temperature must be carefully correlated. When using SB-18, it is necessary to use an electrolyte containing medium (10 mM–100 mM salt), and warm the solution, for example, to a temperature between 37° C. and 42° C., but not below 37° C., and to perform all steps, such as centrifugation, above 37° C. in order to keep the detergent in a micellar form. Varying the SB-18-like detergent that is used in the methods of the invention, as discussed below, may eliminate the need to keep the SB-18-like detergent warm. For example, using $C_{18}$-carboxypropylbetaine (CAS®No. 78195-27-4) at concentrations that do not lyse the cells (in general, below 2 mM) eliminates the rigid temperature constraints imposed by SB-18.

Generally, temperatures above 50° C. seemed to facilitate lysis. Therefore, since the methods of the invention confer an advantage with respect to improving the efficiency of recovery by centrifugation only if the bacterial cells are intact, increasing the temperature above 50° C. should be avoided.

The pH of the detergem containing wash solution should be kept above 5, but below 9. Below pH 5 SB-18-like detergents may begin to display anomolous behavior, and above pH 9 SB-18-like detergents may behave as anionic detergents and be salted-out. However, any pH which permits the SB-18-like detergent to display SB-18-like activity is acceptable. The time of such detergent-containing wash should be at least 60 minutes to permit accumulation of the detergent. Incubations up to 18 hours provided only marginal improvements over the 60 minute incubation result.

Betaines as Detergents

There are generally considered to be three classes of detergents: ionic, including both anionic and cationic; nonionic, and amphoteric (Kirk-Othmer *Encyclopedia of Chemical Technology*, 3rd ed. vol. 22, John Wiley & Sons, New York (1983), p.332–387). The specific class of detergents to which betaines belong is not uniformly accepted. Due to the coexistence of formally charged species, some classify betaines as "amphoteric," however, Laughlin, R. G. *Langmuir* 7:842–847 (1991) argues that these molecules are a subclass of nonionic detergents. What is clear is that betaines have certain peculiar characteristics that place them in a category distinct from both nonionic detergents and ionic detergents. Betaines behave in some respects like ionic detergents, and in other respects like nonionic detergents. In fact, depending on structure, the same molecules can be made to behave like an ionic detergent in certain respects under one condition, and like a nonionic detergent under other conditions.

Detergents are generally described based on their physical characteristics and phase behavior in a temperature (X-axis) versus concentration (Y-axis) plot. In the most simplistic terms, three phases are thought to exist for a pure detergent: the monomer phase, the solid phase, and the micellar phase. Each detergent can be described based on the system parameters that will cause a given phase to exist. Changes to the system parameters cause transitions between the phases that are then used to further characterize behavior. The following general information is summarized from: Shinoda, K., Nakagawa, T., Tamamushi, B., and Isemura, T. eds. *Colloidal Surfactants*, Academic Press, New York (1963); Schick, M. J. ed., *Surfactant Science Series*, vol. 1: *Nonionic Surfactants*, Marcel Dekker, New York (1967); Jungermann, E. ed., *Surfactant Science Series*, vol. 4: *Cationic Surfactants*, Marcel Dekker, New York (1970); Bluestein, B. R. and Hilton, C. L., eds., *Surfactant Science Series*, vol. 12: *Amphoteric Surfactants*, Marcel Dekker, New York (1982); Gloxhuber, C. and Kunstler, K. eds., *Anionic Surfactants*, Marcel Dekker, New York (1992).

For example, all detergents have some degree of solubility in aqueous solutions. At low concentrations, only monomers exist. As the concentration is raised, a phase transition occurs, assuming the temperature is high enough, and micelles begin to form. Under these conditions, and in most cases, further increases in concentration only serve to enrich the micelle concentration. The concentration at which this transition occurs is known as the "critical micellar concentration" (CMC).

As long as the system is above a critical temperature, the CMC occurs at virtually the same concentration at all temperature. Hence, for the purposes of this discussion, the CMC can be visualized as being parallel to the X-axis described above. If the system is below this critical temperature, the equilibrium is between the monomer phase and the solid phase, regardless of concentration. As the temperature is raised, assuming the system is above the CMC, a phase transition between the solid and micellar phases will eventually occur. This temperature, known as the Krafft temperature (Krafft, F. et al., *Ber.* 28:2566–2573 (1895)), is generally referred to as the melting point of the hydrated crystal, and is essentially the same regardless of the concentration. Hence, for the purposes of this discussion, the Krafft temperature can be visualized as being parallel to the Y-axis.

The point at which the CMC and the Krafft temperature intersect is known as the Krafft point. Inherent within this depiction is a characterization of the size (micellar molecular weight and aggregation number) and shape of the micelle formed. Using this basic framework (temperature, concentration, and solvent system, including varying electrolytes and electrolyte concentration), chemists for the last century have defined the unique phase and micellar behavior of different chemical structures. The discussion that follows focusses on clinically relevant conditions (e.g. aqueous solutions) and outlines those features that are believed to be important in the function of SB-18, and SB-18-like detergents in general, and is included as guidance to the artisan wishing to optimize a betaine-like detergent for a given application, for example, detection by amplification methods other than PCR.

While the CMC of detergents decreases with increasing alkyl chain length, the CMC of nonionic detergents is generally $10^2$ fold lower than that of the ionic homologues of equivalent chain length. This suggests that the monomer of the nonionic homologue is less soluble. However, this difference is strongly dependent on the kind and number of nonionic moieties utilized. For example, Hsiao, L. et al., *J. Phys. Chem.* 60:657–660 (1956) show that the CMC of polyoxyethylene phenyl ethers increase with increasing numbers of polyoxyethylene moieties. Tokiwa, F. et al., *Bull. Chem. Soc. Japan* 35:1737–1739 (1954) and Schick, M. J. et al., *J. Phys. Chem.* 66:1326–1333 (1962) show that micellar weight and aggregation number increases with increasing numbers of polyoxyethylene units as well. Ionic detergents on the other hand show only small differences in CMC with different ionic species. Shinoda (Shinoda, K., *Colloidal Surfactants*, Academic Press, New York (1963) pp.54–55) has compiled data on several different ionic homologues to illustrate these minor differences.

In contrast, the CMC of betaines depends on the charge separation distance as well as the nature of the specific ionic groups. For example, Lattes, A. et al., *Surfactants Soln.* 11:127–1139 (1991) show that the CMC of a series of carboxybetaines in water increases as the bridge length goes from methyl, to ethyl, to propyl. Weers, J. G. et al., *Langmuir* 7:854–867 (1991) contradict this data by showing that the trend is reversed. Weers, J. G. et al., *Langmuir* 7:854–867 (1991) further show that: (i) the CMC of the sulfobetaine series first increases going from propyl to butyl, and then decreases going from butyl to hexyl, and (ii) the CMC's of carboxybetaines are lower than the corresponding sulfobetaines. Interestingly, the data of Nandakumar T. N. et al., *J. Oil Tech. Assoc. India* 11:31–34 (1979) contradict Weers, J. G. et al., *Langmuir* 7:854–867 (1991) on this last point: the CMC's of carboxybetaines are higher than the corresponding sulfobetaines. Examination of the CMC dependence on anion moiety can be seen by comparison of the CMC values of $C_{16}$-carboxyethylbetaine ($8.3 \times 10^{-5}$ M: Lattes, A. et al., *Surfactants Soln.* 11:127–1139 (1991)), with $C_{16}$-phosphoethylbetaine ($4 \times 10^{-5}$ M: Tsubone, K. et al., *J. Am. Oil Chem. Soc.* 67:149–153 (1990)), and $C_{16}$-sulfoethylbetaine (insoluble: Weers, J. G. et al. *Langmuir* 7:854–867 (1991); Parris, N. et al., *J. Am. Oil Chem. Soc.* 53:97–100 (1976) report the Krafft point of $C_{16}$-sulfoethylbetaine as >90° C. as well.) Clearly, when compared to the ionic detergents, a more complex relationship of surface activity and ion functionality emerges for the betaines. In fact, the contradictory results possibly be due to the extreme sensitivity of these molecules to system conditions.

The change in CMC with respect to chain length has been described by the equation below (Kevens, H. B. et al., *J. Am. Oil Chem. Soc.* 30:74–80 (1953)) where A is a constant for a homologous series and B is a second constant used to show the dependence of CMC on chain length (m) for the same series:

$$\mathrm{Log}_{10} C = A - Bm$$

Shinoda (Shinoda, K. In: *Colloidal Surfactants*, Academic Press, New York (1963) pp.42–44) has compiled B values for a variety of detergents. In general, B values of ionic detergents are in the range of log 2 (e.g., 0.3), and log 3 (e.g., 0.5) for nonionic detergents. Beckett, A. H. et al., *J. Pharm. Pharmacol.* 15:422–431 (1963); Molyneux, P. et al., *Trans. Faraday Soc.* 61:1043–1052 (1965); and Lattes, A. et al., *Surfactants Soln.* 11:127–1139 (1991) report the B value for a homologous series of carboxy betaines as approximating a log 3 function. Weers, J. G. et al., *Langmuir* 7:854–867 (1991) report the B value of the sulfopropylbetaine series as 0.48.

Clearly, the betaines behave as nonionic detergents, meaning that CMC shows a stronger dependence on alkyl chain length than the corresponding ionic homologues. For example, the CMC of betaines decreases as a log function with each two carbon addition (this is clearly shown in the data of Nandakumar T. N. et al., *J. Oil Tech. Assoc. India* 11:31–34 (1979), and a comparison between ionic detergents and betaines is displayed graphically by Herrmann, K. W. *J. Colloid Inter. Sci.* 22:352–359 (1966).) As discussed above, however, this trend is affected to some degree by bridge length, and ion functionality. For example, the alkylhydroxy-phosphoethylbetaine series of Tsubone, K. et al., *J. Am. Oil Chem. Soc.* 67:394–399 (1990), and the alkyl-phosphoethylbetaine series of Tsubone, K. et al., *J. Am. Oil Chem. Soc.* 67:149–153 (1990) do not show the same degree of dependence. The B values reported by these authors are 0.1025 and 0.025, respectively, suggesting even less dependence on alkyl chain length than their ionic homologues. This deviation of the phosphobetaines is noted by Tsubone, K. et al., *J. Am. Oil Chem. Soc.* 67:149–153 (1990). These results suggest that there is a relationship between acid-base characteristics and the dipole moment created. Again, a complex relationship between behavior, structure and composition is displayed.

Responses to changes in temperature are perhaps the most distinguishing features separating ionic and nonionic detergents. For example, increases in temperature cause the CMC of ionic detergents to increase, whereas the CMC of nonionic detergents decreases. The work of Kuriyama, K. *Kolloid-Z* 180:55–64 (1961) compares sodium dodecyl sufate and methoxypolyoxyethylene decyl ether to clearly demonstrate this dichotomy. The pattern followed by betaines is pH dependent. Tsubone et al. have shown that hydroxyalkyl-phosphobetaines (Tsubone, K. et al., *J. Am. Oil Chem. Soc.* 67:394–399 (1990)) and phosphoethylbetaines (Tsubone, K. et al., *J. Am. Oil Chem. Soc.* 67:394–399 (1990)) behave as ionic detergents at pH 11.0, and as nonionic detergents at pH 6.0. CMC is unaffected by temperature at pH 2.0. Therefore, it would appear that, at low pH some betaines behave anomalously, at high pH all betaines behave as artionic detergents, and interestingly, at intermediate pH's, where the zwitterion is present, betaines follow the nonionic pattern: the CMC decreases with increasing temperature.

Based on the above, changes in miceliar weight and aggregation number in response to temperature are predictable. Micellar weight and aggregation number of ionic detergents decrease slightly with increasing temperature (Nakagawa, T. et al., In: *Colloidal Surfactants*, Academic Press, New York (1963) pp. 123–126). The micellar weight and aggregation number of nonionic detergents on the other hand eventually increases exponentially with increasing temperature (see: Balmbra, R. R. et al., *Trans. Faraday Soc.* 58:1661–1667 (1962), and Kuriyama, K. *Kolloid-Z* 180:55–64 (1961)). This behavior is characteristic of nonionic detergents and results in what is known as a cloud point, or an upper consolute temperature.

The cloud point is observed as the onset of turbidity, and is thought to be caused by dehydration of the hydrophilic portion of the nonionic detergent, thereby causing a reduction in solubility. It should be noted that the cloud point, in contrast to the Krafft temperature, is not a well defined temperature. In essence, micelles still exist; however, micellar weight and aggregation number gradually increase with increasing temperature, and as the temperature is increased further, phase separation eventually occurs. Nilsson, P. et al., *J. Phys. Chem.* 88:6357–6362 (1984) have described a similar phenomenon in sulfatobetaines. These same authors show that sulfobetaines display this behavior to a much lesser degree, whereas carboxybetaines were simply devoid of such behavior. In fact, Bhatia, A. et al., *Colloids and Surfaces* 69:277–292 (1993) show that the micellar weight and aggregation number of $C_{18}$-carboxymethylbetaine decreases with increasing temperature, a response typical of ionic detergents. These results suggest that the ionic/nonionic behavior of betaines can be selected by varying the charges (e.g., dipole moment) appropriately.

Changes in CMC in response to the presence of electrolytes also distinguish these detergents. For example, an increase in electrolyte concentration causes only a small decrease in the CMC of nonionic detergents (Shinoda, K. et al., *Bull. Chem. Soc. Japan* 34:237–241 (1961)). Ionic detergents on the other hand show a marked decrease in CMC when presented with similar changes in electrolyte concentration (Schwuger, V. M. J. *Kolloid-Z.* 233:979–985 (1969)). The net result is a "salting-out" of the ionic detergents. In other words, while the solubility of the gegenion is enhanced, solubility of the alkyl moiety is reduced. Therefore, the temperature must be raised to accommodate the required heat of mixing of the alkyl chains. This phenomenon is also referred to as a Krafft point elevation (see: Tartar, H. V. et al., *J. Phys. Chem.* 43:1173–1179 (1940); Tartar, H. V. et al., *J. Am. Chem. Soc.* 61:539–544 (1939); Nakayama, H. et al., *Bull. Chem. Soc. Japan* 40:1797–1799 (1967); and Tsujii, K. et al. *J. Phys. Chem.* 84:2287–2291 (1980) for examples.)

The most commonly used nonionic detergents have Krafft points below 0° C. and, therefore, do not display this behavior. As the hydrophilic moiety is reduced, however, some nonionic detergents do show a lower consolute boundary. Schott, H. et al., *J. Pharm. Sci.* 65:979–981 (1976) show that Brij 56 (cetyl-polyoxyethylene oxide ($C_{16}E_{10}$): CAS®No. 9004-95-9), and Brij 76 (stearyl-polyoxyethylene oxide ($C_{18}E_{10}$): CAS®No. 9005-00-9) can be salted-out. It should be pointed out, however, that the salting-out observed by Schott, H. et al., *J. Pharm. Sci.* 65:979–981 (1976) is far less dramatic than that seen by Tartar, H. V. et al., *J. Phys. Chem.* 43:1173–1179 (1940). The ability to salt-out nonionic detergents follows the trend: $SCN^{\ominus} > I^{\ominus} > NO_3^{\ominus} > Cl^{\ominus}$ for anions, and $Na^{\oplus} > K^{\oplus} > Li^{\oplus}$ for cations (Schott, H. et al., *J. Pharm. Sci.* 65:979–981 (1976)).

The ability to depress the cloud point follows the reverse trend (Schott, H. et al., *J. Pharm. Sci.* 64:658–664 (1975)). In fact, Schott, H. et al., *J. Pharm. Sci.* 65:979–981 (1976) show that some sodium and potassium nitrate salts can cause the cloud point and Krafft temperature to overlap (Brij 56: cetyl-polyoxyethylene oxide ($C_{16}E_{10}$), for example), thereby causing the formation of an "amorphous gel." The behavior of betaines in the presence of electrolytes is perhaps the most profound difference between this class of detergents and the others. Tsujii, K. et al. *J. Phys. Chem.* 82:1610–1614 (1978) show that $C_{16}$- and $C_{18}$-sulfopropylbetaine can be "salted-in" with added electrolytes. That is to say that the Krafft point is dramatically lowered upon addition of electrolytes (e.g., the melting point of the hydrated crystal is lowered). Tsujii, K. et al., *Yukagaku* 30:495–499 (1981) later showed that this phenomenon was directly correlated to the interbridge distance: if the bridge length was longer than 4–5 Å, the betaine was of the "salting-in type," whereas if the interbridge distance was shorter than 4 Å it was of the "salting-out type." Schott, H. et al, *J. Pharm. Sci.* 64:658–664 (1975) show that some nonionic detergents can be salted-in with respect to raising the cloud point. For example, the cloud point of Brij 96 (oleyl-polyoxyethylene ($C_{18:1}E_{10}$): CAS®No. 9004-98-2), in a 2 molal solution of HCl, is raised by 11.4° C. These differences in temperature are, however, minor in comparison to that observed for the betaines. For example, Tsujii, K. et al., *J. Phys. Chem.* 82:1610–1614 (1978) show that the Krafft point of SB-18 in pure water is 73.4° C. at 2 mM detergent, and 33.6° C. in 1M NaCl (Δ39.8° C.). Tsujii, K. et al. *Yukakagu* 30:495–499 (1981) hypothesize that the salting-in phenomenon is dependent upon the coordination of ions by the zwitterionic headgroup and that there is a minimum distance that allows this to occur productively.

The degree to which a betaine is salted-out (for those that are of the salting-out type) is more dramatic than the salting-out behavior of a nonionic detergent, but less dramatic than that observed for the homologous ionic detergent (e.g., compare the data of Tsujii, K. et al. *J. Phys. Chem.* 82:1610–1614 (1978) with that of Tsujii, K. et al. *Yukakagu* 30:495–499 (1981).) The salting-in behavior of betaines in the presence of different salts follows the classic "lyotropic series" (Tsujii, K. et al. *J. Phys. Chem.* 82:1610–1614 (1978)). That is to say that certain ions are more effective at depressing the Krafft point than other ions. For example, Tsujii, K. et al. *J. Phys. Chem.* 82:1610–1614 (1978) show that the ability to salt-in SB-18 follows the trend: $SCN^{\ominus} > I^{\ominus} > NO_3^{\ominus} > Cl^{\ominus}$ for anions, and $K^{\oplus} \approx NH_4^{\oplus} > Na^{\oplus}$ for cations. However, this trend is exactly reversed with respect to salting-out behavior. For example the effect of salting-out $C_{18}$-carboxymethylbetaine follows the trend, $SCN^{\ominus} > I^{\ominus} > NO_3^{\ominus} > Cl^{\ominus}$ (Tsujii, K. et al. *Yukagaku* 30:495–499 (1981)). This is consistent with the discussions of Schott, H. et al., *J. Pharm. Sci.* 65:979–981 (1976) concerning nonionic behavior.

Changes in micellar weight and aggregation number in response to changes in electrolyte concentration are predictable based on salting-in and salting-out behavior. The micellar weight and aggregation number of ionic detergents increases with increasing electrolyte concentration (Shinoda, K., In: *Colloidal Surfactants*, Academic Press, New York (1963) pp.20–21 review numerous works on this subject). Beeher (Beeher, P., In: *Surfactant Science Series*, vol. 4: *Nonionic Detergents*, Marcel Dekker, New York (1967) pp. 500–504) reviews the effect of electrolytes on the micellar weight and aggregation number of nonionic detergents and concludes that, excluding a few notable exceptions, these parameters are, for the most part, unaffected by changes in electrolyte concentration. Electrolytes, however, are known to depress the cloud point of nonionic detergents (Nakagawa, T, et al., *Colloidal Surfactants*, Academic Press, New York (1963) pp. 129–135). It is interesting to note that the effect of electrolytes on both types of detergents is similar, but opposite: electrolytes raise the Krafft temperature of ionic detergents (e.g., the melting point of the crystal is raised), and lower the cloud point of nonionic detergents (e.g., the temperature at which phase separation occurs is lowered). Bhatia, A. et al., *Colloids and Surfaces* 69:277–292 (1993) show that the micellar weight and aggregation number of $C_{18}$-carboxymethylbetaine increases with increasing $Na^{\oplus}$ concentration, however, the response is not as dramatic as that seen for ionic detergents.

Shinoda, K. *Colloidal Surfactants*, Academic Press, New York (1963) pp. 76–78, reviews a number of works showing that both ionic and nonionic detergents are, in general, pH independent. That is to say that, given the same ionic strength, the phase behavior of these detergents is the same under different pH conditions (e.g., any change associated with pH can generally be attributed to changes in ionic strength as discussed above).

The behavior of the betaines, however, is extremely dependent on pH. Nandakumar T. N. et al., *J. Oil Tech. Assoc. India* 11:31–34 (1979) show that several parameters related to surface activity of carboxymethylbetaines and sulfopropylbetaines are pH dependent. Tsubone et al. have shown that hydroxyalkyl-phosphobetaines (Tsubone, K. et al., *J. Am. Oil Chem. Soc.* 67:394–399 (1990)) and phosphobetaines (Tsubone, K. et al., *J. Am. Oil Chem. Soc.* 67:394–399 (1990)) also display opposing characteristics at different pH values. However, it is imperative to understand that, even with those detergents that are salted-in, the combination of high pH (e.g., the betaine behaves as an ionic detergent) and high salt will produce a salting-out of the betaine. Tsubone, K. et al., *J. Am. Oil Chem. Soc.* 67:149–153 (1990) show that the lower pKa of a $C_n$-phosphoethylbetaine falls in the range 4.7 to 4.9, and the upper pKa fails in the range 8.8 to 9.8. Weers, J. G. et al., *Langmuir* 7:854–867 (1991) show the lower $pK_a$ of $C_{12}$-carboxybetaines having various bridge length. As bridge length increases, the lower $pK_a$ is raised. Therefore, system pH is an important factor to consider when working with betaines. In summary, pH dependence is contingent on the combination of charges utilized in the betaine, and both bridge length and structure. Utilization of the betaines in the methods of the invention under extremely basic conditions are untenable (e.g., the betaines precipitate at pH 14), whereas utilization of the betaines in the methods of the invention under extremely acidic conditions does not appear to have the same limitations.

There is one additional point with respect to the bridge structure and modifications thereof, as it relates to utilization of these molecules. Parris, N. et al., *J. Am. Oil Chem. Soc.* 53:60–63 (1976) compare the Krafft temperatures of sulfopropylbetaines with the corresponding hydroxypropyl sulfobetaines and show a dramatic increase in Krafft point with this modification. Branching of the bridge to produce "iso" forms has an even more dramatic effect (Parris, N. et al., *J. Am. Oil Chem. Soc.* 53:60–63 (1976)). Therefore, the choice of bridge structure and system electrolyte can impact the utility of these molecules even further in the methods of the invention.

The unique feature of the betaines appears to be the dipole moment created by the structural arrangement of opposing charges (Laughlin, R. G. *Langmuir* 7:842–847 (1991)). This arrangement is believed to provide the ability to coordinate water/ion structure in a manner that results in several appealing aqueous phase attributes. As such, this arrangement can assume a variety of forms. Table 3 describes a variety of structures that are clearly betaine-like, and the discussion of Table 3 lists numerous examples of molecules in this category. These include the "reverse betaines," the amine oxide-like detergents, the c-alkyl betaines and the imidazolinium betaine derivatives. One would predict that, owing to the strong dipole moment created by the betaine-like structures inherent in these molecules, reverse betaines, amine oxides, the c-alkyl betaines and imidazolinium betaine derivatives would have similar utility in the methods of the invention. The properties of these molecules are discussed below in view of the properties of betaines described herein.

Zimmer, R. E. (U.S. Pat. No. 3,560,393) describes the synthesis of a wide variety of reverse betaines incorporating phosphate, phosphonate, phosphinate, and ammonium and sulfonium functionalities. Kurosaki, T. et al., *Chem. Soc. Japan* 11:1297–1301 (1990) characterize reverse betaines of the type: alkyl 2-hydroxy-3-trimethylammoniopropyl phosphates ($C_n$-AHTMAP). The $C_n$-AHTMAP compounds are seen to have CMC values similar to that of the corresponding betaines, and a B-value of 0.368, suggesting that the dependence of CMC on alkyl chain length is closer to that of the ionic detergents, than the nonionic detergents. It should be recalled, however, that the B-values of the phosphobetaine series of Tsubone et al. (Tsubone, K. et al., *J. Am. Oil Chem. Soc.* 67:394–399 (1990), and Tsubone, K. et al., *J. Am. Oil Chem. Soc.* 67:394–399 (1990)) appeared even more ionic in character than the corresponding ionic detergents. Unfortunately, no data exist on the pH dependence of reverse betaines.

The amine oxides (AO) are very similar in charge structure to the betaines; however, the bridge has been minimized to a covalent N—O bond. Tsujii, K. et al., *Yukagaku* 30:495–499 (1981), in analyzing the relationship of inter-bridge distance and salting-in/salting-out behavior, include $C_{18}$-AO in their study. These authors show that $C_{18}$-AO behavior parallels $C_{18}$-carboxymethylbetaine behavior; however, the Krafft point is more elevated. Comparison of salting-out behavior of $C_{18}$-AO (Tsujii, K. et al., *Yukagaku* 30:495–499 (1981)) with the salting out behavior of N,N, N-trimethyloctadecylammonium chloride (Tsujii, K. et al., *J. Phys. Chem.* 82:1610–1614 (1978)) shows that the former behaves more like a betaine with a short bridge, than the corresponding cationic detergent. One could speculate that the all important dipole moment characteristic of betaine-like structures is functional in amine oxides, albeit minimized. Further work on amine oxides by Fumikatsu, T. et al., *J. Phys. Chem.* 70:3437–3441 (1966), shows that phase behavior of this class of detergents is pH dependent, and Hermann, K. W. *J. Colloid Inter. Sci.* 22:352–359 (1966) shows that CMC values, B-values, and micellar properties are more closely related to the betaines than the corresponding ionic detergents. The data of Hermann, K. W. *J. Colloid Inter. Sci.* 22:352–359 (1966) even suggests that the amine oxides are more nonionic than the corresponding betaines. McCutcheon's, Volume 1: Emulsifiers & Detergents, North American Edition, MC Publishing, Glen Rock, N.J., p.290 lists the amine oxides as a separate category of detergents.

A large body of information regarding the properties of the c-alkyl betaines appeared in a series of papers by Tori and coworkers (Tori, K. et al., *Kolloid-Z. Z. Polymere* 187:44–51 (1963); Tori, K. et al., *Kolloid-Z. Z. Polymere* 188:47–52 (1963); Tori, K. et al., *Kolloid-Z. Z. Polymere* 189:50–55 (1963); Tori, K. et al., *Kolloid-Z. Z. Polymere* 191:42–48 (1963); and Tori, K. et al., *Kolloid-Z. Z. Polymere* 191:48–52 (1963)). Here again it is seen that the phase behavior of these molecules is similar to the n-alkyl betaines discussed in Table 2. For example, the salting-out behavior, as expected, mimics that of short bridge betaines where the salting-out is not as dramatic as that seen for ionic homologues (Tori, K. et al., *Kolloid-Z. Z. Polymere* 189:50–55 (1963)). In addition, the CMC of c-alkyl betaines decreases with increasing temperature; hallmark behavior of nonionic detergents. Further, Molyneux, P. et al., *Trans. Faraday Soc.* 61:1043–1052 (1965) plot their CMC vs. alkyl chain length data on n-alkyl betaines, with similar n-alkyl betaine data from Beckett, A. H. et al., *J. Pharm. Pharmacol.* 15:422–431 (1963), for comparison with the c-alkyl betaine data of Tori, K. et al., *Kolloid-Z. Z. Polymere* 191:48–52 (1963), and show that the B-values of n-alkyl betaines and c-alkyl betaines are, as might be expected, identical. While the popularity of the c-alkyl betaines has not reached the same proportions as n-alkyl betaines, they are commercially available: the variety seen in the c-alkyl betaine class is only a fraction of the n-alkyl betaine class.

The ability to present a detergent in a functional form (e.g., in the micellar form) in a clinical assay (e.g., aqueous, electrolyte containing solutions) appears to be an important aspect in betaine function in the methods of the invention. Therefore, it would appear that the choice of charge (e.g., $COO^{\ominus}$ vs. $SO_3^{\ominus}$) and bridge structure (e.g., —$CH_2$— vs. —$(CH_2)_3$—, or —$CH_2CH(OH)CH_2$—) plays an important role in productive betaine behavior. However, the phenomenon of salting-in (salting-out) is only relevant when the Krafft temperature of the detergent is above (below) the temperature of the system. For example, if the system temperature is 40° C., and the Krafft temperature of SB-18 is 88° C. (Parris, N. et al., *J. Am. Oil Tech. Soc.* 53:97–100 (1976)), and upon addition of 10 mM NaCl the Krafft temperature becomes 37.5° C. (Tsujii, K. et al. *J. Phys. Chem.* 82:1610–1614 (1978)), then SB-18 is effectively salted-in. If on the other hand the system temperature is 40° C., and the Krafft temperature of, for example, sodium dodecyl sulfonate is 31.5° C. (Tartar, H. V. et al., *J. Am. Chem. Soc.* 61:539–544 (1939)), and upon addition of 8 mM NaCl the critical temperature becomes 34° C. (Tartar, H. V. et al., *J. Phys. Chem.* 43:1173–1179 (1940)), while sodium dodecyl sulfonate is technically salted-out, there would be no effect with respect to the example described here. Alternatively, the analogous temperatures for sodium tetradecyl sulfonate would be 39.5° C. (Tartar, H. V. et al., *J. Am. Chem. Soc.* 61:539–544 (1939)) and 43° C. (Tartar, H. V. et al., *J. Phys. Chem.* 43:1173–1179 (1940)), respectively. Clearly, sodium tetradecyl sulfonate would be nonfunctional under the conditions described in this example. Tartar, H. V. et al., *J. Am. Chem. Soc.* 61:539–544 (1939) also report the critical temperature of sodium octadecyl sulfonate in water as 57° C. In view of this, the critical importance of maintaining the system temperature above 37° C. when using SB-18 as the detergent in the methods of the invention should be stressed. Therefore, careful consideration must be given to correlating the temperature at which processing is performed, with the Krafft temperature of the SB-18-like detergent being used in the method.

The obvious conclusion is that the unique feature of the betaines is that longer alkyl chains can be utilized in a clinical assay that have more attractive solubilizing characteristics.

Betaines as Solubilizing Agents

Solubilization is the action of bringing into solution molecules that are insoluble, or sparingly soluble, in aqueous media (Nakagawa, T., In: *Nonionic Detergents,* (1967) pp.558–603). It is theorized that solubilization operates via one of three modes. First, the solubilizate can be sequestered in the internal portion of the micelle (e.g., compounds that are nonpolar). Second, amphipathic molecules that are both polar and nonpolar to some degree, may associate with the micelle in a fashion similar to other detergent molecules (e.g., the nonpolar portion is sequestered in the core of the micelle, while the polar portion is associated with the surface of the micelle). The third mechanism is invoked with those compounds that are insoluble in both organic media and water. Dimethylphthalate is the classic example (McBain, J. W. et al., *J. Am. Chem. Soc.* 70:3838–3840 (1948)). In this model, it is proposed that molecules are adsorbed on the surface of the micelle. Therefore, it is intuitive that solubilization behavior is dependent on the nature of both the detergent and the solubilizate.

McBain, J. W. et al., *J. Phys. Chem.* 55:655–662 (1951) has compared the solubilization of n-hexane, cyclohexane, cyclohexene, and benzene by potassium laurate, dodecylamine hydrochloride, and Triton X-100, and concluded that ionic detergents solubilize cyclohexane the strongest, whereas Triton X-100 solubilizes benzene the strongest.

Ionic detergent and nonionic detergents, as expected, behave differently when analyzed on a functional level.

Weers, J. G., et al., *Langmuir* 7:854–867 (1991) provide the only controlled solubilization study comparing an anionic (SDS: CAS®No. 151-21-3), cationic ($C_{12}$-trimethylammonium bromide: CAS®No. 1119-94-4), and nonionic detergent ($C_{12}$-ethylene oxide ($C_{12}E_6$)): CAS®NO. 3055-96-7) with $C_{12}$-carboxymethylbetaine (CAS®No. 683-10-3) and $C_{12}$-sulfopropylbetaine (CAS®No. 14933-08-5) betaine. "Oil Blue A" was used as the solubilizate. These authors show that solubilization capacity increased in the order:

anionic<cationic<carboxybetaine<sulfobetaine<nonionic.
Based on the discussion of the work of McBain, J. W. et al., *J. Phys. Chem.* 55:655–662 (1951) above, and given that Oil Blue A is a fused polycyclic hydrocarbon (an anthracene derivative: 1,4-bis((1-methylethyl)amino)-9,10-anthracenedione (CAS®No. 14233-37-5)), this hierarchy would be expected. Interestingly, the sulfobetaine solubilized more Oil Blue A than the carboxybetaine. This is in agreement with the discussion above describing the behavior of carboxybetaines relative to the sulfobetaines: the carboxybetaines appear to lean toward ionic behavior when compared to the sulfobetaines; or alternatively, the sulfobetaines lean toward the nonionic detergents when compared to the carboxybetaines.

Alkyl chain length is directly relate to solubilizing ability. For example, $C_{18}$-detergents would have excellent solubilizing characteristics relative to $C_{12}$-detergents, even $C_{12}$-detergents in other classes: Weers, J. G. et al., *Langmuir* 7:854–867 (1991) also show that the "maximum additive concentration" increases exponentially with increasing alkyl chain length. For example, while $C_{12}$-ethylene oxide ($C_{12}E_6$) solubilizes slightly more Oil Blue A than $C_{12}$-sulfopropylbetaine, $C_{14}$-sulfopropylbetaine solubilizes 4–5 fold more Oil Blue A than $C_{12}$-ethylene oxide ($C_{12}E_6$) (Weers, J. G. et al., *Langmuir* 7:854–867 (1991)).

Inherent within the study of solubilization phenomena is the concept of detergency. Optimal detergency requires a complex mixture of surface active properties (Harris, J. C., In: *Surfactant Science Series,* vol 1: *Nonionic Detergents,* (1964) pp.683–732 review these properties.) One crucial aspect of detergency is the notion that, once something is solubilized, it must be maintained in a dispersed form.

Betaines have excellent dispersion characteristics (Weil, J. K. et al., *J. Am. Oil Chem. Soc.* 53:757–761 (1976)). Fernley, G. W. et al., *J. Am. Oil Chem. Soc.* 55:98–103 (1978) review the use of betaines as detersive agents and compares them favorably to alkyl-sulfonate detergents. However, the solubilizates in the methods of the invention are the lipids and lipoproteins associated with the cell wall of the Mycobacteria.

The cell wall structure of the Mycobacteria (see: McNeil, M. R. et al., *Res. Microbiol.* 142:451–463 (1991) for a comprehensive review), being composed primarily of lipids, lipoproteins and mycolic acids, is extremely thick and hydrophobic. Focussing on the mycolic acid, each mycloic acid has several chains of approximately $C_{14-20}$ ($\Sigma = C_{76}-C_{80}$), and the cell wall unit is isolated as a dimycolate (Noll, H. et al., *Biochim. Biophys. Acta* 20:299–309 (1956)). Given the structure of mycolic acids, the second mode of solubilization would be expected to be operational (e.g., the nonpolar portion is sequestered in the core of the micelle, while the polar portion is associated with the surface of the micelle). Based on the discussion above, ionic detergents would be predicted to be better solubilizers of mycolic acids than nonionic detergents. Therefore, the peripherally associated cell wall components must be stripped and maintained in solution in order to disperse *M. tuberculosis*. Young, D. B. et al., *Res. Microbiol.* 142:55–65 (1991) has shown that Triton X-100 (CAS®No. 9002-93-1) can remove lipoproteins from *M. tuberculosis*, however, FIG. 3 suggests that this detergent cannot disperse the bacteria. Therefore, the long chain betaines would be expected to be better solubilizers of mycolic acids than Triton X-100. Given the enormous size and complex structure of mycolic acids, maintaining them in solution would be expected to be problematic as well. In other words, SB-12, in addition to being a relatively poor solubilizer when compared to SB-18, may not be able to maintain the mycolic acids in a dispersed state. For example, Bhatia, A. et al., *Colloids and Surfaces* 69:277–292 (1993) have compared in detail the micelle structure of $C_{12}$, $C_{16}$, and $C_{18}$-carboxymethylbetaine. The hydrodynamic radius of the $C_{12}$-betaine micelle is 19±2 Å, whereas the micelle structure of both the $C_{16}$ and $C_{18}$-betaine is rod-like and varies depending on surfactant and electrolyte concentration: the persistence length of the $C_{16}$-betaine micelle is 600±100 Å in 1.0M NaCl at 25° C., while the persistence length of the $C_{18}$-betaine micelle is 1400±200 Å in 0.01M NaCl at 40.3° C. Considering that the extended chain length of the $C_{12}$-betaine is 23 Å (Bhatia, A. et al., *Colloids and Surfaces* 69:277–292 (1993)), and further considering the hydrophobic nature of mycolic acids, the possibility that the shorter chain suffactants simply cannot maintain the solubilized mycolic acid in solution would explain the inability of the shorter SB-series detergents to disperse *M. tuberculosis*.

Summary: Betaines as detergents

The betaines have unique characteristics that place them in a distinct class, but that class seems to lie somewhere between the ionic and nonionic categories. Behavior is very complex and is dependent on the bridge structure and type of zwitterion. In some instances, betaines behave like ionic detergents, and in others, betaines behave like nonionic detergents. Hence, the choice of anion and bridge length has profound effects on utility.

For example, overall solubility characteristics are directly related to headgroup hydrophilicity. Headgroup hydrophilicity is in turn dependent on the anion. Since hydrophilicity of the different anions follow the progression $SO_4^{\ominus} < SO_3^{\ominus} < CO_2^{\ominus}$ (Laughlin, R. G., In: *Advances in Liquid Crystals*, Brown, G. H., ed., Academic Press, New York (1978) pp. 41–148), it is expected that carboxybetaines are more soluble than sulfobetaines, which are in turn more soluble than sulfatobetaines. The data of Nandakumar T. N. et al., *J. Oil Tech. Assoc. India* 11:31–34 (1979) and Weers, J. G. et al., *Langmuir* 7:854–867 (1991 ) compare Krafft temperatures of carboxybetaines having different alkyl chain lengths with sulfobetaines of similar chain lengths and clearly show this to be the case. Examination of the data of Parris, N. et al., *J. Am. Oil Tech. Soc.* 53:97–100 (1976), in which the sulfobetaines are similarly compared to the sulfatobetaines, confirms this conclusion. Inclusion of bridge length data suggests that those betaines with a single methylene bridge will be salted-out, analogous to ionic behavior, while betaines with longer bridges will be salted-in. For example, carboxypropylbetaines are expected to be more soluble than carboxymethylbetaines of similar alkyl chain length. Again, Tsujii, K. et al., *Yukakagu* 30:495–499 (1981), have shown that the former is salted-in, while the later is salted-out. Introduction of groups onto the bridge appear to interfere with the solubility of the betaines, thereby compromising attractive features: hydroxypropyl, and "iso" betaines have less desirable characteristics (Parris, N. et al., *J. Am. Oil Chem. Soc.* 53:60–63 (1976)). Shorter bridges would have broader operational pH ranges (Weers, J. G. et al., *Langmuir* 7:854–867 (1991)). Carboxybetaines and sulfobetaines have B-values similar to those of nonionic detergents, whereas the B-values of the phosphobetaines are similar to the ionic detergents. Sulfatobetaines show an upper consolute temperature, whereas the micellar molecular weight and aggregation number of carboxybetaines actually decreases with increasing temperature; akin to ionic behavior. In one regard, however, alkyl structure, all detergents are expected to behave identically. For example, introduction of structural alterations in the alkyl chain, be they one or several double bonds, polar groups such as hydroxyls, esters, amides, or ethers, or other modifications such as the introduction of cyclopropane rings, would all be expected to produce rational changes in character. Given the wide variation in structure, in combination with the known physical characteristics of betaine-like structures, designing a betaine with ideal characteristics for use in the methods of the invention becomes possible. For example, carboxybetaines, while suffering from a higher degree of pH dependence, produce more soluble betaines and would, therefore, permit the use of the longer alkyl chains. In addition, carboxybetaines, which tend toward ionic behavior, would be expected to be the better solubilizers of mycolic acids amongst the betaines. The bridge must be longer than 4~5 Å, therefore, a propyl group would be the minimum. Hodge, D. J. et al., *Langmuir* 7:878–884 (1991) has reported a $C_{20}$-carboxyhexylbetaine with a Krafftpoint of 20° C. $C_{18}$-carboxypropylbetaine (CAS®No. 78195-27-4) would be expected to possess optimal characteristics.

In summary, long chain alkyls are required to disperse *M. tuberculosis*, and these molecules must function in the context of physiologically relevant conditions (e.g., an electrolyte concentration of approximately 100–150 mM). Therein lies the apparent advantage that betaines have over ionic detergents in the methods of the invention: betaines are salted-in, and ionic detergents are salted-out. While explaining the advantages of betaines over nonionic detergents is more speculative, the suggestion is that betaines are, in general, better solubilizers of mycolic acids and other lipids involved in cording than nonionic detergents.

While these arguments do in fact suggest an explanation of why SB-18 was the only detergent to function in the aggregation assay, they do not completely explain the bimodal action of SB-18: that is, why SB-18 also facilitates the recovery of *M. avium* (where aggregation is not a problem). This is discussed below.

Buoyancy of Mycobacteria

The synthesis of lipids by the Mycobacteria is a very complex and diverse subject, with many peculiarities that are species specific (for reviews see Bloch, K. *Adv. Enzymol.* 45:1–84 (1977), Minnikin, D. E., in: The Biology of the Mycobacteria, C. Ratledge et al., eds., vol. 1, Academic Press, New York, 1982, pp.95–184; Ratledge, C., in: The Biology of the Mycobacteria, C. Ratledge et al, eds., vol. 1, Academic Press, New York, 1982, pp.53–92 and Takayama, K. et al., in: The Mycobacteria a source book, part A., G. P. Kubica et al., eds., Marcel Dekker, Inc., New York, 1984, pp. 315–344). In general, however, approximately 60% of the cell wall is lipid, and approximately 50% of the lipid in the cell wall is in the form of mycolic acids (Joklik, W. K. et al., *Zinsser Microbiology*, 20th edition, Appelton & Lange, Norwalk, Conn., 1992, pp. 81 and 499).

Mycolic acid confers a unique character upon this class of microorganism (see Ratledge, in: The Biology of the Mycobacteria, C. Ratledge et al., eds., vol. 1, Academic Press, New York, 1982, pp.53–92 and especially pages pp 65–84 for a detailed description of mycolic acid synthesis).

The result of mycolic acid synthesis is that, in vivo, large quantities of $CO_2$ are generated as a result of synthesizing mycolic acids. For example, synthesis of a mycolic acid residue by the malonyl CoA pathway, containing 80 carbon atoms, would produce approximately 80 $CO_2$ molecules.

There are several pertinent points. First, in vivo, the Mycobacterial cell wall is thicker than its in vitro counterpart (Rastogi, N. et al., *Antimicrob. Agents Chemother.* 20:666–677 (1981)). Second, almost 18% of the dry weight of the Mycobacterium cell (grown in the absence of oleic acid, Tween 80 or BSA) is lipid (Stinson, M. W. et al., *Am. Rev. Resp. Dis.* 104:717–727 (1971)), and in vivo approximately 60% of the cell wall is complex lipid, and 50% of this is mycolic acid (Joklik, W. K. et al., *Zinsser Microbiology*, 20th edition, Appelton & Lange, Norwalk, Conn., 1992, pp. 81, 499 and 503); hence, the Mycobacteria generate large quantities of $CO_2$ during cell wall synthesis. Essentially, the net effect of growth in enriched media containing oleic acid, Tween 80 and BSA would be a reduction in lipid synthesis, and therefore, a substantial decrease in $CO_2$ production. Finally, the fact that the untreated cells are buoyant in a centrifugal field suggests that any buoyancy theory incorporating trapped gas eliminate classical "gas vacuoles" as a possibility (Walsby, A. E. *Bact. Rev.* 36:1–32 (1972)). This led the inventor to the notion that the organisms could simply be degassed to reduce or eliminate buoyancy. For example, as described below, slightly warming the Mycobacteria (cord factor melting point (MP)=43° C.–45° C. (Noll, H. et al., *Biochim. Biophys. Acta* 20:299–309 (1956)), under vacuum, made it possible to remove enough of the trapped $CO_2$ to affect buoyancy.

Preparation of MAC Complex Organisms

For certain microorganisms such as those of the MAC complex, a further processing step, incubation for a sufficient time at an elevated temperature, such as 40° C., under approximately 600 mm Hg vacuum is necessary. There is no minimum time for exposing the MAC organism sample to the detergent-containing wash solution for the purpose of dispersion as the effect is almost instantaneous, but generally 60 minutes is preferred to permit accumulation of the detergent such that buoyancy might be offset. There are believed to be only marginal advantages to exposing the sample to the wash solution beyond 60 minutes. The time for such vacuum degassing step should be at least 20 minutes and 60 minutes is preferred. Incubations up to several hours provide only marginal improvements over a 60 minute incubation when SB-18-like detergents are used. However, incubations of several hours permit most detergents to be used. Exposure of the MAC organisms to the detergent-containing wash solution can be simultaneous with the degassing step, however, there may be practical safety concerns using this embodiment. The temperature of the degassing step should be between 30° C. and 50° C., preferably 40° C. to 42° C. Temperatures below 30° C. probably do not facilitate softening of the waxy-coat on the MAC organisms; temperatures above 50° C. apparently facilitate lysis of the organism. Therefore, since viability is a primary advantage of the methods described herein, and further, since the methods confer an advantage with respect to improving the efficiency of recovery by centrifugation only if the bacterial cells are intact, the processing temperature should not exceed 50° C. for most microorganisms described herein, but temperatures above 50° C. can be used if such temperatures do not lyse the specific species being detected. This can however, be utilized to provide for a desired result. For example, a temperature can be selected that is known to lyse a certain microorganism under the defined processing conditions, but is known not to lyse a second species of microorganism under the same defined processing conditions. In such an example, the methods of the invention would selectively enrich for the non-lysed microorganism.

Without intending to be held to the following explanations, it is believed that the differences observed between MTB complex and MAC complex organisms are due to their respective growth characteristics. In MAC complex organisms, which grow primarily as single cells, the SB-18-like detergents have three effects: (1) the general surface tension disruption effect seen with most detergents, (2) the dispersion effect seen with the MTB complex organisms (albeit less imperative), and (3) an ability to be transported across the membrane and accumulate in the cell. Weir, M. P. et al., *Am. Rev. Res. Dis.* 106:450–457 (1972) have shown that the Mycobacteria are very efficient at actively accumulating lipids, oleic acid for example. Schaefer, W. B. et al., *J. Bacteriol.* 90:1438–1447 (1965) demonstrated that lipid accumulation is observable within two hours, and dramatic lipoidal bodies form within 24 hours. The consequence of lipid accumulation, in contrast to previously held beliefs (Silverstolpe, L., *Nord. Med.* 40/48:2220–2222 (1948); Davis, B. D. et al., *Microbiology*, Harper & Row, New York (1973), p. 847), may be to alter the partial specific volume of the cell in a significant manner sufficient to partially counteract the natural buoyancy.

Without intending on being held to the following explanation, the vacuum degassing step is believed to effectively remove trapped gases, such as $CO_2$, that are formed as a result of the natural metabolism of the microorganism, but trapped in its outer waxy cell wall to some extent. The last theory is based on the observation that marginal, but discernable, improvements in recovery were observed in the absence of added detergent, and that any detergent could be utilized if the organisms were degassed extensively. Overcoming buoyancy by combining detergents with degassing was seen to further facilitate collection by gravity force methods, such as centrifugation, as discussed herein.

The fact that detergents, which am other than SB-18-like, rod-like or approximately-octadecyl, can be used when the organisms are degassed exhaustively suggests that the natural buoyancy of the MAC complex organisms is most likely derived from trapped gasses. Without intending to be held to this explanation, it is believed that once the natural buoyancy of the MAC complex organism is completely eliminated, surface tension is the only remaining factor permitting flotation. Since most detergents are surface tension relievers, many additional detergents can be forced to improve recovery by centrifugation. Extended incubations under vacuum may, however, compromise viability of the organisms.

The vacuum pressure is conveniently 600 mm Hg owing to the general commercial availability of economical vacuum pumps in this range. However, the skilled artisan may use any pressure or means that is sufficient to achieve the desired result of unveiling the microorganism's susceptibility to detergents containing octadecy-like components. After the wash step with a detergent, such as SB-18, and after, if necessary, a degassing step, the microorganisms in the sample are collected by methods known in the art, such as, for example, centrifugation, and lysed, if necessary, for further analysis such as for detection of nucleic acids by amplification. Not all methods of detection require lysis of the microorganism. For example, detection by culture or detection of membrane antigens with an immunoassay would not require lysis. Because the methods of the invention do not lyse, microorganisms having mycolic acid structures in the outer membrane, and especially Mycobacteria, can be detected by either techniques such as amplification or culture following treatment with any of the detergents of the invention.

Accumulation of Detergents

Without intending on being held to the following explanation, accumulation of detergents explains one aspect of SB-18-like activity. To reiterate the foundation of the degassing hypothesis, if culturing the Mycobacteria in the presence of Tween 80 (CAS®No. 9005-65-6)/oleic acid (CAS®No. 112-80-1) causes submerged growth (Dubos, R. J., *Exp. Biol. Med.* 58:361–362 (1945)), and growth of Mycobacteria in the presence of Tween 80/oleic acid causes the formation of lipoidal bodies (Schaefer, W. B. et al., *J. Bacteriol.* 90:1438–1447 (1965)), then one could conclude, in contrast to previously held beliefs (Silverstolpe, L., *Nord. Med.* 40/48:2220–2222 (1948); Davis, B. D. et al., *Microbiology*, Harper & Row, New York (1973), p. 847), that the formation of lipoidal bodies is related to submerged growth, and conceivably even causative. Again, the conclusion must be that an explanation for the for the source of the natural buoyancy of these organisms has, until now, been unrecognized. It is believed that the betaines, analogous to Tween 80/oleic acid, present themselves to the cell in such a way that they are sequestered within the cell, and in doing so alter the partial specific volume of the cell to partially counteract the natural buoyancy of these organisms, thereby enhancing recovery by centrifugation. The fact that the betaines have long been used as components in commercial antibacterial formulations in detergents (Gomi, T., JP 8895298 A2; JP 6395298), anticorrosion formulations (Nemcova, J. et al., CS 202494 B), and dentifrice preparations (Oshino, K. et al., JP 92134025 A2; JP 04134025) suggests that they do indeed enter microbial cells. The fact that the cell wall of *Mycobacterium chelonei* is 1,000× to 10,000× less permeable than that of *E. coli* (Jarlier, V. et al., *J. Bacteriol.* 172:1418–1423 (1990)), suggests that some aspect of betaine nature causes these compounds to be sequestered preferentially.

In order for a molecule to enter a microbial cell, it must first pass through the cell wall (outer membrane) and then through the cell membrane (inner membrane). The permeability of microbial cells is reviewed by Nikaido, H. et al., *Microbiol. Rev.* 49:1–32 (1985), and the permeability of Mycobacterial cells is reviewed by Connell, N. D. et al., In: *Tuberculosis: Pathogenesis, Protection, and Control*, B. R. Bloom, ed., American Society for Microbiology, Washington, D.C. (1994) pp. 333–352. In general, there are three ways a molecule may traverse the outer membrane. The first is through the "hydrophilic pathway", usually involving a porin; the second is via the "hydrophobic pathway", usually involving diffusion through the hydrophobic domain; and the third is referred to as the "self-promoted pathway", or disruption of the cell wall by the agent to permit entrance of the molecule itself (summarized from Hancock, R. E. W. *Ann. Rev. Microbiol.* 38:237–264 (1984)). Once across the cell wall carrier-mediated transport is the most common means for traversing the inner membrane. The two general classes of carrier-mediated transport are: "facilitated diffusion" and "active transport". Both involve the use of specific protein complexes, having some degree of substrate specificity and, therefore, Michaelis-Menten characteristics. Some are energy dependent, whereas others depend on the electrochemical gradient. In summary, the cell wall of the Mycobacteria presents an extreme example of a barrier which must provide some mechanism for the exchange of molecules with the extracellular media.

In the context of the methods of the invention it is imperative to keep in mind the time frames being discussed. For example, most studies which examine the bacteriocidal or bacteriostatic activity of a particular compound grow the bacteria in the presence of said molecule for extended periods of time (e.g., days). Growth over this time period is recorded and efficacy reported. In the methods of the invention the time frames being discussed are limited to several hours. Therefore, it does not seem rational that mechanisms such as the hydrophobic pathway or the self-promoted pathway would be involved.

Therefore, passage of betaines across the outer membrane should use the hydrophilic pathway (e.g., porins) primarily. Porins " . . . are proteins that produce nonspecific, open, water-filled channels allowing the diffusion of small molecules across the membrane." (quoted from: Connell, N. D. et al., In: *Tuberculosis: Pathogenesis, Protection, and Control*, B. R. Bloom, ed., American Society for Microbiology, Washington, D.C. (1994) pp. 336). Trias, J. V. et al., *Science* 258:1479–1481 (1992) report that the porin of *M. chelonae* is a 59 KD protein which produces a pore with a diameter of approximately 2.2 nm, and an exclusion limit between 2,000 and 3,000 daltons. The molecular mass of SB-18 (CAS®No. 13177-41-8) is 419.7 daltons. In addition, Tsubone, K., *J. Am. Oil Chem. Soc.* 67:149–153 (1990), and Tsubone, K., *J. Am. Oil Chem. Soc.* 67:394–399 (1990) study the physical parameters of several N-alkyl-phosphoethylbetaines, and several 2-hydroxyalkyl-phosphoethylbetaines, respectively, and report the occupied area per molecule for the $C_{16}$-betaines as 0.475 $nm^2$, and 0.761 $nm^2$, respectively. Therefore, the cross sectional diameter of the betaine headgroup is approximately 7.8 Å, and 9.8 Å, respectively. Bhatia, A. et al., *Colloids Surf.* 69:277–292 (1993) take the $C_{18}$-carboxybetaine (CAS®No. 820-66-6) headgroup volume as 180 $Å^3$, which gives a diameter of 7.7 Å for this headgroup. For comparison, the headgroup diameter of SDS (CAS®No. 151-21-3) is on the order of 7.5 Å (Shinoda, K. *J. Phys. Chem.* 59:432–435 (1955)). Nonionic detergents, Tween 80 (Oleyl polyoxyethylene (n=20) sorbitan: CAS®No. 9005-65-6) for example, would be expected to have dramatically larger headgroup diameters, and therefore, may be sterically hindered from passing easily through a porin. In support of this, Wayne, L. G. et al., *Am. Rev. Resp. Dis.* 90:588–597 (1964) show that only certain Mycobacteria have the ability to hydrolyze Tween, and in those which cannot hydrolyze Tween, growth is not stimulated by addition of this detergent. The suggestion is that the headgroup must be removed prior to assimilation.

The use of certain nonionic detergents to improve recovery is shown herein. For example, while the headgroup of Tween 80 is to bulky to pass through the porin, other detergents, such as the linear polyoxyethylene ethers of fatty acids (e.g., the "Brij" compounds) useful in the methods of the invention are believed to present themselves in a way that permits passage into the cells and that permits function in the methods of the invention. Hsiao, L. et al., *J. Phys. Chem.* 60:657–660 (1956) show that the area per molecule of polyoxyethylene phenyl ethers is on the same order as that of the betaines (e.g., $C_9$- with an average of 9.5 POE units would have and area of 55 $Å^2$.) It is shown herein, that Brij 96 (oleyl-polyoxyethylene ether ($C_{18:1}E_{10}$): CAS®No.

9004-98-2), while relatively ineffectual at dispersing clumps of *M. tuberculosis*, has SB-18-like activity with respect to offsetting buoyancy. Without intending on being held to the following explanation, nonionic detergents such as Brij 96 function in the methods of the invention as a result of their homologous chemical shape. That is to say that Brij 96 is similar to SB-18-like detergents in that it has the same "rod-like" character and is not sterically hindered from entering the cell. Therefore, "rod-like", as used herein, refers to a nonionic detergent that displays SB-18-like activity, in the absence of degassing, in the methods of the invention. Rod-like detergents would have similar "axial ratios." Axial ratio, as defined by the McGraw-Hill Dictionary of Scientific and Technical Terms, 5th ed., Parker, S. P., ed. McGraw-Hill, Washington, D.C. (1994), p. 168, is: "The ratio of the major axis to the minor axis...." For example, Bhatia, A. et al., *Colloids and Surfaces* 69:277–292 (1993) take the extended chain length (e.g., the major axis) of $C_{12}$-carboxymethylbetaine as 23 Å, and the headgroup volume of the carboxymethylbetaine as approximately 180 Å$^3$. Assuming the headgroup a sphere, the headgroup diameter (e.g., the minor axis) would be approximately 7.7 Å. The major axis would, by definition, be perpendicular to the minor axis. Therefore, the axial ratio of $C_{12}$-carboxymethylbetaine (CAS®No. 683-10-3) would be approximately 3 (23÷7.7=2.99). Tsubone, K., *J. Am. Oil Chem. Soc.* 67:394–399 (1990) report the occupied headgroup area as 0.761 nm$^2$ for 2-hydroxyalkyl phosphoethylbetaines. The minor axis of these betaines would be 9.8 Å, giving the axial ratio of the $C_{12}$-betaine (CAS®No. 124591-53-3) a value of 2.3. Therefore, the axial ratio of betaines would be expected to range from 1.5, for detergents in which the major axis ($R_1$) contains 8-carbon atoms, to approximately 6, for those betaines in which the hydrophobic domain approaches 22-carbon atoms. Rod-like detergents would include all electrically neutral detergents with an alkyl chain length of 8–22 carbon atoms, preferably 12–20 carbon atoms, and most preferably 16–18 carbon atoms, which display SB-18-like activity in the absence of degassing.

Approximately-octadecyl Detergents

It has been discovered that, certain detergents, while impotent in dispersing MTB clumps, can further improve recovery of MAC by centrifugation once the organisms are degassed. For example, after the vacuum treatment discussed above, many additional detergents may be used, especially those that are approximately-octadecyl in structure. That is to say, both SB-16 and SB-18 become more effective in facilitating recovery following degassing. For example, trimethyloctadecyl-ammonium bromide TMA-18: CAS®No. 1120-02-1) and benzyldimethyloctadecylammonium chloride (BenzDMA-18) are now seen to have some degree of efficacy in improving collection with the methods of the invention after degassing was performed. Nonionic, octadecyl detergents such as Tween 80 (CAS®No. 9005-65-6) and Span 80 (CAS®No. 1338-43-8) were also seen to exhibit the same phenomenon after degassing. Once the trapped gasses are removed, the approximately-octadecyl molecules facilitate collection by altering the partial specific volume of the cell as discussed above.

Therefore, "approximately-octadecyl" as used herein will refer to a detergent molecule possessing an octadecyl-like moiety similar to the SB-18-like octadecyl moiety and do not require the presence of the zwitterion function to be effective. Approximately-octadecyl detergents are useful in the methods of the invention when applied to the MAC complex organisms and include SB-18-like detergents. Not all approximately-octadecyl detergents are SB-18-like detergents, but all SB-18-like detergents are approximately-octadecyl detergents. SB-18-like detergents are those useful in the methods of the invention when applied to the MTB complex (i.e., where degassing is not required).

The inability of anionic detergents (e. g., sodium dodecyl sulfate (SDS: CAS®No. 151-21-3)or sodium octadecyl sulfate (SOS): CAS®No. 1120-04-3), or cationic alkyltrimethylammonium salts (e.g., TMA-12 (CAS®No. 1119-94-4) and TMA-18 (CAS®No. 1120-02-1) to work in a manner similar to that of SB-18 can be explained as follows. The Krafft points of the long chain ionic detergents would cause SOS and TMA-18 to be in a microcrystalline form and, therefore, unavailable for rapid uptake. This would be supported by examining the methods of Weir, M. P. et al., *Amer. Rev. Res. Dis.* 106:450–457 (1972): BSA was used to emulsify oleic acid (CAS®No. 112-80-1) prior to use. Emulsification permits the presentation of oleic acid in a manner acceptable for uptake (e.g., in solution). An explanation for the exclusion of anionic detergents that are in solution lies in the fact that the Mycobacterial porins are cation selective. In other words, the channel has several spatially placed anionic amino acids in the mouth of the porin that exclude anionic compounds (Trias, J. V. et al., *Science* 258:1479–1481 (1992); and Trias, J. V. et al., *J. Biol. Chem.* 268:6234–6240 (1993)). Jarlier, V. et al., *J. Bacteriol.* 172:1418–1423 (1990) have shown that cephalosporins use the hydrophilic pathway to gain entry into the cell, and further, anionic cephalosporins diffuse much more slowly into the cell than those with "no net charge." The impediment thwarting the movement of cationic detergents across the outer membrane appears to be due to the fact the porin of Trias, J. V. et al., *J. Biol. Chem.* 268:6234–6240 (1993) is voltage dependent. Accumulation of cationic detergents would simply shut the channel.

Once across the outer membrane, betaines traverse the inner membrane by active transport. Schaefer, W. B. et al., *J. Bacteriol.* 90:1438–1447 (1965) study *M. kansasii*, and Weir, M. P. et al., *Amer. Rev. Res. Dis.* 106:450–457 (1972) study *M. smegmatis*, and show that uptake of oleate is rapid and energy dependent. In addition, Weir, M. P. et al., *Amer. Rev. Res. Dis.* 106:450–457 (1972) further show that the mechanism involved is stereospecific to some degree. McCarthy, C. *Infect. Immun.* 4:199–204 (1971) study *M. avium* and report that 78 nmoles of palmitic acid (CAS®No. 57-10-3) can be sequestered by 1 mg of cells in 30 minutes. There are, however, species specific attributes. Schaefer, W. B. et al., *J. Bacteriol.* 90:1438–1447 (1965) state that MTB complex organisms" . . . did not show the same striking morphological or turbidity changes in media with Tween or oleic acid." Cella, J. A. et al., *J. Am. Chem. Soc.* 74:2061–2062 (1952) conclude that $C_{16}$–$C_{18}$ quaternary ammonium salts provided the best bactericidal activity, and Tsubone, K. et al., *J. Pharm. Sci.* 80:441–444 (1991) clearly shows that $C_{16}$-phosphoethylbetaine (CAS®No. 126712-88-7) is the ideal length for said activity (the $C_{18}$ homologue was reported as being cloudy under assay conditions). Both authors show the short chain compounds to be relatively ineffective antimicrobials. Tsubone, K. et al., *J. Pharm. Sci.* 80:441–444 (1991) also shows extreme species dependence on activity. The conclusion is that the lipid transporter shows a much higher specific activity toward longer chain lipids, and this activity shows wide variations across species. Regardless, there are no major obstacles retarding betaines from entering the cell. The advantage betaines have in the methods of the invention is that they are structurally presented to the cell in an ideal fashion.

If this pathway is involved in SB-18-like activity there may be additional pH and temperature dependent factors. For example, McCarthy, C. *Infect. Immun.* 4:199–204 (1971) shows that the lipid transporter of *M. avium* is both pH and temperature dependent: transport is optimal at 38° C. and pH 6.5. Whereas varying the pH and lowering the temperature during processing would have negative consequences with respect to the chemical structure and phase structure of SB-18, respectively, these parameters might also restrict the ability to accumulate SB-18-like detergents. For example, Tsujii, K. et al., *J. Phys. Chem.* 82:1610–1614 (1978) show that SB-18 in 10 mM NaCl must be kept above 37.5° C. in order to maintain micellar structure. Tsubone, K. et al., *J. Am. Oil Chem. Soc.* 67:149–153 (1990) show that the lower pKa of a $C_n$-phosphoethylbetaine falls in the range 4.7 to 4.9, and the upper $pK_a$ falls in the range 8.8 to 9.8. Weers, J. G. et al., *Langmuir* 7:854–867 (1991) have determined the lower $pK_a$ values of a wide range of $C_{12}$-carboxybetaines and show the dependence on bridge structure. Safeguarding the assay conditions within these pH ranges permits functioning of the betaine as a detersive reagent (e.g., micellar form is maintained, thereby permitting solubilization of mycolic acids and lipids involved with cording). Experiments utilizing mildly acidic buffers (e.g., pH 5.7) have not prevented the collection of *M. tuberculosis* to a discernable degree. This result, however, may be species specific. Therefore, in order to accrue maximum benefit from the utilization of betaines in the methods of the invention, for the detection of a wide variety of organisms, the pH should be maintained above 5.0, but not much greater than 8.0, however, any pH which permits the SB-18-like detergent to display SB-18-like activity is acceptable.

The reason why short chain detergents show reduced activity in the assays described here may actually be due more to the fact that there is a relationship between alkyl chain length and antimicrobial activity. The most interesting finding of Tsubone, K. *J. Pharm. Sci.* 80:441–444 (1991) is that of the nine organisms (both fungi and bacteria) tested, *Propionibacterium acnes* and *Streptococcus mutans* were by far the most dramatically affected by the phosphobetaines as a group. Of the nine organisms, *P. acnes* is the most closely related to the Mycobacteria. In fact, the forward primer sequence (TBv2-119 [SEQ ID No. :1:]) is completely homologous to *P. acnes* in this region of the 16S rRNA gene sequence. The conclusion is that either the betaines are efficiently sequestered, or the structures are extremely potent, or both.

Having now generally described the invention, the same will be more readily understood through reference to the following examples that are provided by way of illustration, and are not intended to be limiting of the present invention.

EXAMPLES

Example 1 Materials and Methods

I. Preparation of SB-18 Wash Buffer

SB-18 Wash Solution (per 500 ml)

A. Add 25 ml of 20× SB-18 Salts (see below) to approximately 475 ml of $H_2O$ (or 5 ml per 100 ml of wash buffer) and autoclave (20 min/liquid cycle).

B. Remove the bottle from the autoclave and immediately add 5 ml of 100× SB-18 (or 1 ml of 100× SB-18 per 100 ml of Wash Buffer). Mix by swirling and place at 40° C.

C. Store the bottles at 40° C. until use. (The bottles can be stored for several days prior to use.)

D. OPTIONAL: Immediately prior to use, thaw the 1.25M DTT to room temperature, and add 2 ml of 1.25M DTT per 500 ml of SB-18 Wash Solution (final concentration: 5 mM or 400 µl of 1.25M DTT per 100 ml of Wash Buffer). Mix well by swirling. It is important that the DTT not be cold when it is added. Note: do not use if precipitate is present.

E. Use as described in the examples below.

F. Discard the remaining contents after use.

At any point in this procedure, if a precipitate is present in the Wash Buffer, do not use it. In addition, the solution should be kept warm at all times prior to and during use. The Krafft temperature of SB-18 under these conditions is approximately 37° C. (Tsujii, K. et al., *Jour. Phys. Chem.* 82:1610–1614 (1978)). Therefore, the solution must be kept above this temperature to avoid crystallization and to ensure stable micelle formation.

II. SB-18 Wash Buffer Components

Figure 10:
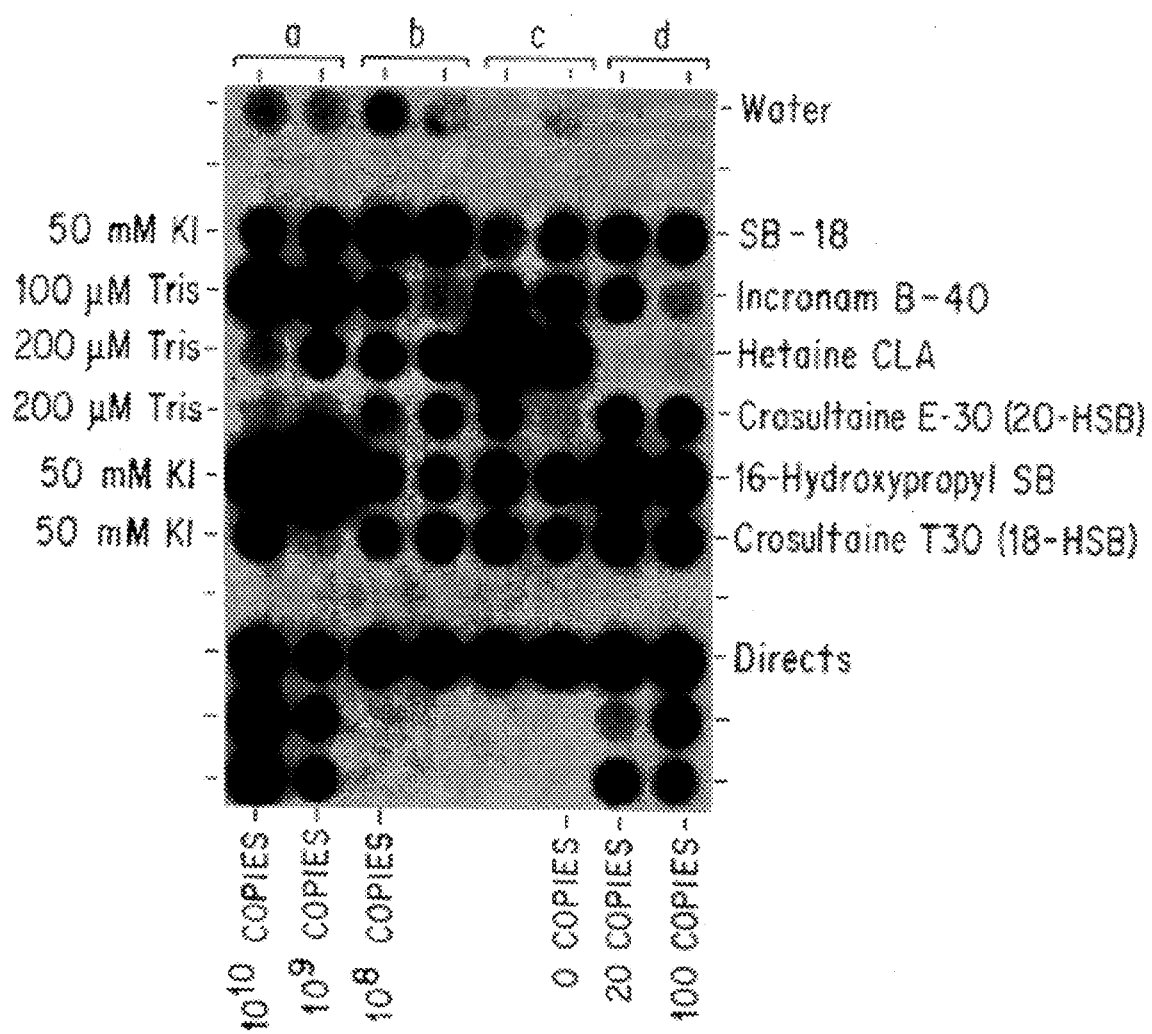
FIG. 10 shows that predictable modifications to assay conditions would permit betaines, which were either compromised or nonfunctional, to function in the in vitro processing of Mycobacterium tuberculosis.

This recipe will make 10 liters of wash buffer. This is enough to process about 400 specimens at 25 ml each. The Examples hereinafter use the buffer defined below, however, as described in Examples 9 and 12, this buffer may be modified to suit the specific SB-18-like detergent being used (Example 9: FIG. 10) as well as the specific processing procedure desired (Example 12: Table 11).

(A) 20× SB-18 Wash Salts

|  | Volume | Conc. | Final Conc. |
|---|---|---|---|
| 1M NaHPO$_4$ pH 8.0 | 40 ml | 200 mM | 10 mM |
| 5M NaCl | 12 ml | 300 mM | 15 mM |
| *[D,L]-Phenylalanine | 1.32 g | 40 mM | 2 mM |

*NOTE:
The use of amino acids, such as phenylalanine, is optional. However, amino acids should only be autoclaved at pH 7.0. Therefore, if amino acids are to be used, the pH of the 20X stock should be reduced to pH 7.0.

$H_2O$ to 200 ml and mix.

Filter sterilize and aliquot into two, 100 ml fractions. Store at room temperature. This solution can be made weekly or monthly and stored.

(B) 100× SB-18 Stock Solution (SB-18 may be conveniently added by first dissolving it in 1:1 isopropanol:water).

A. Transfer 50 ml of the Isopropanol:Water solution (1:1; see below) to a graduated cylinder.

B. Weigh out 3.358 grams of SB-18(N-oetadecyl-N,N-dimethyl-3-ammonio-1-propane sulfonate; Sigma Catalog No. O 8004), place in the cylinder and vortex gently. Let the solution sit for about 20 min and vortex gently about every 5 min.

C. Add more of the Isopropanol:Water solution up to about 75 ml and vortex gently. When the SB-18 has dissolved (about 30 min total), bring the final volume up to 100 ml and mix by inversion.

D. Transfer the solution to a sterile plastic Nalgene bottle.

E. This solution can be stored at room temperature for months.

(C) 1.25M DTT

Dissolve 7.71 grams of dithiothreitol (154.2 g/mole) to 40 ml with water. Aliquot quickly into 2 ml fractions. Store at −20° C.

III. SB-18 Wash Buffer Reagents (A) 1M NaHPO$_4$

| | pH 7.0* | pH 8.0* |
|---|---|---|
| NaH$_2$PO$_4$ (monobasic having 138 g/mole) | 70.38 grams | 11.72 grams |
| Na$_2$HPO$_4$ (dibasic having 142 g/mole) | 69.58 grams | 129.92 grams |

*NOTE:
pH 8.0 is preferred, unless amino acids are to be used in conjunction with SB-18, then pH 7.0 is preferred.

Distilled water to 1 liter.

Filter sterilize into 250 ml aliquots. Store at room temperature.

NOTE: the 1M NaHPO$_4$ buffer may precipitate with time at room temperature. It is best to make up a large volume of the diluted, 20× for extended storage.

(B) 5M NaCl

| NaCl (58.44 g/mole) | 292.2 grams |
|---|---|

H$_2$O to 1 liter. Filter sterilize into 100 ml aliquots. Store at room temperature.

(C) 1:1 Isopropanol:Water

Mix 50 ml of isopropanol with 50 ml of H$_2$O.

IV. 2× Lysis Buffer

| 10× Taq Buffer | 8 ml |
|---|---|
| 0.45% Tween 20 | 180 µl |
| 0.45% NP-40 | 180 µl |
| 200 µg/ml Proteinase K | 160 µl (50 mg/ml Stock) |

H$_2$O to 40 ml.

(A) 10× Taq Buffer

| | Volume | Conc. | Final Conc. |
|---|---|---|---|
| 1M Tris 8.9 | 50 ml | 500 mM | 50 mM |
| 4M KCl | 2.5 ml | 100 mM | 10 mM |

H$_2$O up to 100 ml. Sterile filter and aliquot into 9 ml fractions. Store at −20° C.

(B) Proteinase K (50 mg/ml)

Proteinase K: 500 mg in 10 ml H$_2$O

Aliquot into 175 µl fractions in 0.5 ml microfuge tubes. Store at −20° C.

(C) 1M Tris-HCl pH 8.9

| Tris Base (121.1 g/mole) | 9.472 grams |
|---|---|
| Tris-HCl (157.6 g/mole) | 3.438 grams |

H$_2$O up to 100 ml. Sterile filter. Aliquot: 25 ml each. Store at 4° C.

(D) 4M KCl

| KCl (74.55 g/mole) | 29.82 grams |
|---|---|

H$_2$O up to 100 ml. Sterile filter. Aliquot: 15 ml each. Store at room temperature.

V. Sources used for the exemplified embodiments

| Item | Manufacturer | Catalog No. |
|---|---|---|
| Materials | | |
| 1.5 ml Screwcap tubes | Sarstedt | 72.692/005 |
| 2 ml Screwcap tubes | Sarstedt | 72.694/006 |
| SB-18 Components | | |
| SB-18 | Sigma | O 8004 |
| Isopropyl Alcohol (4 liters) | S/P | 3035-4NY |
| Dithiothreitol | Gibco/BRL | 15508-013 |
| NaH$_2$PO$_4$ (mono) | Sigma | S9638 |
| Na$_2$HPO$_4$ (di) | Sigma | S9763 |
| NaCl | Sigma | S7853 |
| PCR and 2X Lysis Buffer Components | | |
| Tris Base | Sigma | T 6791 |
| Tris-HCl | Sigma | T 6666 |
| KCl | Sigma | P 3911 |
| Tween 20 | Sigma | P 1379 |
| NP-40 | Sigma | N 0896 |
| dU-dNTP's: | Boehringer | |
| dATP | | 1051 440 |
| dCTP | | 1051 458 |
| dGTP | | 1051 466 |
| dUTP | | 1420 470 |
| 50 mM MgCl$_2$ | Gibco/BRL | 18067-017 |
| Uracil DNA Glycosylase | Gibco/BRL | 18054-015 |
| Proteinase K | Gibco/BRL | 25530-031 |
| Taq DNA Polymerase | Perkin Elmer | N808-0105 |

VI. Water

For large volumes, including the SB-18 Wash Solution, Milli-Q purified water was used. For smaller volumes, Gibco/BRL Water was used:

| | 1 liter | 15230-022 |
|---|---|---|
| | 100 ml | 15230-014 |
| Item | Manufacturer | Catalog No. |

"Smaller" volumes include those needed to prepare:
  a. 50X SB-18 Wash Salts, including:
    1M NaHPO$_4$ and 5M NaCl
  b. 100K SB-18 Stock Solution, including:
    Isopropanol:Water (1:1)
  c. 1.25M DTT
  d. 2X Lysis Buffer, including:
    10X Taq Buffer, 1M Tris-HCl pH 8.9, 4M KCl and Proteinase K (50 mg/ml)

VII. Processing Clinical Specimens for Culture

All clinical specimens were sent to our laboratory for routine culture. All clinical specimens were processed by the N-acetyl-L-cysteine/NaOH procedure (Kent, P. T. et al., "Public Health Mycobacteriology" in *A Guide for the Level III Laboratory*, U.S. Department of Health and Human Service, Centers for Disease Control, 1985, pp. 31–46). The bacterial pellets were resuspended in 1 ml of sterile water, and portions removed for planting on BACTEC 12B media (Beeton Dickinson, Towson, Md.), incubation on Lowenstein-Jensen agar (Beeton Dickinson, Towson, Md.) and for smear analysis (Kent, P. T. et al., "Public Health Mycobacteriology" in *A Guide for the Level III Laboratory*, U.S. Department of Health and Human Service, Centers for Disease Control, 1985, pp. 57–70). The remaining sediment was then either frozen at −20° C. or further processed for PCR as described below. All positive BACTEC cultures were identified by either the Gen-Probe culture assay (GenProbe, San Diego, Calif.), or standard biochemical analysis (Kent, P. T. et al., "Public Health Mycobacteriology" in *A Guide for the Level III Laboratory*, U.S. Department of Health and Human Service, Centers for Disease Control, 1985, pp. 71–157)).

VIII. Direct Amplification of Sediment

Table 4: 200 μl of the sediment were directly transferred to a screw cap microfuge tube containing 200 μl of 2× lysis buffer (40 mM Tris-HCl [pH8.3], 100 mM KCl, 0.45% Tween 20, 0.45% NP-40 and 200 μg/ml proteinase K). The specimens were incubated at 60° C. for 60 minutes and then boiled for 15 minutes. A 50 μl aliquot was then removed for amplification by PCR.

IX. Sediment Washes

Sediments were washed with different solutions as described below. Table 5: there were three wash conditions as follows: (i) Water Wash: 25 ml of sterile water were added to the sediment, vortexed and then immediately subjected to centrifugation at 3,500× g for 20 minutes at 4° C. (ii) Dithiothreitol (DTT) Wash: 25 ml of 10 mM $KHPO_4$ (potassium phosphate buffer, a mixture of KHPO4 and $K_2HPO_4$), pH8.0, with 5 mM DTT were added to the sediment, vortexed, incubated at room temperature for 20 minutes and then subjected to centrifugation at 7,410× g for 20 minutes at 4° C. (iii) Tween 20/NP-40 Wash: 25 ml of 10 mM $KHPO_4$ (pH8.0) and 5 mM DTT with 0.05% Tween 20 and 0.05% NP-40 were added to the sediment, vortexed, incubated at room temperature for 20 minutes with shaking and then subjected to centrifugation at 7,410× g for 20 minutes at 4° C. In all cases the tubes were decanted, and 200 μl of sterile water were added to resuspend the pellet. Two hundred μl were then transferred to a screw cap microfuge tube containing 200 μl of 2× lysis buffer. The specimens were incubated at 60° C. for 60 minutes and then boiled for 15 minutes. All tubes were subjected to a one minute spin at 12,000× g prior to removal of a 50 μl aliquot for amplification.

Table 6: 25 ml of 10 mM $NaHPO_4$ (pH7.0), 45 mM NaCl, 5 mM DTT, and either 200 μM or 2 mM N-octadecyl-N,N-dimethyl-3-ammonio-1-propane sulfonate (SB-18 [Sigma Cat. No. O 8004]), were added to the sediment, vortexed, incubated at 37° C. for 60 minutes with shaking (140 rpm) and then subjected to centrifugation at 7,410× g for 20 minutes at 37° C. The tubes were decanted and the pellets resuspended by addition of 200 μl of sterile water. 200 μl were then transferred to a screw cap microfuge tube containing 200 μl of 2× lysis buffer. The specimens were incubated at 60° C. for 60 minutes and then boiled for 30 minutes. All tubes were subjected to a one minute spin at 12,000× g prior to removal a 50 μl aliquot for amplification.

Table 9: 25 ml of 10 mM $NaHPO_4$ (pH7.0), 15 mM NaCl, 5 mM DTT, and 2 mM SB-18, were added to the sediment, vortexed, and incubated at 37° C. for 60 minutes with shaking (140 rpm). The caps were then loosened and the tubes placed in a vacuum oven preheated to 40° C. 600 mm Hg vacuum was then applied for 60 minutes. All tubes were removed from the vacuum oven, the caps tightened and then subjected to centrifugation at 7,410× g for 20 minutes at 37° C. The tubes were decanted and the pellets resuspended by addition of 200 μl of sterile water. Two hundred μl were then transferred to a screw cap microfuge tube containing 200 μl of 2× lysis buffer. The specimens were incubated at 60° C. for 60 minutes and then boiled for 15 minutes. All tubes were subjected to a one minute spin at 12,000× g prior to removal of a 50 μl aliquot for amplification. For the final validation, all samples were amplified in duplicate.

X. PCR System

The PCR system developed is unique and is based on the 16S rRNA gene sequences as published by Rogall, T. et al., *Int. J. Sys. Bacteriol.* 40:323–330 (1990). The primers were designed such that they had the ability to provide optimal amplification of the following groups/species of Mycobacteria: *M. tuberculosis* (TB complex: [MTB]), *M. avium—M. intracellulare* and *M. paratuberculosis* (MAC complex), *M. kansasii* and *M. marinum*. The forward primer was designed against nucleotides 119–144 (according to the nomenclature of Rogall, T. et al., *Int. J. Sys. Bacteriol.* 40:323–330 (1990)) of the second variable (V2) region of the 16S rRNA gene sequence of these Mycobacteria. The sequence of the forward primer (TBv2-119) is: 5'-AAA CTG GGT CTA ATA CCG GAT AGG A-3' [SEQ ID No. :1:]. The reverse primer was designed against nucleotides 431–453 of the third variable (V3) region. The sequence of the reverse primer (TBv3-453) is: 5'-CCA CCT ACC GTC AAT CCG AGA-3' [SEQ ID No. :2:]. The amplification product was approximately 335 base pairs (depending on the species amplified). The genus specific probe was designed against a central portion of the amplification product and is common to all Mycobacteria. Its sequence is: 5'-GCG GGC iCA TCC CAC ACC GC-3' [SEQ ID No. :3:]. The MTB-species specific probe was designed against a distinct portion of the amplification product and is specific to organisms of the TB complex. Its sequence is: 5'-GAC CAC GGG ATG CAT GTC TTG TG-3' [SEQ ID No. 4:].

The amplification protocol utilizes the 9600 Thermal Cycler (Perkin Elmer, Norwalk, Conn.) and incorporates the uracil DNA glycosylase (UDG [Life Technologies, Inc. Gaithersburg, Md.]) sterilization scheme in all reactions (Longo, M. C. et al., *Gene* 93:125–128 (1990)). Each 100 μl reaction contained a final concentration of 200 μM dATP/dCTP/dGTP and 400 μM dUTP (dU-dNTP's: Boehringer, Indianapolis, Ind.), 3.0 mM $MgCl_2$, 25 pmoles each primer with 2.5 units of Taq DNA polymerase (Perkin Elmer, Norwalk, Conn.). The final buffer concentration was 50 mM Tris-HCl pH 8.9, 10 mM KCl and 0.225% each Tween20/NP-40. AmpliWax (Perkin Elmer, Norwalk, Conn.) was also incorporated to optimize efficiency. The reactions were made as follows: 25 μl (containing 2.5 units of Taq, 0.25 units of UDG, dU-dNTP's, and 25 pmoles TBv2-119 in 1× buffer) is placed in a 0.2 ml microfuge tube with an AmpliWax bead, heated to 80° C. for 5 minutes and then cooled. 25 μl (containing the $MgCl_2$, 0.75 unit of UDG and 25 pmoles TBv3-453 in 1× buffer) was then layered over the AmpliWax. The specimen was added in a volume of 50 μl in 1×-PCR Buffer. The cycling profile was: 45° C. for 5 minutes, 94° C. for 7 minutes, then 40 cycles of 94° C. for 20 seconds, 61° C. for 1 second and 72° C. for 10 seconds; followed by a soak file at 72° C. Following thermal cycling the reactions were frozen at −20° C.

A positive amplification control was cloned using the CloneAmp System (Life Technologies, Inc. Gaithersburg, Md.). The TBv2-119 and TBv3-453 primers were modified according to the manufacturer. A colony of *Mycobacterium tuberculosis* ATCC #27294 (ATCC, Rockville, Md.) grown on a slant was placed in 200 μl of PCR lysis buffer and boiled for 30 minutes. A 10 μl aliquot was removed and subjected to amplification as described above except that 200 μM dTTP was used in place of 400 μM dUTP, and the enzyme UDG was omitted from the reaction. The product was cloned into DH5α cells according to the procedure of the manufacturer (Life Technologies, Inc. Gaithersburg, Md.). The plasmid (pOL332) was purified by Applied Biotechnologies, Inc. (Ellicot City, Md.) and sequenced using the Cycle Sequencing Kit (Life Technologies, Inc. Gaithersburg, Md.) to confirm identity. The purified plasmid was quantified by $A_{260}$ readings and then diluted for use as a positive amplification control. All amplification runs included duplicate reactions containing 20 and 100 copies of this plasmid. Additionally, duplicate negative controls were also amplified with each run. This plasmid was also used as a hybridization control on each blot.

XI. Detection

Amplified samples were removed from −20° C. and prepared for blotting by addition of 100 µl of 2×-denaturation solution (1M NaOH/2M NaCl). The reaction tubes were then placed back in the thermal cycler and heated to 60° C. for 15 minutes. All probes were 5'-end labelled using $\gamma$-[$^{32}$P]ATP and polynucleotide kinase (Life Technologies, Inc. Gaithersburg, Md.) according to the manufacturer. The probe was purified using a Chromaspin column according to the manufacturer (Clontech, Palo Alto, Calif.). The samples were dot blotted onto Nytran Plus (Schleicher & Schuell, Keene, N.H.) and probed according to the recommendations of the manufacturer. Briefly, the filter was baked at 80° C. for one hour and then prehybridized for three hours at 42° C. in 10× Denhardt's, 6× SSPE, 1% SDS and 100 µg/ml denatured herring sperm DNA. The filter was then placed in 6× SSPE and 3% SDS with the 5'-$^{32}$P-labelled probe and incubated overnight at either 61° C. (genus probe [SEQ ID No. :3:]) or 65° C. (TB-specific probe [SEQ ID No. :4:]). The filter was washed three times at room temperature in 6× SSPE for 10 minutes each, and then once either at 61° C. for 3 minutes in 1× SSPE for the Genus probe [SEQ ID No. :3:], or at 65° C. for 3 minutes in 1× SSPE for the TB-specific probe [SEQ ID No. :4:]. The filter was then subjected to autoradiography. Filters were then stripped by boiling in 0.1% SDS for 15 minutes and reprobed as necessary.

XII. Optimization of the PCR

The positive control was used as a means to optimize the system. $MgCl_2$ concentration, nucleotide concentration, various amplification profiles and annealing temperatures were examined in order to optimize the system. PCR products were analyzed by agarose gel electrophoresis and ethidium bromide staining, as well as dot blotting and hybridization. The amplification conditions described above could routinely amplify 20 copies to detectable levels. We have noticed the same phenomenon described by Carmody, M. W. et al., *Biotechniques* 15:692–699 (1993). Specifically, the quantity of dU-PCR product visualized on the gel appears to be greater than the quantity estimated by hybridization (when compared to known quantities of the blotted dT-plasmid). We have attempted to use "UDG hot-start," as described by Loewy, Z. G. et al., *J. Clin. Micro.* 32:135–138 (1994), but have not seen the same enhancement of signal.

XIII. Organization of the Dot Blots

As described above, the PCR reaction is denatured and covalently immobilized to a nylon membrane in a two-dimensional array. Creation of the two dimensional array is accomplished using a dot-blot manifold apparatus ("The Convertible," Life Technologies, Inc., Gaithersburg, Md.) which is configured in the standard 96 well format (e.g. 8 wells by 12 wells).

Figure 2:
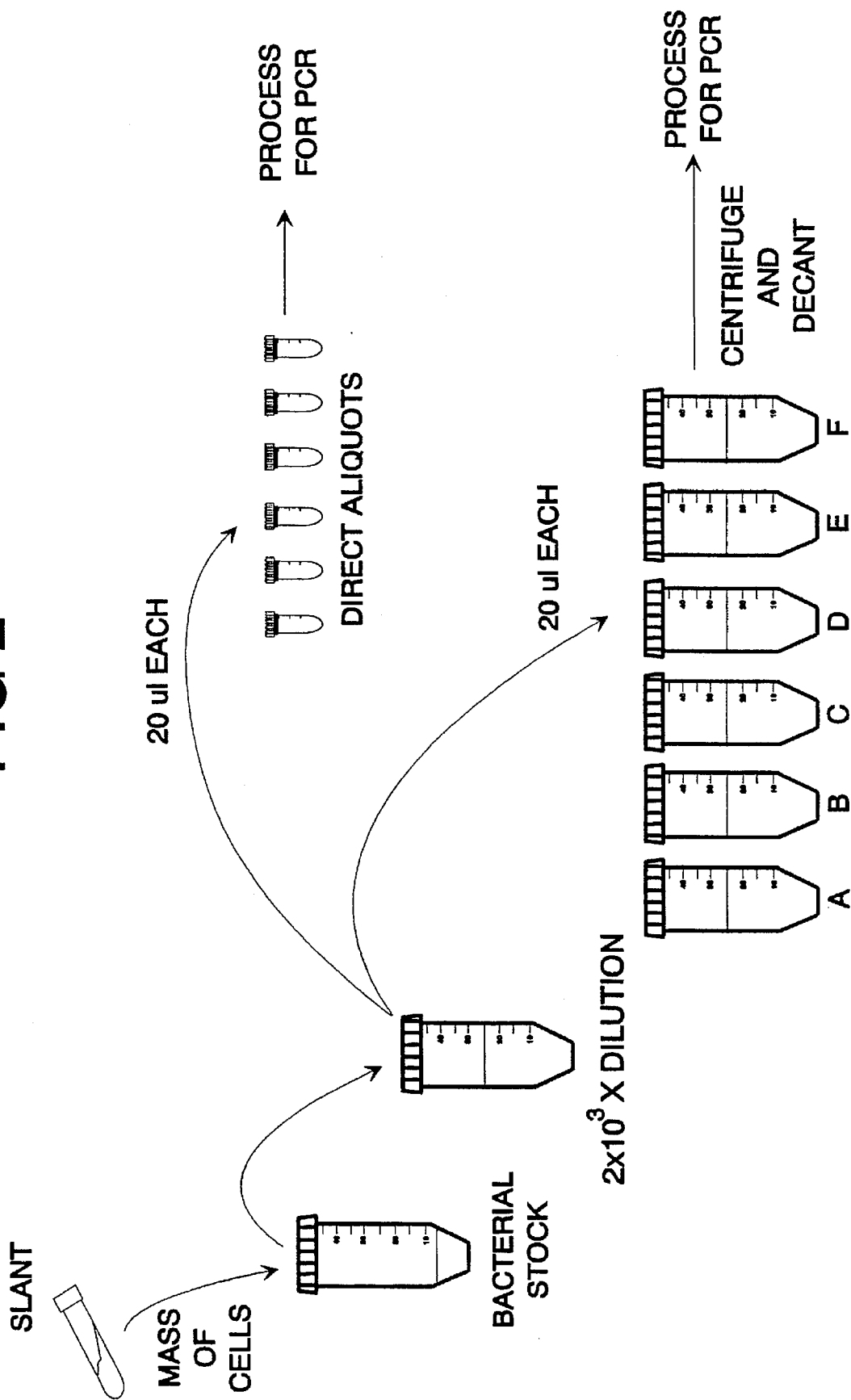
FIG. 2 shows a sketch describing the "processing assay": an in vitro protocol designed to mimic the processing of Mycobacteria in clinical samples.
Figure 2A:
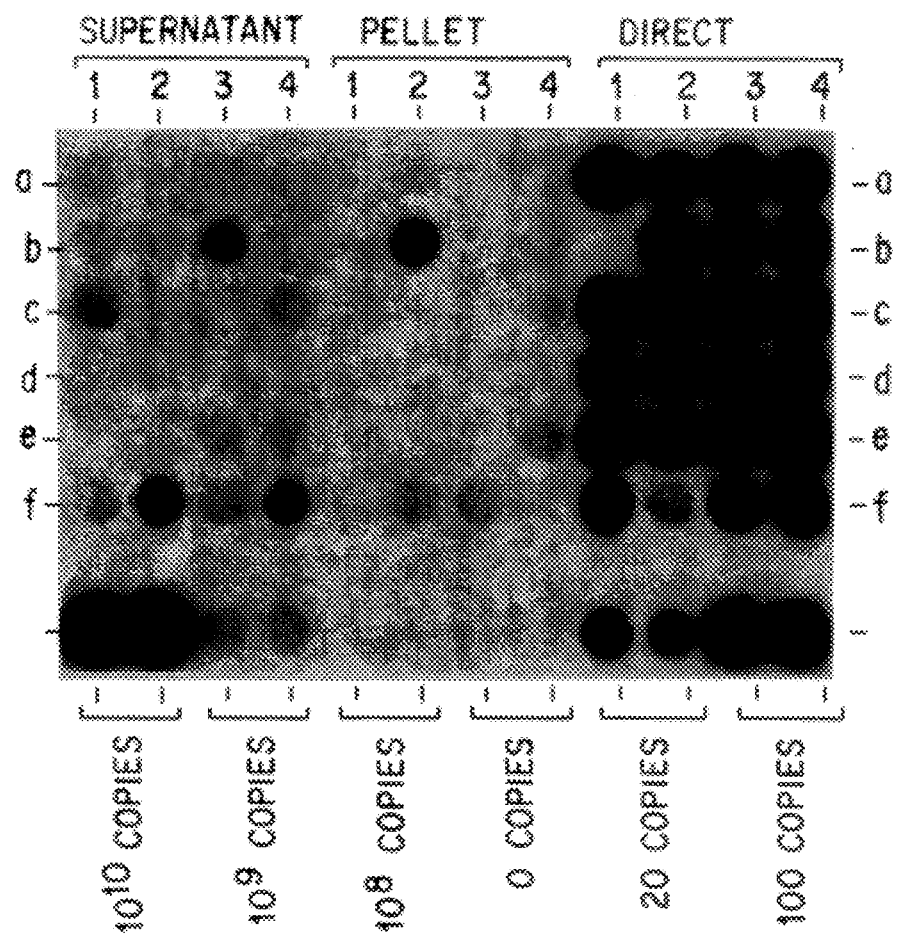
FIG. 2A shows the dot blot results highlighting the efficiency of recovery of Mycobacterium tuberculosis during in vitro processing, as outlined in FIG. 2, when water is the extraction solution.
Figure 13:
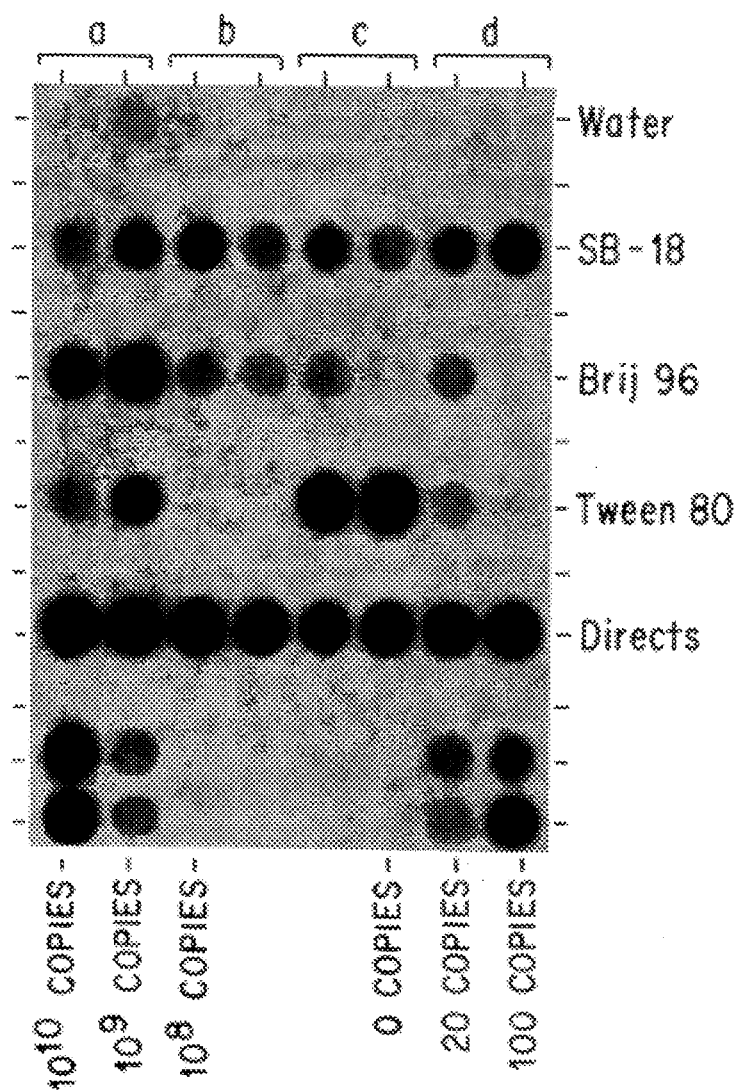
FIG. 13 shows that Brij 96, an approximately-octadecyl nonionic structural homologue of both SB-18 and Tween 80, shows SB-18-like activity.
Figure 14:
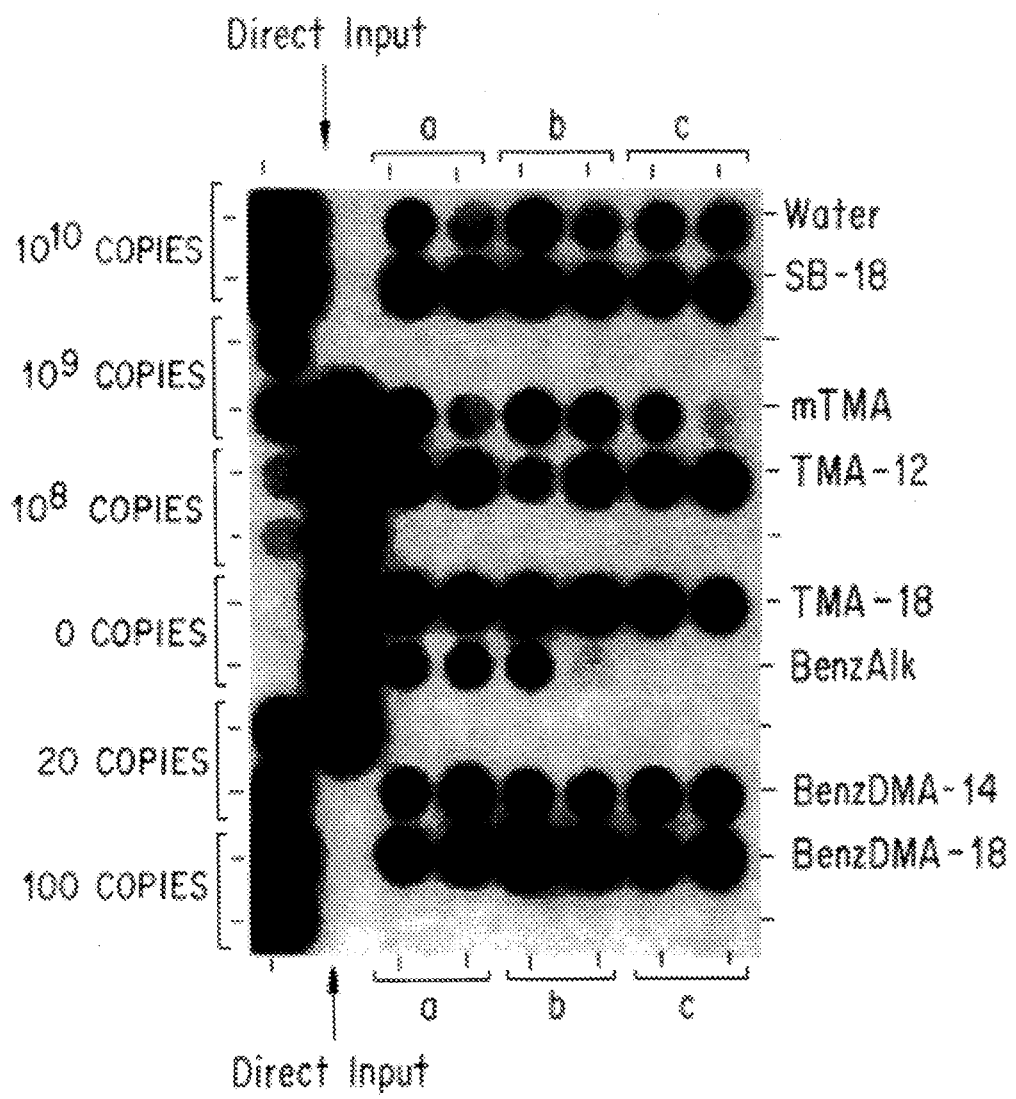
FIG. 14 shows that limited vacuum desgassing of Mycobacterium avium unveils a class of approximately-octadecyl detergents that have some degree of efficacy in improving collection by centrifugation.
Figure 16:
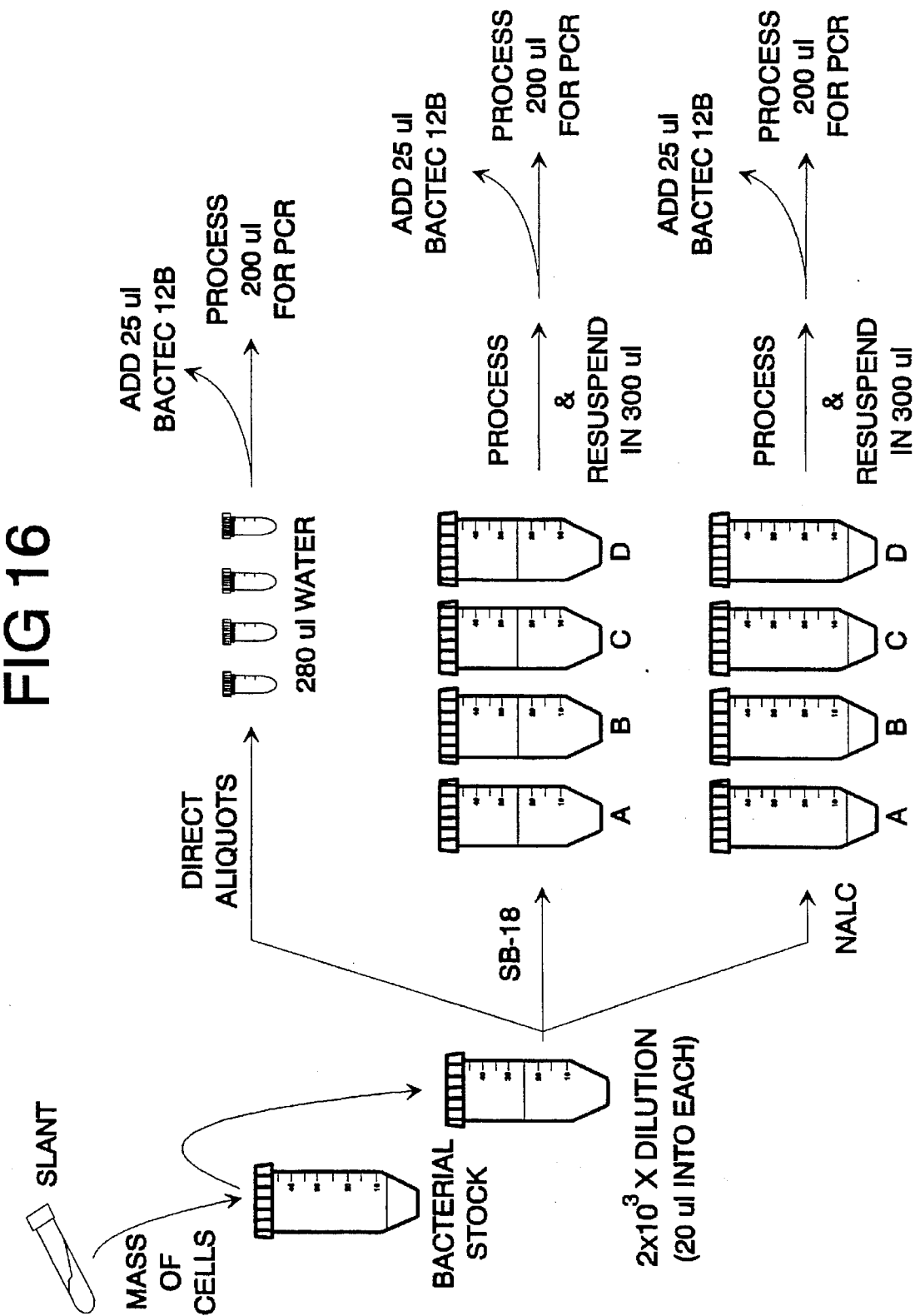
FIG. 16 is a schematic of the experimental protocol designed to compare the SB-18 processing procedure outlined in FIG. 11 with the NALC/NaOH processing procedure.
Figure 16B:
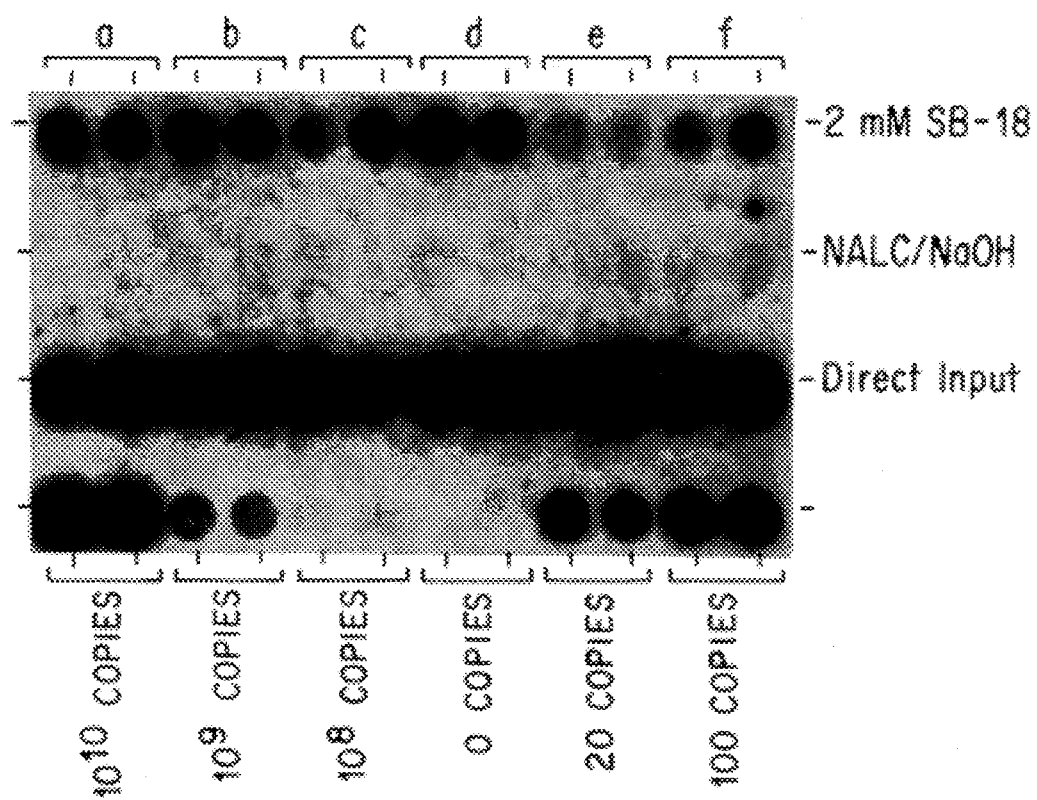
FIG. 16B presents the amplification results when the samples of FIG. 16 are subjected to PCR.

The bottom row in FIGS. 2A and 16B, or, the bottom two rows in FIGS. 3, 4A, 5, 6, 7, 7A, 8, 9, 9A, 9B, 9C, 9D, 10, 11A, 12, and 13, or, column 1 in FIG. 14, present the results from the hybridization and amplification controls. The hybridization controls are those wells labeled "$10^8$, $10^9$, and $10^{10}$" and are spotted in duplicate, on the same row in FIGS. 2A, 16A, and in the same column in FIGS. 3, 4A, 5, 6, 7, 7A, 8, 9, 9A, 9B, 9C, 9D, 10, 11A, 12, 13 and 14. The indicated number of copies of the pOL332 plasmid were used as hybridization controls, and can be compared from blot to blot to assess the exposure.

Similarly, amplification controls consist of duplicate reactions containing "0, 20 and 100" starting copies of the pOL332 plasmid, and can be used within an experiment to assess the efficiency of a given amplification run. The amplification controls are also spotted in duplicate, on the same row in FIGS. 2A, 16A, and in the same column in FIGS. 3, 4A, 5, 6, 7, 7A, 8, 9, 9A, 9B, 9C, 9D, 10, 11A, 12, 13 and 14.

The majority of the experiments utilize multiple replicates which, at the start of the experiment, are presumed to be identical. These replicate samples are labelled "a," "b," "c," "d," etc., and are amplified in, at least duplicates, as indicated by the bracket spanning the label. Every experimental well is shown in at least duplicate as indicated by the bracket. Several experiments simply compare "test conditions" whereas many of the experiments utilize several internal controls: "assay negative control," "assay positive control" and "assay input control." The assay input control (also known as the "Direct Input" or "Direct Aliquot") represents the maximum number of copies aliquoted in a given experiment (e.g., the maximum intensity dot). Comparison of this series with the assay controls or test conditions represents the efficiency of processing. The assay negative control (water) actually represents low efficiency recovery, and the assay positive control (2 mM SB-18) actually represents high efficiency recovery. Comparison of the assay negative, assay positive and assay input controls with the various test conditions permits a conclusion regarding whether modifications improve efficiency of recovery.

XIV. Resolution of Discrepant Results

During the empirical work all samples that were found to be culture positive, but PCR negative, were checked for inhibitors. In these instances, 1000 copies of the positive control were spiked into discrepant samples to check for inhibition of amplification. During the validation, there were several instances in which duplicate amplifications of the same sample gave different results (e.g., one was positive and one was negative). These samples were rerun in duplicate and the results resolved in a manner analogous to that described by Jackson et al., *J. Clin. Microbiol.* 31:3123–3128 (1993): if at least one of the second set of reactions was positive, the sample was deemed positive.

XV. Specificity of the PCR

To examine the specificity of the system with the primers and probes described above, three categories of organisms were checked for their ability to be amplified. The three categories were based on primer complementarity as follows: (i) those that should amplify optimally, (ii) those that may amplify, but with reduced efficiency due to minor mismatches in the primer sequences, and (iii) those that should not amplify due to missing sequences in the primers. The following American Type Culture Collection (ATCC, Rockville, Md.) strains were used to examine the first category: *M. tuberculosis* (ATCC #27294), *M. avium* (ATCC #25291), *M. intracellulare* (ATCC #13950), *M. kansasii* (ATCC #12478), *M. paratuberculosis* (ATCC #19698), *M. marinum* (ATCC #927), *M. szulgai* (ATCC #35799), and *M. gastri* (ATCC #15754). The following ATCC strains were used to examine the second category: *M. xenopi* (ATCC #19250), *M. gordonae* (ATCC #14470), *M. malmoense* (ATCC #29571), *M. terra* (ATCC #15755), and *M. nonchromogenicum* (ATCC #19530). The following ATCC strains were used to examine the third category: *M. fortuitum* (ATCC #6841) represented the fast growing Mycobacterium that should not amplify; unrelated but similar organisms included *Propionibacterium acnes* (ATCC #6919), *Corynebacterium xerosis* (ATCC #373), and *Rhodococcus equi*

(ATCC #6939); other organisms found in high numbers in sputum and bronchial specimens (Murray, P. R. et al., in: *Manual of Clinical Microbiology*, 5th edition, A. Balows et al., eds., Am. Soc. Microbiol., Washington, DC., 1991, pp. 488–490) were represented by *Prevotella melaninogenica* (ATCC #25845) and *Peptostreptococcus magnus* (ATCC #15794). All Mycobacterium were grown on slants prior to use. All other organisms were grown as suggested by the ATCC.

PCR products were analyzed by both agarose gel electrophoresis and ethidium bromide staining, as well as dot blotting and hybridization. All organisms in the first category amplified with equal efficiency. Organisms in the second category fell into two subpopulations based on the complementarity to the primers. *M. gordonae* (1 mismatch in the forward primer and 2 mismatches in the reverse primer) amplified only at high copy number. *M. malmoense* (1 mismatch in the forward primer only) amplified with reduced efficiency. In the second subpopulation *M. terra*, *M. nonchromogenicum* and *M. xenopi* each had numerous primer mismatches and would not amplify. None of the organisms in the third category would amplify, even at high copy number.

Example 2

Direct Boiling of Samples in PCR Buffer Was Not Sufficient

Initially, to better recover Mycobacteria in a form amenable to amplification, boiling the sediment directly as described by Victor, T. et al., *J. Clin. Microbiol.* 30:1514–1517 (1992) was attempted. Seventy-six frozen NALC/NaOH sediments were placed in PCR buffer directly and boiled (Table 4). As described above, for direct amplification of the sediment, 200 µl of the sediment were directly transferred to a screw cap microfuge tube containing 200 µl of 2× lysis buffer (40 mM Tris-HCl [pH8.3], 100 mM KCl, 0.45% Tween 20, 0.45% NP-40 and 200 µg/ml proteinase K). The specimens were incubated at 60° C. for 60 minutes and then boiled for 15 minutes. A 50 µl aliquot were then removed for amplification by PCR.

TABLE 4

Correlation of PCR with Culture When the NALC/NaOH Sediment is Amplified Directly
The results of direct PCR amplification of the NALC/NaOH sediments are shown. Sediment was removed prior to processing for amplification and grown in BACTEC 12B culture bottles as described above. All positive MTB or MAC cultures were identified using the Gen-Probe culture assay (Gen-Probe, San Diego, CA). All others were identified by biochemical analysis (Kent, P.T. et al., "Public Health Mycobacteriology" in A Gidde for the Level III Laboratory, U.S. Department of Health and Human Service, Centers for Disease Control, 1985, pp. 71–157).

| Condition | # Species | Correlation Culture | PCR | % Correlation | Total PCR Positives |
|---|---|---|---|---|---|
| Sediment | 76 MTB Complex | *5 | 1 | 20% | 5 |
|  | MAC Complex | 2 | 0 | 0% |  |
|  | Other | 1 | — | — |  |

*All 5 specimens were from the same patient.

As shown in Table 4, only 1 of 7 culture positive samples was detected by amplification (14.3%) when sediment was used directly. In each case, it was possible to amplify the organism from culture suggesting that the primer pair was functional on these isolates. Each false negative was determined to be the result of inhibition of the PCR assay as a result of the NALC/NaOH extraction.

Example 3

Amplification Inhibition Effects

Our laboratory typically uses 3% NaOH to process clinical specimens (Kent, P. T. et al., "Public Health Mycobacteriology," in *A Guide for the level III Laboratory*, U.S. Department of Health and Human Service, Centers for Disease Control, (1985) pp. 31–46). The concentration of NaOH (e.g., $OH^{\ominus}$) in the 3% stock is 0.75M, at pH 14. The total $Na^{\oplus}$ concentration in the 3% stock (including the 1.45% sodium citrate) is 0.8M. To examine potential PCR inhibition effects due to salt concentration (e.g., $Na^{\oplus}$) or pH (e.g., $OH^{\ominus}$ concentration), the experiments shown in FIG. 1 were performed. Five ml of NALC/NaOH (0.5% NALC, 1.45% sodium citrate and 3% NaOH) were diluted 10 fold with 45 ml of water. The final concentration of the diluted components was 3.1 mM NALC, 5.6 mM sodium citrate and 75 mM NaOH. Various amounts of the diluted NALC/NaOH were then transferred to a 1.5 ml microfuge tube containing 200 µl of 2× lysis buffer. Approximately 1000 copies of the pOL332 positive control plasmid were spiked into each mixture, and all volumes were adjusted to a final volume of 400 µl with water. All tubes were incubated at 95° C. for 15 minutes and then 50 µl of each were amplified in duplicate. The results are shown in FIG. 1 (see Section XIII in Example 1 for an explanation of the format of the data). The percentage indicates the mount of NALC/NaOH in the final amplification reaction tube. For example, 25% would mean that 25 µl of the NALC/NaOH solution (at 3.1 mM NALC, 5.6 mM sodium titrate and 75 mM NaOH) were placed in the amplification reaction at a final volume of 100 µl. Copy controls of 0, 20 and 100 copies were amplified simultaneously. Hybridization controls of $10^8$, $10^9$, and $10^{10}$ copies were blotted as well.

The results shown in FIG. 1 suggest that the diluted NALC/NaOH solution must be further diluted by greater than a factor of 10 in the final amplification mixture for the PCR reaction to function efficiently. Therefore, either the addition of salt or $OH^{\ominus}$ must be less than approximatley 5 mM for the amplification to function efficiently. Since the PCR is more sensitive to changes in pH (relative to the slight increase in salt) it would seem that inhibition is due to alterations in pH. Given the variability of specimen consistency, it is virtually impossible to remove all NALC/NaOH by simple decanting. These data confirm that further processing of the sediment is necessary when the NALC/NaOH is used as a first step to process the specimen. This conclusion is further substantiated by the data of Noordhoek, G. T. et al., *J. Clin. Micro.* 32:277–284 (1994): the two laboratories that had the worst performances in this study did not further purify the NALC/NaOH sediment.

Example 4

Effect of Adding Secondary Wash Steps with Water and DTT

I. Water Wash

To decrease the cost per sample and increase the efficiency when it is desired to process large numbers of samples, the applicability of a secondary wash step (2°-Wash) to further remove inhibitors, such as NALC/NaOH, was examined (Table 5).

Amplification conditions were as described above in Materials and Methods.

Initially, a simple water wash to rinse the button (the sediment) was used. Twenty-five ml of sterile water were added to the sediment, vortexed and then immediately subjected to centrifugation at 3,500× g for 20 minutes at 4° C. The tubes were decanted, and 200 µl of sterile water were added to resuspend the pellet. Two hundred µl were then transferred to a screw cap microfuge tube containing 200 µl of 2× lysis buffer. The specimens were incubated at 60° C. for 60 minutes and then boiled for 15 minutes. All tubes were subjected to a one minute spin at 12,000× g prior to removal of a 50 µl aliquot for amplification.

Upon incorporating this water wash step, correlations improved to 33% (Table 5:7 PCR positives out of 21 culture positives [n=407]). As above, it was possible to amplify the organism from the culture; however, contrary to the above, inhibition did not appear to be the primary problem as several specimens were negative upon repeated amplification. Furthermore, isolation of *M. avium* also appeared to be a significant problem. In general, while correlations were low, these results were consistent with the majority of the studies discussed in Table 1. Of the 33 methodologies reporting correlations of less than 100% in Table 1, 21 include some form of buffer exchange step. The remaining twelve did not include a buffer exchange step and nine refer to inhibitors as a problem.

II. DTT Wash

Shawar, R. M. et al., *J. Clin. Micro.* 31:61–65 (1993) and Hermans, P. W. M. et al., *J. Clin. Micro.* 28:1204–1213 (1990) have shown that sputum suppresses the PCR. Presumably the acidic mucopolysaccharides are inhibitory (Ochert, A. S. et al., *PCR Methods and Applications* 3:365–368 (1994)). Alternatively, the "viscous" nature of the sputum may also be affecting the efficiency of the amplification. Buck, G. E. et al., *J. Clin. Micro.* 30:1331–1334 (1992) refer specifically to the viscosity as being a contributing factor to false negatives. Some extreme examples of this condition, a condition that is directly proportional to disease state, have also been observed in the preliminary studies. Therefore, in an attempt to overcome this problem, the composition of the 2°-Wash was changed such that it would further liquify sputum.

To better liquify the sputum, 10 mM KHPO$_4$, pH8.0, and 5 mM dithiothreitol (DTT) were included in the wash step, similar to the protocol of Hirsch, S. R. et al., *J. Lab. Clin. Med.* 74:346–353 (1969) and the RCF was increased during the centrifugation step as recommended by Ratnam, S. et al., *J. Clin. Microbiol.* 23:582–585 (1986) and Rickman, T. W. et al., *J. Clin. Microbiol.* 11:618–620 (1980). Twenty-five ml of 10 mM KHPO$_4$ (pH8.0), with 5 mM DTT were added to the sediment, vortexed, incubated at room temperature for 20 minutes and then subjected to centrifugation at 7,410× g for 20 minutes at 4° C. In all cases, the tubes were decanted, and 200 µl of sterile water added to resuspend the pellet. Two hundred µl were then transferred to a screw cap microfuge tube containing 200 µl of 2× lysis buffer. The specimens were incubated at 60° C. for 60 minutes and then boiled for 15 minutes. All tubes were subjected to a one minute spin at 12,000× g prior to removal of a 50 µl aliquot for amplification.

As shown in Table 5, 175 random specimens were washed using these conditions. The consistency of the samples appeared to improve significantly and the correlation again improved, this time to 60% (6 PCR positives out of 10 culture positives). As before, with one exception (see Footnote c in Table 5) it was possible to amplify the organism from the culture (or off the slant), and only one false negative could be attributed to inhibition. However, "statistical drop-outs" were again observed among replicates of the same sample.

While washing the sediment appeared to alleviate inhibition, to some 10 degree, clearly false negatives were not entirely due to inhibition: under these conditions, sample bias appeared to dominate the false negative problem.

TABLE 5

Correlation of PCR with Culture Using Various Wash Conditions
The results of various assay conditions, and their correlation of PCR with culture, by washing the sediments are shown. All specimens were first processed by the NALC/NaOH procedure (Kent, P.T. et al., "Public Health Mycobacteriology" in A Guide for the Level III Laboratory, U.S. Department of Health and Human Service, Centers for Disease Control, 1985, pp. 31–46). Sediment was removed prior to washing and grown in BACTEC 12B culture bottles. All positive MTB, MAC or *M. kansasii* cultures were identified using the Gen-Probe culture assay (Gen-Probe, San Diego, CA). All others were identified by biochemical analysis (Kent, P.T. et al., "Public Health Mycobacteriology" in A Guide for the Level III Laboratory, U.S. Department of Health and Human Service, Centers for Disease Control, 1985, pp. 71–157). The Condition represents further processing of the sediment by washing. Three different secondary wash conditions were used: (i) water, (ii) 10 mM KHPO$_4$ (pH8.0) and 5 mM DTT, and (iii) 10 mM KHPO$_4$ (pH8.0) and 5 mM DTT containing 0.05% Tween 20 and 0.05% NP-40, as described in Materials and Methods.

| Condition | # | Species | Correlation Culture | Correlation PCR | % Correlation | Total PCR Positives |
|---|---|---|---|---|---|---|
| 2°-Water Wash | 407 | MTB Complex | 1 | 1 | 100% | 32 |
|  |  | MAC Complex | 20 | 6 | [a]30% |  |
|  |  | Other | 3 | — | — |  |
| 2°-DTT Wash | 175 | MTB Complex | 4 | 3 | [b]75% | 10 |
|  |  | MAC Complex | [c]5 | 2 | [d]50% |  |
|  |  | *M. kansasii* | [e]2 | 1 | 50% |  |
|  |  | Other | 4 | — | — |  |
| 2°-Tween20/NP-40 Wash | 359 | MTB Complex | 5 | 4 | [f]80% | 20 |
|  |  | MAC Complex | 21 | 9 | [g]43% |  |

TABLE 5-continued

Correlation of PCR with Culture Using
Various Wash Conditions

The results of various assay conditions, and their correlation of PCR with culture, by washing the sediments are shown. All specimens were first processed by the NALC/NaOH procedure (Kent, P.T. et al., "Public Health Mycobacteriology" in A Guide for the Level III Laboratory, U.S. Department of Health and Human Service, Centers for Disease Control, 1985, pp. 31–46). Sediment was removed prior to washing and grown in BACTEC 12B culture bottles. All positive MTB, MAC or *M. kansasii* cultures were identified using the Gen-Probe culture assay (Gen-Probe, San Diego, CA). All others were identified by biochemical analysis (Kent, P.T. et al., "Public Health Mycobacteriology" in A Guide for the Level III Laboratory, U.S. Department of Health and Human Service, Centers for Disease Control, 1985, pp. 71–157). The Condition represents further processing of the sediment by washing. Three different secondary wash conditions were used: (i) water, (ii) 10 mM KHPO$_4$ (pH8.0) and 5 mM DTT, and (iii) 10 mM KHPO$_4$ (pH8.0) and 5 mM DTT containing 0.05% Tween 20 and 0.05% NP-40, as described in Materials and Methods.

| Condition | # | Species | Correlation Culture | PCR | % Correlation | Total PCR Positives |
|---|---|---|---|---|---|---|
| Accumulated 2°- Wash Results | 941 | Other | 3 | — | — | 62 |
| | | MTB Complex | 10 | 8 | 80% | |
| | | MAC Complex | 46 | 17 | 37% | |
| | | *M. kansasii* | 2 | 1 | 50% | |
| | | Other | 10 | — | — | |

*False negatives were due to both low copy number and inhibition.
*b*The 1 false negative was due to inhibition.
*c*Repeated attempts to amplify one of these specimens out of culture were unsuccessful.
*d*The 2 false negatives were due to low copy number.
*One of these was BACTEC negative and produced only one colony on the slant (e.g., low copy number).
*f*The 1 false negative was due to inhibition.
*g*The 12 false negatives were due to low copy number.

Example 5

Partitioning of the Mycobacteria During Centrifugation

During the experimentation described above, the question of whether or not Mycobacteria could be being lost during the wash step was investigated. FIG. 2 describes the experimental design of an assay used to mimic processing (hereafter referred to as the "processing assay"). *Mycobacterium tuberculosis* grown on slants were used as a source in these experiments.

A small mass of cells was first transferred to 5 ml of 10 mM KHPO$_4$ (pH8.0) and vortexed to generate a bacterial stock. The stock was then diluted 2×10$^3$ fold and 20 µl transferred into 15 ml of 2°-Wash buffer. This transfer was repeated five more times for a total of six samples. At the same time, six 20 µl aliquots were removed directly from the 2×10$^3$ fold dilution into six aliquots containing 380 µl of lysis buffer for amplification directly. These latter aliquots (hereafter referred to as "directs," "direct input" or "direct aliquot" controls) serve as controls for total target input in a given experiment. The tubes containing the wash buffer were then subjected to centrifugation (7,410× g at 4° C. for 20 min). Following centrifugation, aliquots of the supernatant (200 µl) were placed in 200 µl of 2× lysis buffer. The supernatant was then poured off, the pellet resuspended in 200 µl of water and 200 µl of the resuspended pellet was mixed with 200 µl of 2× lysis buffer. Fifty µl aliquots of each series were subjected to PCR, in quadruplicate.

Input in this experiment was estimated to be approximately 10,000 copies. Therefore, the direct aliquot should represent amplification of approximately 1,000 copies. If the organisms were lysed, or homogeneously distributed in the supernatant, amplification reactions would contain approximately 20 copies. Amplification of the pellet presumably represents the efficiency of recovery by centrifugation. The results are shown in FIG. 2A (see Section XIII in Example 1 for an explanation of the format of the data).

In FIG. 2A, the PCR products were denatured, blotted, probed and subjected to autoradiography as described above in Materials and Methods. The six different "specimens" are represented as a, b, c, d, e and f, and should be identical. The quadruplicate amplifications of the supernatant fraction and pellet for a given specimen are shown on the same line (1, 2, 3 and 4). The quadruplicate amplifications of the direct input aliquots, corresponding to a given specimen, are shown in the same line. Copy controls of 0, 20 and 100 copies were amplified simultaneously. Hybridization controls of 10$^8$, 10$^9$ and 10$^{10}$ copies were blotted as well. The results (FIG. 2A) show that some pellets are negative, some supernatant fractions are positive, and both fractions show sample bias.

One possible explanation for the above result was that the Mycobacteria are lysing. Osmotically lysing these organisms is not trivial. Thacore, H. et al., *Rev. Infect. Dis.* 3:960–972 (1981) and Sato, H. et al., *Can. J. Microbiol.* 12:255–261 (1966) report that extreme measures are required to generate spheroplasts and "ghosts" of MTB. Alternatively, Thacore, H. et al., *Proc. Soc. Exptl. Biol. Med.* 114:43–47 (1963) show that cells grown in the presence of EDTA stick to the walls of the flask. This, however, is easily overcome by addition of lysozyme to the media. The correct explanation is presumably due to partitioning of the Mycobacterium resulting from buoyancy. The observations of FIG. 2A are not surprising in light of the results of Klein, G. C. et al., *Am. J. Clin. Pathol.* 22:581–585 (1952): both the sediment and the supernatant were culture positive in 88.8% and 82.4% of all specimens centrifuged at 2,000 rpm and 3,000 rpm, respectively; and the sediment was culture negative while the supernatant was culture positive in 2.7% and 2.2% of all specimens centrifuged at 2,000 rpm and 3,000 rpm, respectively.

Example 6

Influence of the Cell Wall on Recovery of the Mycobacteria

Dubos, R. J. et al., *J. Exp. Med.* 83:409–423 (1946) concluded that submerged growth in the presence of Tween 80 (CAS®No. 9005-65-6) was due to "wetting" of the cell surface. If surface tension is responsible for the aberrant results, and surface tension can be overcome by the addition of nonionic detergents, then it seems logical that these reagents should improve correlation to culture. However, as shown below, this was not the case.

Young, D. B. et al., *Res. Microbiol.* 142:55–65 (1991) have demonstrated that the peripherally associated lipoproteins can be stripped by incubation in the nonionic detergent Triton X-100 (CAS®No. 9002-93-1). The nonionic detergents Tween 20 (CAS®No. 9005-64-5) and NP-40 (CAS®No. 127087-87-0), which are commonly used as additives in the PCR, were, therefore, included in the secondary wash step in an attempt to affect the surface tension (or stickiness) of mycobacterial cells (Table 5).

NALC/NaOH processed sediments were washed with a Tween 20/NP-40 wash: 25 ml of 10 mM $KHPO_4$ (pH8.0) and 5 mM DTT with 0.05% Tween 20 and 0.05% NP-40 were added to the sediment, vortexed, incubated at room temperature for 20 minutes with shaking and then subjected to centrifugation at 7,410× g for 20 minutes at 4° C. In all cases the tubes were decanted, and 200 µl of sterile water were added to resuspend the pellet. Two hundred µl were then transferred to a screw cap microfuge tube containing 200 µl of 2× lysis buffer. The specimens were incubated at 60° C. for 60 minutes and then boiled for 15 minutes. All tubes were subjected to a one minute spin at 12,000 × g prior to removal of a 50 µl aliquot for amplification.

As shown in Table 5, of 359 specimens amplified, 26 were culture positive for either MTB complex (5 specimens) or MAC complex (21 specimens). MTB was amplified out of only 4 specimens (80%) and MAC was amplified out of 9 specimens (43%). Again, a lack of inhibition was shown in all but one of the false negatives; the organisms could be amplified out of culture, and statistical dropouts were observed to dominate false negatives.

Thus, accumulating the wash results shown in Table 5, MTB correlations of 80% with culture were achieved (even though there was a small relative number of MTB isolates [n=10]). The results concerning the ability to isolate MAC complex organisms by this protocol were strikingly different: correlation with culture was 37% (n=46). This dichotomy is also reflected in the art shown in Table 1.

Figure 3:
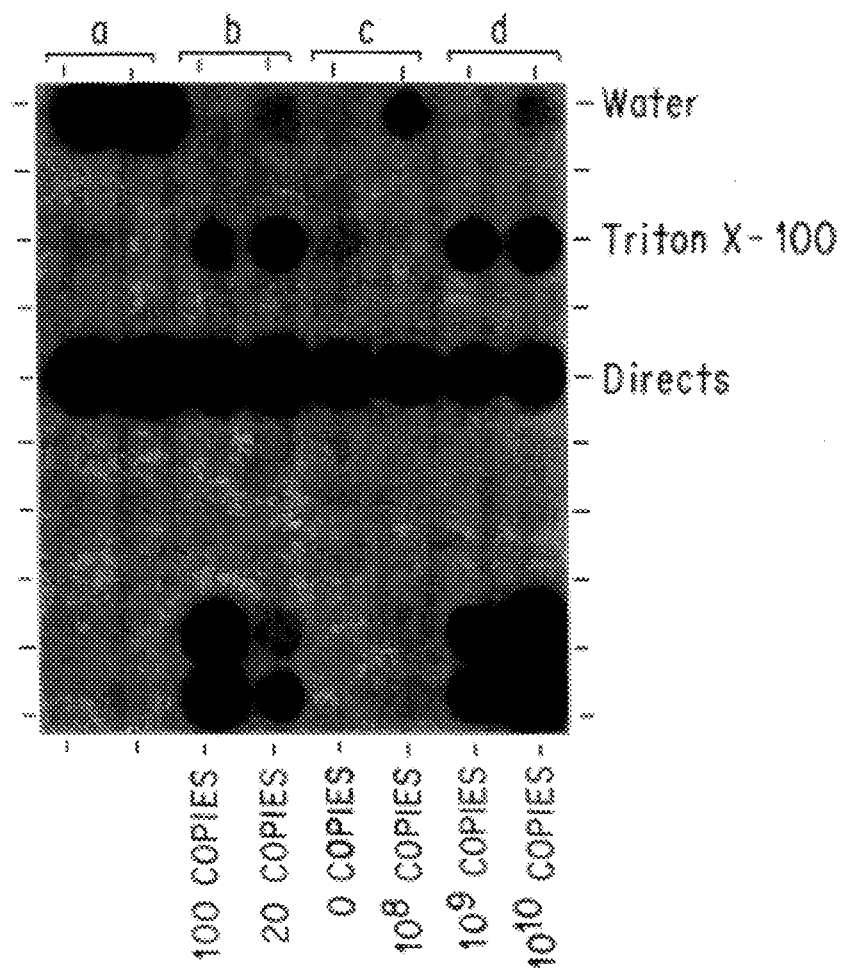
FIG. 3 shows the effect of addition of 0.1% Triton X-100 to the extraction solution.

To further support this finding, the processing experiment outlined in FIG. 2 was repeated using *M. tuberculosis* in the presence of 0.1% Triton X-100 (CAS®No. 9002-93-1). FIG. 3 shows the result of this experiment. The processing assay described in FIG. 2 was used in this experiment with the exception that the 2°-Wash buffer contained either water or 10 mM Tris-HCl pH 8.0 supplemented with 0.1% Triton X-100 and 5 mM DTT. In addition, only four aliquots were taken and the tubes were incubated at room temperature for 20 minutes with shaking. Duplicate amplifications of four aliquots are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$ and $10^{10}$ copies were blotted as well.

The results shown in FIG. 3 are in agreement with the above data (Table 5): nonionic detergents would not be expected to improve the efficiency of recovery. In fact, large variations, which can be attributed to clumping, were observed. Note the overexposure of this blot (FIG. 3) relative to other blots. This was necessary to observe these results.

A conclusion consistent with these results is that while additional steps must be taken to further relieve the samples of inhibitors, simply "wetting" the cells does not appear to completely resolve the problem. This is further substantiated by the fact that of the five studies shown in Table 1 that used nonionic detergents to wash sediments prior to amplification (Clarridge, J. E. et al., *J. Clin. Micro.* 31:2049–2056 (1993); Irula, J. V. et al., *J. Clin. Micro.* 31:1811–1814 (1993); Kolk, A. H. J. et al., *J. Clin. Micro.* 30:2567–2575 (1992); Shawar, R. M. et al., *J. Clin. Micro.* 31:61–65 (1993); and Sritharan, V. et al., *Mol. Cell. Probes* 5:385–395 (1991)), none achieve 100% correlation to culture. Robinson, L. et al., *J. Lab. Clin. Med.* 27:84–91 (1941) reported years earlier that agents that alleviated surface tension were impotent in enhancing recovery by centrifugation. If, contrary to Dubos' suggestion (Dubos, R. J. *Exp. Biol. Med.* 58:361–362 (1945); Dubos, R. J. et al., *J. Exp. Med.* 83:409–423 (1946)), Tween 80, oleic acid and BSA affected pellicle growth through an in vivo process, as opposed to compensating for surface tension, then clumps would still be expected to be present in the experiment described here (FIG. 3). Based on the results presented here (Table 5) and in the art (Table 1), no advantage is obtained by the inclusion of these nonionic detergents in the wash buffer.

Example 7

Aggregation and Dispersion of the Mycobacteria

While peripherally associated lipid components were undoubtedly being removed by Triton X-100 in the above experiment (FIG. 3), the cells were still aggregated. As a next step, attempts to improve recovery by dispersion were initiated. FIG. 4 details the experimental design of an assay (hereafter referred to as the "aggregation assay") that was developed to assess the ability of different detergents to disperse clumps of MTB. This assay relies on the fact that aggregation exacerbates sample bias: multiple aliquots will produce similar amplification results only if the clumps have been dispersed. More specifically, each aliquot from the same sample will have equal numbers of organisms only if they are homogeneously distributed throughout the solution. This situation is expected to be most pronounced at low copy number. In theory, dispersion of clumps should improve the probability of accurate diagnosis, even at relatively low copy number, because all aliquots will have a higher probability of harboring target.

Implementation of the protocol designed to assess the ability of detergents to disperse Mycobacteria (FIG. 4) utilized *Mycobacterium tuberculosis* grown on slants as the source in these experiments. A small mass of cells was first transferred to 5 ml of 10 mM $KHPO_4$ (pH 8.0) and vortexed to generate a bacterial stock. The stock was then diluted $2 \times 10^3$ fold by transfer of 10 µl into 20 ml of 2°-Wash Buffer. The various aspects of the 2°-Wash Buffer were changed, including the detergent and its concentration, the buffer used as well as the ionic strength and pH of the buffer, the time of incubation, the temperature of incubation, and plus or minus agitation. Following the incubation, 20 µl were transferred into 25 ml of a normalizing buffer (10 mM KHPO$_4$ pH 8.0, 0.05% Tween 20, 0.05% NP-40 and 5 mM DTT). This transfer was repeated three more times for a total of four samples. At the same time, four 20 µl aliquots were removed directly from the 2×10$^3$ fold dilution into four different microfuge tubes containing 380 µl of lysis buffer for amplification directly. These latter aliquots (hereafter referred to as "directs," "direct input" or "direct aliquot" controls) serve as controls for total input in a given experiment. The tubes containing the normalizing buffer were subjected to centrifugation at 7,410× g for 20 minutes at 4° C. In all cases the tubes were decanted, and 200 µl of sterile water added to resuspend the pellet. Two hundred µl aliquots were immediately removed and placed in 200 µl of 2× lysis buffer. All tubes were prepared for PCR as described in Materials and Methods. Fifty µl aliquots of each series were subjected to PCR, in duplicate, to compensate for the dilution and normalize input.

Figure 4A:
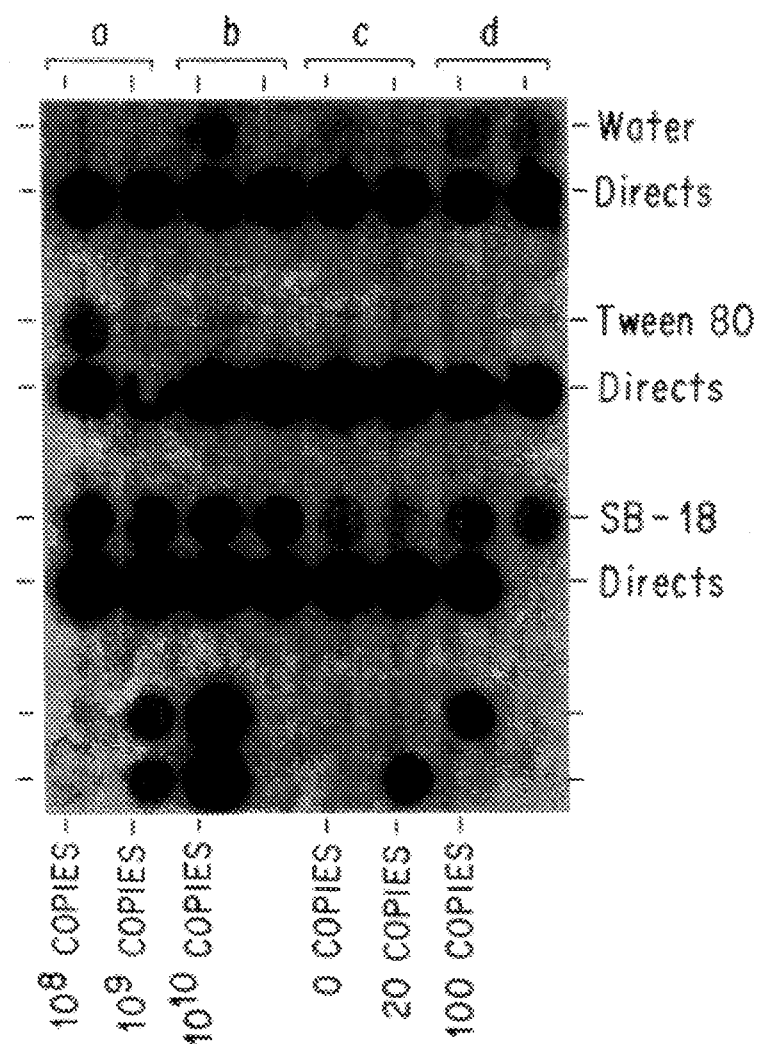
FIG. 4A shows the dot blot results of attempts to disperse the Mycobacteria. Data from three representative conditions are shown: water, 0.1% Tween 80 and 2 mM SB-18.

For the data shown in FIG. 4A, the PCR products from each assay were denatured, blotted, probed and subjected to autoradiography as described in Materials and Methods (above). The duplicate amplifications of the four different "specimens" for each condition are represented as a, b, c and d and should be identical. The duplicate amplifications of the direct aliquots from each condition are shown on the appropriately labeled line. Copy controls of 0, 20 and 100 copies were amplified simultaneously. Hybridization controls of 10$^8$, 10$^9$ and 10$^{10}$ copies were blotted as well.

FIG. 4A shows a representative result comparing no detergent (e.g., water), 0.1% Tween 80 in 10 mM Tris-HCl pH 8.0, and 2 mM N-octadecyl-N,N-dimethyl-3-ammonio-1-propane sulfonate (SB-18:CAS®No. 13177-41-8) in 10 mM NaHPO$_4$, 15 mM NaCl. All tubes were incubated at 37° C. for 60 minutes with agitation (140 rpm) prior to aliquoting into normalizing buffer. Of those compounds tested, the only detergent to consistently show significant activity in this assay was the sulfopropylbetaine, SB-18. SB-16 (CAS®No. 2281-11-0) showed some dispersion activity: SB-16 was seen to function, albeit inconsistently. Other detergents, and other detergents in the sulfopropylbetatine series, but with a length of less than 16 alkyl carbons (SB-10 (CAS®No. 15163-36-7), SB-12 (CAS®No. 14933-08-5), and SB-14 (CAS®No. 14933-09-6), were impotent in disaggregating MTB clumps. Dispersion of MTB clumps improves the probability that, even at low copy number, all aliquots will have target.

Attempts to confirm the dispersion theory by acid-fast smear were unsuccessful. Apparently, inclusion of any detergent significantly compromises the ability to heat fix cells to the slide.

Example 8

SB-18 Facilitates the Isolation of Mycobacteria by Centrifugation

The above results were extended by using the processing assay described in FIG. 2. There was a direct correlation between the efficacy of the detergent in disruption of clumps, and recovery in the processing assay. FIG. 5 shows a representative result using both *M. avium* and *M. tuberculosis* in the presence and absence of 2 mM SB-18. The schematic described in FIG. 2 was followed for the experiment shown in FIG. 5. The 2°-Wash Buffer contained 10 mM $NaHPO_4$ pH 7.0, 15 mM NaCl, 2 mM SB-18, 2 mM Phenylalanine and 5 mM DTT, and was compared with water. In addition, the tubes were incubated at 37° C. for 60 minutes with shaking (140 rpm). Duplicate amplifications of four aliquots are represented as a, b, c, and d, and should be identical. The duplicate amplifications of the direct aliquots, corresponding to a given species, are shown on the appropriately labeled line. Copy controls of 0, 20 and 100 copies were amplified simultaneously. Hybridization controls of $10^8$, $10^9$, and $10^{10}$ copies were blotted as well.

This blot was chosen because the characteristic dumping of *M. tuberculosis* and the more diffuse distribution characteristic of *M. avium* is clearly discernible. In addition, with regard to the clumping seen in this blot, it has been observed that phenylalanine, while improving recovery of MAC organisms, compromises the efficacy of SB-18 dispersion activity. Regardless, significant improvements in recovery were routinely observed with both organisms.

Table 6 describes the results of processing NALC-NaOH sediments with a wash buffer supplemented with 2 mM SB-18.

TABLE 6

Correlation of PCR with Culture
when SB-18 is Included in the Wash Buffer
The results of inclusion of SB-18 in the 2°-Wash Buffer are presented as described in Material and Methods. The composition of the buffer used to wash the sediment in this series of samples was 10 mM $NaHPO_4$ (pH 7.0), 45 mM NaCl, 5 mM DTT, and either 200 µM or 2 mM SB-18. Sediment was removed prior to washing and grown in BACTEC 12B culture bottles. All positive MTB, MAC or *M. kansasii* culture were identified using the Gen-Probe culture assay (Gen-Probe, San Diego, CA). All other organisms were identified by biochemical analysis (Kent, P.T. et al., "Public Health Mycobacteriology" in A Guide for the Level III Laboratory, U.S. Department of Health and Human Service, Centers for Disease Control, 1985, pp. 71–157). The sediments were washed for 60 minutes at 37° C. with shaking (140 rpm). Following sediment wash, the samples were subjected to centrifugation and further processed for PCR as described in Materials and Methods.

| Condition | # | Species | Correlation Culture | Correlation PCR | % Correlation | Total PCR Positives |
|---|---|---|---|---|---|---|
| 2° SB-18 Wash | 754 | MTB Complex | 5 | 5 | 100% | 143 |
| | | MAC Complex | 23 | 15 | 65% | |

TABLE 6-continued

Correlation of PCR with Culture
when SB-18 is Included in the Wash Buffer
The results of inclusion of SB-18 in the 2°-Wash Buffer are
presented as described in Material and Methods. The
composition of the buffer used to wash the sediment in this
series of samples was 10 mM NaHPO$_4$ (pH 7.0), 45 mM NaCl,
5 mM DTT, and either 200 µM or 2 mM SB-18. Sediment
was removed prior to washing and grown in BACTEC 12B
culture bottles. All positive MTB, MAC or *M. kansasii* culture
were identified using the Gen-Probe culture assay (Gen-Probe,
San Diego, CA). All other organisms were identified by
biochemical analysis (Kent, P.T. et al., "Public Health
Mycobacteriology" in A Guide for the Level III Laboratory,
U.S. Department of Health and Human Service, Centers for
Disease Control, 1985, pp. 71–157). The sediments were
washed for 60 minutes at 37° C. with shaking (140 rpm).
Following sediment wash, the samples were subjected to
centrifugation and further processed for PCR as described in
Materials and Methods.

| Condition | # Species | Correlation Culture | PCR | % Correlation | Total PCR Positives |
|---|---|---|---|---|---|
| | *M. kansasii* | 1 | 1 | 100% | |
| | Other | 16 | 3 | — | |

Of 754 samples washed with buffer containing SB-18, 23 samples were culture positive for *M. avium*, 5 were culture positive for *M. tuberculosis*, and was culture positive for *M. kansasii*. Correlation to culture was as follows: *M. avium*, 65%; *M. tuberculosis*, 100%; and *M. kansasii*, 100%. While the actual number of culture positive specimens was low, clearly there was a discernable improvement in overall correlation. Of the eight *M. avium* samples missed on a preliminary screen, resolution of discrepants showed that five were due to low copy numbers (multiple amplifications were seen to be both positive and negative), one was confirmed to be the result of the presence of inhibitors, and two were "unexplained" (multiple amplification were all negative, but the presence of inhibitors was excluded). In addition, a correlation with culture positive *M. gordonae* samples began to appear. The fact that positive *M. gordonae* amplifications were observed in vitro only when high copy numbers were introduced was construed as further evidence that the overall efficiency of recovery had improved significantly.

Figure 5:
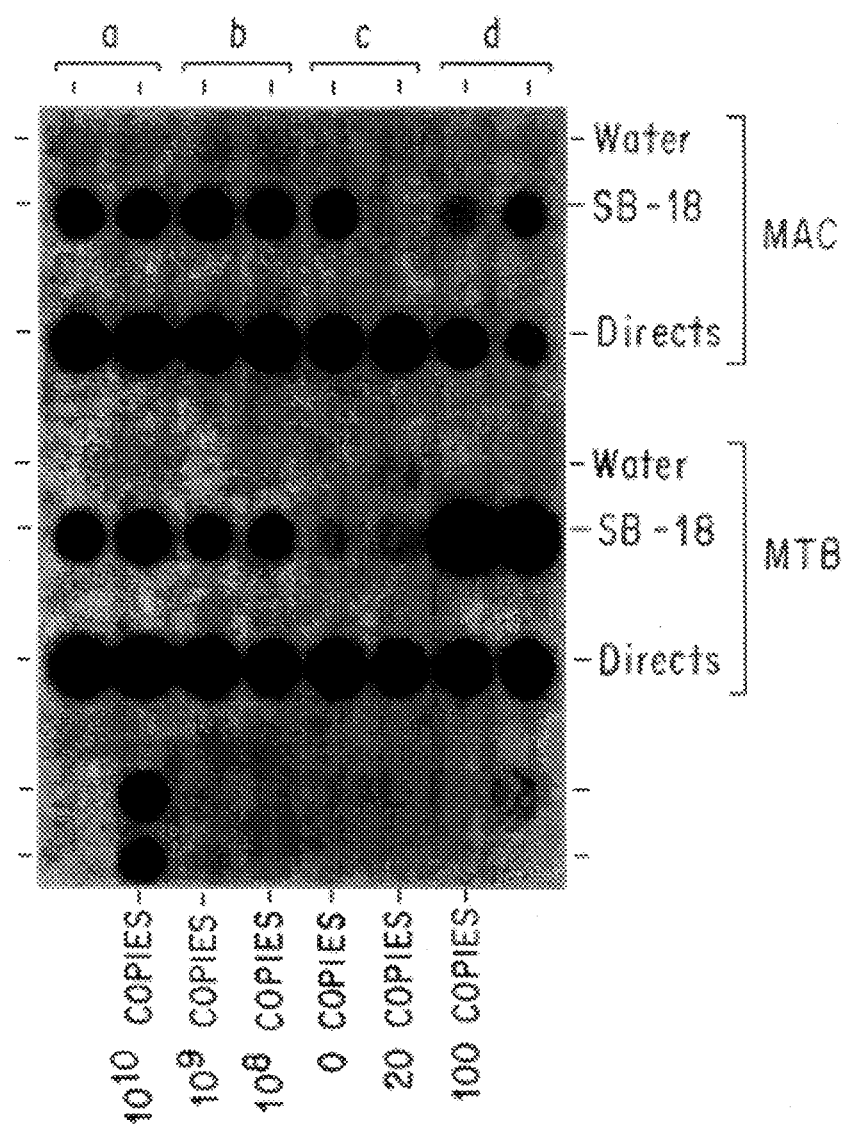
FIG. 5 shows the effect of in vitro processing for both Mycobacterium avium and Mycobacterium tuberculosis when 2 mM SB-18 is included in the extraction solution.

While the ability to isolate both *M. avium* and *M. tuberculosis* from clinical sediments and off slants for experimental purposes was again improved, there were several observations from the in vitro work that merit discussion. First, due to the difference in input from experiment to experiment, meaningful results were extremely difficult to obtain. At very low copy number input, dramatic sample bias was observed with those detergents that did not affect MTB aggregation, interpretation was all but impossible. At high input copy number, meaningful differences could not be observed because amplification of all reactions had proceeded into the linear phase. Careful balancing between these two extremes was required, and proved difficult to accomplish. A priori, it is estimated that between 100 and 1,000 copies were required to obtain meaningful results. Less that 100 copies produced dramatic sample bias in the centrifuged specimens, and greater that 1,000 copies produced relatively homogeneous solutions that were guaranteed to contain cells, regardless of the nature of the processing solution. The second observation addresses the relative differences that were expected. For example, using simple water or nonionic detergent washes, there was an 80% correlation to culture with MTB (Table 5). The suggestion is that only marginal improvements (approximately 20%) are required to achieve 100% correlation. *M. avium*, on the other hand, would require more than a doubling in efficiency to achieve 100% correlation. In light of the first observation noted immediately above, this notion further complicates accruing meaningful data. Regardless, significant improvements under the conditions described were obtained and suggests that the losses were substantially greater than originally envisioned." Unexplained" results for MAC organisms can only be rationalized by invoking near quantitative losses during processing. The third observation is that differences in the ability to isolate *M. tuberculosis* and *M. avium* continued: the two organisms seemed to behave differently, both in vivo and in vitro, with MTB showing more dramatic improvements as a result of SB-18 addition (FIG. 5). Further, the fact that MAC organisms grow in a single cell fashion suggests that the mechanisms of action of SB-18 function are not solely through dispersion.

Attempts to improve the assay focussed on incorporating additives. Whereas mixing detergents seemed counterproductive, and is in accordance with the findings of Linfield W. M. et al., *J. Am. Oil Chem. Soc.* 40:114–117 (1963), incorporation of amino acids into the buffer improved the consistency of recovery modestly, but compromised the ability to disperse MTB. It may be that amino acids are simply being actively sequestered, thereby compromising the natural buoyancy of the Mycobacteria to some degree. Regardless, all empirical data suggested that some input material was still being lost.

Example 9

The Use of Betaines in Isolating Mycobacteria

SB-18 (CAS®No. 13177-41-8) and SB-16 (CAS®No. 2281-11-0) (albeit to a lesser degree) were the only detergents tested above that functioned in the aggregation assay (FIG. 4A shows the results using SB-18). Further, the results of FIG. 5 suggested that the mechanism by which SB-18 functions is not simply one of dispersion. Therefore, a series of experiments were undertaken in an attempt to elucidate features of SB-18 that facilitated improvements in detection (FIGS. 6–9D).

Figure 6:
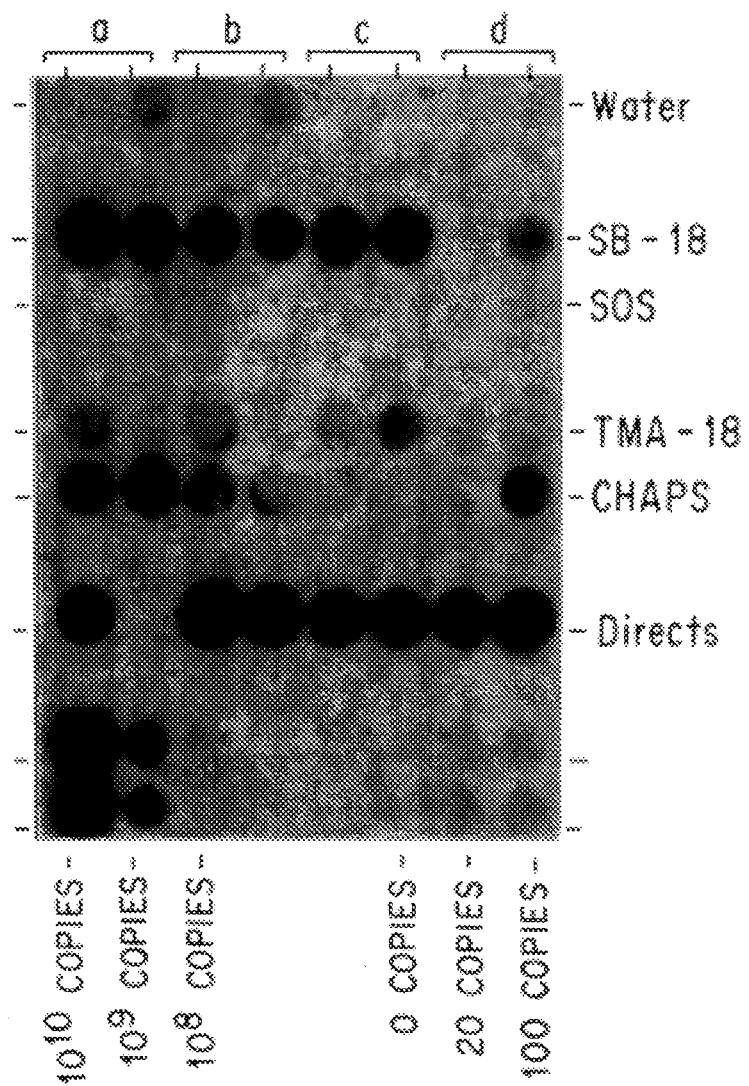
FIG. 6 shows the dot blot result of in vitro processing of Mycobacterium tuberculosis when different ionic homologues of SB-18 are used in the extraction solution.

The results shown in FIG. 6 are based upon a modification of the processing assay shown in FIG. 2 and utilized several ionic homologues of SB-18: sodium octadecylsulfate (SOS: CAS®No. 1120-04-3), trimethyloctadecylammonium bromide (TMA-18: CAS®No. 1120-02-1) and 3-[(3-cholamidopropyl)-dimethylammonio]-1-propane sulfonate (CHAPS: CAS®No. 75621-03-3). SOS and TMA-18 are anionic and cationic octadecyl detergents, respectively, and CHAPS is a zwitterionic bile salt with the (N,N-dimethylammonio) propane sulfonate moiety. All wash buffers contained 10 mM $NaHPO_4$ pH 8.0 and 15 mM NaCl, with the exception of the water control. Four replicate tubes were manufactured for each series and supplemented with either 2 mM SB-18, 200 µM SOS, 2 mM TMA-18 or 2 mM CHAPS. A 2 mM solution of SOS produced a white precipitate that inhibited the PCR reaction. Therefore, a 200 µM solution was used. All tubes were inoculated with 20 µl of the $M.$ $tuberculosis$ bacterial stock and incubated at 37° C. for 60 minutes with shaking (140 rpm) prior to centrifugation. Duplicate amplifications of the four replicates are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

The results show that SB-18 is the only detergent within this tested series that functioned effectively. Repeated experiments have led to the following conclusions: (a) SOS, in addition to being very expensive, precipitates under the conditions used, and (b) while both TMA-18 and CHAPS appeared to perform better than either SOS or the water control, neither gave the signal routinely seen with SB-18.

The results shown in FIGS. 7 and 7A are based on a modification of the processing assay shown in FIG. 2 and use the SB-series of detergents: SB-12, SB-14, SB-16, and SB-18 with both *Mycobacterium tuberculosis* and *Mycobacterium avium*, respectively. These homologues differ only by alkyl chain length. All 2°-Wash Buffers contained 10 mM $NaHPO_4$ pH 8.0, 15 mM NaCl and 5 mM DTT, with the exception of the water control. Four replicate tubes were processed for each series and all were supplemented to a final concentration of 2 mM with the appropriate detergent. All tubes were inoculated with either 20 µl of an *M. tuberculosis* bacterial stock (FIG. 7), or 20 µl of an *M. avium* bacterial stock (FIG. 7A). All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

As shown in FIG. 7, both SB-18 and SB-16 appeared to produce results of both equal intensity and uniform distribution. Alternatively, SB-14, while showing excellent promise in facilitating the recovery of *M. tuberculosis* by centrifugation, produced results that were characteristic of nonuniform distribution due to clumping. SB-12, while clearly performing better than water, did not perform as well as the homologues with higher alkyl chain lengths. In regard to the results of FIG. 7A, all detergents in this series appeared to function relatively equally in terms of facilitating the recovery of *M. avium*. These results were fairly typical with the exception that, when using *M. tuberculosis*, SB-16 generally produced less uniform results than SB-18.

Upon completion of the experimentation that resulted in FIG. 3, it was recognized that clumping was still a major concern. As discussed in Example 7, the line of research pursued was aimed at alleviating this phenomenon. The utility of SB-18 in the method of the invention was originally discovered during a random screening of detergents and was identified based on its ability to disperse clumps of *M. tuberculosis*. The fact that all SB-series detergents facilitated the collection of both *M. tuberculosis* and *M. avium*, in combination with the fact that *M. avium* grows as a single cell (e.g., no dispersion required), suggests that the SB-series of detergents have a commonality that allows them to function in the methods of the invention. Stated differently: in addition to the long chain SB-homologues being able to disperse cords, all SB-18-like detergents have, in some as yet undefined fashion, the ability to facilitate recovery of this class of organisms. Therefore, these data suggest a bimodal mechanism of SB-18 action. The inventor demonstrates below how this bimodal attribute of SB-18 extends to other molecules.

The SB-series of detergents, also known as the sulfopropylbetaines, are a subset of a large, broad class of zwitterionic detergents known as the betaines. The SB-series of zwitterionic detergents are available through customary sources (e.g., Aldrich, Milwaukee, Wis.; CalBiochem, La Jolla, Calif.; Fluka, Ronkonkoma, N.Y.; and Sigma, St. Louis). There are numerous manufacturers of homologous structures, and four different samples were initially obtained from three different manufacturers: the Henkel Corporation (Hoboken, N.J.) provided "Velvetex AB-45" and "Velvetex BK-35"; Inolex Chemical Company (Philadelphia, Pa.) provided "Lexaine® C"; and Goldschmidt Chemical Corporation (Hopewell, Va.) provided "TEGO® Betain L 5351." Velvetex AB-45 (CAS®Number 68424-94-2) is a cococarboxymethylbetaine ($R_1$=coconut oil, $\alpha$=—$CH_2$—, $R_2$,$R_3$=—$CH_3$, $R_4$=—$CH_2$—, $\beta$=$N^{\oplus}$ and $\gamma$=—$COO^{\ominus}$: see Table 2 for structure codes); Velvetex BK-35 (CAS®Number 61789-40-0), Lexaine®C (CAS®Number 61789-39-7), and TEGO® Betain L 5351 (CAS®Number "proprietary"), are all cocoamidopropyl carboxymethylbetaines ($\alpha$=—C(O)$NHC_3H_6$—). Coconut oil has a complex composition; however, use of this oil in the synthesis of betaines would cause $R_1$ to be composed of the following mixture of alkyl chains: 45.4% lauric ($C_{12}$), 18.0% myristic ($C_{14}$), 10.5% palmitic ($C_{16}$), 2.3% stearic ($C_{18}$), 0.4% arachidic ($C_{20}$), 7.4% oleic ($C_{18:1}$), and 5.4% other (the oil composition was compiled from the CRC Handbook of Chemistry and Physics, 55th ed. CRC Press, Cleveland, Ohio (1974) pp.D-192–193).

The results shown in FIG. 8 are based on a modification of the processing assay shown in FIG. 2, and utilized the commercially available betaine preparations described above: Velvetex AB-45, Velvetex BK-35, Lexaine® C, and TEGO® Betain L 5351. Two mM SB-18 was used as the positive control, and water was used as the negative control. All 2°-Wash Buffers contained 10 mM $NaHPO_4$, pH 8.0 and 15 mM NaCl, with the exception of the water control. Four replicate tubes were prepared for each series and supplemented to a final concentration of 10 mM with the appropriate cocobetaine detergent. All tubes were inoculated with 20 µl of an *M. tuberculosis* bacterial stock. All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

Clearly, these commercial preparations show some degree of "SB-18-like activity" with regard to improving the ability to collect these organisms by centrifugation. Given the composition of the alkyl moiety, and the results presented in FIG. 7, these preparations would, a priori, be expected to, and did, behave in a manner intermediate between SB-12, SB-14 and SB-16. For example, they improved recovery, but had a limited capacity with respect to dispersing these organisms. It should be noted that since three of the reagents are reported to have identical structures (Velvetex BK-35, Lexaine® C, and TEGO® Betain L 5351), they would be expected to, and did, function identically. (Note that two have different CAS®Numbers.) The fact that all three do function with equal efficiency suggests that performance is independent of manufacturer. In addition, even though these preparations are impure, they functioned in this assay.

Additional sources of betaine-like molecules were examined below. The background on these molecules is presented so that the results of testing a wide variety of homologous structures can be better discussed.

Background on Betaines

The betaines are zwitterionic detergent molecules that are essentially a center of positive charge separated from a center of negative charge. The alkyl can be bound to either the cation, the anion, or the bridge separating the charges. Table 2 gives the generic structure of the most common class of betaines, and the discussion of Table 2 gives numerous examples. Table 3 gives several structural variations on the betaine theme, and the discussion of Table 3 gives several examples of these subclasses. The cation, in the vast majority of cases, is a quaternary nitrogen. The anion shows a much higher degree of diversity. For example, ammonio-versions of carboxybetaines, phosphobetaines and sulfobetaines are readily available commercially.

In addition to the sources mentioned above, the 1994 edition of "McCutcheon's" (McCutcheon's, Volume 1: Emulsifiers & Detergents, North American Edition, MC Publishing, Glen Rock, N.J., p.290–291) lists 93 commercially available "Betaine Derivatives." A large body of scientific information, technical expertise and manufacturing capabilities relating to betaines exists today.

The results presented herein indicate that a combination of structural and behavioral idiosyncracies facilitate betaine action in the methods of the invention. Given the variety and unique character displayed by this class of zwitterionic detergents (Tables 2 and 3), a large variety of betaines, representing a broad spectrum of structural variations, were examined to assess the ability of these homologues to improve the collection of *Mycobacterium tuberculosis*. Table 7 summarizes the structures, sources and CAS®Numbers of the betaines used to generate FIGS. 9 through 9D.

TABLE 7

Summary of betaine-like structures tested

Figure 9:
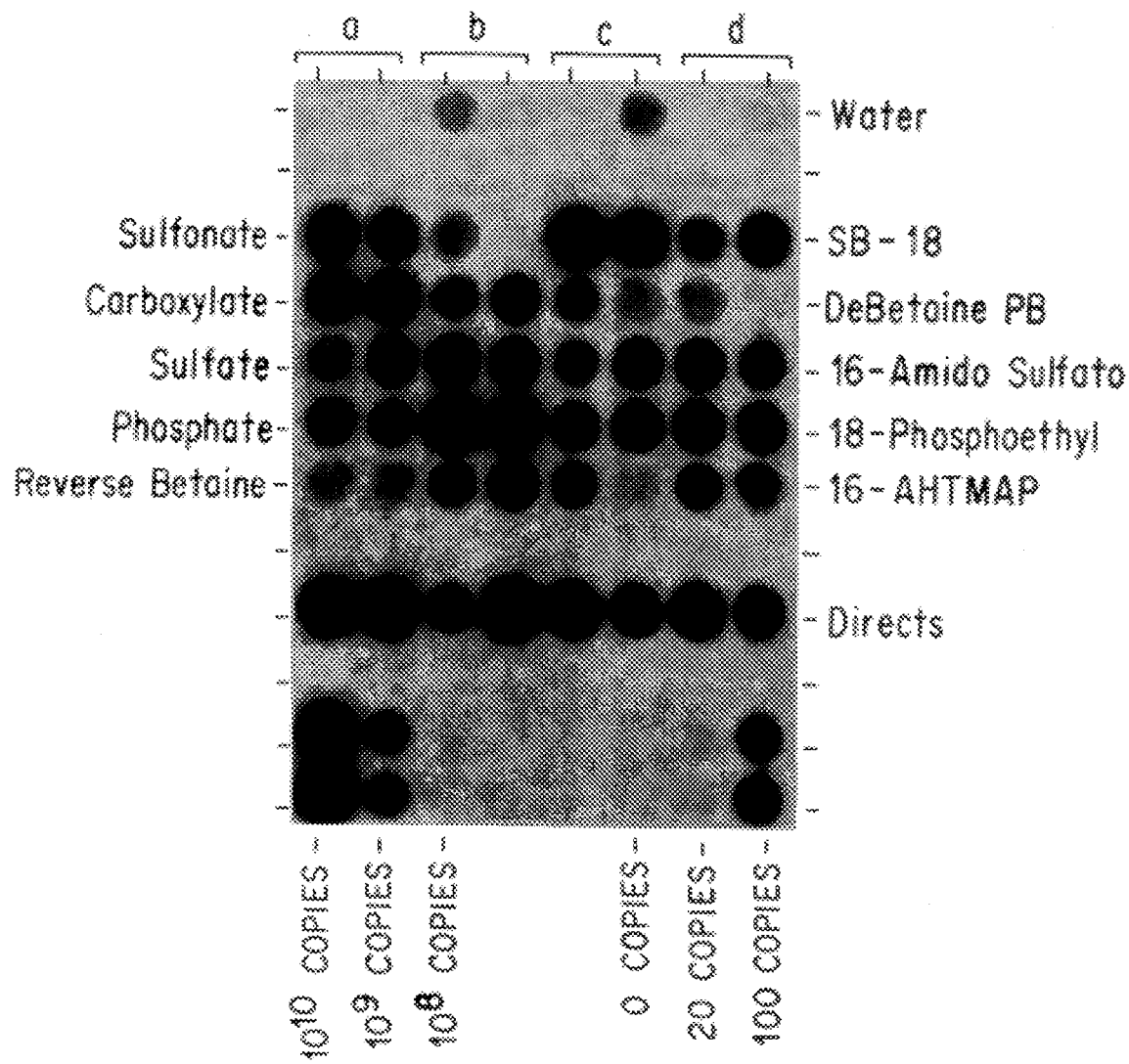
FIG. 9 shows the dot blot results of in vitro processing of Mycobacterium tuberculosis when betaines having a variety of charge combinations and structural relationships are used in the extraction solution.
Figure 9A:
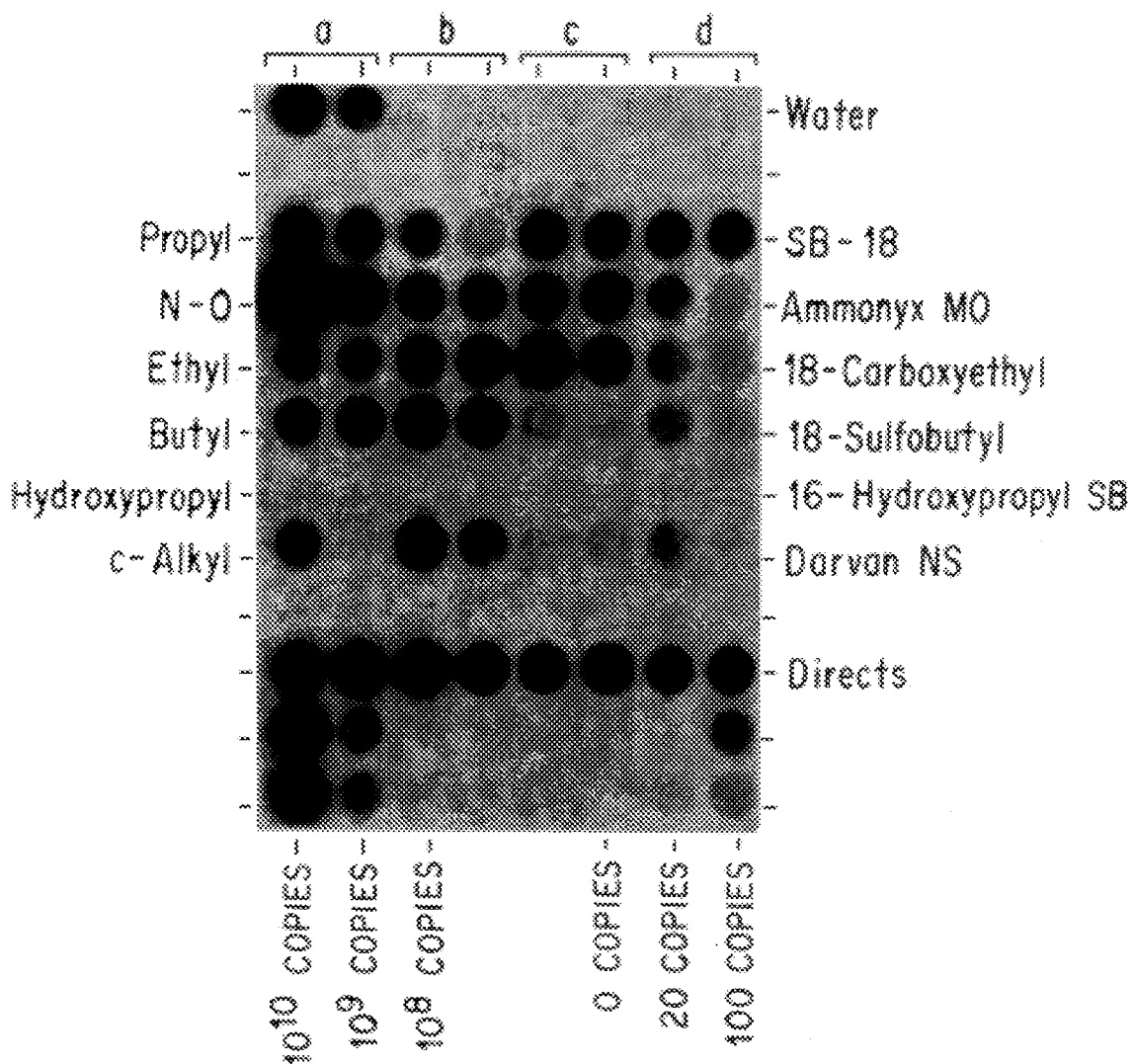
FIG. 9A shows the dot blot results of in vitro processing of Mycobacterium tuberculosis when betaines having a variety of "bridge" structures are used in the extraction solution.
Figure 9B:
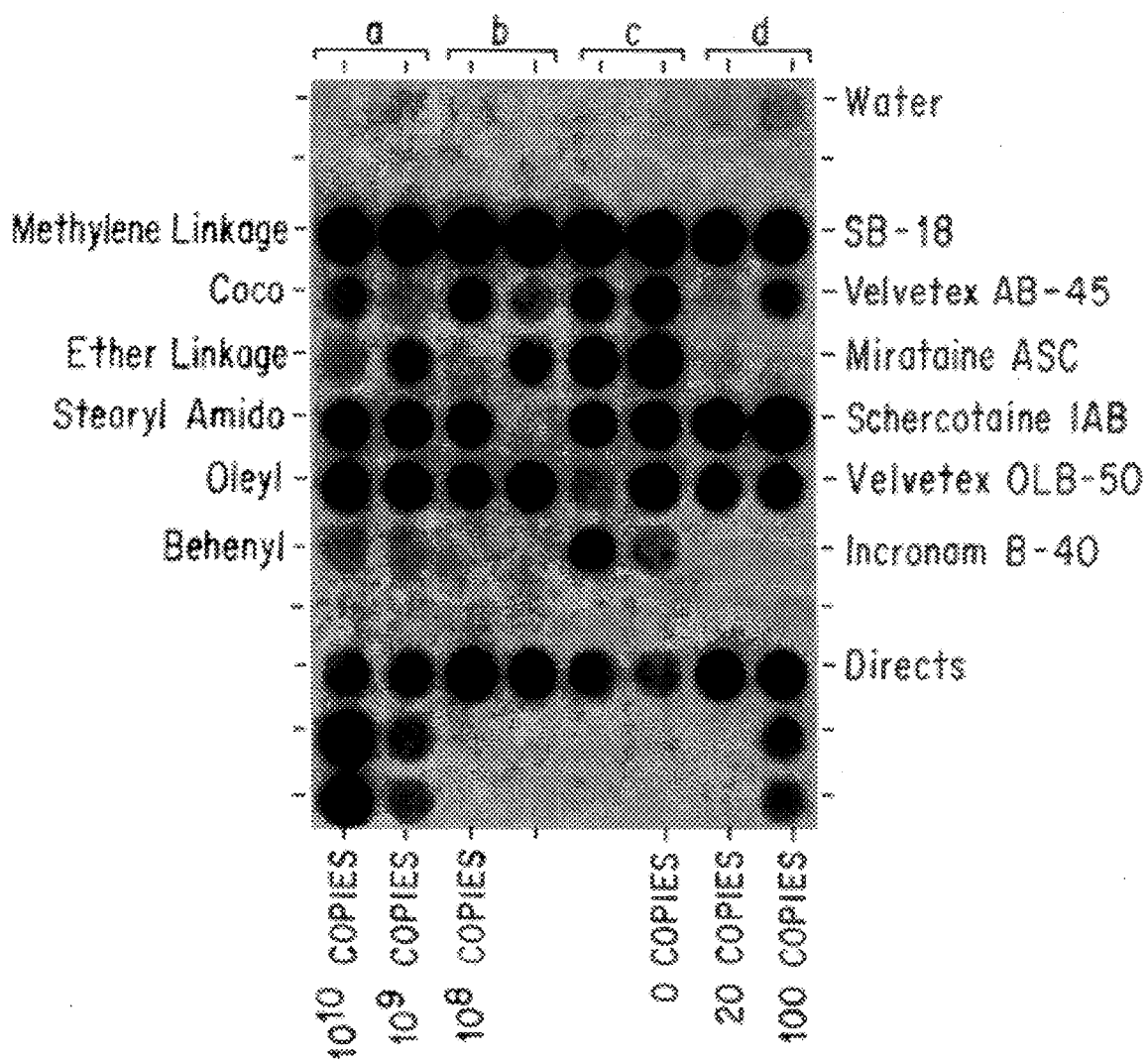
FIG. 9B shows the dot blot results of in vitro processing of Mycobacterium tuberculosis when betaines having a variety of alkyl and alkyl "linkage" structures are used in the extraction solution.

| Trade Name | Manufacturer | Structure | CAS ® No. |
|---|---|---|---|
| FIG. 9: Charge Combinations | | | |
| DeTaine PB | DeForest | Cetyl carboxymethylbetaine (—COO$^\ominus$) | 693-33-4 |
| Custom | ECOCHEM | $C_{16}$-amidopropyl sulfatoethylbetaine (—OSO$_3^\ominus$) | 58930-11-3 |
| Custom | ECOCHEM | $C_{18}$-phosphoethylbetaine (—OPO$_3^\ominus$) | 126712-89-8 |
| Custom | KAO Chemical | $C_{16}$-AHTMAP: "Reverse Betaine" (—N$^\oplus$(CH$_3$)$_3$) | 99485-86-6 |
| FIG. 9A: Bridge Structure | | | |
| Ammonyx MO | Stepan | Myristyl dimethylamine oxide (—O$^\ominus$) | 3332-27-2 |
| Custom | ECOCHEM | $C_{18}$-Carboxyethylbetaine | 30612-73-8 |
| Custom | ECOCHEM | $C_{18}$-Sulfobutylbetaine | 22313-73-1 |
| Custom | ECOCHEM | $C_{16}$-Hydroxypropyl sulfobetaine | 7425-12-9 |
| Darvan NS | R.T. Vanderbilt | c-Decyl Betaine and c-Cetyl Betaine | 95-56-0 |
| FIG. 9B: Alkyl and Alkyl Linkage | | | |
| Velvetex AB-45 | Henkel | Coco carboxymethylbetaine | 68424-94-2 |
| Mirataine ASC | Rhone-Poulenc | Alkylether hydroxypropyl sulfobetaine | 108797-84-8 |
| Schercotaine IAB | Scher | Isostearylamidopropyl carboxymethylbetaine | 6179-44-8 |
| Velvetex OLB-50 | Henkel | Oleyl carboxymethylbetaine | 871-37-4 |
| Incronam B-40 | Croda | Behenyl carboxymethylbetaine | 84082-44-0 |
| FIG. 9C: Natural Oils | | | |
| TEGO Betaine L5351 | Goldschmidt | Cocoamidopropyl carboxymethylbetaine | "Proprietary" |
| Crosultaine C-50 | Croda | Cocoamidopropyl hydroxypropyl sulfobetaine | 68139-30-0 |
| Incronam BA-30 | Croda | Babassuamidopropyl carboxymethylbetaine | — |
| Rewoteric AM-R40 | Sherex | Ricinamidopropyl carboxymethylbetaine | 71850-81-2 |
| Schercotaine WOAB | Scher | Wheat Germ Oil Amido | "None Assigned" |
| FIG. 9D: Natural Oils | | | |
| Chembetaine S | Chemron | Soyamidopropyl carboxymethylbetaine | — |
| Hetaine CLA | Heterene | Canolamidopropyl betaine | — |
| Crosultaine T-30 | Croda | Tallowamidopropyl hydroxypropyl sulfobetaine | — |
| Rewoteric TEG | Sherex | Tallow Glycinate | 70750-46-8 |
| Crosultaine E-30 | Croda | Erucamidopropyl hydroxypropyl sulfobetaine | — |

Examination of Betaine Charge Structure

Comparison of FIGS. 6, 7, 7A, and 8, and the discussions on betaine structure, suggest that it is not the unique combination of sulfonate, quaternary dimethylamine, and octadecyl chain that facilitate SB-18-like activity. To the contrary, it is the fact that an anion is separated from a cation, and the two are covalently attached in the same molecule. The purpose of the experiment shown in FIG. 9 was to examine the role of the dipole moment created by the coexistence of opposing charges in SB-18-like molecules. The results shown in FIG. 9 are based on a modification of the processing assay shown in FIG. 2, and utilized several betaines that vary based on charges and charge structure. Two molecules were derived from commercial sources, and three were custom syntheses. The SB-18 control (CAS®No. 13177-41-8) is a $C_{18}$-sulfopropylbetaine and was purchased from Sigma, St. Louis, Mo. SB-18 combines a quaternary dimethylamine, with a sulfonate ($-SO_3^{\ominus}$) group. DeTaine PB (CAS®No. 693-33-4) is a $C_{16}$-carboxymethylbetaine and was obtained as a sample from DeForest, Inc., Boca Raton, Fla. DeTaine PB combines a quaternary dimethylamine, with a carboxyl ($-COO^{\ominus}$) group. Two of the three custom syntheses were contracted to Ecochem, Inc. of Chaska, Minn. (all chemical characterizations were performed by Ecochem.) The first custom betaine, $C_{16}$-amidopropyl sulfatoethylbetaine (CAS®No. 58930-11-3), combines a quaternary dimethylamine, with a sulfate ($-OSO_3^{\ominus}$) group. The $C_{16}$-amidopropyl sulfatoethylbetaine ($C_{16}$-AmStB) was synthesized according to the procedure of Parris N. et al., *J. Am. Oil Chem. Soc.* 53:97–100 (1976). The second custom betaine, $C_{18}$-phosphoethylbetaine (CAS®No. 126712-89-8), combines a quaternary dimethylamine, with a phosphate ($-OPO_3^{\ominus}$) group. The $C_{18}$-phosphoethylbetaine was synthesized according to the procedure of Tsubone, K. et al., *J. Am. Oil Chem. Soc.* 67:149–153 (1990). The third of the three custom betaines, $C_{16}$-alkyl 2-hydroxy-3-trimethylammoniopropyl phosphate ($C_{16}$-AHTMAP: CAS®No. 99485-86-6), falls into the category of "reverse betaine" as described in Table 3. $C_{16}$-AHTMAP combines a quaternary trimethylamine ($\gamma=-N^{\oplus}(CH_3)_3$), with a phosphate ($-OPO_3^{\ominus}$) group, however, the unique feature of this molecule is the fact that the alkyl is linked to the anion. $C_{16}$-AHTMAP was received as a kind gift from the Kao Institute for Fundamental Research, Tochigi, Japan, and was synthesized according to the procedure of Kurosaki, T. et al., *Chem. Soc. Japan* 11:1297–1301 (1990). The structure of the $C_{16}$-AHTMAP compound was confirmed by Ecochem of Chaska, Minn. SB-18 was considered the positive control, and water was used as the negative control. All Wash Buffers contained 10 mM $NaHPO_4$, pH 8.0 and 15 mM NaCl, with the exception of the water control and the $C_{16}$-AmStB, which was dispersed in 1 mM Tris-HCl, pH 8.0. Four replicate tubes were prepared for each series and supplemented to a final concentration of 2 mM with the appropriate detergent with the exception of $C_{16}$-AmStB which was used at a final concentration of 200 µM. All tubes were inoculated with 20 µl of an *M. tuberculosis* bacterial stock. All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

As shown in FIG. 9, all the tested detergents appear to work equally well in this assay. Based on the arguments presented herein, and the fact that the reverse betaine functions in a manner similar to SB-18, demonstrates that all betaine-like molecules possess SB-18-like activity. The basis for this commonality is believed to be the close proximal coexistence of opposing charges, thereby creating an electrically neutral molecule with a large dipole moment. The result of this combination is best summarized by Laughlin, R. G. *Langmuir* 7:842–847 (1991): "Zwitterionic functional groups possess the greatest polarity found within the nonionic class of hydrophilic groups." The fact that different ionic groups can be used interchangeably in the assay described here identifies the degree of polarity of the headgroup as the distinguishing feature of these detergents. For example, the degree of polarity produced by a polyoxyethylene group, while electrically neutral and of approximately the same molecular size as, say, the ammoniopropanesulfonate moiety of SB-18, is insignificant in comparison. This is exemplified by comparing the CMC and Krafft points of Brij 76 (CAS®No. 9005-00-9) and SB-18 with sodium octadecyl sulfonate. Brij 76 (stearyl-ethylene oxide ($C_{18}E_{10}$)) has a CMC of approximately $3\times10^{-5}$M (estimated from: Schott, H. et al., *J. Phar. Sci.* 64:658–664 (1975) based on the oleyl equivalent), a Kraft point of 45.5° C. and a cloud point of 64° C. (Schott, H. et al., *J. Phar. Sci.* 65:979–981 (1976)). SB-18 has a CMC of approximately $2\times10^{-6}$ (Nandakumar, T. N. et al., *J. Oil Tech. Assoc. India* 11:31–34 (1979)), and a Kraft point of 89° C. in pure water and 37.5° C. in 10 mM NaCl (Tsujii, K. et al. *J. Phys. Chem.* 82:1610–1614 (1978)). The critical temperature of sodium ocatadecyl sulfonate is 57° C. at a concentration of $7.5\times10^{-4}$ M (Tartar, H. V. et al., *J. Am. Chem. Soc.* 61:539–544 (1939)). SB-18 is the least soluble (e.g., lowest CMC), but has the lowest Krafft temperature in the presence of salt (e.g., lowest melting temperature of the hydrated crystal). Clearly, the relationship between CMC, Krafft temperature and polarity is complex; however, it appears that the dramatic ability of the zwitterion to structure water in the presence of electrolytes is the key to function. Therefore, referring to Tables 2 and 3 and examining the cations and anions listed, a large variety of additional ions are envisioned, which could be combined to produce a functional betaine in the methods of the invention.

Examination of Betaine Bridge Structure

The results presented in FIG. 9 suggest that the important feature of betaine structure is the presence of opposing charges. These data, in conjunction with the importance of betaine bridge structure, also suggest that insofar as the combination of bridge structure and alkyl chain permits the formation of micelles within the context of the assay, a betaine will display SB-18-like activity. Examination of the structures used in FIG. 9 shows that DeTaine PB has a methyl bridge, the sulfatoethylbetaine and the phosphoethylbetaine have an ethyl bridge, SB-18 has a propyl bridge, and $C_{16}$-AHTMAP has a hydroxypropyl bridge. The results shown in FIG. 9A reveal additional bridge structures and charge combinations.

The results shown in FIG. 9A are based on a modification of the processing assay shown in FIG. 2, and utilize several betaines that vary based on the bridge structure separating the charges. Two molecules were derived from commercial sources, and three were custom syntheses. Ammonyx MO (CAS®No. 3332-27-2) is a $C_{14}$-dimethylamine oxide (the bridge is an NO bond: $N^{\oplus}—O^{\ominus}$), and was obtained as a sample from Stepan Company, Northfield, Ill. It should also be noted that Ammonyx MO can be considered another variation on the dipole moment structure discussed in FIG. 9. Danran NS is a c-alkylbetaine as described in Table 3 (the alkyl is attached to the bridge), and was obtained as a sample from R. T. Vanderbilt, Norwalk, Conn. The manufacturer states that Danran NS is a mixture of c-decyl betaine (CAS®No. 96-55-9) and c-cetyl betaine (CAS®No. 95-56-0). The proportions of each are not stated. The three custom syntheses were contracted to Ecochem, Inc. of Chaska, Minn. (all chemical characterizations were performed by Ecochem).

The first custom betaine, $C_{18}$-carboxyethylbetaine (CAS®No. 30612-73-8), has an ethyl bridge ($R_4$=—$CH_2CH_2$—) and was synthesized according to the procedure of Weers, J. G. et al., Langmuir 7:854–867 (1991). The second custom betaine, $C_{18}$-sulfobutylbetaine (CAS®No. 22313-73-1), has a butyl bridge ($R_4$=—$CH_2CH_2CH_2CH_2$—) and was synthesized according to the procedure of Parris, N. et al., J. Am. Oil Chem. Soc. 53:97–100 (1976). The third custom betaine, $C_{16}$-hydroxypropyl sulfobetaine (CAS®No. 7425-12-9), has a 2-hydroxypropyl bridge ($R_4$=—$CH_2CH(OH)CH_2$—) and was synthesized according to the procedure of Parris, N. et al., J. Am. Oil Chem. Soc. 53:60–63 (1976). Two mM SB-18 was used as the positive control, and water was used as the negative control. All wash buffers contained 10 mM $NaHPO_4$ (sodium phosphate buffer, a mixture of $NaHPO_4$ and $Na_2HPO_4$), pH 8.0 and 15 mM NaCl, with the exception of the water control. Four replicate tubes were prepared for each series and supplemented to a final concentration of 2 mM with the appropriate detergent, with the exception of Darvan NS, which was brought to a final concentration of 10 mM. All tubes were inoculated with 20 µl of an M. tuberculosis bacterial stock. All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

Again, with the exception of $C_{16}$-hydroxypropyl sulfobetaine, all tested compounds functioned in the methods of the invention. Specifically, all tested compounds showed some SB-18-like activity. Interestingly, Darvan NS, which is a combination of $C_{10}$ and $C_{16}$ betaines, worked marginally. While the proportions of each are not known, Darvan NS is an extremely thin liquid, even more so that the coco-derivatives, suggesting that it has a very high concentration of the $C_{10}$ derivative. Regardless, the c-alkyl showed some degree of SB-18-like activity. Additional experiments with the amine oxide showed this structure to have excellent efficacy, although clumping was consistently observed. Unfortunately, increases in AO chain length under clinical conditions might not be permissible. For example, the Krafft temperature of the $C_{18}$-AO is approximately 43° C., and was of the salting-out type (Tsujii, K. et al., *Yukagaku* 30:495–499 (1981)). In addition, as predicted in FIG. 9, the amine oxides provide another example of the structural variability of the dipole moment. Both the $C_{18}$-carboxyethylbetaine and the $C_{16}$-sulfobutylbetaine, in general, behaved in a manner similar to SB-18: several processing experiments using these two betaines usually produced fairly uniform results.

The inability of $C_{16}$-hydroxypropyl sulfobetaine to facilitate recovery of the bacteria by centrifugation can be explained by the fact that the detergent precipitated upon addition to the $NaHPO_4$. Based on information concerning the interaction of betaine bridge structure with various ions, the skilled artisan could modify the system parameters such that $C_{16}$-hydroxypropyl sulfobetaine can be used. For example, if a 4–5 Å charge separation was the minimum intercharge distance that permitted salting-in (propyl distance would be approximately 5.5 Å. (Tsujii, K. et al. *Yukagaku* 30:495–499 (1981)), and facilitation of salting-in behavior followed the trend: $SCN^{\ominus}>I^{\ominus}>NO_3^{\ominus}>Cl^{\ominus}$ for anions, and $K^{\oplus}\approx NH_4^{\oplus}>Na^{\oplus}$ for cations (Tsujii, K. et al. *J. Phys. Chem.* 82:1610–1614 (1978)), then one could modify buffer composition to facilitate the utilization of $C_{16}$-hydroxypropyl sulfobetaine. The results of these experiments are presented and discussed in FIG. 10.

From these data one would be led to concur with Laughlin, R. G. *Langmuir* 7:842–847 (1991) that betaine efficacy is, for the most part, more dependent on the charge structure than bridge structure. In other words, insofar as the bridge permits the formation of micelles under the system conditions, it would appear that it is the coexistence of charges on the same molecule that facilitate the use of these detergents in the methods of the invention. The importance of the bridge structure, therefore, appears to function primarily in permitting productive presentation of a given detergent within the context of the assay conditions. For example, if the bridge permits the formation of micelles given the temperature, electrolyte, and electrolyte concentration of the assay, then the betaine will show SB-18-like activity.

Examination of Alkyl and Alkyl Linkage on Betaine Function

Closer scrutiny of the structures used in the experiments resulting in FIGS. 9 and 9A reveal that a complex array of alkyl structures has been used in the methods of the invention. For example, $C_{10}$, $C_{14}$, $C_{16}$ and $C_{18}$ straight chain hydrocarbons were the foundation of the hydrophobic domains ($R_1$) in these examples. In addition, the sulfatobetaine uses an amidopropyl linkage to covalently connect the alkyl to the quaternary nitrogen. The implication is that betaine function is even less dependent on alkyl structure. That is to say that, insofar as the combination of charges, bridge structure, and alkyl structure permit the formation of micelles within the context of the assay, a betaine will display SB-18-like activity. In an effort to further exemplify this notion, several additional betaines were tested. The results shown in FIG. 9B are based on a modification of the processing assay shown in FIG. 2, and utilize several betaines that vary based on alkyl structure, composition and linkage to the quaternary nitrogen. All five molecules were derived from commercial sources. Velvetex AB-45 (CAS®No. 68424-94-2) uses coconut oil as the source for the alkyl chain (the composition of coconut oil is given above), and was obtained as a sample from the Henkel Corporation, Emery Group Cospha, Hoboken, N.J. The alkyl linkage of Velvetex AB-45 is simply an extension of the alkyl chain. Mirataine ASC (CAS®No. 108797-84-8) uses a 3-butoxy-2-hydroxy functionality as part of the connection linking the alkyl moiety to the quaternary nitrogen, and was obtained as a sample from Rhone-Poulenc, Surfactants & Specialty Division, Cranberry, N.J. Information on this CAS®Number states the structure as: "1-propanaminium,3-butoxy-2-hydroxy-N-(-2-hydroxy-3-sulfopropyl)-N,N-dimethyl-, inner salt." The viscosity of this liquid suggests that an alkyl of approximately dodecyl structure is linked to the butoxy, however, the exact structure is unknown. Schercotaine IAB (CAS®No. 6179-44-8) uses an amidopropyl array to link the alkyl moiety to the quaternary nitrogen, and was obtained as a sample from Scher Chemical, Inc., Clifton, N.J. The manufacturer states that the alkyl is an "isostearyl," indicating that the molecule may branch in some undefined fashion. Information on this CAS®Number, however, simply states the alkyl structure as "octadecyl." Velvetex OLB-50 (CAS®No. 871-37-4) uses an oleyl group ($C_{18:1}$) as the alkyl chain (e.g., introduction of a double bond), and was obtained as a sample from the Henkel Corporation, Emery Group Cospha, Hoboken, N.J. Incronam B-40 is an extraordinarily long alkyl chain ($C_{22}$), and was obtained as a sample from Croda, Inc., Parsippany, N.J. No CAS®Number was given for Intronare B-40; however, a similar product sold outside the United States by the same manufacturer, having the same trade name, lists its active ingredient as "bethanamido" and its CAS®No. as 84082-44-0. Information on this CAS®Number states its alkyl composition as a mixture of $C_8$–$C_{22}$. Both are sold as pastes, indicating a predominance of exceptionally long alkyl chains. The Incronam B-40 detergent stock could only be generated by dissolving a portion of the paste in a 10:1, isoamyl alcohol:water mixture. Two mM SB-18 was used as the positive control, and water was used as the negative control. All wash buffers contained 10 mM $NaHPO_4$, pH 8.0 and 15 mM NaCl, with the exception of the water control. Four replicate tubes were prepared for each series and supplemented to a final concentration of 2 mM with the appropriate detergent, with the exception of Incronam B-40 which was brought to a final concentration of 200 µM. Flocculation of the detergent occurred under these conditions. All tubes were inoculated with 20 µl of an *M. tuberculosis* bacterial stock. All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

Again, all these betaines, with the exception of Incronam B-40, show SB-18-like activity. Velvetex AB-45 produced slightly more uniform results in these experiments than those seen in FIG. 8. Mirataine ASC, which has an unknown chain length, was an extremely thin liquid and appeared unable to disperse the Mycobacteria. These results, owing to clumping, were typically seen with the shorter chain betaines. Schercotaine IAB and Velvetex OLB-50 are both octadecyl detergents, the former being a saturated chain and the latter being unsaturated. Both of these betaines produced results routinely seen with SB-18: processing with these betaines produced fairly uniform results, however, slightly more variation was observed with the unpurified samples. The obvious conclusion is that insofar as the alkyl moiety permits the formation of micelles under the system conditions, it would appear that it is the coexistence of charges on the same molecule that facilitate the use of these detergents in the methods of the invention. Incronam B-40, similar to $C_{16}$-hydroxypropyl sulfobetaine (FIG. 9A), precipitated upon addition to the $NaHPO_4$ and was, therefore, not expected to show the same degree of efficacy. Based on information concerning the interaction of betaine bridge structure with various electrolytes, Incronam B-40 would be predicted to present a more difficult problem than $C_{16}$-hydroxypropyl sulfobetaine (FIG. 9A). For example, if a 4~5 Å charge separation was the minimum intercharge distance that permitted salting-in (methyl distance would be approximately 3.1 Å (Tsujii, K. et al. *Yukagaku* 30:495–499 (1981)), and salting-out behavior is exacerbated following the trend: $SCN^{\ominus}>I^{\ominus}>NO_3^{\ominus}>Cl^{\ominus}$ for anions, and $K^{\oplus}\approx NH_4^{\oplus}>Na^{\oplus}$ for cations (Tsujii, K. et al. *J. Phys. Chem.* 82:1610–1614 (1978)), then one would be limited with respect to modifications of buffer composition in efforts to facilitate the utilization of Incronam B-40. In other words, one would be restricted to simply minimizing electrolytes, a situation analogous to ionic detergents in general. The results of efforts pursuing this line of research are presented and discussed in FIG. 10.

Betaines Derived from Natural Oils

The vast majority of commercially available betaines are derived from natural oils, primarily coconut oil. Based on the results of FIGS. 8, 9, 9A, and 9B, these betaines should function in the methods of the invention as well. The results shown in FIGS. 9C and 9D utilize several different betaines, the alkyls of all are derived exclusively from natural oils. These structure differ based on alkyl length, alkyl structure, alkyl mixtures, linkage to the quaternary nitrogen, bridge structures, and anion moiety. In essence, these betaines provide a unique opportunity to further examine relationships between the various aspects of betaine anatomy. Each experiment will be presented first, followed by a discussion of both FIGS.

The results shown in FIG. 9C are based on a modification of the processing assay shown in FIG. 2, and utilize several betaines that are derived exclusively from natural oils. All five molecules were derived from commercial sources. TEGO Betaine L5351 (CAS®No. "Proprietary") is a carboxymethylbetaine that uses coconut oil as the source for the alkyl chain in combination with an amidopropyl linkage. TEGO Betaine L5351 was obtained as a sample from the Henkel Corporation, Emery Group Cospha, Hoboken, N.J. Coconut oil derived from *Cocos nucifera* is a complex mixture of fatty acids with the following composition: 45.4% lauric ($C_{12}$), 18.0% myristic ($C_{14}$), 10.5 % palmitic ($C_{16}$), 2.3 % stearic ($C_{18}$), 0.4% arachidic ($C_{20}$), 7.4 % oleic ($C_{18:1}$), and 5.4 % other (the oil composition was compiled from the CRC Handbook of Chemistry and Physics, 55th ed. CRC Press, Cleveland, Ohio (1974) pp.D-192–193). Crosultaine C-50 (GAS®No. 68139-30-0) is a sulfobetaine that uses a hydroxypropyl bridge and coconut oil as the source for the alkyl chain, in combination with an amidopropyl linkage. Crosultaine C-50 was obtained as a sample from Croda, Inc., Parsippany, N.J. Incronam BA-30 (no CAS®No. stated) is a carboxymethylbetaine that presumably uses "babassu oil" as the foundation of the hydrophobic domain, in combination with an amidopropyl linkage. Incronam BA-30 was obtained as a sample from Croda, Inc., Parsippany, N.J. Babassu oil derived from *Attalea funifera* is a complex mixture of fatty acids with the following composition: 44.1% lauric ($C_{12}$), 15.4% myristic ($C_{14}$), 8.5% palmitic ($C_{16}$), 2.7% stearic ($C_{18}$), 0.2% arachidic ($C_{20}$), 16.1% oleic ($C_{18:1}$), 1.4% linoleic ($C_{18:2}$), and 11.6% other (the oil composition was compiled from the CRC Handbook of Chemistry and Physics, 55th ed. CRC Press, Cleveland, Ohio (1974) pp.D-192–193). Rewoteric AM-R40 (CAS®No. 71850-81-2) is a carboxymethylbetaine that presumably uses castor oil as the source for the alkyl chain in combination with an amidopropyl linkage. Rewoteric AM-R40 was obtained as a sample from the Sherex Chemical Company, Dublin, Ohio. Castor oil derived from *Ricinus communis* is a complex mixture of fatty acids, but is composed primarily of ricinoleic acid (87%), and oleic (7.4%) and linoleic acid (3.1%) (the oil composition was compiled from the CRC Handbook of Chemistry and Physics, 55th ed. CRC Press, Cleveland, Ohio (1974) pp.D-192–193). Ricinoleic acid, or 12-hydroxy-9-octadecenoic acid (cis) is an unsaturated-$C_{18}$ chain that has the structure:

$C_6H_{13}CH(OH)CH_2CH=CH(CH_2)_7COOH$. Linoleic acid, or 9,12-octadecadienoic acid, is also an unsaturated-$C_{18}$ chain with the following structure: $CH_3(CH_2)_4 CH=CHCH_2CH=CH(CH_2)_7COOH$. Schercotaine WOAB (CAS®No. "none assigned") is presumably a carboxymethylbetaine that uses wheat germ oil as the source for the alkyl chain in combination with an amidopropyl linkage. Schercotaine WOAB was obtained as a sample from the Scher Chemicals, Inc., Clifton, N.J. Wheat germ oil derived from *Triticum aestivum* is a complex mixture of fatty acids, but is composed primarily of linoleic acid (52.3%), oleic (28.1%) and linolenic acid (3.6%). The balance of approximately 16% is a mixture of lauric, myristic, palmitic, stearic and arachidic acids (the oil composition was compiled from the CRC Handbook of Chemistry and Physics, 55th ed. CRC Press, Cleveland, Ohio (1974) pp.D-192–193). Linolenic acid, or 9,12,15-octadecatrienoic acid (cis, cis, cis), yet another unsaturated-C,s chain, has the structure: $CH_3 [CH_2CH=CH]_3(CH_2)_7COOH$. 2 mM SB-18 was used as the positive control, and water was used as the negative control. All wash buffers contained 10 mM $NaHPO_4$, pH 8.0 and 15 mM NaCl, with the exception of the water control. Four replicate tubes were prepared for each series. Incronam BA-30, Rewoteric AM-R40, and Schercotaine WOAB were added to the respective wash buffers to a final concentration of 2 mM, and TEGO Betaine L5351 and Crosultaine C-50 were brought to a final concentration of 10 mM. None of these detergents precipitated upon addition to the sodium phosphate buffer. All tubes were inoculated with 20 μl of an *M. tuberculosis* bacterial stock. All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

The results shown in FIG. 9D are based on a modification of the processing assay shown in FIG. 2, and utilize several betaines that are also derived exclusively from natural oils. These structures differ based on alkyl length, alkyl structure, alkyl mixtures, linkage to the quaternary nitrogen, bridge structures, and anion moiety. All five molecules were derived from commercial sources. Chembetaine S (CAS®No.: none stated) is a carboxymethyl betaine that uses soybean oil as the source for the alkyl chain in combination with an amidopropyl linkage. Chembetaine S was obtained as a sample from the Chemron Corporation, Paso Robles, Calif. Soybean oil derived from *Glycine soja* is a complex mixture of fatty acids, but is composed primarily of linoleic (50.7%), oleic (28.9%) and palmitic (9.8%) acids. Additional components include: linolenic (6.5 %), stearic (2.4 %), and arachidic (0.9 %) (the oil composition was compiled from CRC Handbook of Chemistry and Physics, 55th ed. CRC Press, Cleveland, Ohio (1974) pp.D-192–193). Hetaine CLA (CAS®No. "none") is a betaine of unknown structure that uses canola oil as the source for the alkyl chain, in combination with an amidopropyl linkage. Hetaine CLA was obtained as a sample from Heterene, Inc., Paterson, N.J. The composition of "canola oil" has not been ascertained. Crosultaine T-30 (no CAS®No. given) is a sulfobetaine that has a hydroxypropyl bridge and tallow as the source for the alkyl chain, in combination with an amidopropyl linkage. Crosultaine T-30 was obtained as a sample from Croda, Inc., Parsippany, N.J. Tallow is typically derived from either beef (*Bovis taurus*) or mutton (*Ovis aries*). Tallow derived from beef has the following composition: 49.6% oleic acid, 27.4% palmitic acid, 14.1% stearic acid, 6.3 % myristic acid, and 2.5 % linoleic acid. Tallow derived from mutton has the following composition: 36.0 % oleic acid, 24.6 % palmitic acid, 30.5% stearic acid, 4.6% myristic acid, and 4.3% linoleic acid (the oil composition was compiled from CRC Handbook of Chemistry and Physics, 55th ed. CRC Press, Cleveland, Ohio (1974) pp.D-192–193). The source of the tallow used to manufacture Crosultaine T-30 is not known. Rewoteric TEG (CAS®No. 70750-46-8) is a bis-hydroxyethyl glycinate that has tallow as the source for the alkyl chain. Rewoteric TEG was obtained as a sample from the Sherex Chemical Company, Dublin, Ohio. The source of the tallow used to manufacture Rewoteric TEG is not known. Crosultaine E-30 (no CAS®No. given) is a sulfobetaine that uses a hydroxypropyl bridge and rapeseed oil as the source for the alkyl chain, in combination with an amidopropyl linkage. Crosultaine E-30 was obtained as a sample from Croda, Inc., Parsippany, N.J. Rapeseed oil derived from *Brassica campestris* is a complex mixture of fatty acids, but is composed primarily of erucic (50%), oleic (32%) and linoleic acid (15%) (the oil composition was compiled from CRC Handbook of Chemistry and Physics, 55th ed. CRC Press, Cleveland, Ohio (1974) pp.D-192–193). Erucic acid, or cis-13-docosenoic acid, has an unsaturated-$C_{20}$ chain with the structure: $CH_3(CH_2)_7CH{=}CH(CH_2)_{11}COOH$.

Initially, Hetaine CLA, Crosultaine T-30, and Crosultaine E-30 all precipitated upon addition to the $NaHPO_4$ (final concentration: 2 mM detergent). Therefore, the conditions were changed and 50 mM Tris-HCl pH8.0 was used instead. Two mM SB-18 was used as the positive control (in the typical 10 mM $NaHPO_4$, pH8.0, 15 mM NaCl buffer), and water was used as the negative control. Detergent wash buffers contained 50 mM Tris-HCl pH8.0, with the exception of the water control. Four replicate tubes were prepared for each series. Chembetaine S and Rewoteric TEG were added to the respective wash buffers to a final concentration of 2 mM, and Hetaine CLA, Crosultaine T-30 and Crosultaine E-30 were brought to a final concentration of 200 µM. In the Tris buffer, Hetaine CLA and Crosultaine E-30 appeared turbid, whereas Crosultaine T-30 remained clear. Crosultaine T-30, however, precipitated upon final centrifugation in one of the experiments (not shown). All tubes were inoculated with 20µl of an *M. tuberculosis* bacterial stock. All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

The betaines presented in FIGS. 9C and 9D were selected to examine the effect of mixtures of alkyl moieties, complex alkyl structures, different charge combinations and different linkages with respect to efficacy in the methods of the invention. As concluded with FIG. 9B, modifications to alkyl structure have very little impact with respect to the methods of the invention, insofar as these structures permit micelle formation under the prevailing system parameters. In other words, if the combination of charges, bridge structure and alkyl are such that micelle formation can occur, then the betaines will enhance the recovery of Mycobacteria by centrifugation. Tallow, coconut, babassu, soybean, rapeseed, and wheat germ oils provide a wide spectrum of complex mixtures of saturated and unsaturated alkyl chains, and castor oil utilizes a hydroxylated alkyl. Excluding Rewoteric TEG, the hydrophobic moieties are linked to the quarternary nitrogen via an amidopropyl group, and as a group, these structures are used in conjunction with a either the carboxymethyl- or the hydroxypropylsulfo- moiety. Based on information concerning bridge structure relative to betaine performance, the methylene bridge and hydroxypropyl bridge both reduce the ability to utilize longer alkyl chains in the assay described here. This reduced solubility, however, is overcome to some degree by the use of the amidopropyl linkage.

Figure 9C:
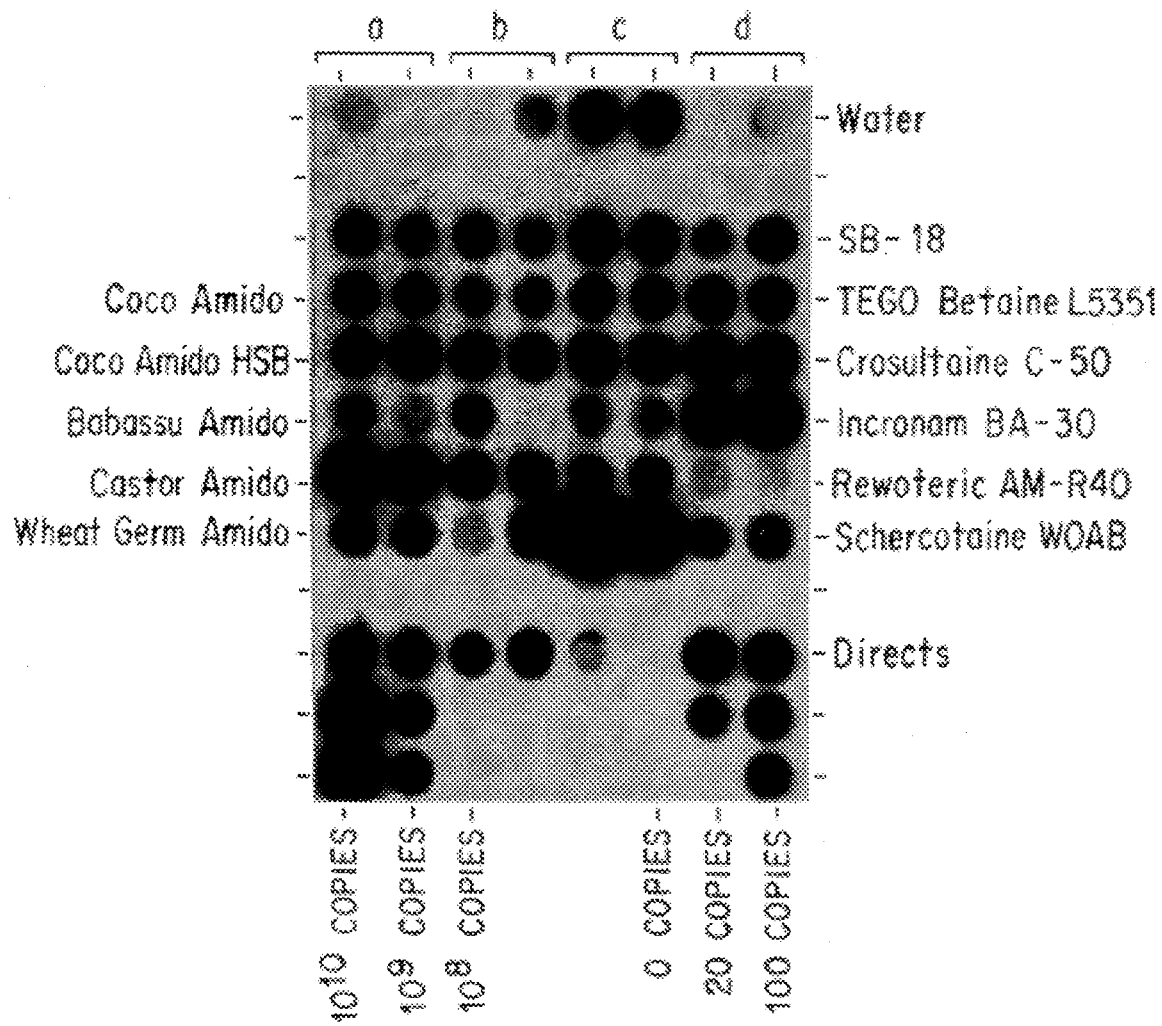
FIG. 9C shows the dot blot results of in vitro processing of Mycobacterium tuberculosis when betaines, which have their hydrophobic domains derived exclusively from natural oils, are used in the extraction solution.

Both TEGO Betaine L5351 and Crosultaine C-50 produced more uniform results in this experiment than was typically seen (FIG. 9C). Incronam BA-30, another oil consisting of primarily short chains, produced an amplification pattern more characteristic of clumping, but still displayed SB-18-like activity with respect to improving recovery in general (FIG. 9C). The results shown here with Rewoteric AM-R40 and Schercotaine WOAB were fairly typical: the amplification pattern due to clumping was observed here as well (FIG. 9C). Another detergent, which were primarily octadecyl and which typically showed more clumping than expected, was Chembetaine S. A priori one would expect the octadecyl detergents to behave similarly. For example, SB-18, $C_{18}$-carboxyethylbetaine and $C_{18}$-sulfobutylbetaine (FIG. 9A), Velvetex OLB-50 and Schercotaine IAB (FIG. 9B), Rewoteric AM-R40 and Schercotaine WOAB (FIG. 9C), and Chembetaine S, Crosultaine T-30, Rewoteric TEG and Crosultaine E-30 (FIG. 9D), are all composed primarily of saturated or unsaturated octadecyl-like chains. Whereas all worked better than the shorter chains in improving the efficiency of collection, they varied with respect to alleviating clumping. Perhaps increasing the complexity of the detergents by using the mixtures of various chain lengths, or including double bonds or other functionalities such as hydroxyl groups, compromises the ability to solubilize the mycolic acids and lipids associated with cording. Alternatively, many of these commercial preparations are unpurified, and perhaps this factor affected the overall efficacy.

Figure 9D:
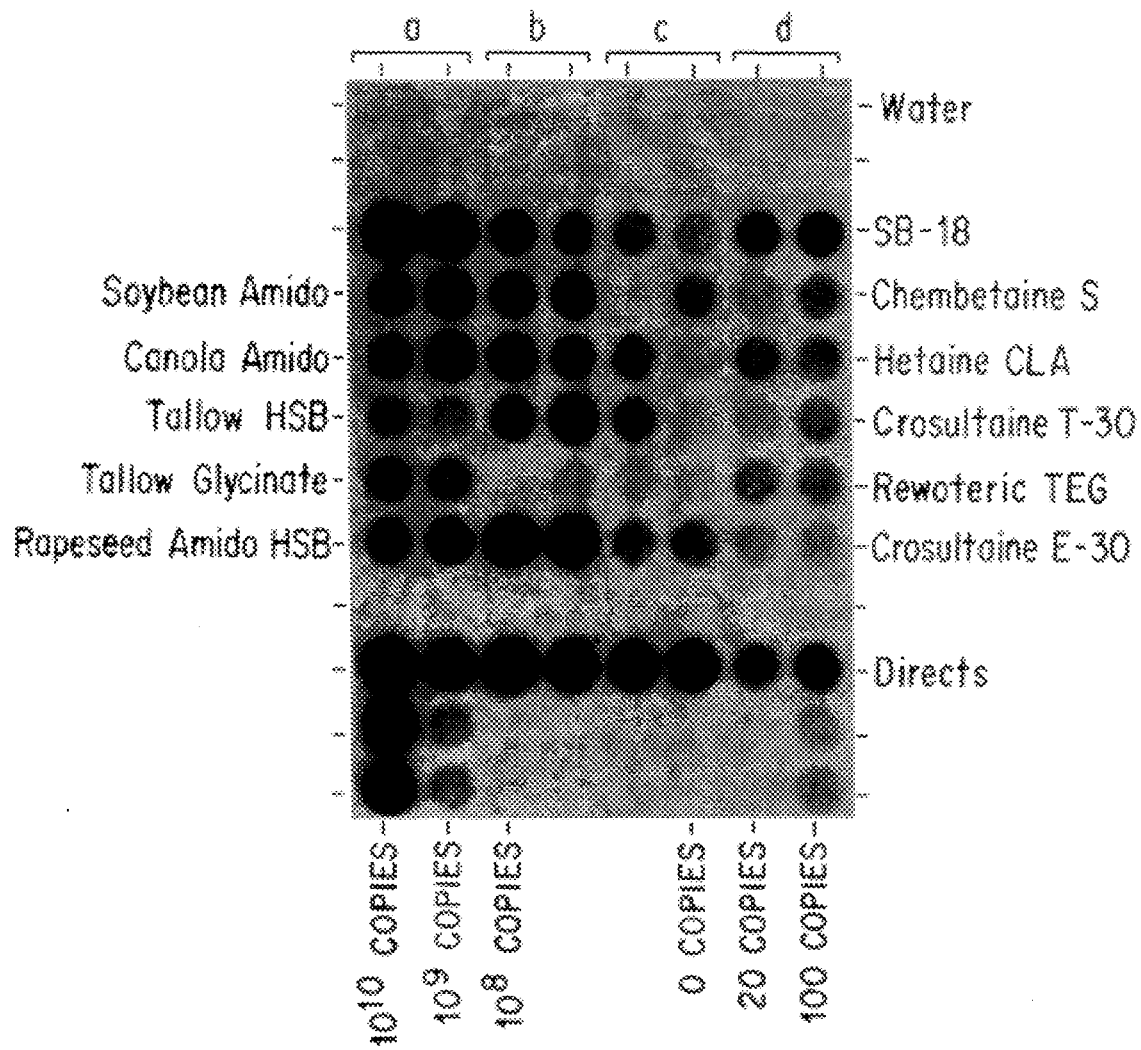
FIG. 9D shows the dot blot results of in vitro processing of Mycobacterium tuberculosis when betaines, which have their hydrophobic domains derived exclusively from natural oils, are used in the extraction solution.

Perhaps the most interesting combinations tested in FIGS. 9C and 9D were those provided by Hetaine CLA, Crosultaine T-30, and Crosultaine E-30. If by "canola oil," the manufacturer of Hetaine CLA means corn oil, then corn oil derived from *Zea mays* is a complex mixture of fatty acids, but is composed primarily of oleic (49.6%), linoleic (34.3%) and palmitic (10.2%) acids (the oil composition was compiled from the CRC Handbook of Chemistry and Physics, 55th ed. CRC Press, Cleveland, Ohio (1974) pp.D-192–193). The fact that Velvetex OLB-50 (oleyl carboxymethylbetaine) functioned without problem suggests that the alkyl mixture of Hetaine CLA, which is very viscous, is something different, possibly involving groups that accentuate nonionic character (e.g., hydroxypropyl sulfobetaine). The fact that Crosultaine T-30 presented minor solubility problems, while Rewoteric TEG functioned without incident (e.g., they both use tallow), speaks to the nature of both the solubility of the anion (—COO$^\ominus$ vs. —SO$_3^\ominus$), and the hydroxylation of the bridge. Crosultaine E-30 is perhaps one of the most extreme betaines: it is composed primarily of unsaturated $C_{20}$ and $C_{18}$ moieties, and it utilizes a hydroxypropyl bridge with a sulfonate anion (—SO$_3^\ominus$).

The most interesting aspect of FIG. 9D, however, was the presentation of what appeared to be a turbid solution (e.g., a cloud point) with both Hetaine CLA and Crosultaine E-30. Contrary to $C_{16}$-hydroxypropyl sulfobetaine (FIG. 9A), both of these betaines functioned in the methods of the invention. These results are not paradoxical. To the contrary, the cloud point is thought to be caused by dehydration of the hydrophilic portion of the nonionic detergent, and since the cloud point, in contrast to the Krafft temperature, is not a well defined temperature, micelles can still exist when turbidity is observed. In general, at the onset of turbidity micellar weight and aggregation number gradually increase with increasing temperature, and as the temperature is increased further, phase separation eventually occurs (Nakagawa, T. et al., In: *Colloidal Surfactants*, Academic Press, New York (1963) pp. 121–135). Hence, since Hetaine CLA and Crosultaine E-30 did not undergo phase separation they would be expected to function in the processing assay.

Nilsson, P. et al., *J. Phys. Chem.* 88:6357–6362 (1984) have observed cloud points in sulfobetaines, and Faulkner, P. G. et al., *Langmuir* 5:924–926 (1989) described the changes that take place upon hydroxylation of the bridge in sulfobetaines. The interesting aspect of these results is that one betaine, $C_{16}$-hydroxypropyl sulfobetaine, behaved as an ionic detergent and was salted-out in phosphate buffer; whereas a different, but very closely related betaine, Crosultaine E-30 (a $C_{20:1}$—, $C_{18}$—& $C_{18:2}$-amidopropyl hydroxypropyl sulfobetaine), behaved as a nonionic detergent and became turbid (for the purpose of this discussion, the structure of Hetaine CLA is unknown). In addition to suggesting several very interesting aspects of betaine structure relative to the interaction the amidopropyl linkage, the hydroxypropyl bridge, and alkyl chain length, these observations suggest predictable responses with respect to the addition of electrolytes. For example, the solubility of hydroxypropyl sulfobetaine should improve with a different ion (e.g., potassium iodide (KI) as opposed to NaHPO$_4$), owing to the Krafft point elevation effect (Tsujii, K. et al. *J. Phys. Chem.* 82:1610–1614 (1978); Tsujii, K. et al., *Yukagaku* 30:495–499 (1981)), while addition of the same ion would be expected to exacerbate the cloud point of Hetaine CLA and Crosultaine E-30 (Schott, H. et al., *J. Pharm. Sci.* 64:658–664 (1975); Schott, H. et al., *Pharm. Sci.* 65:979–981 (1976)). In fact, as predicted, addition of 100 mM KI provided a clear solution of $C_{16}$-hydroxypropyl sulfobetaine, but caused a worsening of the turbidity with Crosultaine E-30 and Hetaine HLA. Therefore, utilization of the latter two would require minimizing the salt concentration. In general, it would appear that the amidopropyl function enhances nonionic character. For example, the amidopropyl moiety increases the overall headgroup by augmenting the hydrophylic portion of the detergent, similar to increasing the number of polyoxyethylene groups as discussed by Hsiao, L. et at., *J. Phys. Chem.* 60:657–660 (1956).

One of the major problems with using the commercial samples provided here, however, are their respective purifies. For example, SB-18 (Sigma, St. Louis, Mo.) is provided as a purified inner salt, which is stated to be 98% pure. Incronam B-40, Hetaine CLA, Crosultaine T-30, and Crosultaine E-30 are all provided as crude mixtures of reaction products. The percent active material stated by the manufacturer for each of these materials is: 44%–48%; 38%–42%; 30%–34%; and 30%–34 9, respectively. In addition, the salt (NaCl) content of each is stated to be: 4.2%–4.6%; 5%; 2.4%–4.0%; and 2.5%–4.0%, respectively. Attempting to generate a 2 mM solution of any one of these detergents would, by default, also produce a solution 3–4 mM in NaCl that, in some instances, would create a solution that is unusable.

FIG. 10 examines different assay parameters, as modified to facilitate the utilization of the $C_{16}$-hydroxypropyl sulfobetaine, Incronam B-40, Hetaine CLA, Crosultaine T-30, and Crosultaine E-30. Assay conditions were modified as follows: The $C_{16}$-hydroxypropyl sulfobetaine and Crosultaine T-30 buffer consisted of 10 mM Tris-HCl pH 8.0 and 50 mM KI. Each was a clear solution at 2 mM detergent. The Incronam B-40, Hetaine CLA, and Crosultaine E-30 buffer was simply 200 μM Tris-HCl pH 8.0. Each detergent was a clear solution at 200 μM. Each buffer was also equilibrated to 37° C. The SB-18 control used the 10 mM Tris-HCl pH 8.0 and 50 mM KI buffer. Four replicate tubes were manufactured for each series. All tubes were inoculated with 20 μl of an *M. tuberculosis* bacterial stock. All tubes were then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

While Hetaine CLA, Crosultaine T-30, and Crosultaine E-30 were shown to function under the original condition (FIG. 9D), Incronam B-40 and $C_{16}$hydroxypropyl sulfobetaine were severely compromised with respect to function. What this experiment shows is that, based on the physical nature of the betaines, predictable modifications to assay conditions can be implemented to permit the utilization of a compound that would not otherwise function. In addition, this experiment shows the importance of functional presentation of the detergent (e. g., in a micellar phase).

Conclusion

Whereas $C_{12}$–$C_{16}$ alkyl chains permit improvements in the isolation of all Mycobacteria, the $C_{18}$–$C_{22}$ alkyl chains also permit disruption of cording Mycobacteria. A dimethyl, quaternary nitrogen, in combination with a carboxyl anion ($—COO^{\ominus}$) yields the highest degree of solubility in an economically efficient manner. The most preferred bridge structure is a straight chain alkyl (e.g., no modifications), with a minimum of three carbon atoms (e.g., propyl bridge). While the effect of the amidopropyl linkage is difficult to discern, for simplicity, the linkage would need only be an extension of the hydrophobic domain. $C_{18}$-carboxypropylbetaine (CAS®No. 78195-27-4) combines the optimal characteristics of solubility, bridge structure, and ionic character, while still being relatively simple to synthesize (JP Appl. No. 79100920[54-100920]; JP 8125139).

For the $C_{18}$-carboxypropylbetaine (CAS®No. 78195-27-4) used herein, the following procedure (communicated by Dr. Lafayette D. Foland at the Clorox Technical Center, Pleasanton, Calif.) was used to prepare the compound:

(1) Add 1 equivalent (0.1 mole or 29.7 grams) of N,N-dimethyloctadecylamine (297 grams/mole: GAS®No. 124-28-7) to 1.1 equivalents (0.11 moles or 19.9 grams) of bromobutyric acid ethyl ester (195 grams/mole: CAS®No. 2969-81-5) under argon to form a neat solution.

(2) Place the flask in an oil bath at 50° C.–60° C. and stir the solution (under argon) overnight. Large, white chunks will form. [Note: this is a fairly exothermic reaction. When scaling this reaction up, it is important to monitor the temperature so as not to burn up the intermediate product.]

(3) Add 600 mls of isopropyl alcohol directly to the reaction products and immediately add 150 grams of the activated anion exchange resin AG 1-X8 (Bio-Rad No. 140–1422), or an equivalent anion exchange resin, such as Amberlite IRA-400OH (Sigma IRA-440C) with a hydroxide counterion to the flask and stir the suspension overnight. [Note: Activate (or reactivate) the anion exchange resin by mixing 150 grams of the resin with 1 liter of 5% NaOH. Wash the resin in a column with 5 liters of distilled water prior to use. The amount of resin can be reduced substantially and this can be determined using routine methods.]

(4) Remove the anion exchange resin by filtration.

(5) Remove the solvent on a Rotovap and place the resulting solid on a high vacuum line overnight.

(6) Recrystallize the material twice as follows:

Place the dried betaine in 400 mls of ether and bring to a boil. Titrate methanol into the flask until the material is just dissolved. Cool the flask to room temperature (a white crystal will begin to form almost immediately). Place the flask at 0°–4° C. overnight. Remove the crystallized material by filtration and place on a high vacuum line overnight. [Note: The material released from the anion exchange resin is fairly pure, and if 95% purity is acceptable, then only one recrystallization, or possibly no recrystallization, would be necessary. Note also, that a diprotic apolar solvent could be substituted for the ether.]

This procedure will yield approximately 20 grams of purified $C_{18}$-carboxypropylbetaine (approximately 50% yield). N,N-dimethyloctadecylamine is available from AKZO, Inc. (No. Armeen DM18D), American Tokyo Kasei, Inc. (No. D1609) and Pfaltz & Bauer, Inc. (No. D42680). Bromobutyric acid methyl ester is available from Aldrich (No. 16,711-8) and Fluka (No. 16540). Note that bromobutyric acid ethyl ester can be used in place of the iodobutyric acid methyl ester used in the Kazuo (JP 8125139) patent; similarly, Ambefiite IRA-400OH anion exchange from Sigma may be used in place of AG 1-X8 from Bio-Rad. The intermediate product, having 412 grams/mole, would have 2.4 mmoles/gram. The Ambefiite resin has a 4 meq/gram capacity according to the Sigma catalog. A single recrystallation to reduce the salt concentration is generally sufficient.

Note that $C_{18}$-carboxypropylbetaine (CAS®No. 78195-27-4) is extremely bacteriostatic and concentrations of this compound in the assays of the invention that are greater than 2 mM may result in an undesired lysis of the bacteria.

The important aspects of assay conditions, therefore, are temperature, pH, ionic strength and specific electrolyte. For example, a pH above 5.0, but below 9.0, would, in general, be absolutely required for many betaines to maintain the zwitterion. The processing temperature must be maintained above the Krafft temperature of the specific SB-18-like detergent being used. For example, the processing temperature for SB-18 must be kept at or above 37° C. (Tsujii, K. et al., *J. Phys. Chem.* 82:1610–1614 (1978)), whereas the processing temperature of $C_{18}$-carboxypropylbetaine (CAS®No. 78195-27-4) must be maintained at a temperature of only 25 ° C. (Tsujii, K. et al., *Yukakagu* 30:495–499 (1981)). Ionic strength is interrelated with the ion used. For example, in order to maximize salting-in with sodium chloride, a higher concentration is required than when using a salt such as potassium iodide.

When considering the option of PCR amplification as a method of detection, potassium chloride, although not ideal, is satisfactory and produces the necessary effect at useful concentrations relative to the amplification reaction conditions.

The results indicate that a logical combination of betaine structure and assay design choices are possible, acid can be optimized as desired by the artisan. SB-18 is the most effective betaine that is currently readily available commercially in a purified form, although, as noted earlier, betaines such as $C_{18}$-carboxypropylbetaine (CAS®No. 78195-27-4) are easily synthesized in the laboratory or by a custom synthesis commercial provider.

Figure 7:
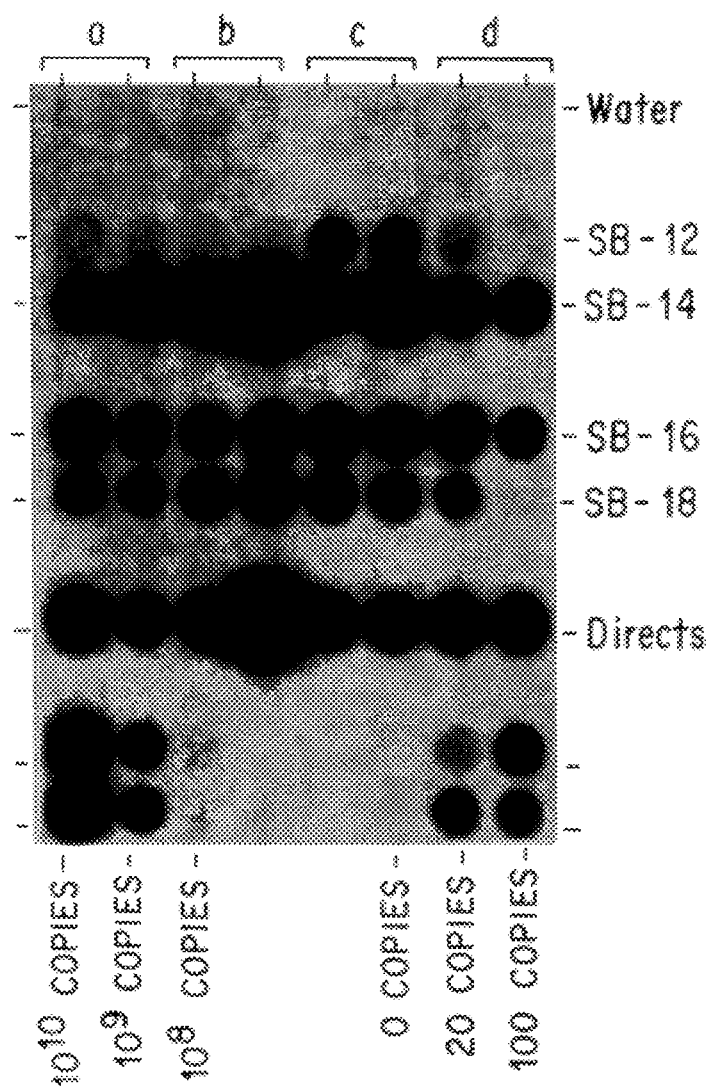
FIG. 7 shows the dot blot results of in vitro processing of Mycobacterium tuberculosis when different SB-series detergents are used in the extraction solution.
Figure 7A:
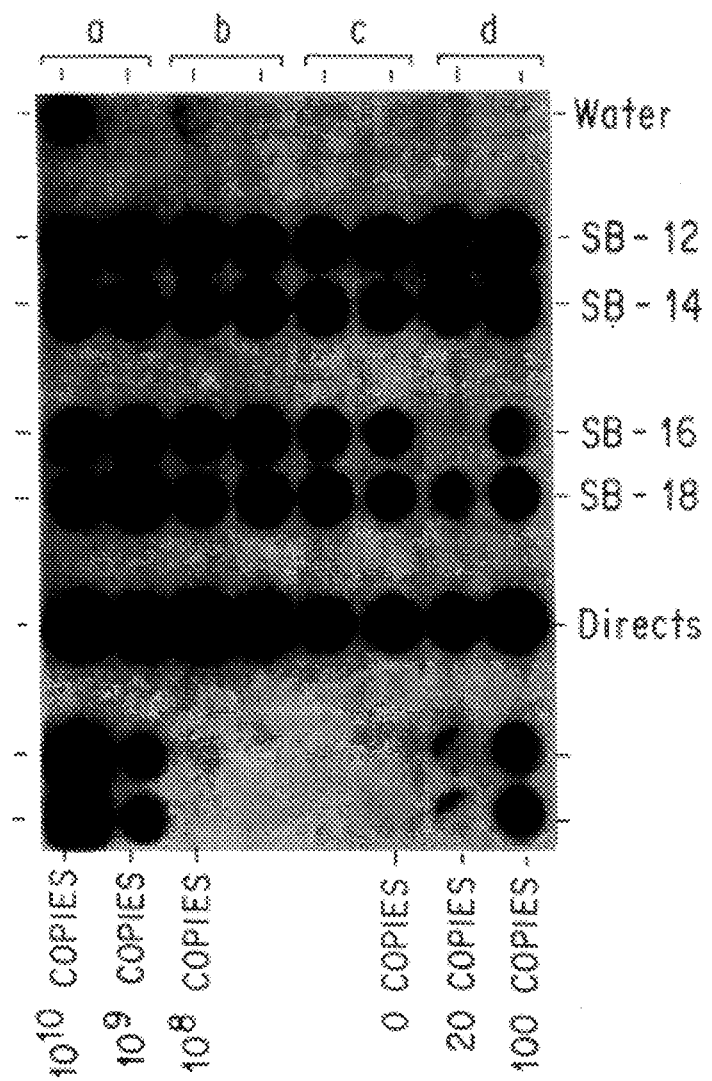
FIG. 7A shows the dot blot results of in vitro processing of Mycobacterium avium when different SB-series detergents are used in the extraction solution.
Figure 8:
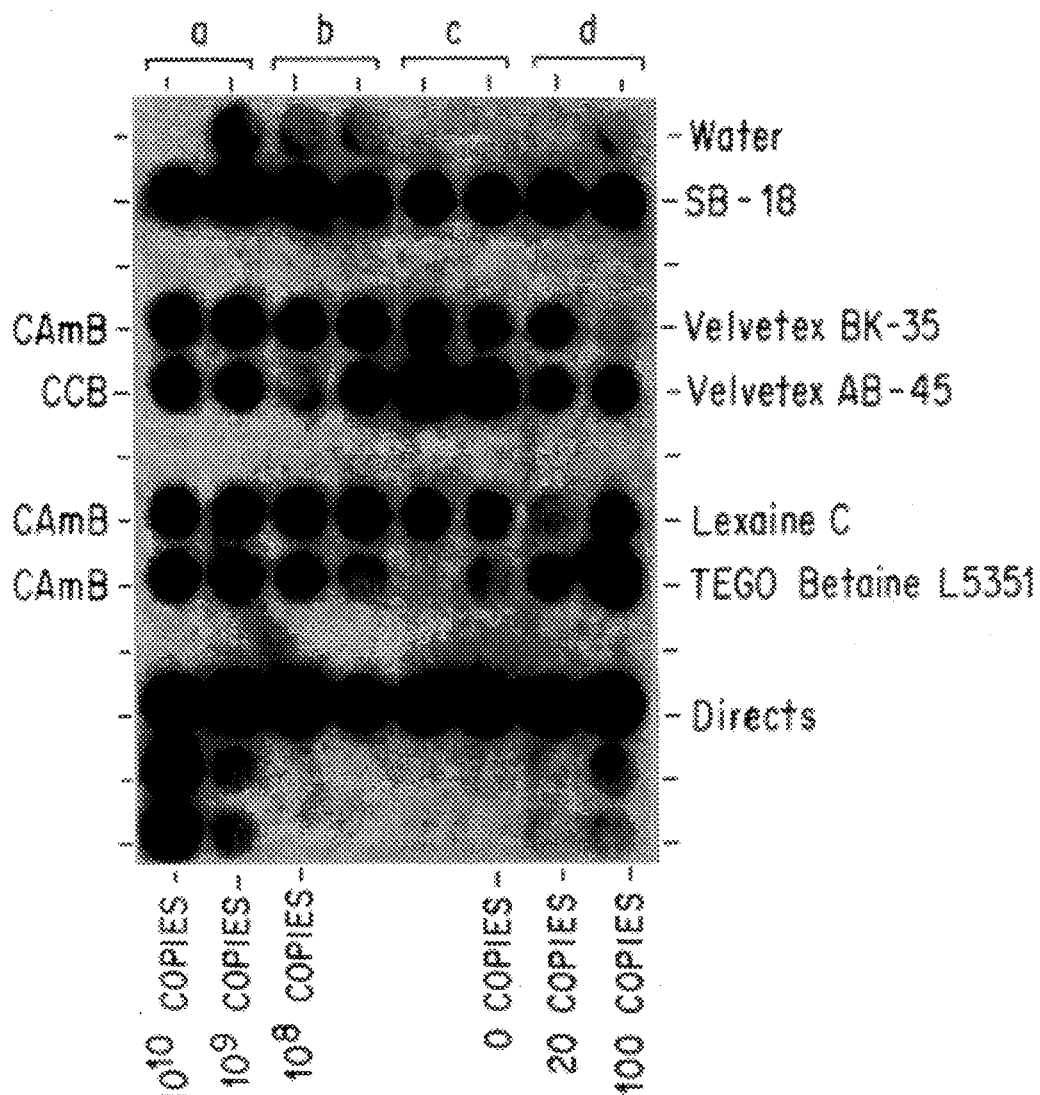
FIG. 8 shows the dot blot results of in vitro processing of Mycobacterium tuberculosis when cococarboxybetaines (e.g., SB-18-like detergents) are used in the extraction solution.

The accumulated data of FIGS. 6, 7 and 7A, 8, 9 through 9D, and FIG. 10 show: (1) that SB-18 is unique among the listed homologous ionic detergents in that it facilitates dispersion of Mycobacteria and collection of the same by centrifugation (FIG. 6); (2) that the sulfopropylbetaine series all have some degree of efficacy in facilitating recovery of both classes of Mycobacteria (FIGS. 7 and 7A); (3) that a wide variety of homologous "betaine-like" detergents display "SB-18-like activity" in the methods of the invention, and that these characteristics follow predictable behavior patterns (FIGS. 8, 9, 9A, 9B, 9C, and 9D); and (4) that by modifying system parameters, based on an understanding of the behavior of this class of molecules, betaines that would not otherwise function in the methods of the invention can be provided in a manner that allows them to display SB-18-like activity (FIG. 10).

In conclusion, the polarity of the dipole moment created by the separation of charges promotes functional presentation of a detergent molecule in a clinical assay. More importantly, with respect to the dispersion of cording Mycobacteria, the dipole created allows longer chain alkyl moieties to be used in aqueous, electrolyte containing solutions. The consequence of this is the ability to utilize detergents that have superior solubilization capacities under reaction conditions that are commonplace in the clinical laboratory. As previously stated, however, the ability to disperse these organisms does not fully explain the ability of shorter chain molecules to facilitate the collection of organisms that do not clump. The other half of the answer will be better understood following the next Example.

Example 10

Degassing M. tuberculosis and M. avium

Arguably, the hydrophobic nature of the cell wall of this class of organisms is directly responsible for pellicular growth. Numerous publications reference Dubos, R. J. *Exp. Bid. Med.* 58:361–362 (1945) and state that Tween 80 permits "rapid," "diffuse," and "submerged growth" as a result of "wetting." The results of FIGS. 4A and Table 6, however, suggest that, regardless whether surface tension and clumping are directly related to pellicle growth, the fact is that the mechanisms by which Tween 80 relieves these phenomena are different from that of SB-18. Since *M. avium* grows in a more diffuse fashion, and shows minimal clumping, it is expected that MTB would be more dramatically affected by the experiment described in FIG. 5. Again, the implication is that Tween 80 must be acting in vivo to elicit submerged growth. Regardless, it would seem logical that, in the absence of surface tension, the essence of submerged growth and buoyancy must in some way be intimately related.

Silverstolpe, L. *Nord. Med.* 40/48:2220–2222 (1948) determined that the range of specific gravity of the tubercle bacilli was from 1.07 to 0.79, with a mean slightly less than 1.00. Silverstolpe, L. *Nord. Med.* 40/48:2220–2222 (1948) concludes: "Bakteriernas jämförelsevis låga specifika vikt kan förklaras av deras fetthalt . . . ." Literally translated: "The comparatively low specific weight of the bacteria can be explained by their fat content . . . ." The notion that it is the actual quantity of lipid in the cell wall that is responsible for the low specific gravity is accepted in the art. In a popular 1973 microbiology text the authors state: ". . . The striking abundance of lipids in the cell wall (60% of the dry weight) accounts for the hydrophobic character of the organisms, which tend to adhere to each other during growth in aqueous media and to float at the surface . . . " (Davis, B. D. et al., *Microbiology*, Harper & Row, New York, 1973, p. 847). However, according to the invention, the lipid content is not ultimately responsible for the low specific gravity of the Mycobacteria.

Presumably, according to the art's line of reasoning, the partial specific volume of the lipids in the cell compensate for the partial specific volume of the remaining components to permit flotation. This suggests that, in the absence of surface tension, the additional lipid component in the cell wall of *M. avium* is directly responsible for its enhanced difficulty of recovery during centrifugation (Table 1). While this seems plausible, Stinson, M. W. et al., *Am. Rev. Resp. Dis.* 104:717–727 (1971) showed that in glycerol containing, media lipids account for 17.7% of the dry weight of the cell, while in the presence of Tween 80, the lipid content increases to 34.1%. Since Tween 80 permits submerged growth, this hypothesis cannot be a rational explanation for buoyancy: the lipid content has increased by almost two fold yet paradoxically the cells submerge.

Schaefer, W. B. et al., *J. Bacteriol.* 90:1438–1447 (1965) had shown this incongruity years earlier by publishing dramatic micrographs showing the production of lipoidal bodies in Mycobacteria in the presence of either oleic-BSA or Tween 80-BSA containing media. Weir, M. P. et al., *Amer. Rev. Res. Dis.* 106:450–457 (1972) and McCarthy, C. *Infect. Immun.* 4:199–204 (1971) have also characterized the rapid uptake of oleic acid under culture conditions. It appears that the evidence necessary to support the hypothesis that there is a relationship between buoyancy and total lipid content is lacking. In fact, one would be led to objectively conclude from the comparison of these findings that perhaps the accumulation of lipids is facilitating submerged growth to some degree.

The above commentary leads one to conjecture that submerged growth in the presence of Tween 80 (CAS®No. 9005-65-6) must result from some other change in cell structure. The report of Yamori, S. et al, *Microbiol. Immunol.* 35:921–926 (1991) confirms that upon the addition of OADC (oleic acid, BSA, dextrose, catalase, and NaCl) to Tween 80 containing media, significant cell wall changes are taking place. These authors conclude that drug sensitivities change as a result of the cell wall changing (e.g., the cell wall becomes more permeable). In addition, Rastogi, N. et al., *Antimicrob. Agents Chemother.* 20:666–677 (1981) had shown a decade earlier that the cell wall thins significantly when passaged in culture, and that further, in enriched media containing oleic, BSA & Tween 80, biochemical characteristics change as well. Taken together, these observations imply that, while surface tension may be involved in pellicle growth, neither surface tension nor lipid composition can fully explain "buoyancy" or "low-specific-gravity." Instead changes in cell wall structure must be responsible for submerged growth. Therefore, there must have been other possibilities, for example, (i) the process by which these lipids are inserted into the wall, (ii) the structures formed upon incorporation, or (iii) a combination of both.

In general, there are two ways that lipid can be responsible for growth that is confined to the surface. The first, as implied by Dubos, R. J. *Exp. Bid. Med.* 58:361–362 (1945), is surface tension. A second theory, which would stem from the work of Silverstolpe, L. *Nord. Med.* 40/48:2220–2222 (1948), relies on the "partial specific volume of lipids" of these organisms.

As described herein, according to the invention, it believed that the most efficient way for the Mycobacteria, which are obligate aerobes, to maintain buoyancy, in the absence of surface tension or partial specific lipid volumes, is by the trapping of gasses (e.g., $CO_2$) generated as a byproduct of cell wall construction. Approximately 80 $CO_2$ molecules are produced for each mycolic acid residue synthesized by the malonyl CoA pathway. The $CO_2$ production of an organism closely related to the Mycobacteria, *Propionibacterium shermanii*, produces the eyes (e.g., the holes) in Swiss cheese (Sherman, J. M. J. *Bacteriol.* 6:379–392 (1921)). At a molecular level the cell wall can simply be envisioned to have macromolecular pockets of $CO_2$ trapped within the labyrinthian network of solidified mycolic acids and glycolipids. Since the melting temperature of cord factor (6,6'-dimycolate of $\alpha,\alpha$-D-trehalose) is 43° C.–45° C. (Noll, H. et al., *Biochim. Biophys. Acta* 20:299–309 (1956)), the waxy consistency of the cell wall could act to trap macromolecular pockets of gas. It is believed that placing the buffer under vacuum causes dissolved $CO_2$ to be removed from the buffer such that a concentration gradient is created. This in turn allows the $CO_2$ trapped in the cell wall to dissolve into the buffer. This process is expected to be reasonably inefficient, and is expected to be even less efficient in the presence of cording.

Figure 11:
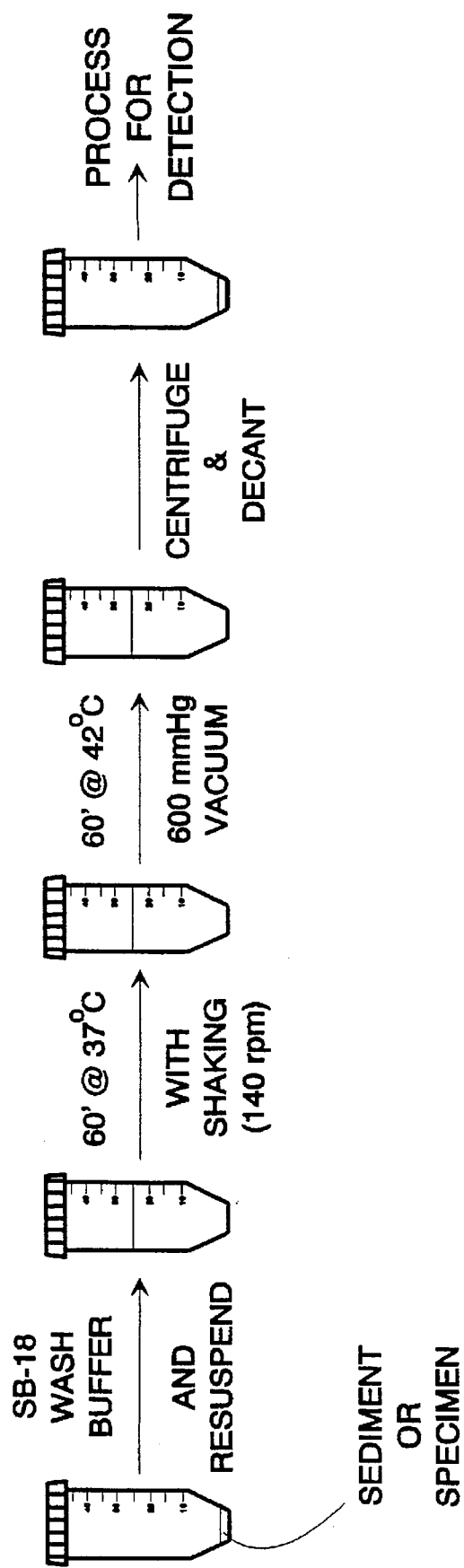
FIG. 11 is a schematic of the experimental protocol for studying the effect of vacuum pressure on in vitro processing.
Figure 11A:
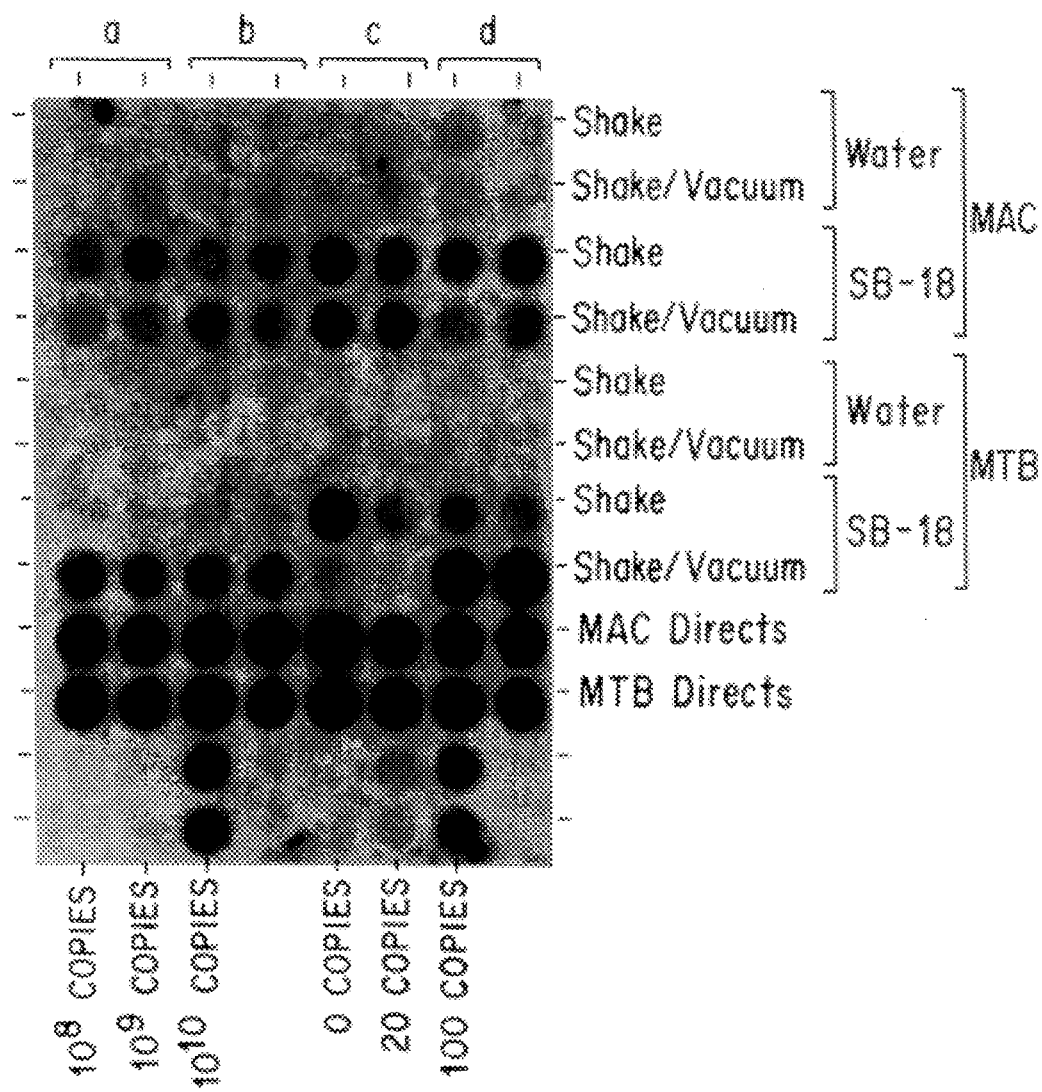
FIG. 11A shows the effect of vacuum pressure on in vitro processing for both Mycobacterium tuberculosis and Mycobacterium avium.

FIG. 11 shows the outline of the final configuration of the overall processing protocol. FIG. 11A shows the results of degassing in the presence and absence of SB-18 for both *M. tuberculosis* and *M. avium*.

For the data presented in FIG. 11A, the schematic shown in FIG. 2 was modified as described by FIG. 11. The wash buffer contained either water or 10 mM $NaHPO_4$, pH 7.0, 15 mM NaCl, 2 mM SB-18, 2 mM phenylalanine and 5 mM DTT. In addition, the tubes were first incubated at 37° C. for 60 minutes with shaking (140 rpm) and then either centrifuged directly or subjected to vacuum (600 mm Hg) for 60 minutes at 40° C. before centrifugation. Prior to degassing the caps were loosened. Both *M. avium* and *M. tuberculosis* were tested in this experiment. Duplicate amplifications of four aliquots are represented as a, b, c, and d, and should be identical. The duplicate amplifications of the direct aliquots, corresponding to a given species, are shown on the appropriately labeled line. Copy controls of 0, 20 and 100 copies were amplified simultaneously. Hybridization controls of $10^8$, $10^9$ and $10^{10}$ copies were blotted as well.

Clearly, both surface tension and buoyancy play significant roles in explaining the behavior of these organisms during processing for amplification. Even in the absence of any added detergent there is generally a greater recovery when the organisms are subjected to vacuum (see MAC recovery in water with vacuum degassing in the absence of added detergent.) Numerous experiments have led to the conclusion that while both surface tension and trapped gas are involved in both *M. tuberculosis* and *M. avium*, the dominant feature of *M. tuberculosis* is surface tension, and the dominant characteristic in *M. avium* is trapped gas. That is to say, that while SB-18 improves the recovery of both classes of Mycobacteria, MTB is more dramatically affected by the detergent, while MAC is affected by degassing to a greater extent than MTB. In addition, degassing MTB under these conditions is probably more effective due to the fact that SB-18 disperses the organisms.

Figure 12:
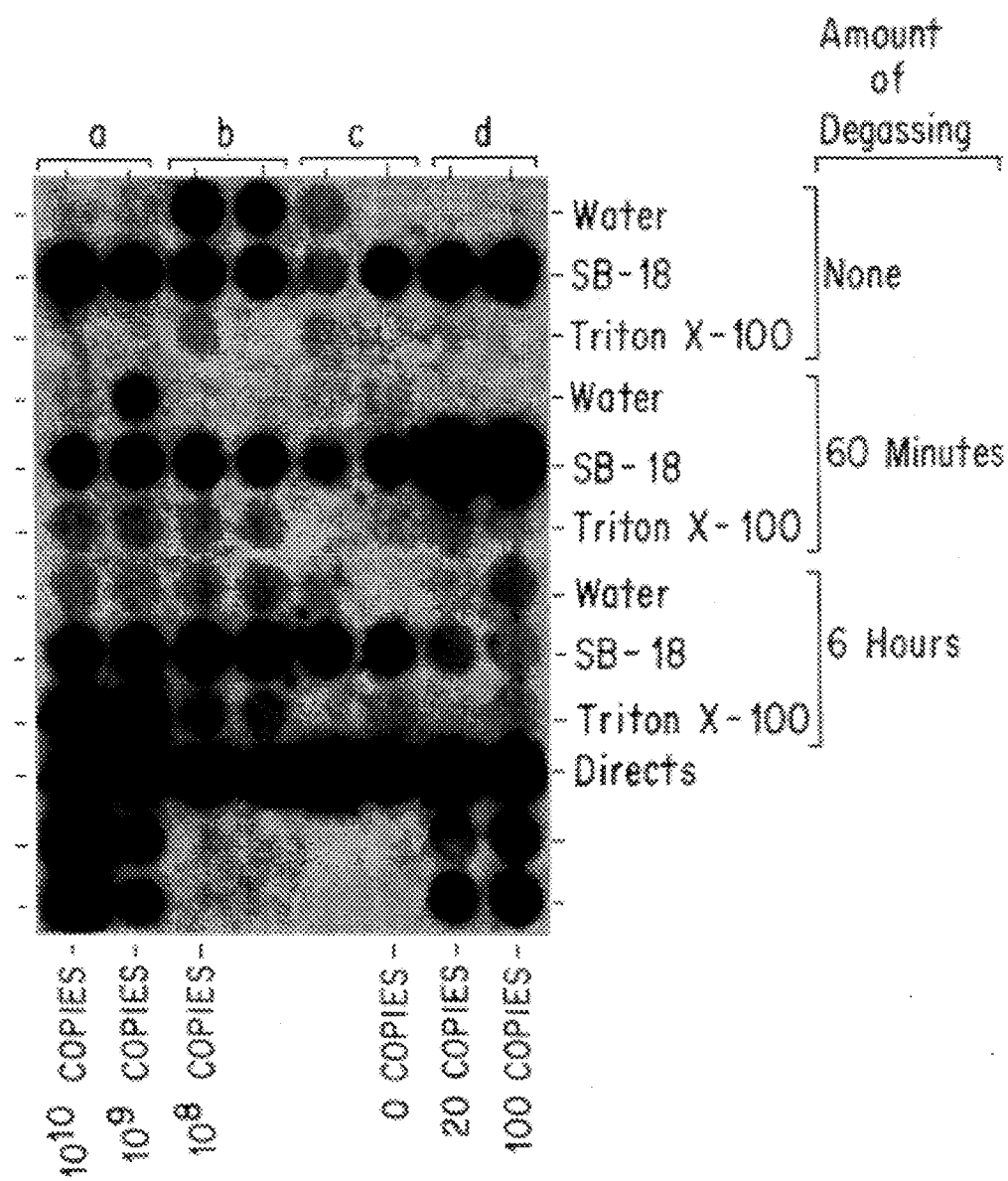
FIG. 12 shows that extended degassing of Mycobacterium tuberculosis is required to permit Triton X-100 to improve the efficacy of recovery during in vitro processing.

If the trapped gas hypothesis is correct, then extended degassing should permit literally any detergent to improve the recovery of *M. tuberculosis*. For example, since the problems surrounding MTB false negatives involve clumping, surface tension and buoyancy, if buoyancy could be compensated to some degree by degassing, then only clumping and surface tension would remain. Since most detergents, given the appropriate concentration, can overcome surface tension, only sample bias would remain. FIG. 12 examines this.

For the data presented in FIG. 12, the schematic shown in FIG. 2 was again used as described by FIG. 11. The wash buffer contained either water, or 0.1% Triton X-100 (CAS®No. 9002-93-1) in 10 mM Tris-HCl, pH 8.0, or 10 mM $NaHPO_4$, pH 7.0, 15 mM NaCl, 2 mM SB-18 (CAS®No. 3177-41-8), and 5 mM DTT. In addition, three sets of tubes for each condition were generated. Following inoculation, all tubes were first incubated at 37° C. for 60 minutes with shaking (140 rpm). One set of tubes was centrifuged directly while the remaining two sets for each of the three conditions was subjected to vacuum (600 mm Hg). One set of tubes was subjected to vacuum for only 60 minutes at 40° C. before centrifugation, and the final set of tubes was subjected to vacuum for 6 hours at 40° C. before centrifugation (prior to degassing the caps were loosened). Only *M. tuberculosis* was tested in this experiment. Duplicate amplifications of four aliquots are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$ and $10^{10}$ copies were blotted as well.

Clearly, extended degassing improves the ability to recover these organisms by centrifugation. Inclusion of any detergent under these conditions, while not disrupting cord formation, alleviates surface tension to a degree such that collection by centrifugation is enhanced. It should be noted that degassing is expected to be more efficient in the presence of those detergents that disrupt cord formation.

Other Detergents with SB-18-like activity

The following studies examined whether other detergents, analogous to the betaines, present themselves to the cell in such a way that they are sequestered within the cell, and in doing so alter the partial specific volume of the cell to partially counteract the natural buoyancy of these organisms, thereby enhancing recovery by centrifugation.

For example, assuming that the passage of betaines across the outer membrane uses the hydrophilic pathway (Connell, N. D. et al., In: *Tuberculosis: Pathogenesis, Protection, and Control*, B. R. Bloom, ed., American Society for Microbiology, Washington, D.C. (1994) pp.333–352), and passage across the inner membrane uses the lipid transporter (Schaefer, W. B. et al., *J. Bacteriol.* 90:1438–1447 (1965); Weir, M. P. et al., *Amer. Rev. Res. Dis.* 106:450–457 (1972) and McCarthy, C. *Infect. Immun.* 4:199–204 (1971)) then one could presumably use a class of nonionic detergents with similar characteristics, for example, an approximately-octadecyl detergent that minimized headgroup volume. While the headgroup of Tween 80 is too bulky to pass through the porin, other detergents, such as the linear polyoxyethylene ethers of fatty acids (e.g., the "Brij" compounds) might present themselves in a manner that permits passage into the cells and that permits function in the methods of the invention.

Hsiao, L. et al., *J. Phys. Chem.* 60:657–660 (1956) show that the area per molecule of polyoxyethylene phenyl ethers is on the same order as that of the betaines (e.g., $C_9$- with an average of 9.5 POE units would have and area of 55 $Å^2$.) FIG. 13 compares SB-18 with Brij 96 (oleyl-polyoxyethylene ether ($C_{18:1}E_{10}$)) and Tween 80 (oleyl polyoxyethylene sorbitan (n=20)) in the processing assay.

The experiment of FIG. 13 follows the processing assay outlined in FIG. 2, and utilizes 2 mM SB-18, 1% Brij 96

(CAS®No. 9004-98-2) and 1% Tween 80 (CAS®No. 9005-65-6) in 10 mM NaHPO4 pH 8.0, 15 mM NaCl. Water was used as the negative control. Four replicate tubes were prepared for each series. All tubes were inoculated with 20 μl of an *M. tuberculosis* bacterial stock, and then incubated at 37° C. for 60 minutes with shaking (140 rpm) prior to centrifugation. Duplicate amplifications of the four replicates for each detergent series are represented as a, b, c, and d, and should be identical. The duplicate amplifications of the direct aliquots are shown on the appropriately labeled line. Copy controls of 0, 20 and 100 copies were amplified simultaneously. Hybridization controls of $10^8$, $10^9$, and $10^{10}$ copies were blotted as well.

Utilization of Brij 96 in numerous experiments similar to that presented in FIG. 13 showed comparable results. Brij 96 displays SB-18-like activity with respect to compensating buoyancy, however, as expected, Brij 96 has a limited capacity with respect to dispersion of *M. tuberculosis*. Regardless, the results of Tween 80 presented here (FIG. 13) agree with the results of FIG. 4A: Tween 80 neither improves recovery of, nor disperses these organisms. In support of the hypothesis that Brij 96 can enter the cell, Dubos, R. J. et at., *J. Exptl. Med.* 83:409-423 (1946) has shown that homologues of Brij 96 can be used to stimulate growth in culture. Unfortunately, Dubos reported that these compounds were seen to form precipitates in the presence of serum and other proteins. The utility of precipitating proteins using linear polymers of polyoxyethylene has been known for some time (see: Yamamoto, K. R. et al., *Virology* 40:734 (1970) as one example). This would limit the usefulness of these detergents for the processing of clinical specimens.

Further problems with using these nonionic detergents are that they have a very narrow range within which to operate. For example, based on the observations here, longer alkyl chains are preferred, longer alkyl chains have reduced solubilities. Brij 96 has a Krafft point below 2° C. and a cloud point of 54° C., whereas Brij 76 (stearyl-polyoxyethylene ether ($C_{18}E_{10}$): CAS®No. 9005-00-9), has a Krafft point of approximately 46° C. and a cloud point of 64° C. (Schott, H. et al., *J. Pharm. Sci.* 64:658-664 (1975); Schott, H. et al., *J. Pharm. Sci.* 65:979-981 (1976)). Brij 72 (stearyl-polyoxyethylene ether ($C_{18}E_2$): CAS®No. 9005-00-9) and Brij 92 (oleyl-polyoxyethylene ether ($C_{18:1}E_2$): CAS®No. 9004-98-2)) are both insoluble under these assay conditions. Increasing solubility requires increasing the number of POE units. As the number of POE units increases, so does the headgroup area (Hsiao, L. et al., *J. Phys. Chem.* 60:657-660 (1956)).

In addition, within this narrow range, nonionic detergents behave unusually. For example, Schott, H. et al., *J. Pharm. Sci.* 65:979-981 (1976) show that some sodium and potassium nitrate salts can cause the cloud point and Krafft temperature of Brij 56 (cetyl-polyoxyethylene ether ($C_{16}E_{10}$): CAS®No. 9004-95-9), to overlap, thereby causing the formation of an "amorphous gel." Brij 56 has a Krafft point of 32.5° C. and a cloud point of 67° C. (Schott, H. et al., *J. Pharm. Sci.* 65:979-981 (1976)). Again, the advantage of betaines appears to be related to the fact that long chain alkyls can be used reliably under clinical conditions to disperse any cording and compensate buoyancy.

The data in FIG. 14 demonstrate that certain classes of detergents have a higher propensity to facilitate collection by centrifugation once the organisms are subjected to limited vacuum degassing. FIG. 14 shows a representative result using *M. avium* when a modified version of the assay shown in FIG. 11 is followed. Washes using both water and 2 mM SB-18 (10 mM NaHPO$_4$ pH 7.0, 15 mM NACl, 2 mM SB-18, 2 mM phenylalanine and 5 mM DTT) were compared to several different detergents in the same sodium phosphate buffer (10 mM NaHPO$_4$ pH 7.0, 15 mM NaCl, and 5 mM DTT). Two series of quarternary ammonium detergents were used to examine both chemical structure and alkyl chain length. The first series of detergents were the long chain alkyl-trimethylammonium salts. They included (a) dodecyltrimethylammonium bromide (TMA-12: CAS®No. 1119-94-4), (b) mixed alkyl-trimethylammonium bromide (mTMA: mTMA is predominantly the tetradecyl homolog ($C_{14}$) with some of the $C_{12}$ and $C_{16}$ homologs being present), and (c) octadecyltrimethylammonium bromide (TMA-18: CAS®No. 1120-02-1). The second series of detergents used were the long chain alkyl-benzyldimethylammonium salts. They included: (d) benzalkonium chloride (BenzAlk (CAS®No. 8001-54-5)): BenzAlk is predominantly the $C_{12}$ homolog, with some $C_{14}$ and $C_{16}$ being present); (e) benzyldimethyltetradecylammonium chloride (BenzDMA-14: CAS®No. 139-08-2); and (f) benzyldimethylstearyl ammonium chloride (BenzDMA-18). Each was made in a fashion similar to that described for SB-18 (Example 1), and added to the buffer at a final concentration of 2 mM. The tubes were first incubated at 37° C. for 60 minutes with shaking (140 rpm), and then incubated for 60 minutes at 40° C. under 600 mm Hg vacuum. Duplicate amplifications of three aliquots are represented as a, b, and c, and should be identical. The duplicate amplifications of the direct input aliquots are shown on the appropriately labeled line. Copy controls of 0, 20 and 100 copies were amplified simultaneously. Hybridization controls of $10^8$, $10^9$, and $10^{10}$ copies were blotted as well.

In accordance with the data presented here, while all detergents were seen to perform with added efficacy, the approximately-octadecyl detergents, which are sequestered more actively, are marginally better at improving the recovery of cells by centrifugation once degassing has compensated buoyancy. Similar experiments showed that the nonionic, octadecyl detergents Tween 80 and Span 80, while being previously unable to neither improve recovery of organisms that had not been degassed, nor disaggregate Mycobacterial cells, produced results similar to those observed in FIG. 14 (Tween 80 is known to contain small amounts of hydrolyzed detergent, and Span 80 is simply the sorbitan ester of stearic acid).

Therefore, degassing the Mycobacteria unveils a class of "approximately-octadecyl" detergents (also called "approximately-octadecyl-like" detergents), which class includes the SB-18-like detergents and which may now be used like the SB-18-like detergents, to more efficiently collect the microorganisms. Since MAC complex organisms grow primarily as single cells, the detergents used in the experiment of FIG. 14 easily disrupt surface tension and disperse the cells. It is believed that these detergents, due to their approximately-octadecyl character, are more efficiently transported across the membrane and accumulate in the cell as discussed above.

Therefore, longer alkyl chain lengths appear to be important for two reasons. First, longer chains facilitate dispersion, and second, longer chains are more actively sequestered. Long chain detergents, being less soluble, require special conditions to function. For example, ionic detergents require a minimization of electrolytes, and non-ionic detergents require larger headgroups. Clinical specimens require operating within the context of electrolyte containing solutions, and active transport of detergents into bacterial cells requires minimization of the headgroup. Therein lies the advantage of betaines: they function more efficiently in electrolyte containing solutions and they minimize headgroup volume. In summary, betaines appear to provide a unique opportunity to enhance rapid diagnosis of Mycobacterial infections because long chain alkyls can be used reliably under clinical conditions to disperse any cording and compensate buoyancy.

Additional features related to designing betaines for the methods described herein come from the work of Tsubone, K. et al., J. Pharm. Sci. 80:441–444 (1991). These authors show that the efficacy of antimicrobial activity was seen to be dependent on alkyl chain length, bridge length and the length of $R_2$ and $R_3$ ($R_2$ and $R_3$ as defined in Table 2). For example, appeared to be the ideal chain length in most cases (the phosphoethylbetaine apparently precipitated), methyl groups in the $R_2$ and $R_3$ positions appeared to convey the highest level of antimicrobial activity due to steric effects, and a $C_2$ bridge displayed the highest anitmicrobial activity, while $C_3$ showed the minimum of activity. Increases in bridge length beyond $C_3$ showed a steady increase in antimicrobial activity. In a later paper the authors show that these phenomena correlate with the ability to chelate divalent cations (Tsubone, K. J. Pharm. Sci. 80:1051–1054 (1991)).

In conclusion, since it is both the nature, combination and spatial relationship of the charged species that make the betaines unique, and it is the specific combination of ions that causes intra-family variance of the betaines; based on the above discussion one could design betaines for desired characteristics. For example, longer alkyl chain lengths would be more efficiently sequestered and able to alleviate problems associated with cording. Maintaining the bridge as a propyl group would minimize bacteriostatic activity. The $R_2$ and $R_3$ groups would be minimized at methyl groups to avoid steric hindrance. Regardless, the notion of minimization of bacteriostatic activity with a propyl bridge (e.g., SB-18 is a sulfopropylbetaine) immediately raised the question of viability.

The Viability of SB-18 Processed Mycobacteria

With respect to M. tuberculosis, this protocol produces viable organisms. Table 8 shows the crude BACTEC culture data comparing $^{14}CO_2$ release of untreated Mycobacteria (A and B); cells incubated in PCR lysis buffer with no additional treatment (C and D); cells incubated in lysis buffer and treated at 60° C. for 1 hour and then treated at 95° C. for 15 minutes (E and F); and cells processed by the SB-18 protocol (G and H).

TABLE 8

Preliminary Data Indicating that SB-18 Processed M. tuberculoisis cells are Viable
The preliminary culture results of processing M. tuberculosis, as outlined in FIG. 2, are presented. The numbers represent the $^{14}CO_2$ counts released for a given sample as recorded by the BACTEC 460TB counter (Becton Dickinson, Sparks, MD). Each sample was checked regularly during a 6 week period. The cultures were inoculated on 2/16. Four sets of BACTEC 12-B cultures, with two replicates each, were inoculated with 20 µl of Bacterial Stock: untreated Mycobacteria (A and B); cells incubated in PCR lysis buffer with no additional treatment (C and D), or treated at 60° C. for 1 hour followed by treatment at 95° C. for 15 minutes (E and F); and cells processed by the SB-18 protocol (G and H) described in FIG. 2. Each replicate sample was cultured in duplicate, and was labelled as either 1 or 2. A reading > 15 is considered positive. Once a culture was recorded as positive, it was marked with a "+" and analysis of that culture was terminated.

|  | Sample | Week 1 | | | Week 2 | | | 3 | 4 | 5 | 6 |
|---|---|---|---|---|---|---|---|---|---|---|---|
|  |  | 2/18 | 2/21 | 2/23 | 2/25 | 3/2 | 2/28 | 3/5 | 3/12 | 3/19 | 3/26 |
| Positive | A-1 | 11 | 138 | + | + | + | + | + | + | + | + |
| Control | A-2 | 9 | 108 | + | + | + | + | + | + | + | + |
|  | B-1 | 6 | 72 | + | + | + | + | + | + | + | + |
|  | B-2 | 6 | 84 | + | + | + | + | + | + | + | + |
| 2X Lysis | C-1 | 2 | 20 | + | + | + | + | + | + | + | + |
| Buffer | C-2 | 3 | 38 | + | + | + | + | + | + | + | + |
| & | D-1 | 2 | 18 | + | + | + | + | + | + | + | + |
| Untreated | D-2 | 2 | 15 | 36 | + | + | + | + | + | + | + |
| 2X Lysis | E-1 | 0 | 0 | 4 | 4 | 0 | 0 | 3 | 4 | 6 | 0 |
| Buffer | E-2 | 0 | 0 | 4 | 4 | 0 | 0 | 4 | 4 | 3 | 0 |
| & | F-1 | 0 | 0 | 4 | 4 | 0 | 0 | 4 | 4 | 3 | 0 |
| 60° C./60' | F-2 | 0 | 0 | 4 | 4 | 3 | 0 | 5 | 4 | 4 | 0 |
| 95° C./15' |  |  |  |  |  |  |  |  |  |  |  |
| SB-18 | G-1 | 3 | 35 | + | + | + | + | + | + | + | + |
| Processing | G-2 | 3 | 43 | + | + | + | + | + | + | + | + |
|  | H-1 | 16 | 231 | + | + | + | + | + | + | + | + |
|  | H-2 | 4 | 97 | + | + | + | + | + | + | + | + |

Whereas the SB-18 protocol produces viable organisms, and extended degassing enhances the efficacy of any detergent in facilitating collection by centrifugation, because the Mycobacteria are obligate aerobes, degassing for extended periods of time would be expected to compromise viability.

Table 9 shows the results of combining SB-18 treatment with degassing of NALC/NaOH sediments.

TABLE 9

Correlation of PCR with Culture using SB-18 in the Wash Buffer and Vacuum Degassing of the Washed Sediments
The results of including a vacuum degassing step, in addition to inclusion of SB-18 in the 2°-Wash Buffer are presented. All specimens were first processed by the NALC/NaOH procedure (Kent, P.T. et al., "Public Health Mycobacteriology" in A Guide for the Level III Laboratory, U.S. Department of Health and Human Service, Centers for Disease Control (1985), pp. 31–46). Sediment was removed prior to washing and grown in BACTEC 12B culture bottles. All positive MTB, MAC or M. kansasii cultures were identified using the Gen-Probe culture assay (Gen-Probe, San Diego, CA). All other organisms were identified by biochemical analysis (Kent, P.T. et al., "Public Health Mycobacteriology" in A Guide for the Level III Laboratory, U.S. Department of Health and Human Service, Centers for Disease Control (1985), pp. 71–157). The composition of the buffer used to wash the NALC/NaOH sediments in this series of samples was 10 mM NaHPO$_4$, pH 8.0, 15 mM NaCl, 5 mM DTT, and 2 mM SB-18. The sediments were washed for 60 minutes at 37° C. with shaking (140 rpm). Following sediment wash, the samples were subjected to 600 mm Hg at 40° C. for 60 minutes. Samples were then subjected to centrifugation (5,000 × g for 20 minutes at 37° C.) and further processed for PCR as described in Materials and Methods.

| Condition | # | Species | Correlation Culture | Correlation PCR | % Correl. | Total PCR Positives |
|---|---|---|---|---|---|---|
| SB-18 | 504 | MTB Complex | 4 | 3 | 75% | 55 |
| Wash-Vacuum | | MAC Complex | 13 | 9 | 70% | |
| Degassing | | M. kansasii | 4 | 4 | 100% | |
| | | Other | 4 | — | — | |

Of 504 samples washed with SB-18 at 37° C., and degassed under 600 mm Hg at 40° C., and amplified in duplicate, 13 samples were culture positive for MAC complex, 4 were culture positive for MTB complex, and 4 were culture positive for M. kansasii. Analysis of the results showed that 9 of the MAC culture-positive samples were also positive by PCR (70%); three of the MTB culture-positive specimens were also positive by PCR (75%); and all M. kansasii culture positive specimens were PCR positive (100%). Three of the MAC samples missed contained inhibitors, and one was unexplained. The MTB sample missed displayed statistical drop-out characteristics upon resolution (e.g., low copy number). Three of the MAC culture/PCR positive samples displayed characteristics consistent with statistical drop-outs (e. g., one of the duplicate amplifications was negative and one was positive). Those samples that were seen to exhibit sample bias also required extended incubations in culture for detection by this method.

The correct conclusion here is that deficient results are not a consequence of problems inherent with the SB-18/ degassing procedure. Instead, all the data presented above, in combination with the fact that the samples are first processed by NALC/NaOH, suggests that the integrity of the samples are significantly compromised prior to being processed by the SB-18/degassing procedure. The fact that MAC specimens still exhibit statistical drop-outs and unexplained results further suggests that deficient results will be forthcoming as long as contemporary protocols are used as a means to initially process samples.

Safety Note

Figure 15:
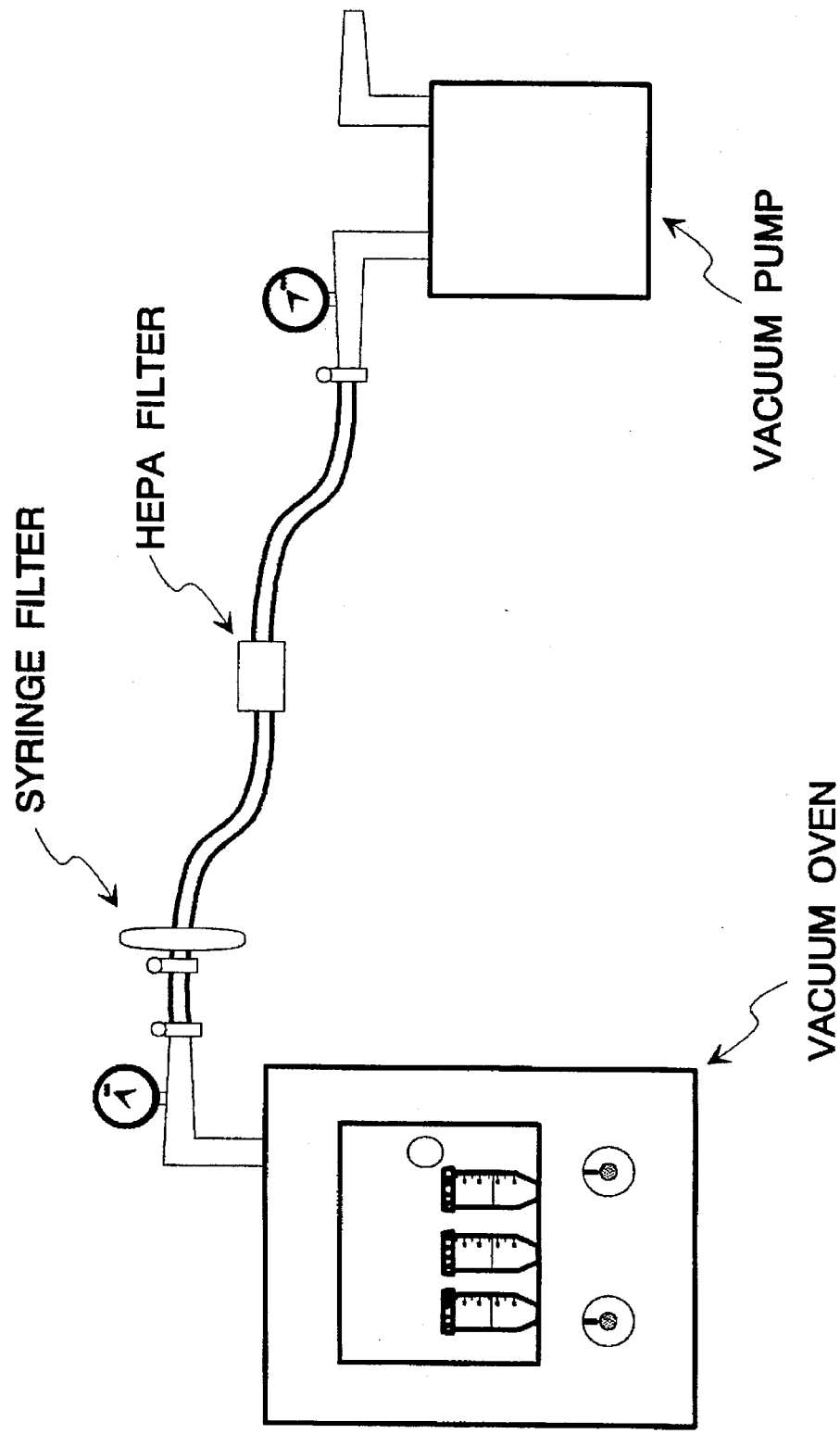
FIG. 15 describes the design of the vacuum degassing apparatus used for these experiments.

Since the caps of the specimen tubes must be loosened prior to vacuum degassing, large amounts of aerosol would be generated in the event of an accident. Therefore, the following guidelines were adopted to ensure the safety of laboratory personnel. First, all data were generated using a consecutive detergent wash, vacuum degassing methodology. This was solely for safety reasons: as the degassing step requires the caps be loosened, and the detergent wash step requires agitation, accomplishing the two steps simultaneously may cause the caps to become detached and personnel to become exposed to the specimens. Second, the apparatus shown in FIG. 15 was set up in a laminar flow hood. The artisan should ensure that the air flow in the laminar flow hood is not obstructed by the vacuum oven. Third, all air evacuated from the vacuum oven passes through two sets of filters to remove dust borne particles. The first filter is a 0.2 μsyringe-type filter (Gelman, Ann Arbor, Mich.), that can be fitted into the vacuum line. This filter is attached to the vacuum oven through a short piece of vacuum tubing. Hose clamps are used to immobilize it so that the possibility of accidental detachment is eliminated. The syringe filter is removed monthly, autoclaved and disposed. The second filter is a 0.3 μHEPA-CAP filter (Whatman, Clifton, N.J.), and is also fitted into the vacuum line. This filter is connected to the syringe filter without hose clamps so that it can be detached, decontaminated and stored if necessary. The HEPA-CAP filter is changed quarterly. Finally, the vacuum oven is decontaminated on the same schedule with the hood.

Example 11

The SB-18-Degassing Protocol is Superior to NALC/NaOH Processing

The schematic in FIG. 2 was modified such that a direct comparison, by both culture and amplification, between untreated M. tuberculosis, M. tuberculosis processed using SB-18 and degassing, and M. tuberculosis processed by NALC/NaOH, was made. The assay shown in FIG. 16 represents the necessary modifications. Table 10 presents the raw data of $^{14}CO_2$ counts released from BACTEC 12B cultures (Becton Dickinson, Sparks, Md.) for each of the three conditions. This data is plotted in FIG. 16A, and FIG. 16B presents the amplification results when aliquots of the processed samples, the same samples used to inoculate the cultures, were amplified by PCR.

In this experiment the protocol of FIG. 16 is followed. *M. tuberculosis* cells were scraped off a slant and suspended in water. The cells were further diluted to generate a bacterial stock that was then used to inoculate all samples. Two sets of tubes, consisting of six replicates each, were generated for each processing protocol. The SB-18 processing solution consisted of 15 ml of 10 mM $NaHPO_4$, pH 8.0, 15 mM NaCl, 2 mM SB-18, and 5 mM DTT. Twenty µl of cells were added to each SB-18 tube and then all were first incubated at 37° C. for 60 minutes with shaking (140 rpm) and then subjected to vacuum (600 mm Hg) for 60 minutes at 40° C. (prior to degassing the caps were loosened). The tubes were then subjected to centrifugation (5,000× g for 20 minutes at 37° C.) and decanted. Five milliliters of NALC/NaOH (Kent, P. T. et at., "Public Health Mycobacteriology" in *A Guide for the Level III Laboratory*, U.S. Department of Health and Human Service, Centers for Disease Control (1985), pp. 31–46) were placed in each replicate for this set and 20 µl of the cell stock added. The NALC/NaOH tubes were incubated for 15 minutes at room temperature, diluted with 45 mls. of sterile water, and then subjected to centrifugation (3,000× g for 20 minutes at 4° C.) and then decanted. All pellets were resuspended in 300 µl of sterile water. Six positive control samples were generated to monitor viability and maximum amplification signal strength. The input controls were manufactured by simply mixing 280 µl of sterile water with 20 µl of the bacterial stock. All samples were then split for analysis by both culture and amplification. This was accomplished in the following manner: duplicate 25 µl aliquots were used to inoculate BACTEC 12B cultures, and a 200 µl aliquot of this sample was added to 200 µl of 2X lysis buffer. The culture bottles were checked routinely for $^{14}CO_2$ release on a BACTEC 460TB counter. Amplification was carried out as described in Materials and Methods. Duplicate amplifications of the six samples from each set are represented as a, b, c, d, e, and f and should be identical (FIG. 16B). Copy controls of 0, 20 and 100 copies were amplified simultaneously. Hybridization controls of $10^8$, $10^9$ and $10^{10}$ copies were blotted as well.

There are two major points to be made and several minor observations concerning this data. The first major point: all SB-18 treated cultures turned positive, and the second major point: not a single NALC/NaOH culture turned positive. While NALC/NaOH is known to compromise the viability of the Mycobacteria (Krasnow, I. et al., *Am. J. Clin. Path.* 45:352–355 (1966); Kubica, G. P. W. et al., *Ant. Rev. Resir. Dis.* 87:775–779 (1963)), the amplification results (FIG. 16B) confirm that, as expected, large losses of microorganisms are, in fact, taking place. In some instances, these losses are quantitative. Since the clinical data presented in Table 9 utilized NALC/NaOH processed sediments, it should be clear that the degree to which the samples are compromised prior to SB-18 washing and degassing is not trivial.

The first minor observation is that the positive controls required almost two weeks to surpass the threshold (15 cpm). Comparing this to the dam of Table 8, in which the positive controls and the SB-18 treated cells were positive by day 5, indicates the extremely low copy numbers used in this experiments. Second, the data in Table 10 suggest that the SB-18 processed cells lag the control cells by approximately a week. There are three explanations for this: (a) as discussed in Example 10, the SB-18 is expected to have some bacteriostatic activity; (b) the positive controls represent true, maximal input, whereas losses are undoubtedly taking place with the processed cells (with low copy number this effect is exacerbated); and finally, (c) the decanted tubes were not further processed (e.g., the volume of the sample upon addition of the water was, in all cases, greater than 300 µl), resulting in a dilution effect. While the extent to which the detergent is bacteriostatic cannot yet be determined, if in fact it is, SB-18 is clearly not bacteriocidal. In regard to "c" above, this experiment was repeated and the supernatant transferred to a microfuge tube and further processed to minimize both bacteriostatic and dilution effects. In this experiment the SB-18 and control results were indistinguishable, and two of twelve NALC/NaOH cultures were positive.

The conclusion is unavoidable that the deficiency with the above diagnoses of *M. tuberculosis* infections is rooted in the processing protocols currently being used in the art. Small, P. M., et al., *New Engl. J. Med.* 330:1703–1709 (1994), and Allard, D. et al., *New Engl. J. Med.* 330:1710–1716 (1994) changed the thinking of the medical community (Hamburg, M. A. et al., *New Engl. J. Med.* 330:1750–1751 (1994)) by publishing restriction fragment length polymorphism (RFLP) studies suggesting that greater than a third of TB infections in the United States were due to recent transmissions. Previously, it was estimated that 90% of infections were latent and arose from inactive foci. The data presented in these Examples (and especially Example 11) strongly imply that, owing to a combination of slow growth, buoyancy, aggregation, defective processing protocols, and a lack of dependable and sensitive diagnostic assays, the true percentage of cases that arise from latent infections or recent transmissions has not been established.

Of the two primary sources of false negative results, inhibitor and low copy numbers, the methods of the invention especially solve the latter. The detergent disrupts cording and offsets buoyancy to some degree, and the degassing further alleviates buoyancy. As a result, organisms that display these characteristics may now be more efficiently collected for detection. Further, since the methods of the invention enhance the ability to efficiently collect and extract low numbers of microorganisms that are in the sample, the methods of the invention thus enhance the efficacy of the detection assay when it is necessary to work with low copy numbers.

Examples 12 and 13 are presented as additional examples of how the use of SB-18-like detergents would be applied in practice to biological or other specimens. Given that clinical laboratories must follow the recommended guidelines published by the Centers for Disease Control (Kent, P. T. et al., "Public Health Mycobacteriology," in *A Guide for the Level III Laboratory*, U.S. Department of Health and Human Service, Centers for Disease Control, (1985) pp. 31–46), Example 12 is given. Example 13 is given in view of the results presented herein, suggesting that contemporary methodologies must be abandoned in order for amplification based technologies to be used reliably in the clinical laboratory.

TABLE 10

Comparison of SB-18 Processing with NALC/NaOH Processing

The culture results of the processing experiment outlined in FIG. 16 are presented. The numbers represent the $^{14}CO_2$ counts released for a given sample as recorded by the BACTEC 460TB counter (Becton Dickinson, Sparks, MD). Each sample was checked regularly during an 8 week period ("Days in Culture"). Three sets of cultures, with six replicates each, were initiated: "Input," representing the positive control group (samples A–F); "SB-18," representing *M. tuberculosis* processed by the methods of the invention, and as outlined in FIG. 11 (samples G–L); and "NALC," representing *M. tuberculosis

TABLE 10-continued

Comparison of SB-18 Processing with NALC/NaOH Processing

The culture results of the processing experiment outlined in FIG. 16 are presented. The numbers represent the $^{14}CO_2$ counts released for a given sample as recorded by the BACTEC 460TB counter (Becton Dickinson, Sparks, MD). Each sample was checked regularly during an 8 week period ("Days in Culture"). Three sets of cultures, with six replicates each, were initiated: "Input," representing the positive control group (samples A–F); "SB-18," representing *M. tuberculosis* processed by the methods of the invention, and as outlined in FIG. 11 (samples G–L); and "NALC," representing *M. tuberculosis* process (ii) Vortex to resuspend the pellet and incubate at 37° C. for 60 min (140 rpm or hard enough to break up the cultures to disperse them into the fluid) just prior to the next step. The 37° C. temperature facilitates dispersion and is necessary to keep the detergent from precipitating. (iii) Incubate for 60 min at 40° C. under approximately 600 mm Hg vacuum (the caps of the tubes should be loose for this step).

(iv) Proceed to Step 7.

7. Spin the tube for 20 min at 37° C. Note: In the examples, an IEC Model PR$_{7000}$M clinical centrifuge was used. The maximum speed/g-force rated for this rotor, 5,200 rpm/7410× g, was used.

8. While the tubes are spinning, aliquot 200 μl of 2X Lysis Buffer into the appropriate number of labelled 1.5 ml screwcap microfuge tubes (leave the tubes at 4° C.).

9. After centrifugation, decant the supernatant, being careful not to dislodge the pellet. Decant as completely as possible.

10. Add 200 μl of water to the pellet.

11. Resuspend the pellet by vortexing.

12. Transfer 200 μl of the specimen to the appropriately labelled 1.5 ml screwcap microfuge tube containing 200 μl of the 2X Lysis Buffer (from step 8 above).

13. Vortex and incubate the tubes at 60° C. for 60 min.

14. Vortex and incubate the tubes at 95° C. for 30 min.

15. Vortex and immediately perform PCR, or store at −20° C. The tubes should be subjected to a quick centrifugation step immediately prior to removing an aliquot for amplification.

Note on Monitoring the pH of the SB-18 Wash Buffer

Examples 10 and 11 suggest that the pH of the wash buffer should be monitored such that maximal SB-18-like activity is achieved. Table 11 examines the pH of two different SB-18 wash buffers upon addition of diluted NALC/NaOH. If the methods of Example 12 are to be followed, the wash solution must have a higher buffer strength such as 50 mM Tris-HCl.

TABLE 11

Addition of NALC/NaOH to SB-18 Buffer
The TABLE below shows the pH of the SB-18 wash buffer upon addition of various amounts of diluted NALC/NaOH. Three different concentrations of NALC/NaOH have been used (2%, 3% or 4%). These three represent the most common concentrations of NALC/NaOH used in the clinical laboratory to process specimens for Mycobacterial detection (Kent, P.T. et al., "Public Health Mycobacteriology," in A Guide for the Level III Laboratory, U.S. Department of Health and Human Service, Centers for Disease Control, (1985) pp. 31–46). These percentages refer to the percent NaOH of the solution added to the actual specimen. During actual sample processing, and after a short incubation to decontaminate the specimen, this solution is then further diluted with either water or phosphate buffered saline (PBS) prior to centrifugation. For the purposes of this experiment, and in order mimic clinical processing, 5 mls of each NALC/NaOH solution was added to a 50 ml conical and then immediately diluted with 45 mls of water. Various amounts (e.g., 1 ml, 2 mls, 3 mls, 4 mls, or 5 mls) of the diluted NALC/NaOH solutions were then added to 25 mls of either: (A) 10 mM NaHPO$_4$, pH 8.0, 15 mM NaCl; or (B) 50 mM Tris-HCl pH 8.0, 50 mM KCl, and the pH recorded.
Addition of NALC/NaOH to SB-18 Buffer

|  | Neet | 1 ml | 2 mls | 3 mls | 4 mls | 5 mls |
|---|---|---|---|---|---|---|
| (A) 25 mls of 10 mM NaBPO$_4$, pH 8.0, 15 mM NaCl | | | | | | |
| 2% NaOH | 8.24 | 9.94 | 10.66 | 10.92 | 11.08 | 11.21 |
| 3% NaOH | 8.20 | 10.30 | 10.87 | 11.11 | 11.27 | 11.39 |
| 4% NaOH | 8.24 | 10.60 | 11.06 | 11.23 | 11.40 | 11.53 |

TABLE 11-continued

Addition of NALC/NaOH to SB-18 Buffer
The TABLE below shows the pH of the SB-18 wash buffer upon addition of various amounts of diluted NALC/NaOH. Three different concentrations of NALC/NaOH have been used (2%, 3% or 4%). These three represent the most common concentrations of NALC/NaOH used in the clinical laboratory to process specimens for Mycobacterial detection (Kent, P.T. et al., "Public Health Mycobacteriology," in A Guide for the Level III Laboratory, U.S. Department of Health and Human Service, Centers for Disease Control, (1985) pp. 31–46). These percentages refer to the percent NaOH of the solution added to the actual specimen. During actual sample processing, and after a short incubation to decontaminate the specimen, this solution is then further diluted with either water or phosphate buffered saline (PBS) prior to centrifugation. For the purposes of this experiment, and in order mimic clinical processing, 5 mls of each NALC/NaOH solution was added to a 50 ml conical and then immediately diluted with 45 mls of water. Various amounts (e.g., 1 ml, 2 mls, 3 mls, 4 mls, or 5 mls) of the diluted NALC/NaOH solutions were then added to 25 mls of either: (A) 10 mM NaHPO$_4$, pH 8.0, 15 mM NaCl; or (B) 50 mM Tris-HCl pH 8.0, 50 mM KCl, and the pH recorded.
Addition of NALC/NaOH to SB-18 Buffer

|  | Neet | 1 ml | 2 mls | 3 mls | 4 mls | 5 mls |
|---|---|---|---|---|---|---|
| (B) 25 mls of 50 mM Tris-HCl pH 8.0, 50 mM KCl | | | | | | |
| 2% NaOH | 7.70 | 7.70 | 7.74 | 7.83 | 7.89 | 7.93 |
| 3% NaOH | 7.70 | 7.74 | 7.82 | 7.88 | 7.97 | 8.04 |
| 4% NaOH | 7.70 | 7.71 | 7.8 | 7.91 | 8.03 | 8.14 |

Example 13

Procedure for Preparation of Mycobacterium for Culture, Smear or Amplification Using SB-18 or Degassing as the Principal Processing Step This Example is given in view of the results presented herein, suggesting that contemporary methodologies must be abandoned in order for amplification based technologies to be used reliably in the clinical laboratory.

The following procedure solves the problems mentioned above and is useful especially for the immediate isolation of Mycobacteria for culture, smear or amplification from samples that have not been processed by any standard method, but rather the sample is processed directly with the method of the invention. This procedure can be used for the isolation of Mycobacteria from clinical specimens (including, for example, sputum, cerebrospinal fluid (CSF) and urine), and is useful especially for the preparation of Mycobacterium, including, but not limited to, *M. tuberculosis* Complex, *M. avium* Complex, and *M. kansasii*. This procedure can be used for the isolation of Mycobacteria from semi-solid material (including, but not limited to, *M. paratuberculosis* from cow feces, *M. avium* from bird feces or other Mycobacteria from soil). Additionally, other Mycobacteria (including, but not limited to, *M. avium* Complex and *M. paratuberculosis*) can be isolated from biological fluids, such as milk or whole blood. This procedure can be used for the isolation of Mycobacteria, including, but not limited to, *M. gordonae* from an environmental source such as water. This procedure can be used for the isolation of Mycobacteria from any exotic source, such as fish or reptile scales, amphibian skin samples, or other tissue samples, human or otherwise, (including, but not limited to, *M. tuberculosis* complex (MTB), *M. avium* complex (MAC), *M. marinum*, *M. fortuitum*, and *M. chelonae*).

NOTES:

(a) Steps 1–4 demonstrate how to use a sample that has not been first processed by any standard procedure but rather, the sample is processed by the method of the invention.

(b) Steps 11–14 are described for use in conjunction with PCR. These steps may be modified such that the resultant processed sediment can be used in conjunction with any of the detection methods described above.

(c) Begin this procedure at either Step 1, 2, 3, or 4 depending on the application.

(d) Any sample that requires clarification or purification or both prior to either beginning this procedure or prior to any step can be accomplished by techniques known in the art, including, for example, centrifugation, gel exclusion chromatography and/or ion exchange chromatography, and/or filtration. The clarification and/or purification method used is at the discretion of the artisan, and will depend on the application. Step 4 is included to exemplify this.

1. SB-18 Detergent Wash:
(i) To the specimen (1–2 grams or 1–2 mls) add approximately 25 ml of SB-18 wash buffer. Note: The wash buffer should be poured into a 50 ml conical with the original specimen.
(ii) Vortex to suspend the sample and incubate at 37° C. for 60 min (140 rpm or hard enough to break up the cultures to disperse them into the fluid). The 37° C. temperature facilitates dispersion and is also necessary to keep the detergent from precipitating.
(iii) Proceed to Step 5.

2. Vacuum Degassing:
(i) Suspend approximately 1–2 grams of sample, or 1–2 mls of a liquid sample, in 6 ml of sterile water, or any other desired buffer, in a 50 ml conical tube. (Water samples should be taken at the surface of the medium in question.)
(ii) Incubate for 60 min at 40° C. under approximately 600 mm Hg vacuum (the caps of the tubes should be loose for this step).
(iii) Proceed to Step 5.

3. SB-18 Detergent Wash and Vacuum Degassing:
(i) To the specimen (1–2 grams or 1–2 mls) add approximately 25 ml of SB-18 wash buffer. Note: The wash buffer should be poured into a 50 ml conical with the original specimen.
(ii) Vortex to suspend the sample and incubate at 37° C. for 60 min (140 rpm or hard enough to break up the cultures to disperse them into the fluid). The 37° C. temperature facilitates dispersion and is also necessary to keep the detergent from precipitating.
(iii) Incubate for 60 min at 40° C. under approximately 600 mm Hg vacuum (the caps of the tubes should be loose for this step).
(iv) Proceed to Step 5.

4. SB-18 Detergent Wash Following Clarification and/or Purification (Vacuum Degassing Optional):
(i) Suspend approximately 1–2 grams of sample, or 1–2 mls of a liquid sample; in 6 ml of sterile water in a 50 ml conical tube.
(ii) Vortex the sample and let stand at room temperature for 10 minutes.
(iii) Set up tubes with 1.25X SB-18 Secondary Wash Buffer and store at 37° C.
(iv) Clarify the sample by centrifugation at 2,700 rpm (2,000× g) at 25 ° C. for 10 minutes, or at whatever force is necessary to clarify the sample without compromising the further processing of the Mycobacteria from the supernatant fraction (this step is optional if there are no visible particulates in the sample).
(v) Remove from the centrifuge and let stand for 10 minutes at room temperature.
(vi) Carefully decant part or most of the supernatant fraction from each sample directly through a G-50 column (Pharmacia, Piscataway, N.J.) into the appropriately labelled 50 ml conical containing the 1.25X-SB- 18 wash buffer. Remove the desired volume but leave the portion closest to the pellet. Transfer as little of the pellet as possible.
(vii) Vortex to mix the contents and then incubate at 37° C. for 60 minutes with shaking (140 rpm).
(viii) Loosen the caps and incubate for 60 minutes at 40° C. under approximately 600 mm Hg vacuum (this step is optional).
(ix) Proceed to Step 5.

5. Spin the tube for 20 min at 37° C. Note: In the examples, an IEC Model $PR_{7000}M$ clinical centrifuge was used. The maximum speed/g-force rated for this rotor, 5,200 rpm/7410× g, was used.

6. While the tubes are spinning, aliquot 200 µl of 2X Lysis Buffer into the appropriate number of labelled 1.5 ml screwcap microfuge tubes (leave the tubes at 4° C.).

7. After centrifugation, decant the supernatant, being careful not to dislodge the pellet. Decant as completely as possible.

8. Add 200µl of water to the pellet.

9. Resuspend the pellet by vortexing.

10. Remove a 100 µl aliquot for culture if desired. Typically there will be 100 to 200 µl of the supernatant remaining in the bottom of the conical. Adding more than 200 µl of water to the pellet is usually unnecessary: there will be enough fluid for culture, smear and amplification. Note: For smear analysis, as much of the detergent as possible must be removed.

11. Transfer 200µl of the specimen to the appropriately labelled 1.5 ml screwcap microfuge tube containing 200 µl of the 2X Lysis Buffer (from step 6 above).

12. Vortex and incubate the tubes at 60° C. for 60 min.

13. Vortex and incubate the tubes at 95° C. for 30 min.

14. Vortex and immediately perform PCR, or store at –20° C. The tubes should be subjected to a quick centrifugation step immediately prior to removing an aliquot for amplification.

Comparison of NALC/NaOH and SB-18 Processed Clinical Samples

Table 12 compares thirteen samples that have been processed by both NALC/NaOH and SB-18. The specimens used were discarded samples from the clinical laboratory, a portion of which had been processed by NALC/NaOH. The initial volume of these samples exceeded the maximum recommended volume suggested by Kent, P. T. et al., "Public Health Mycobacteriology," in *A Guide for the Level III Laboratory*, U.S. Department of Health and Human Service, Centers for Disease Control, (1985) pp. 31–46. Therefore, the remainder of the original specimens, which were to be discarded following inoculation of the culture with the NALC/NaOH sediments, were used. Typically less than 1 ml remained for SB-18 processing. Cultures 1, 10, 12 and 13 were culture positive by both methods. However, the SB-18 sample from culture 1 did not contain acid fast material. Growth in this culture was later shown to result from a strain of Pseudomonas. Cultures 10, 12, and 13 all contained acid fast material by both methods. The SB-18 sediments were amplified and samples 4, 10, 12 and 13 were PCR positive. Sample 1 contained inhibitors, and 4 was derived from a patient who had been diagnosed in the past with an *M. tuberculosis* infection. This patient is assumed to be on drug therapy. Sample 4 was smear negative. The results of Table 12, although very limited, suggest that samples can be processed by SB-18 and amplified to assess the presence of Mycobacterial DNA. In addition, SB-18 has significant bacteriocidal and bacteriostatic activity. However, Pseudomonas, which is also fairly impermeable (Jarlier, V. et al., *J. Bacteriol.* 172:1418–1423 (1990)), appears to be of concern with respect to culturing SB-18 processed samples. It should be noted that SB-18 samples 10, 12, and 13, which represent significantly less material; produced culture positive samples more quickly.

Note: The whole blood should be drawn in an ACD (acid-citrate-dextrose) collection tube (Becton-Dickinson) and used within 24 hours. The collection tube should be mixed thoroughly after collection. Note: This protocol has been optimized for use with CB-18 (CAS No. 78195-27-4). The buffer used was 20 mM Tris-HCl pH 8.0, 2 mM NaCl, and 1 mM CB-18.

TABLE 12

Processing Clinical Specimens Directly with SB-18
Culture data, showing thirteen clinical specimens which had been processed by both NALC/NaOH and the SB-18 protocol, are compared. Specifically, the NALC/NAOH procedure was that according to Kent, P.T. et al., "Public Health Mycobacteriology," in A Guide for the level III Laboratory, U.S. Department of Health and Human Service, Centers for Disease Control (1985), pp. 31–46 (3% final), and the SB-18 procedure was that described above and initiated at Step 3, and then continued as directed in Steps 5 through 14. The NALC/NaOH sediments were checked for acid fast material according to the procedure of Kent, P.T. et al., "Public Health Mycobacteriology," in A Guide for the level III Laboratory, U.S. Department of Health and Human Service, Centers for Disease Control (1985), pp. 71–157. The specimens used were discarded samples from the clinical laboratory, a portion of which had been processed by NALC/NaOH. The numbers represent the $^{14}CO_2$ counts released for a given sample as recorded by the BACTEC 460TB counter (Becton Dickinson, Sparks, MD). Each culture was checked regularly during the time period. A value above 15 was considered positive. Positive cultures were then checked for acid fast material according to the procedure of Kent, P.T. et al., "Public Health Mycobacteriology," in A Guide for the level III Laboratory, U.S. Department of Health and Human Service, Centers for Disease Control (1985), pp. 71–157. Once the sample was shown to be acid fast positive, the culture was terminated, indicated as "+". An ND indicates that the sample was not seven weeks old.
Comparison of NALC/NaOH and SB-18 Processed Clinical Samples

| # | Method | WEEK 1 | | | WEEK 2 | | | WEEK 3 | WEEK 4 | WEEK 5 | WEEK 6 | WEEK 7 |
|---|--------|---|---|---|---|---|---|---|---|---|---|---|
| 1 | SB-18 | 5 | 200 | + | + | + | + | + | + | + | + | + |
|   | NALC  | 5 | 0 | 0 | 15 | 999 | + | + | + | + | + | + |
| 2 | SS-18 | 5 | 3 | 0 | 3 | 0 | 0 | 3 | 4 | 0 | 0 | 0 |
|   | NALC  | 5 | 0 | 0 | 3 | 0 | 0 | 3 | 0 | 0 | 3 | 0 |
| 3 | SB-18 | 5 | 3 | 0 | 3 | 0 | 0 | 4 | 3 | 0 | 0 | 0 |
|   | NALC  | 5 | 0 | 3 | 3 | 0 | 0 | 2 | 3 | 0 | 3 | 0 |
| 4 | SB-18 | 4 | 3 | 4 | 3 | 0 | 0 | 3 | 3 | 0 | 0 | 0 |
|   | NALC  | 4 | 0 | 3 | 3 | 0 | 0 | 4 | 3 | 0 | 0 | 0 |
| 5 | SB-18 | 1 | 5 | 4 | 3 | 0 | 0 | 0 | 0 | 0 | 3 | ND |
|   | NALC  | 1 | 5 | 3 | 0 | 0 | 0 | 0 | 0 | 0 | 3 | ND |
| 6 | SB-18 | 2 | 4 | 3 | 2 | 0 | 0 | 0 | 0 | 0 | 4 | ND |
|   | NALC  | 1 | 4 | 3 | 2 | 0 | 0 | 0 | 0 | 0 | 3 | ND |
| 7 | SS-18 | 6 | 0 | 4 | 3 | 0 | 0 | 0 | 4 | 4 | 3 | ND |
|   | NALC  | 0 | 4 | 3 | 4 | 0 | 0 | 0 | 0 | 3 | 4 | ND |
| 8 | SB-18 | 6 | 0 | 0 | 3 | 0 | 0 | 0 | 3 | 3 | 3 | ND |
|   | NALC  | 5 | 0 | 3 | 3 | 0 | 0 | 0 | 3 | 3 | 3 | ND |
| 9 | SB-18 | 5 | 0 | 0 | 4 | 0 | 0 | 0 | 4 | 2 | 3 | ND |
|   | NALC  | 0 | 0 | 3 | 3 | 0 | 0 | 0 | 0 | 2 | 3 | ND |
| 10 | SB-18 | 5 | 0 | 0 | 66 | + | + | + | + | + | + | + |
|   | NALC  | 5 | 0 | 5 | 14 | 874 | + | + | + | + | + | + |
| 11 | SB-18 | 1 | 0 | 0 | 3 | 1 | 0 | 3 | 0 | 0 | 0 | ND |
|   | NALC  | 1 | 0 | 0 | 3 | 0 | 0 | 3 | 0 | 0 | 0 | ND |
| 12 | SB-18 | 1 | 0 | 3 | 12 | 16 | 47 | 506 | + | + | + | + |
|   | NALC  | 1 | 0 | 0 | 3 | 3 | 83 | + | + | + | + | + |
| 13 | SB-18 | 2 | 7 | 372 | + | + | + | + | + | + | + | + |
|   | NALC  | 1 | 3 | 173 | + | + | + | + | + | + | + | + |

Example 14

Method for Quantitative Isolation of *M. avium* Complex from Whole Blood (1) Add 1 ml of fresh whole blood to 10 mls of buffer containing the SB-18-like or approximately-octadecyl detergent and vortex to mix the solutions.

Higher concentrations of CB-18 (e.g., 2 mM) appear to facilitate lysis of these organisms. Modification to this protocol should be optimized for each SB-18-like or approximately-octadecyl detergent being used.

(2) Incubate at 37° C. for 60 minutes with shaking (140 rpm).

(3) Loosen the caps and transfer to a vacuum oven. Incubate at 42° C. for 60 minutes under 600 mm Hg.

(4) Tighten the caps and centrifuge at 3,500× g for 20 minutes at 30° C.

Note: Care should be taken when subjecting 15 ml conical tubes to centrifugation. First, the appropriate rotor adapters should be used. Second, polystyrene tubes should not be used, due to the possibility of fracture: polypropylene tubes should be used.

(5) Decant the tubes and add 500 µl of wash buffer containing the same SB-18-like or approximately-octadecyl detergent and resuspend the pellet. [Note: a small gelatinous pellet typically forms. Do not attempt to remove all the supernatant from the tube.]

(6) Transfer the resuspended pellet to a 1.5 ml screw cap microfuge tube with a disposable transfer pipette.

(7) Place the tubes in a microfuge and spin for 10 minutes at room temperature at maximum speed (the temperature of this step will vary depending on the detergent employed in the protocol).

(8) Aspirate the supernatant and add 300 µl of sterile water to the specimen.

(9) Resuspend the pellet and transfer 200 µl to 2X lysis buffer for amplification. Process the specimen for amplification and detection as described in Example 1.

(10) The remaining sediment is transferred to a BACTEC 12B culture bottle (Becton-Dickinson) for analysis.

Example 15

Modified Oxalic Acid Decontamination Procedure

Potential Pseudomonas contamination is the biggest problem when using the protocol of Example 13. If this is a concern, the Pseudomonas can be eliminated by digestion with oxalic acid, or predigestion of the contaminated sputum with oxalic acid. The protocol for such decontamination follows. This protocol modifies the oxalic acid procedure described on pages 43–44 of Kent et al., "Public Health Mycobacteriology" in *A Guide for the Level III Laboratory*, U.S. Department of Health and Human Service, Centers for Disease Control (1985), pp. 31–46.

(1) Place between 0.5–2 mls of raw specimen or 2 mls of contaminated culture in a 50 ml conical tube.

(2) To the specimen, or contaminated culture, add an equal volume of 5% oxalic acid (ethanedioic acid, CAS No. 6153-56-6). 5% Oxalic acid: 5 grams of oxalic acid dihydrate (126.01 grams/mole) in 100 ml water.

(3) Incubate at room temperature for 15 minutes.

(4) Add one-tenth (1/10) of a volume of "NaOH Neutralization Solution" to the mixture and vortex immediately. For example, if 2 ml of oxalic acid were added to the specimen, then 200 µl of the NaOH Neutralization Solution would be added to the specimen. NaOH Neutralization Solution: 31.76 grams of sodium hydroxide (40 grams/mole) in 100 ml of water (final concentration: 7.94M).

(5) Add buffer containing the SB-18-like or approximately-octadecyl detergent to the specimen to a final volume of approximately 25 ml.

(6) Incubate at 37° C. for 60 minutes with shaking (140 rpm).

(7) Loosen the caps and transfer to a vacuum oven. Incubate at 42° C. for 60 minutes under 600 mm Hg.

(8) Tighten the caps and centrifuge at 5,000× g for 20 minutes at 37° C.

(9) Decant the tubes and add 300 µl of sterile water to the specimen.

(10) Resuspend the pellet and transfer 200 µl to 2X lysis buffer for amplification. Process the specimen for amplification and detection as described in Example 1.

(11) The remaining sediment is transferred to a BACTEC 12B culture bottle (Becton-Dickinson) for analysis.

Example 16

The method of any of Examples 12, 13, 14 or 15 except that a desired non-Mycobacterium microorganism, or a desired Mycobacterium group or complex or Mycobacterium species, or a Mycobacteria complex such as *M. tuberculosis* (MTB) complex, *M. avium* (MAC) complex, MAIS complex and *M. fortuitum* complex, as well as fast growing and slow growing Mycobacteria including specified and unspecified photochromogens, nonphotochromogens, scotochromogens, and especially *M. africanum, M. asiaticum, M. avium, M. bovis, M. bovis* (BCG), *M. butyricum, M. chelonae, M. duvalii, M. flavescens, M. fortuitum, M. gastri, M. gordonae, M. haemophilum, M. intracellularae, M. kansasii, M. leprae, M. lepraemurium, M. linda, M. lufu, M. marinum, M. malmoense, M. microti, M. mucoscum, M. nonchromogenicum, M. paratuberculosis, M. peregrinum, M. phlei, M. rhodochrous, M. scrofulaceum, M. shimoidei, M. simiae, M. smegmatis, M. szulgai, M. terrae, M. thermoresistable, M. triviale, M. tuberculosis, M. ulcerans, M. vaccae, M. xenopi* is detected by detection of its genetic material or detection of an antigen indicative of the presence of such microorganism.

Example 17

The method shown in any of Examples 12–16, except that the detergent is an SB-18-like detergent as defined in Tables 2 and 3, other than SB-18.

Example 18

The method shown in any of Examples 12–16, except that the detergent is an approximately-octadecyl detergent, other than SB-18.

Example 19

The method shown in any of Examples 12–16, except that at least two different approximately-octadecyl detergents are used in the processing steps.

Example 20

A listing of the CAS®Number, chemical name and structure for the CAS®Numbers referred to herein is provided as Table 13.

TABLE 13

| CAS ® No. | Name & Structure |
|---|---|
| 1. 57-10-3 | Palmitic Acid<br>$HO_2C-(CH_2)_{14}-Me$ |
| 2. 68-12-2 | Dimethyl Formamide and N,N-dimethyl-formamide<br>$H_3C-\underset{\underset{CH_3}{\mid}}{N}-CH=O$ |
| 3. 75-12-7 | Formamide<br>$H_2N-CH=O$ |
| 4. 95-56-0 | c-hexadecyl betaine and 1-carboxy-N,N,N-trimethyl-1-hetadecanaminium, inner salt |
| 5. 96-55-9 | c-decyl betaine and 1-carboxy-N,N,N-trimethyl-1-undecanaminium, inner salt<br>$^-O_2C-\underset{\underset{N^+Me_3}{\mid}}{CH}-(CH_2)_9-Me$ |
| 6. 112-80-1 | Oleic Acid and<br>(Z)-9-octadecenoic acid<br>$HO_2C\overset{(CH_2)_7}{\diagup}\underset{Z}{=}\overset{(CH_2)_7}{\diagdown}Me$ |
| 7. 139-08-2 | Benz DMA-14.Cl⁻ and<br>benzyldimethyltetradecylammonium chloride<br>$Ph-CH_2-\underset{\underset{Me}{\mid}}{\overset{\overset{Me}{\mid}}{N^+}}-(CH_2)_{13}-Me \quad .Cl^-$ |
| 8. 143-07-7 | dodecanoic acid<br>$HO_2C-(CH_2)_{10}-Me$ |
| 9. 151-21-3 | SDS and Sodium dodecyl sulfate and Sulfuric acid monododecyl ester sodium salt<br>$HO_3SO-(CH_2)_{11}-Me$<br>$.Na$ |
| 10. 302-95-4 | Deoxycholic acid and 12-α-dihydroxy-3-α-5-β-cholan-24-oic acid monosodium salt<br>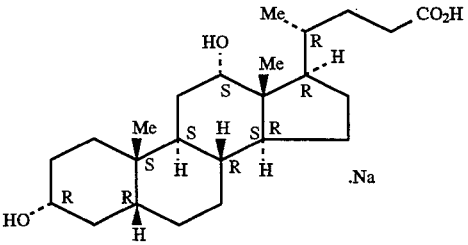 |
| 11. 334-48-5 | decanoic acid<br>$HO_2C-(CH_2)_8-Me$ |
| 12. 683-10-3 | N-(carboxymethyl)-N,N-dimethyl-1-dodecanaminium, inner salt<br>$^-O_2C-CH_2-\underset{\underset{Me}{\mid}}{\overset{\overset{Me}{\mid}}{N^+}}-(CH_2)_{11}-Me$ |
| 13. 686-83-9 | 1-carboxy-N,N,N-trimethyl-1-tridecanaminium, inner salt<br>$^-O_2C-\underset{\underset{N^+Me_3}{\mid}}{CH}-(CH_2)_{11}-Me$ |
| 14. 686-84-0 | 1-carboxy-N,N,N-trimethyl-1-nonadecanaminium, inner salt<br>$^-O_2C-\underset{\underset{N^+Me_3}{\mid}}{CH}-(CH_2)_{17}-Me$ |

TABLE 13-continued

| CAS ® No. | Name & Structure |
|---|---|
| 15. 693-33-4 | N-(carboxymethyl)-N,N-dimethyl-1-hexadecanaminium, inner salt $$^-O_2C-CH_2-\overset{\underset{\mid}{Me}}{\underset{\mid}{N^+}}-(CH_2)_{15}-Me$$ $$Me$$ |
| 16. 820-66-6 | N-(carboxymethyl)-N,N-dimethyl-1-octadecanaminium, inner salt $$^-O_2C-CH_2-\overset{\underset{\mid}{Me}}{\underset{\mid}{N^+}}-(CH_2)_{17}-Me$$ $$Me$$ |
| 17. 871-37-4 | Oleyl carboxymethylbetaine and N-(carboxymethyl)-N,N-dimethyl-9-octadecen-1-aminium, inner salt $$^-O_2C\diagdown \overset{+}{N}-(CH_2)_8\underset{Z}{=\!=\!=}(CH_2)_7\diagdown Me$$ $$\diagup\quad\diagdown$$ $$Me\quad Me$$ |
| 18. 1119-94-4 | TMA-12.Br$^-$ and N,N,N-trimethyl-1-dodecanaminium bromide $$Me_3{}^+N-(CH_2)_{11}-Me$$ $$.Br^-$$ |
| 19. 1119-97-7 | TMA-14.Br and N,N,N-trimethyl-1-tetradecylammonium bromide $$Me_3{}^+N-(CH_2)_{13}-Me$$ $$.Br^-$$ |
| 20. 1120-02-1 | TMA-18-Br and N,N,N-trimethyl-1-octadecanaminium bromide $$Me_3{}^+N-(CH_2)_{17}-Me$$ $$.Br^-$$ |
| 21. 1120-04-3 | SOS and octadecyl sodium sulfate $$HO_3SO-(CH_2)_{17}-Me$$ $$.Na$$ |
| 22. 1338-39-2 | Span 20 and monododecanoate sorbitan $$\underset{\mid}{CH_2}-O-\overset{\overset{O}{\|}}{C}-CH_2(CH_2)_9CH_3$$ $$HO-\underset{\mid}{C}-H$$ (sorbitan ring with OH, O, OH) |
| 23. 1338-41-6 | Span 60 and monooctadecanoate sorbitan $$\underset{\mid}{CH_2}-O-\overset{\overset{O}{\|}}{C}-CH_2(CH_2)_{16}CH_3$$ $$HO-\underset{\mid}{C}-H$$ (sorbitan ring with OH, O, OH) |
| 24. 1338-43-8 | Span 80 and (Z)-mono-9-octadecenoate sorbitan $$\underset{\mid}{(CH_2)_7}\underset{Z}{=\!=\!=}(CH_2)_7-CH_3$$ $$HO-\underset{\mid}{C}-H$$ (sorbitan ring with OH, O, OH) |
| 25. 1462-54-0 | N-dodecyl-beta-alanine $$Me-(CH_2)_{11}-NH-CH_2-CH_2-CO_2H$$ |

TABLE 13-continued

| CAS ® No. | Name & Structure |
|---|---|
| 26. 1643-20-5 | Dimethylaurylamine oxide and N,N-dimethyl-1-dodecanamine N-oxide $$Me-\overset{O^-}{\underset{Me}{N^+}}-(CH_2)_{11}-Me$$ |
| 27. 2281-11-0 | SB-16 and $C_{16}$-sulfopropylbetaine and N,N-dimethyl-N-(3-sulfopropyl)-1-hexadecanaminium, inner salt $$^-O_3S-(CH_2)_3-\overset{Me}{\underset{Me}{N^+}}-(CH_2)_{15}-Me$$ |
| 28. 2571-88-2 | N,N-dimethyl-1-octadecanamine N-oxide $$Me-\overset{O^-}{\underset{Me}{N^+}}-(CH_2)_{17}-Me$$ |
| 29. 2601-33-4 | N-(carboxymethyl)-N,N-dimethyl-1-tetradecanaminium, inner salt $$^-O_2C-CH_2-\overset{Me}{\underset{Me}{N^+}}-(CH_2)_{13}-Me$$ |
| 30. 2644-45-3 | N-(carboxymethyl)-N,N-dimethyl-1-decanaminium, inner salt $$^-O_2C-CH_2-\overset{Me}{\underset{Me}{N^+}}-(CH_2)_9-Me$$ |
| 31. 2956-38-9 | N-(carboxymethyl)-N,N-dimethyl-1-undecanaminium, inner salt $$^-O_2C-CH_2-\overset{Me}{\underset{Me}{N^+}}-(CH_2)_{10}-Me$$ |
| 32. 3055-96-7 | 6-Lauryl Ether and 3,6,9,12,15,18-hexaoxatriacontan-1-ol $$HO-CH_2-CH_2-O-CH_2-CH_2-O-CH_2-CH_2-O-CH_2-CH_2-O-CH_2-CH_2-O-CH_2-CH_2-O-(CH_2)_{11}-Me$$ |
| 33. 3332-27-2 | myristyl dimethyl amine oxide and N,N-dimethyl-1-tetradecanamine N-oxide $$Me-\overset{O^-}{\underset{Me}{N^+}}-(CH_2)_{13}-Me$$ |
| 34. 4292-10-8 | N-(carboxymethyl)-N,N-dimethyl-3-((1-oxododecyl)amino)-1-propanaminium, inner salt $$^-O_2C-CH_2-\overset{Me}{\underset{Me}{N^+}}-(CH_2)_3-NH-\overset{O}{\underset{}{C}}-(CH_2)_{10}-Me$$ |
| 35. 6179-44-8 | Isostearylamidopropyl carboxymethylbetaine and N-(carboxymethyl)-N,N-dimethyl-3-((1-oxooctadecyl)amino)-1-propanaminium, inner salt $$^-O_2C-CH_2-\overset{Me}{\underset{Me}{N^+}}-(CH_2)_3-NH-\overset{O}{\underset{}{C}}-(CH_2)_{16}-Me$$ |
| 36. 6232-16-2 | N-(carboxymethyl)-N,N-diethyl-1-dodecanaminium, inner salt $$^-O_2C-CH_2-\overset{Et}{\underset{Et}{N^+}}-(CH_2)_{11}-Me$$ |

TABLE 13-continued

| CAS ® No. | Name & Structure |
|---|---|
| 37. 7128-91-8 | N,N-dimethyl-1-hexadecanamine N-oxide $$Me-\overset{O}{\underset{\underset{Me}{\mid}}{\overset{\parallel}{N}}}-(CH_2)_{15}-Me$$ |
| 38. 7281-04-1 | Benz DMA-12.Br and N-dodecyl-N,N-dimethyl-benzenemethanaminium bromide $$Ph-CH_2-\overset{Me}{\underset{\underset{Me}{\mid}}{\overset{\mid}{N^+}}}-(CH_2)_{11}-Me \quad .Br^-$$ |
| 39. 7425-12-9 | $C_{16}$-hydroxypropylsulfobetaine and N-(2-hydroxy-3-sulfopropyl)-N,N-dimethyl-1-hexadecanaminium, inner salt $$^-O_2S-CH_2-\overset{OH}{\underset{\mid}{CH}}-CH_2-\overset{Me}{\underset{\underset{Me}{\mid}}{\overset{\mid}{N^+}}}-(CH_2)_{15}-Me$$ |
| 40. 8001-54-5 N/A | Benz Alk.Cl$^-$ and alkyldimethylbenzylammonium chloride |
| 41. 9002-92-0 | Brij 35 and α-dodecyl-ω-hydroxy-poly(oxy-1,2-ethanediyl) $$HO+CH_2-CH_2-O+_n (CH_2)_{11}-Me$$ Brij 35; n = 23 |
| 42. 9002-93-1 | Triton X-100 and α-[4-(1,1,3,3-tetramethylbutyl)phenyl]-ω-hydroxy poly(oxy-1,2-ethanediyl) $$Me_3C-CH_2-\overset{Me}{\underset{\underset{Me}{\mid}}{\overset{\mid}{C}}}-\text{Ph}-O+CH_2-CH_2-O+_n H$$ Trition X-100; n = 23 |
| 43. 9003-39-8 | Polyvinyl pyrrolidone 360,000 and 1-ethenyl-2-pyrrolidinone homopolymer |
| 44. 9004-95-9 | Brij 52 and Brij 56 and Brij 58 and α-hexadecyl-ω-hydroxy-poly(oxy-1,2-ethanediyl) $$HO+CH_2-CH_2-O+_n (CH_2)_{15}-Me$$ Brij 52: n = 2 Brij 56: n = 10 Brij 58: n = 20 |
| 45. 9004-98-2 | Brij 92 and Brij 96 and Brij 99 and (Z)-9-octadecen-1-ol monoether with polyethylene glycol $$HO+CH_2-CH_2-O+_n (CH_2)_8-CH=CH-(CH_2)_7-Me$$ Brij 92: n = 2 Brij 96: n = 10 Brij 99: n = 20 |
| 46. 9005-00-9 | Brij 72 and Brij 76 and Brij 78 α-octadecyl-ω-hydroxy-poly(oxy-1,2-ethanediyl) $$HO+CH_2-CH_2-O+_n (CH_2)_{17}-Me$$ Brij 72: n = 2 Brij 76: n = 10 Brij 78: n = 20 |

TABLE 13-continued

| CAS ® No. | Name & Structure |
|---|---|
| 47. 9005-64-5<br>N/A | Tween 20 and poly(oxy-1,2-ethanediyl) monododecanoate sorbitan derivatives (n = 20) |
| 48. 9005-65-6<br>N/A | Tween 80 and (Z)-poly(oxy-1,2-ethanediyl)mono-9-octadecenoate sorbitan derivatives (n = 20) |
| 49. 9005-67-8<br>N/A | Tween 60 and poly(oxy-1,2-ethanediyl)monooctadecanoate sorbitan derivatives (n = 20) |
| 50. 13177-41-8 | SB-18 and $C_1$-sulfopropylbetaine and N,N-dimethyl-N-(3-sulfopropyl)-1-octadecanaminium, inner salt<br>$^-O_3S-(CH_2)_3-\overset{\overset{\displaystyle Me}{\mid}}{\underset{\underset{\displaystyle Me}{\mid}}{N^+}}-(CH_2)_{17}-Me$ |
| 51. 13177-42-9 | N-(2-hydroxy-3-sulfopropyl)-N,N-dimethyl-1-tetradecanaminium, inner salt<br>$^-O_3S-CH_2-\overset{\overset{\displaystyle OH}{\mid}}{CH}-CH_2-\overset{\overset{\displaystyle Me}{\mid}}{\underset{\underset{\displaystyle Me}{\mid}}{N^+}}-(CH_2)_{13}-Me$ |
| 52. 13197-76-7 | N-(2-hydroxy-3-sulfopropyl)-N,N-dimethyl-1-dodecanaminium, inner salt<br>$^-O_3S-CH_2-\overset{\overset{\displaystyle OH}{\mid}}{CH}-CH_2-\overset{\overset{\displaystyle Me}{\mid}}{\underset{\underset{\displaystyle Me}{\mid}}{N^+}}-(CH_2)_{11}-Me$ |
| 53. 14233-37-5 | 1,4-bis((1-methylethyl)amino)-9,10-anthracenedione<br><br>i-PrNH, O on anthraquinone ring with i-PrNH and O substituents |
| 54. 14351-50-9 | N,N-dimethyl-9-octadecen-1-amine N-oxide<br>$Me-(CH_2)_7-\overset{Z}{=}-(CH_2)_8-\underset{\underset{\displaystyle O}{\parallel}}{\overset{\overset{\displaystyle Me}{\diagup}}{N}}\diagdown Me$ |
| 55. 14933-08-5 | SB-12 and $C_{12}$-sulfopropylbetaine and N,N-dimethyl-N-(3-sulfopropyl)-1-dodecanaminium, inner salt<br>$^-O_3S-(CH_2)_3-\overset{\overset{\displaystyle Me}{\mid}}{\underset{\underset{\displaystyle Me}{\mid}}{N^+}}-(CH_2)_{11}-Me$ |
| 56. 14933-09-6 | SB-14 and $C_{14}$-sulfopropylbetaine and N,N-dimethyl-N-(3-sulfopropyl)-1-tetradecanaminium, inner salt<br>$^-O_3S-(CH_2)_3-\overset{\overset{\displaystyle Me}{\mid}}{\underset{\underset{\displaystyle Me}{\mid}}{N^+}}-(CH_2)_{13}-Me$ |
| 57. 15163-30-1 | N-(3-carboxypropyl)-N,N-dimethyl-1-dodecanaminium, inner salt<br>$^-O_2C-(CH_2)_3-\overset{\overset{\displaystyle Me}{\mid}}{\underset{\underset{\displaystyle Me}{\mid}}{N^+}}-(CH_2)_{11}-Me$ |

TABLE 13-continued

| CAS ® No. | Name & Structure |
|---|---|
| 58. 15163-34-5 | dodecyldipropyl(3-sulfopropyl)-ammonium hydroxide, inner salt $$^-O_3S-(CH_2)_3-\underset{\underset{n\text{-Pr}}{\mid}}{\overset{\overset{n\text{-Pr}}{\mid}}{N^+}}-(CH_2)_{11}-Me$$ |
| 59. 15163-35-6 | N,N-dimethyl-N-(3-(sulfooxy)propyl)-1-dodecanaminium, inner salt $$^-O_3S-O-(CH_2)_3-\underset{\underset{Me}{\mid}}{\overset{\overset{Me}{\mid}}{N^+}}-(CH_2)_{11}-Me$$ |
| 60. 15163-36-7 | N,N-dimethyl-N-(3-sulfopropyl)-1-decanaminium, inner salt $$^-O_3S-(CH_2)_3-\underset{\underset{Me}{\mid}}{\overset{\overset{Me}{\mid}}{N^+}}-(CH_2)_9-Me$$ |
| 61. 15178-76-4 | N,N-dimethyl-N-(3-sulfopropyl)-1-octanaminium, inner salt $$^-O_3S-(CH_2)_3-\underset{\underset{Me}{\mid}}{\overset{\overset{Me}{\mid}}{N^+}}-(CH_2)_7-Me$$ |
| 62. 16527-85-8 | N-(2-carboxyethyl)-N,N-dimethyl-1-dodecanaminium, inner salt $$^-O_2C-CH_2-CH_2-\underset{\underset{Me}{\mid}}{\overset{\overset{Me}{\mid}}{N^+}}-(CH_2)_{11}-Me$$ |
| 63. 16545-85-0 | 1-carboxy-N,N,N-trimethyl-1-pentadecanaminium, inner salt $$^-O_2C-\underset{\underset{}{\mid}}{\overset{\overset{N^+Me_3}{\mid}}{CH}}-(CH_2)_{13}-Me$$ |
| 64. 19223-55-3 | 2-hydroxy-N,N-dimethyl-N-(3-((1-oxododecyl)amino)propyl)-3-sulfo-1-propanaminium, inner salt $$^-O_3S-CH_2-\overset{\overset{OH}{\mid}}{CH}-CH_2-\underset{\underset{Me}{\mid}}{\overset{\overset{Me}{\mid}}{N^+}}-(CH_2)_3-NH-\overset{\overset{O}{\|}}{C}-(CH_2)_{10}-Me$$ |
| 65. 19223-56-4 | N-(2-hydroxy-3-sulfopropyl)-N,N-dimethyl-1-octadecanaminium, inner salt $$^-O_3S-CH_2-\overset{\overset{OH}{\mid}}{CH}-CH_2-\underset{\underset{Me}{\mid}}{\overset{\overset{Me}{\mid}}{N^+}}-(CH_2)_{17}-Me$$ |
| 66. 22313-73-1 | N,N-dimethyl-N-(4-sulfobutyl)-1-octadecanaminium, inner salt $$^-O_3S-(CH_2)_4-\underset{\underset{Me}{\mid}}{\overset{\overset{Me}{\mid}}{N^+}}-(CH_2)_{17}-Me$$ |
| 67. 23609-76-9 | N-(carboxymethyl)-N,N-dimethyl-1-tridecanaminium, inner salt $$^-O_2C-CH_2-\underset{\underset{Me}{\mid}}{\overset{\overset{Me}{\mid}}{N^+}}-(CH_2)_{12}-Me$$ |
| 68. 23609-77-0 | N-(carboxymethyl)-N,N-dimethyl-1-pentadecanaminium, inner salt $$^-O_2C-CH_2-\underset{\underset{Me}{\mid}}{\overset{\overset{Me}{\mid}}{N^+}}-(CH_2)_{14}-Me$$ |

TABLE 13-continued

| CAS ® No. | Name & Structure |
|---|---|
| 69. 24020-67-5 | N,N-dimethyl-N-(2-sulfoethyl)-1-dodecanaminium, inner salt<br><br>$^-O_3S-CH_2-CH_2-\overset{\overset{\displaystyle Me}{\mid}}{\underset{\underset{\displaystyle Me}{\mid}}{N^+}}-(CH_2)_{11}-Me$ |
| 70. 25322-68-3 | PEG 1450 and α-hydro-ω-hydroxy-poly(oxy-1,2-ethanediyl)<br>$HO\!-\!\!\left[CH_2-CH_2-O\right]_{\!n}\!\!-\!H$<br><br>PEG 1450: n 24 |
| 71. 26483-35-2 | N,N-dimethyl-1-docosanamine N-oxide<br><br>$Me-\overset{\overset{\displaystyle O}{\|}}{\underset{\underset{\displaystyle Me}{\mid}}{N}}-(CH_2)_{21}-Me$ |
| 72. 26873-85-8 | Ficoll 400,000 and β-D-fructofuranosyl α-D-glucopyranoside polymer with (chloromethyl)oxirane |
| 73. 29557-49-1 | (2-(dodecylhydroxyphosphinyl)ethyl)trimethyl-ammonium hydroxide, inner salt<br><br>$Me_3N^+\!-\!CH_2\!-\!CH_2\!-\!\overset{\overset{\displaystyle O^-}{\mid}}{\underset{\underset{\displaystyle O}{\|}}{P}}\!-\!(CH_2)_{11}\!-\!Me$ |
| 74. 30612-73-8 | N-(2-carboxyethyl)-N,N-dimethyl-1-octadecanaminium, inner salt<br><br>$^-O_2C-CH_2-CH_2-\overset{\overset{\displaystyle Me}{\mid}}{\underset{\underset{\displaystyle Me}{\mid}}{N^+}}-(CH_2)_{17}-Me$ |
| 75. 32020-40-9 | (2-(dodecylhydroxyphosphinyl)ethyl)dimethyl-sulfonium hydroxide, inner salt<br><br>$Me\!-\!\overset{\overset{\displaystyle Me}{\mid}}{S^+}\!-\!CH_2\!-\!CH_2\!-\!\overset{\overset{\displaystyle O^-}{\mid}}{\underset{\underset{\displaystyle O}{\|}}{P}}\!-\!(CH_2)_{11}\!-\!Me$ |
| 76. 32020-41-0 | (3-hydroxypropyl)trimethyl-ammonium hydroxide, hydrogen decylphosphonate, inner salt<br><br>$Me_3N^+\!-\!(CH_2)_3\!-\!O\!-\!\overset{\overset{\displaystyle O^-}{\mid}}{\underset{\underset{\displaystyle O}{\|}}{P}}\!-\!(CH_2)_{11}\!-\!Me$ |
| 77. 32020-42-1 | (2-hydroxyethyl)dimethyl-sulfonium hydroxide, hydrogen decylphosphonate, inner salt<br><br>$Me\!-\!\overset{\overset{\displaystyle Me}{\mid}}{S^+}\!-\!CH_2\!-\!CH_2\!-\!O\!-\!\overset{\overset{\displaystyle O^-}{\mid}}{\underset{\underset{\displaystyle O}{\|}}{P}}\!-\!(CH_2)_9\!-\!Me$ |
| 78. 32020-43-2 | diethyl(2-hydroxyethyl)-sulfonium hydroxide, decylhydrogen phosphate, inner salt<br><br>$Me\!-\!(CH_2)_9\!-\!O\!-\!\overset{\overset{\displaystyle O^-}{\mid}}{\underset{\underset{\displaystyle O}{\|}}{P}}\!-\!O\!-\!CH_2\!-\!CH_2\!-\!\overset{\overset{\displaystyle Et}{\mid}}{S^+}\!-\!Et$ |

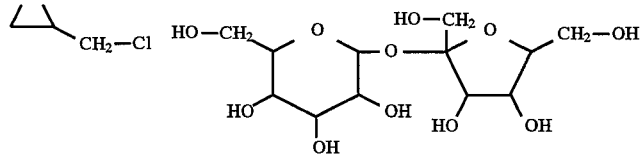

TABLE 13-continued

| CAS ® No. | Name & Structure |
|---|---|
| 79. 32954-43-1 | N-(carboxymethyl)-N,N-dimethyl-3-((1-oxohexadecyl)amino)-1-propanaminium, inner salt<br><br>$^-O_2C-CH_2-\underset{\underset{Me}{\mid}}{\overset{\overset{Me}{\mid}}{N^+}}-(CH_2)_3-NH-\overset{\overset{O}{\parallel}}{C}-(CH_2)_{14}-Me$ |
| 80. 34135-76-7 | N-(2-hydroxy-3-sulfopropyl)-N,N-dimethyl-1-decanaminium, inner salt<br><br>$^-O_3S-CH_2-\overset{\overset{OH}{\mid}}{CH}-CH_2-\underset{\underset{Me}{\mid}}{\overset{\overset{Me}{\mid}}{N^+}}-(CH_2)_9-Me$ |
| 81. 34236-95-8 | N,N-dimethyl-N-(3-(sulfooxy)propyl)-1-hexadecanaminium, inner salt<br><br>$^-O_3S-O-(CH_2)_3-\underset{\underset{Me}{\mid}}{\overset{\overset{Me}{\mid}}{N^+}}-(CH_2)_{15}-Me$ |
| 82. 35489-44-2 | N-(1,3-dimethyl-3-sulfobutyl)-N,N-dimethyl-1-dodecanaminium, inner salt<br><br>$Me-\underset{\underset{SO_3^-}{\mid}}{\overset{\overset{Me}{\mid}}{C}}-CH_2-\overset{\overset{Me}{\mid}}{CH}-\underset{\underset{Me}{\mid}}{\overset{\overset{Me}{\mid}}{N^+}}-(CH_2)_{11}-Me$ |
| 83. 36051-36-2 | N,N-dimethyl-N-(sulfomethyl)-1-octadecanaminium, inner salt<br><br>$^-O_3S-CH_2-\underset{\underset{Me}{\mid}}{\overset{\overset{Me}{\mid}}{N^+}}-(CH_2)_{17}-Me$ |
| 84. 42416-43-3 | N-(2-carboxyethyl)-N,N-dimethyl-1-hexadecanaminium, inner salt<br><br>$^-O_2C-CH_2-CH_2-\underset{\underset{Me}{\mid}}{\overset{\overset{Me}{\mid}}{N^+}}-(CH_2)_{15}-Me$ |
| 85. 52562-28-4 | N,N-dimethyl-N-(3-((1-oxododecyl)amino)propyl)-3-sulfo-1-propanaminium, inner salt<br><br>$^-O_3S-(CH_2)_3-\underset{\underset{Me}{\mid}}{\overset{\overset{Me}{\mid}}{N^+}}-(CH_2)_3-NH-\overset{\overset{O}{\parallel}}{C}-(CH_2)_{10}-Me$ |
| 86. 52562-29-5 | N,N-dimethyl-N-(3-((1-oxohexadecyl)amino)propyl)-3-sulfo-1-propanaminium, inner salt<br><br>$^-O_3S-(CH_2)_3-\underset{\underset{Me}{\mid}}{\overset{\overset{Me}{\mid}}{N^+}}-(CH_2)_3-NH-\overset{\overset{O}{\parallel}}{C}-(CH_2)_{14}-Me$ |
| 87. 52667-78-4 | N,N-dimethyl-N-(sulfomethyl)-1-dodecanaminium, inner salt<br><br>$^-O_3S-CH_2-\underset{\underset{Me}{\mid}}{\overset{\overset{Me}{\mid}}{N^+}}-(CH_2)_{11}-Me$ |
| 88. 56505-82-9 | N-(2-hydroxy-3-sulfopropyl)-N,N-dimethyl-2-tetradecanaminium, inner salt<br><br>$Me-\underset{\underset{Me-CH-(CH_2)_{11}-Me}{\mid}}{\overset{\overset{Me}{\mid}}{N^+}}-CH_2-\overset{\overset{OH}{\mid}}{CH}-CH_2-SO_3^-$ |

TABLE 13-continued

| CAS ® No. | Name & Structure |
|---|---|
| 89. 58930-04-4 | N,N-dimethyl-N-(2-sulfoethyl)-1-tetradecanaminium, inner salt<br><br>$^-O_3S-CH_2-CH_2-\overset{\overset{\displaystyle Me}{\mid}}{\underset{\underset{\displaystyle Me}{\mid}}{N^+}}-(CH_2)_{13}-Me$ |
| 90. 58930-05-5 | N,N-dimethyl-N-(2-sulfoethyl)-1-hexadecanaminium, inner salt<br><br>$^-O_3S-CH_2-CH_2-\overset{\overset{\displaystyle Me}{\mid}}{\underset{\underset{\displaystyle Me}{\mid}}{N^+}}-(CH_2)_{15}-Me$ |
| 91. 58930-06-6 | N,N-dimethyl-3-((1-oxohexadecyl)amino)-N-(2-sulfoethyl)-1-propanaminium, inner salt<br><br>$^-O_3S-CH_2-CH_2-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{14}-Me$ |
| 92. 58930-07-7 | N,N-dimethyl-N-(4-sulfobutyl)-1-hexadecanaminium, inner salt<br><br>$^-O_3S-(CH_2)_4-\overset{\overset{\displaystyle Me}{\mid}}{\underset{\underset{\displaystyle Me}{\mid}}{N^+}}-(CH_2)_{15}-Me$ |
| 93. 58930-08-8 | N,N-dimethyl-N-(3-((oxohexadecyl)amino)propyl)-4-sulfo-1-butanaminium, inner salt<br><br>$^-O_3S-(CH_2)_4-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{14}-Me$ |
| 94. 58930-09-9 | N,N-dimethyl-N-(2-(sulfooxy)ethyl)-1-tetradecanaminium, inner salt<br><br>$^-O_3S-O-CH_2-CH_2-\overset{\overset{\displaystyle Me}{\mid}}{\underset{\underset{\displaystyle Me}{\mid}}{N^+}}-(CH_2)_{13}-Me$ |
| 95. 58930-10-2 | N,N-dimethyl-N-(2-(sulfooxy)ethyl)-1-hexadecanaminium, inner salt<br><br>$^-O_3S-O-CH_2-CH_2-\overset{\overset{\displaystyle Me}{\mid}}{\underset{\underset{\displaystyle Me}{\mid}}{N^+}}-(CH_2)_{15}-Me$ |
| 96. 58930-11-3 | N,N-dimethyl-3-((1-oxohexadecyl)amino)-N-(2-(sulfooxy)ethyl)-1-propanaminium, inner salt<br><br>$^-O_3S-O-CH_2-CH_2-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{14}-Me$ |
| 97. 58930-12-4 | N,N-dimethyl-N-(3-(sulfooxy)propyl)-1-tetradecanaminium, inner salt<br><br>$^-O_3S-O-(CH_2)_3-\overset{\overset{\displaystyle Me}{\mid}}{\underset{\underset{\displaystyle Me}{\mid}}{N^+}}-(CH_2)_{13}-Me$ |
| 98. 58930-13-5 | N,N-dimethyl-3-((1-oxohexadecyl)amino)-N-(3-(sulfooxy)propyl)-1-propanaminium, inner salt<br><br>$^-O_3S-O-(CH_2)_3-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{14}-Me$ |

TABLE 13-continued

| CAS ® No. | Name & Structure |
|---|---|
| 99. 58930-14-6 | N,N-dimethyl-N-(4-(sulfooxy)butyl)-1-dodecanaminium, inner salt<br><br>$^-O_3S-O-(CH_2)_4-\overset{\overset{\displaystyle Me}{\mid}}{\underset{\underset{\displaystyle Me}{\mid}}{N^+}}-(CH_2)_{11}-Me$ |
| 100. 58930-15-7 | N,N-dimethyl-N-(4-(sulfooxy)butyl)-1-hexadecanaminium, inner salt<br><br>$^-O_3S-O-(CH_2)_4-\overset{\overset{\displaystyle Me}{\mid}}{\underset{\underset{\displaystyle Me}{\mid}}{N^+}}-(CH_2)_{15}-Me$ |
| 101. 58930-16-8 | N,N-dimethyl-N-(3-((1-oxohexadecyl)amino)propyl)-4-(sulfooxy)-1-butanaminium, inner salt<br><br>$^-O_3S-O-(CH_2)_4-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{14}-Me$ |
| 102. 59272-84-3 | N-(carboxymethyl)-N,N-dimethyl-3-((1-oxotetradecyl)amino)-1-propanaminium, inner salt<br><br>$^-O_2C-CH_2-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{12}-Me$ |
| 103. 59942-40-4<br>N/A | N,N-dimethyl-N-(methyl-2-sulfoethyl)-1-dodecanaminium, inner salt |
| 104. 59942-41-5<br>N/A | N,N-dimethyl-N-(methyl-2-sulfoethyl)-1-tetradecanaminium, inner salt |
| 105. 59942-42-6<br>N/A | N,N-dimethyl-N-(methyl-2-sulfoethyl)-1-hexadecanaminium, inner salt |
| 106. 61789-37-9<br>N/A | cocoamidopropyl carboxymethylbetaine |
| 107. 61789-39-7 | 3-amino-N-(carboxymethyl)-N,N-dimethyl-1-propanaminium, N-coco acyl derivs., chlorides, sodium salt |
| 108. 61789-40-0<br>N/A | 3-amino-N-(carboxymethyl)-N,N-dimethyl-1-propanaminium, N-coco acyl derivs., inner salt |
| 109. 63663-10-5 | 2-hydroxy-N,N-dimethyl-N-(3-((1-oxotetradecyl)amino)propyl)-3-sulfo-1-propanaminium, inner salt<br><br>$^-O_3S-CH_2-\overset{\overset{\displaystyle OH}{\mid}}{CH}-CH_2-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{12}-Me$ |
| 110. 63663-11-6 | 2-hydroxy-N,N-dimethyl-N-(3-((1-oxohexadecyl)amino)propyl)-3-sulfo-1-propanaminium, inner salt<br><br>$^-O_3S-CH_2-\overset{\overset{\displaystyle OH}{\mid}}{CH}-CH_2-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{14}-Me$ |
| 111. 63663-12-7 | 2-hydroxy-N,N-dimethyl-N-(3-[(1-oxooctadecyl)amino)propyl]-3-sulfo-1-propanaminium inner salt<br><br>$^-O_3S-CH_2-\overset{\overset{\displaystyle OH}{\mid}}{CH}-CH_2-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{16}-Me$ |

TABLE 13-continued

| CAS ® No. | Name & Structure |
|---|---|
| 112. 63663-13-8 | N,N-dimethyl-N-(3-((1-oxohexadecyl)amino)propyl)-2-sulfo-1-propanaminium, inner salt Me—CH(SO$_3^-$)—CH$_2$—N$^+$(Me)(Me)—(CH$_2$)$_3$—NH—C(=O)—(CH$_2$)$_{14}$—Me |
| 113. 64463-49-6 | N,N-dimethyl-N-(4-sulfobutyl)-1-dodecanaminium, inner salt $^-$O$_3$S—(CH$_2$)$_4$—N$^+$(Me)(Me)—(CH$_2$)$_{11}$—Me |
| 114. 65180-40-7 | N-dodecyl-N,N-dimethyl-4-sulfo-benzenemethanaminium, inner salt $^-$O$_3$S—C$_6$H$_4$—CH$_2$—N$^+$(Me)(Me)—(CH$_2$)$_{11}$—Me |
| 115. 65180-41-8 | N,N-dimethyl-4-sulfo-N-tetradecyl-benzenemethanaminium, inner salt $^-$O$_3$S—C$_6$H$_4$—CH$_2$—N$^+$(Me)(Me)—(CH$_2$)$_{13}$—Me |
| 116. 65180-42-9 | N-hexadecyl-N,N-dimethyl-4-sulfo-benzenemethanaminium, inner salt $^-$O$_3$S—C$_6$H$_4$—CH$_2$—N$^+$(Me)(Me)—(CH$_2$)$_{15}$—Me |
| 117. 65180-43-0 | N,N-dimethyl-N-octadecyl-4-sulfo-benzenemethanaminium, inner salt $^-$O$_3$S—C$_6$H$_4$—CH$_2$—N$^+$(Me)(Me)—(CH$_2$)$_{17}$—Me |
| 118. 65180-44-1 | N,N-dimethyl-N-(3-((1-oxododecyl)amino)propyl)-4-sulfo-benzenemethanaminium, inner salt $^-$O$_3$S—C$_6$H$_4$—CH$_2$—N$^+$(Me)(Me)—(CH$_2$)$_3$—NH—C(=O)—(CH$_2$)$_{10}$—Me |
| 119. 65180-45-2 | N,N-dimethyl-N-(3-((1-oxotetradecyl)amino)propyl)-4-sulfo-benzenemethanaminium, inner salt $^-$O$_3$S—C$_6$H$_4$—CH$_2$—N$^+$(Me)(Me)—(CH$_2$)$_3$—NH—C(=O)—(CH$_2$)$_{12}$—Me |

TABLE 13-continued

| CAS ® No. | Name & Structure |
|---|---|
| 120. 65180-46-3 | N,N-dimethyl-N-(3-((1-oxohexadecyl)amino)propyl)-4-sulfo-benzenemethanaminium, inner salt<br><br>$^-O_3S\text{-}C_6H_4\text{-}CH_2\text{-}N^+(Me)(Me)\text{-}(CH_2)_3\text{-}NH\text{-}C(=O)\text{-}(CH_2)_{14}\text{-}Me$ |
| 121. 65180-47-4 | N,N-dimethyl-N-(3-((1-oxooctadecyl)amino)propyl)-4-sulfo-benzenemethanaminium, inner salt<br><br>$^-O_3S\text{-}C_6H_4\text{-}CH_2\text{-}N^+(Me)(Me)\text{-}(CH_2)_3\text{-}NH\text{-}C(=O)\text{-}(CH_2)_{16}\text{-}Me$ |
| 122. 66451-67-0 | N-(carboxymethyl)-N,N-dimethyl-1-oxo-1-dodecanaminium, inner salt<br><br>$^-O_2C\text{-}CH_2\text{-}N^+(Me)(Me)\text{-}C(=O)\text{-}(CH_2)_{10}\text{-}Me$ |
| 123. 66451-68-1 | N-(carboxymethyl)-N,N-dimethyl-1-oxo-1-octadecanaminium, inner salt<br><br>$^-O_2C\text{-}CH_2\text{-}N^+(Me)(Me)\text{-}C(=O)\text{-}(CH_2)_{16}\text{-}Me$ |
| 124. 66516-99-2 | N-(carboxymethyl)-N,N-dimethyl-1-oxo-1-hexadecanaminium, inner salt<br><br>$^-O_2C\text{-}CH_2\text{-}N^+(Me)(Me)\text{-}C(=O)\text{-}(CH_2)_{14}\text{-}Me$ |
| 125. 67030-70-0 | N,N-dimethyl-N-(3-sulfopropyl)-1-pentadecanaminium, inner salt<br><br>$^-O_3S\text{-}(CH_2)_3\text{-}N^+(Me)(Me)\text{-}(CH_2)_{14}\text{-}Me$ |
| 126. 68139-30-0 | cocoamidopropyl hydroxypropylsulfobetaine and N-(3-aminopropyl)-2-hydroxy-N,N-dimethyl-3-sulfo-1-propanaminium N-coco acyl derivs., inner salts |
| 127. 68155-09-9<br>N/A | cocoamidopropyl dimethyl amine oxide |
| 128. 68334-21-4<br>N/A | 1-(carboxymethyl)-4,5-dihydro-1-(hydroxyethyl)-2-norcoco alkyl-Imidazolinium, inner salt |
| 129. 68424-94-2<br>N/A | cococarboxymethylbetaine |
| 130. 69725-38-3<br>N/A | N-(2-carboxyethyl)-N,N-dimethyl-1-tetradecanaminium, inner salt |
| 131. 69775-75-3 | N,N-dimethyl-N-(sulfomethyl)-1-hexadecanaminium, inner salt<br><br>$^-O_3S\text{-}CH_2\text{-}N^+(Me)(Me)\text{-}(CH_2)_{15}\text{-}Me$ |
| 132. 70750-46-8<br>N/A | Tallow bishydroxyethyl glycinate or bis(hydroxyethyl)tallow alkyl betaine |

TABLE 13-continued

| CAS ® No. | Name & Structure |
|---|---|
| 133. 71497-51-3 | N-(2-hydroxy-3-sulfopropyl)-N,N-dimethyl-1-tetradecanaminium, inner salt<br>Me—(CH$_2$)$_{12}$—Me=D1<br>$^-$O$_3$S—CH$_2$—CH(OH)—CH$_2$—N$^+$(D1)(Me)—Me |
| 134. 71502-45-9 | N-(2-hydroxy-3-sulfopropyl)-N,N-dimethyl-1-pentadecanaminium, inner salt<br>$^-$O$_3$S—CH$_2$—CH(OH)—CH$_2$—N$^+$(Me)(Me)—(CH$_2$)$_{14}$—Me |
| 135. 71695-31-3 | 4-carboxy-N-dodecyl-N,N-dimethyl-benzenemethanaminium, inner salt<br>$^-$O$_2$C—C$_6$H$_4$—CH$_2$—N$^+$(Me)(Me)—(CH$_2$)$_{11}$—Me |
| 136. 71695-32-4 | N-(3-carboxypropyl)-N,N-dimethyl-1-hexadecanaminium, inner salt<br>$^-$O$_2$C—(CH$_2$)$_3$—N$^+$(Me)(Me)—(CH$_2$)$_{15}$—Me |
| 137. 71695-33-5 | 4-carboxy-N-hexadecyl-N,N-dimethyl-benzenemethanaminium, inner salt<br>$^-$O$_2$C—C$_6$H$_4$—CH$_2$—N$^+$(Me)(Me)—(CH$_2$)$_{15}$—Me |
| 138. 71695-34-6 | 2-carboxy-N-dodecyl-N,N-dimethyl-benzenemethanaminium, inner salt<br>o-(CO$_2^-$)C$_6$H$_4$—CH$_2$—N$^+$(Me)(Me)—(CH$_2$)$_{11}$—Me |
| 139. 71695-35-7 | 2-carboxy-N-hexadecyl-N,N-dimethyl-benzenemethanaminium, inner salt<br>o-(CO$_2^-$)C$_6$H$_4$—CH$_2$—N$^+$(Me)(Me)—(CH$_2$)$_{15}$—Me |
| 140. 71850-81-2 | ricinamidopropyl carboxymethylbetaine and N-(carboxymethyl)-3-((12-hydroxy-1-oxo-9-octadecenyl)amino)-N,N-dimethyl-1-propanaminium, inner salt<br>Me—(CH$_2$)$_5$—CH(OH)—R—CH=CH(Z)—(CH$_2$)$_7$—C(O)—NH—(CH$_2$)$_3$—N$^+$(Me)(Me)—CH$_2$—CO$_2^-$ |

TABLE 13-continued

| CAS ® No. | Name & Structure |
|---|---|
| 141. 73565-98-7 | N-(5-carboxypentyl)-N,N-dimethyl-1-hexadecanaminium, inner salt<br><br>$^-O_2C-(CH_2)_5-\overset{\overset{\displaystyle Me}{\mid}}{\underset{\underset{\displaystyle Me}{\mid}}{N^+}}-(CH_2)_{15}-Me$ |
| 142. 73602-79-6 | 2-hydroxy-N,N-dimethyl-N-(3-((1-oxododecyl)amino)propyl)-3-(phosphonooxy)-1-propanaminium, inner salt<br><br>$^-HO_3P-O-CH_2-\overset{\overset{\displaystyle OH}{\mid}}{CH}-CH_2-\overset{\overset{\displaystyle Me}{\mid}}{\underset{\underset{\displaystyle Me}{\mid}}{N^+}}-(CH_2)_3-NH-\overset{\overset{\displaystyle O}{\|}}{C}-(CH_2)_{10}-Me$ |
| 143. 75621-03-3 | CHAPS and N,N-dimethyl-N-(3-sulfopropyl)-3-[[(3α,5β,7α,12α)-3-7-12-trihydroxy-24-oxocholan-24-yl]amino]-1-propanaminium, inner salt |
| 144. 76392-97-7 | N-(5-carboxypentyl)-N,N-dimethyl-1-dodecanaminium, inner salt<br><br>$^-O_2C-(CH_2)_5-\overset{\overset{\displaystyle Me}{\mid}}{\underset{\underset{\displaystyle Me}{\mid}}{N^+}}-(CH_2)_{11}-Me$ |
| 145. 78195-27-4 | N-(3-carboxypropyl)-N,N-dimethyl-1-octadecanaminium, inner salt<br><br>$^-O_2C-(CH_2)_3-\overset{\overset{\displaystyle Me}{\mid}}{\underset{\underset{\displaystyle Me}{\mid}}{N^+}}-(CH_2)_{17}-Me$ |
| 146. 84082-44-0<br>N/A | Behenyl carboxymethylbetaine and 3-amino-N-(carboxymethyl)-N,N-dimethyl-1-propanaminium N-C8-22 acyl derivs, inner salt |
| 147. 89367-17-9 | N,N-dimethyl-N-(3-(phosphonooxy)propyl)-1-hexadecanaminium, inner salt<br><br>$^-HO_3P-O-(CH_2)_3-\overset{\overset{\displaystyle Me}{\mid}}{\underset{\underset{\displaystyle Me}{\mid}}{N^+}}-(CH_2)_{15}-Me$ |
| 148. 92764-22-2 | N,N-dimethyl-N-(3-(sulfooxy)propyl)-1-decanaminium, inner salt<br><br>$^-O_3S-O-(CH_2)_3-\overset{\overset{\displaystyle Me}{\mid}}{\underset{\underset{\displaystyle Me}{\mid}}{N^+}}-(CH_2)_9-Me$ |
| 149. 92764-24-4 | N,N-dimethyl-N-(2-(sulfooxy)ethyl)-1-decanaminium, inner salt<br><br>$^-O_3S-O-CH_2-CH_2-\overset{\overset{\displaystyle Me}{\mid}}{\underset{\underset{\displaystyle Me}{\mid}}{N^+}}-(CH_2)_9-Me$ |

TABLE 13-continued

| CAS ® No. | Name & Structure |
|---|---|
| 150. 99485-86-6 | 3(((hexadecyloxy)hydroxyphosphinyl)oxy)-2-hydroxy-N,N,N-trimethyl-1-propanaminium, inner salt $$\text{Me}-(\text{CH}_2)_{15}-\text{O}-\underset{\underset{\text{O}}{\|}}{\overset{\text{O}^-}{\text{P}}}-\text{O}-\text{CH}_2-\overset{\text{OH}}{\underset{}{\text{CH}}}-\text{CH}_2-\text{N}^+\text{Me}_3$$ |
| 151. 99485-87-7 | 2-hydroxy-3-((hydroxy(octadecyloxy)phosphinyl)oxy)-N,N,N-trimethyl-1-propanaminium, inner salt $$\text{Me}-(\text{CH}_2)_{17}-\text{O}-\underset{\underset{\text{O}}{\|}}{\overset{\text{O}^-}{\text{P}}}-\text{O}-\text{CH}_2-\overset{\text{OH}}{\underset{}{\text{CH}}}-\text{CH}_2-\text{N}^+\text{Me}_3$$ |
| 152. 99485-91-3 | 3-(((dodecyloxy)hydroxyphosphinyl)oxy)-2-hydroxy-N,N,N-trimethyl-1-propanaminium, inner salt $$\text{Me}-(\text{CH}_2)_{11}-\text{O}-\underset{\underset{\text{O}}{\|}}{\overset{\text{O}^-}{\text{P}}}-\text{O}-\text{CH}_2-\overset{\text{OH}}{\underset{}{\text{CH}}}-\text{CH}_2-\text{N}^+\text{Me}_3$$ |
| 153. 108797-84-8 | 3-butoxy-2-hydroxy-N-(2-hydroxy-3-sulfopropyl)-N,N-dimethyl-1-propanaminium, inner salt $$\text{n-BuO}-\text{CH}_2-\overset{\text{OH}}{\underset{}{\text{CH}}}-\text{CH}_2-\underset{\underset{\text{Me}}{|}}{\overset{\text{Me}}{\text{N}^+}}-\text{CH}_2-\overset{\text{OH}}{\underset{}{\text{CH}}}-\text{CH}_2-\text{SO}_3^-$$ |
| 154. 120139-51-7 | N-(4-carboxybutyl)-N,N-dimethyl-1-dodecanaminium, inner salt $$^-\text{O}_2\text{C}-(\text{CH}_2)_4-\underset{\underset{\text{Me}}{|}}{\overset{\text{Me}}{\text{N}^+}}-(\text{CH}_2)_{11}-\text{Me}$$ |
| 155. 124046-26-0 N/A | babassuamidopropyl dimethyl amine oxide |
| 156. 124591-53-3 | 2-hydroxy-N,N-dimethyl-N-(2-(phosphonooxy)ethyl)-1-dodecanaminium, inner salt $$^-\text{HO}_3\text{P}-\text{O}-\text{CH}_2-\text{CH}_2-\underset{\underset{\text{Me}}{|}}{\overset{\text{Me}}{\text{N}^+}}-\text{CH}_2-\overset{\text{OH}}{\underset{}{\text{CH}}}-(\text{CH}_2)_9-\text{Me}$$ |
| 157. 124591-54-4 | 2-hydroxy-N,N-dimethyl-N-(2-(phosphonooxy)ethyl)-1-tetradecanaminium, inner salt $$^-\text{HO}_3\text{P}-\text{O}-\text{CH}_2-\text{CH}_2-\underset{\underset{\text{Me}}{|}}{\overset{\text{Me}}{\text{N}^+}}-\text{CH}_2-\overset{\text{OH}}{\underset{}{\text{CH}}}-(\text{CH}_2)_{11}-\text{Me}$$ |
| 158. 124591-57-7 | 2-hydroxy-N,N-dimethyl-N-(2-(phosphonooxy)ethyl)-1-hexadecanaminium, inner salt $$^-\text{HO}_3\text{P}-\text{O}-\text{CH}_2-\text{CH}_2-\underset{\underset{\text{Me}}{|}}{\overset{\text{Me}}{\text{N}^+}}-\text{CH}_2-\overset{\text{OH}}{\underset{}{\text{CH}}}-(\text{CH}_2)_{13}-\text{Me}$$ |
| 159. 126712-86-5 | N,N-dimethyl-N-(2-(phosphonooxy)ethyl)-1-dodecanaminium, inner salt $$^-\text{HO}_3\text{P}-\text{O}-\text{CH}_2-\text{CH}_2-\underset{\underset{\text{Me}}{|}}{\overset{\text{Me}}{\text{N}^+}}-(\text{CH}_2)_{11}-\text{Me}$$ |

TABLE 13-continued

| CAS ® No. | Name & Structure |
|---|---|
| 160. 126712-87-6 | N,N-dimethyl-N-(2-(phosphonooxy)ethyl)-1-tetradecanaminium inner salt<br><br>$^{-}HO_3P-O-CH_2-CH_2-\overset{\overset{\displaystyle Me}{\mid}}{\underset{\underset{\displaystyle Me}{\mid}}{N^+}}-(CH_2)_{13}-Me$ |
| 161. 126712-88-7 | N,N-dimethyl-N-(2-(phosphonooxy)ethyl)-1-hexadecanaminium, inner salt<br><br>$^{-}HO_3P-O-CH_2-CH_2-\overset{\overset{\displaystyle Me}{\mid}}{\underset{\underset{\displaystyle Me}{\mid}}{N^+}}-(CH_2)_{15}-Me$ |
| 162. 126712-89-8 | N,N-dimethyl-N-(2-(phosphonooxy)ethyl)-1-octadecanamimum, inner salt<br><br>$^{-}HO_3P-O-CH_2-CH_2-\overset{\overset{\displaystyle Me}{\mid}}{\underset{\underset{\displaystyle Me}{\mid}}{N^+}}-(CH_2)_{17}-Me$ |
| 163. 126712-90-1 | N,N-diethyl-N-(2-(phosphonooxy)ethyl)-1-hexadecanaminium, inner salt<br><br>$^{-}HO_3P-O-CH_2-CH_2-\overset{\overset{\displaystyle Et}{\mid}}{\underset{\underset{\displaystyle Et}{\mid}}{N^+}}-(CH_2)_{15}-Me$ |
| 164. 126712-91-2 | N-(2-(phosphonooxy)ethyl)-N,N-dipropyl-1-hexadecanaminium, inner salt<br><br>$\text{n-Pr}-\overset{\overset{\displaystyle CH_2-CH_2-O-PO_3H^-}{\mid}}{\underset{\underset{\displaystyle \text{n-Pr}}{\mid}}{N^+}}-(CH_2)_{15}-Me$ |
| 165. 126712-92-3 | N,N-dibutyl-N-(2-(phosphonooxy)ethyl)-1-hexadecanaminium, inner salt<br><br>$\text{n-Bu}-\overset{\overset{\displaystyle CH_2-CH_2-O-PO_3H^-}{\mid}}{\underset{\underset{\displaystyle \text{n-Bu}}{\mid}}{N^+}}-(CH_2)_{15}-Me$ |
| 166. 126712-93-4 | N-ethyl-N-(2-(phosphonooxy)ethyl)-N-propyl-1-hexadecanaminium, inner salt<br><br>$\text{n-Pr}-\overset{\overset{\displaystyle Et}{\mid}}{\underset{\underset{\displaystyle CH_2-CH_2-O-PO_3H^-}{\mid}}{N^+}}-(CH_2)_{15}-Me$ |
| 167. 126712-94-5 | N-butyl-N-ethyl-N-(2-(phosphonooxy)ethyl)-1-hexadecanaminium, inner salt<br><br>$\text{n-Bu}-\overset{\overset{\displaystyle Et}{\mid}}{\underset{\underset{\displaystyle CH_2-CH_2-O-PO_3H^-}{\mid}}{N^+}}-(CH_2)_{15}-Me$ |
| 168. 127087-87-0<br>N/A | NP.40 and<br>α-(4-nonylphenyl)-ω-hydroxy-poly(oxy-1,2-ethanediyl) branched |
| 169. 128506-41-2 | 3-(decyloxy)-2-hydroxy-N,N-dimethyl-N-(2-(phosphonooxy)ethyl)-1-propanaminium, inner salt<br><br>$Me-(CH_2)_9-O-CH_2-\overset{\overset{\displaystyle OH}{\mid}}{CH}-CH_2-\overset{\overset{\displaystyle Me}{\mid}}{\underset{\underset{\displaystyle Me}{\mid}}{N^+}}-CH_2-CH_2-O-PO_3H^-$ |

TABLE 13-continued

| CAS ® No. | Name & Structure |
|---|---|
| 170. 128506-42-3 | 3-(dodecyloxy)-2-hydroxy-N,N-dimethyl-N-(2-(phosphonooxy)ethyl)-1-propanaminium, inner salt<br>$$\text{Me}-(\text{CH}_2)_{11}-\text{O}-\text{CH}_2-\overset{\overset{\text{OH}}{\vert}}{\text{CH}}-\text{CH}_2-\overset{\overset{\text{Me}}{\vert}}{\underset{\underset{\text{Me}}{\vert}}{\text{N}^+}}-\text{CH}_2-\text{CH}_2-\text{O}-\text{PO}_3\text{H}^-$$ |
| 171. 128506-46-7 | 2-hydroxy-N,N-dimethyl-N-(2-(phosphonooxy)ethyl)-3-(tetradecyloxy)-1-propanaminium, inner salt<br>$$\text{Me}-(\text{CH}_2)_{13}-\text{O}-\text{CH}_2-\overset{\overset{\text{OH}}{\vert}}{\text{CH}}-\text{CH}_2-\overset{\overset{\text{Me}}{\vert}}{\underset{\underset{\text{Me}}{\vert}}{\text{N}^+}}-\text{CH}_2-\text{CH}_2-\text{O}-\text{PO}_3\text{H}^-$$ |
| 172. 132621-79-5 | N-(2-carboxyethyl)-N,N-dimethyl-1-tridecanaminium, inner salt<br>$$^-\text{O}_2\text{C}-\text{CH}_2-\text{CH}_2-\overset{\overset{\text{Me}}{\vert}}{\underset{\underset{\text{Me}}{\vert}}{\text{N}^+}}-(\text{CH}_2)_{12}-\text{Me}$$ |
| 173. 132621-80-8 | N-(6-carboxyhexyl)-N,N-dimethyl-1-dodecanaminium, inner salt<br>$$\text{Me}-(\text{CH}_2)_{11}-\overset{\overset{\text{Me}}{\vert}}{\underset{\underset{\text{Me}}{\vert}}{\text{N}^+}}-(\text{CH}_2)_6-\text{CO}_2^-$$ |
| 174. 132621-81-9 | N,N-dimethyl-N-(6-sulfohexyl)-1-hexadecanaminium, inner salt<br>$$^-\text{O}_3\text{S}-(\text{CH}_2)_6-\overset{\overset{\text{Me}}{\vert}}{\underset{\underset{\text{Me}}{\vert}}{\text{N}^+}}-(\text{CH}_2)_{15}-\text{Me}$$ |
| 175. 132630-63-8 | 2-hydroxy-3-((hydroxy(tetradecyloxy)phosphinyl)oxy)-N,N,N-trimethyl-1-propanaminium, inner salt<br>$$\text{Me}-(\text{CH}_2)_{13}-\text{O}-\overset{\overset{\text{O}^-}{\vert}}{\underset{\underset{\text{O}}{\vert\vert}}{\text{P}}}-\text{O}-\text{CH}_2-\overset{\overset{\text{OH}}{\vert}}{\text{CH}}-\text{CH}_2-\text{N}^+\text{Me}_3$$ |
| 176. 134590-60-6 | N,N-dimethyl-N-(2-(phosphonooxy)ethyl)-octadecen-1-aminium, inner salt<br>$$^-\text{HO}_3\text{P}-\text{O}-\text{CH}_2-\text{CH}_2-\overset{\overset{\text{Me}}{\vert}}{\underset{\underset{\text{Me}}{\vert}}{\text{N}^+}}-(\text{CH}_2)_{17}-\text{Me}$$ |
| 177. 134842-83-4 | N,N-dimethyl-N-(2-(phosphonooxy)ethyl)-1-decanaminium, inner salt<br>$$^-\text{HO}_3\text{P}-\text{O}-\text{CH}_2-\text{CH}_2-\overset{\overset{\text{Me}}{\vert}}{\underset{\underset{\text{Me}}{\vert}}{\text{N}^+}}-(\text{CH}_2)_9-\text{Me}$$ |
| 178. 134842-84-5 | N,N-dimethyl-N-(2-(phosphonooxy)ethyl)-1-undecanaminium, inner salt<br>$$^-\text{HO}_3\text{P}-\text{O}-\text{CH}_2-\text{CH}_2-\overset{\overset{\text{Me}}{\vert}}{\underset{\underset{\text{Me}}{\vert}}{\text{N}^+}}-(\text{CH}_2)_{10}-\text{Me}$$ |
| 179. 134842-85-6 | N-ethyl-N-methyl-N-(2-(phosphonooxy)ethyl)-1-hexadecanaminium, inner salt<br>$$^-\text{HO}_3\text{P}-\text{O}-\text{CH}_2-\text{CH}_2-\overset{\overset{\text{Et}}{\vert}}{\underset{\underset{\text{Me}}{\vert}}{\text{N}^+}}-(\text{CH}_2)_{15}-\text{Me}$$ |

TABLE 13-continued

| CAS ® No. | Name & Structure |
|---|---|
| 180. 134842-86-7 | N,N-dimethyl-N-(4-(phosphonooxy)butyl)-1-hexadecanaminium, inner salt<br><br>$^-HO_3P-O-(CH_2)_4-\overset{\overset{\displaystyle Me}{\vert}}{\underset{\underset{\displaystyle Me}{\vert}}{N^+}}-(CH_2)_{15}-Me$ |
| 181. 134842-87-8 | N,N-dimethyl-N-(6-(phosphonooxy)hexyl)-1-hexadecanaminium, inner salt<br><br>$^-HO_3P-O-(CH_2)_6-\overset{\overset{\displaystyle Me}{\vert}}{\underset{\underset{\displaystyle Me}{\vert}}{N^+}}-(CH_2)_{15}-Me$ |
| 182. 144077-11-2 | N,N-dimethyl-N-(3-((1-oxotridecyl)amino)propyl)-4-(sulfooxy)-1-butanaminium, inner salt<br><br>$^-O_3S-O-(CH_2)_4-\overset{\overset{\displaystyle Me}{\vert}}{\underset{\underset{\displaystyle Me}{\vert}}{N^+}}-(CH_2)_3-NH-\overset{\overset{\displaystyle O}{\Vert}}{C}-(CH_2)_{11}-Me$ |
| 183. 144077-12-3 | 2-hydroxy-N,N-dimethyl-N-(3-((1-oxooctadecyl)amino)propyl)-3-(phosphonooxy)-1-propanaminium, inner salt<br><br>$^-HO_3P-O-CH_2-\overset{\overset{\displaystyle OH}{\vert}}{CH}-CH_2-\overset{\overset{\displaystyle Me}{\vert}}{\underset{\underset{\displaystyle Me}{\vert}}{N^+}}-(CH_2)_3-NH-\overset{\overset{\displaystyle O}{\Vert}}{C}-(CH_2)_{16}-Me$ |
| 184. 145578-49-0 | N,N-dimethyl-N-(2-(phosphonooxy)ethyl)-1-heptadecanaminium, inner salt<br><br>$^-HO_3P-O-CH_2-CH_2-\overset{\overset{\displaystyle Me}{\vert}}{\underset{\underset{\displaystyle Me}{\vert}}{N^+}}-(CH_2)_{16}-Me$ |
| 185. 146959-90-2 | N-(3-carboxypropyl)-N,N-dimethyl-1-tetradecanaminium, inner salt<br><br>$^-O_2C-(CH_2)_3-\overset{\overset{\displaystyle Me}{\vert}}{\underset{\underset{\displaystyle Me}{\vert}}{N^+}}-(CH_2)_{13}-Me$ |
| 186. 146959-91-3 | N-(3-carboxypropyl)-N,N-dimethyl-1-pentadecanaminium, inner salt<br><br>$^-O_2C-(CH_2)_3-\overset{\overset{\displaystyle Me}{\vert}}{\underset{\underset{\displaystyle Me}{\vert}}{N^+}}-(CH_2)_{14}-Me$ |
| 187. 148716-30-7 | N,N-dimethyl-N-(2-(phosphonooxy)ethyl)-9-octadecen-1-aminium, inner salt<br><br>$^-HO_3P-O-CH_2-CH_2-\overset{+}{\underset{Me\ \ Me}{N}}-(CH_2)_8-\underline{Z}-(CH_2)_7-Me$ |
| 188. 150147-53-8 | N-(3-carboxypropyl)-N,N-dimethyl-1-undecanaminium, inner salt<br><br>$^-O_2C-(CH_2)_3-\overset{\overset{\displaystyle Me}{\vert}}{\underset{\underset{\displaystyle Me}{\vert}}{N^+}}-(CH_2)_{10}-Me$ |

What is claimed is:

1. A method for decreasing the buoyancy of a microorganism that contains mycolic-acid like structures in the outer membrane of said microorganism, said method comprising contacting said microorganism with a solution comprising an SB-18-like or rod-like detergent under conditions that permit the recovery of said microorganism from said solution.

2. The method of claim 1, wherein said detergent is an SB-18-like detergent.

3. The method of claim 1, wherein said detergent is a rod-like detergent.

4. A method for dispersing a clump of corded microorganisms that contains mycolic-acid like structures in the outer membrane of said microorganism, said method comprising contacting said clump with a solution comprising an SB-18-like or rod-like detergent under conditions that disperses said clump.

5. The method of claim 4, wherein said detergent is an SB-18-like detergent.

6. The method of claim 4, wherein said detergent is a rod-like detergent.

7. The method of claim 2 or 5, wherein said SB-18-like detergent is selected from the group consisting of a CB-like, SB-like, HSB-like, PB-like, StB-like, PhB-like, So-like, Rev-B-like, AO-like, cAB-like, ImB-like detergent and Brij 96.

8. The method of claim 7, wherein said SB-like and HSB-like detergents have the structure

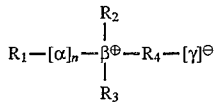

wherein $R_1$ is $C_8$–$C_{22}$;

α is —$CH_2$—, —$CH(OH)$—, —$(CO)$—$NH$—$CH_2CH_2CH_2$—, —$O$—, or —$C(O)$—;

n is 0 or 1;

β is —$N^\oplus$—, —$P^\oplus$—, or —$S^\oplus$—;

$R_2$ is —H, —$CH_3$, —$CH_3$, —$C_2H_5$, —$C_3H_7$, or —$C_4H_9$;

$R_3$ is —H, —$C_3$, —$C_2H_5$, —$C_3H_7$, or —$C_4H_9$;

$R_4$ is —$CH_2$—, —$C_2H_4$—, —$C_3H_6$—, —$C_4H_8$—, —$C_5H_{10}$—, —$C_6H_{12}$—, —$CH_2$—$C_6H_4$—, —$C_mH_{2m}$—, —$CH(OH)CH_2CH_2$—, —$CH_2CH(OH)CH_2$—, or —$C_mH_{2m-1}(OH)$— where m is $\geq 1$; and γ is —$SO_3^{63}$.

9. The method of claim 8, wherein said SB-like detergent is selected from the group consisting of N,N-dimethyl-N-(sulfomethyl)-1-dodecanaminium, inner salt (CAS®No. 52667-78-4), N,N-dimethyl-N-(sulfomethyl)-1-hexadecanaminium, inner salt (CAS®No. 69775-75-3), N,N-dimethyl-N-(sulfomethyl)-1-octadecanaminium, inner salt (CAS®No. 36051-36-2), N,N-dimethyl-N-(2-sulfoethyl)-1-dodecanaminium, inner salt (CAS®No. 24020-67-5), N,N-dimethyl-N-(2-sulfoethyl)-1-tetradecanaminium, inner salt (CAS®No. 58930-04-4), N,N-dimethyl-N-(2-sulfoethyl)-1-hexadecanaminium, inner salt (CAS®No. 58930-05-5), N,N-dimethyl-3-((1-oxohexadecyl)amino)-N-(2-sulfoethyl)-1-propanaminium, inner salt (CAS®No. 58930-06-6), N,N-dimethyl-N-(3-sulfopropyl)-1-octanaminium, inner salt (CAS®No. 15178-76-4), N,N-dimethyl-N-(3-sulfopropyl)-1-decanaminium, inner salt (CAS®No. 15163-36-7), N,N-dimethyl-N-(3-sulfopropyl)-1-dodecanaminium, inner salt (CAS®No. 14933-08-5), N,N-dimethyl-N-(3-sulfopropyl)-1-tetradecanaminium, inner salt (CAS®No. 14933-09-6), N,N-dimethyl-N-(3-sulfopropyl)-1-pentadecanaminium, inner salt (CAS®No. 67030-70-0), N,N-dimethyl-N-(3-sulfopropyl)-1-hexadecanaminium, inner salt (CAS®No. 2281-11-0), N,N-dimethyl-N-(3-sulfopropyl)-1-octadecanaminium, inner salt (CAS®No. 13177-41-8), dodecyldipropyl(3-sulfopropyl)-ammonium hydroxide, inner salt (CAS®No. 15163-34-5), N,N-dimethyl-N-(3-((1-oxododecyl)amino)propyl)-3-sulfo-1-propanaminium, inner salt (CAS®No. 52562-28-4), N,N-dimethyl-N-(3-((1-oxohexadecyl)amino)propyl)-3-sulfo-1-propanaminium, inner salt (CAS®No. 52562-29-5), N,N-dimethyl-N-(methyl-2-sulfoethyl)-1-dodecanaminium, inner salt (CAS®No. 59942-40-4), N,N-dimethyl-N-(methyl-2-sulfoethyl)-1-tetradecanaminium, inner salt (CAS®No. 59942-41-5), N,N-dimethyl-N-(methyl-2-sulfoethyl)-1-hexadecanaminium, inner salt (CAS®No. 59942-42-6), N,N-dimethyl-N-(3-((1-oxohexadecyl)amino)propyl)-2-sulfo-1-propanaminium, inner salt (CAS®No. 63663-13-8), N,N-dimethyl-N-(4-sulfobutyl)-1-dodecanaminium, inner salt (CAS®No. 64463-49-6), N,N-dimethyl-N-(4-sulfobutyl)-1-hexadecanaminium, inner salt (CAS®No. 58930-07-7), N,N-dimethyl-N-(4-sulfobutyl)-1-octadecanaminium, inner salt (CAS®No. 22313-73-1), N-(1,3-dimethyl-3-sulfobutyl)-N,N-dimethyl-1-dodecanaminium, inner salt (CAS®No. 35489-44-2), N,N-dimethyl-N-(3-((oxohexadecyl)amino)propyl)-4-sulfo-1-butanaminium, inner salt (CAS®No. 58930-08-8), N,N-dimethyl-N-(6-sulfohexyl)-1-hexadecanaminium, inner salt (CAS®No. 132621-81-9), N,N-dodecyl-N,N-dimethyl-4-sulfo-benzenemethanaminium, inner salt (CAS®No. 65180-40-7), N,N-dimethyl-4-sulfo-N-tetradecyl-benzenemethanaminium, inner salt (CAS®No. 65180-41-8), N-hexadecyl-N,N-dimethyl-4-sulfo-benzenemethanaminium, inner salt (CAS®No. 65180-42-9), N,N-dimethyl-N-octadecyl-4-sulfo-benzenemethanaminium, inner salt (CAS®No. 65180-43-0), N,N-dimethyl-N-(3-((1-oxododecyl)amino)propyl)-4-sulfo-benzenemethanaminium, inner salt (CAS®No. 65180-44-1), N,N-dimethyl-N-(3-((1-oxotetradecyl)amino)propyl)-4-sulfo-benzenemethanaminium, inner salt (CAS®No. 65180-45-2), N,N-dimethyl-N-(3-((1-oxohexadecyl)amino)propyl)-4-sulfo-benzenemethanaminium, inner salt (CAS®No. 65180-46-3), N,N-dimethyl-N-(3-((1-oxooctadecyl)amino)propyl)-4-sulfo-benzenemethanaminium, inner salt (CAS®No. 65180-47-4), N-(2-hydroxy-3-sulfopropyl)-N,N-dimethyl-1-decanaminium, inner salt (CAS®No. 34135-76-7), N-(2-hydroxy-3-sulfopropyl)-N,N-dimethyl-1-dodecanaminium, inner salt (CAS®No. 13197-76-7), N-(2-hydroxy-3-sulfopropyl)-N,N-dimethyl-2-tetradecanaminium, inner salt (CAS®No. 56505-82-9), N-(2-hydroxy-3-sulfopropyl)-N,N-dimethyl-1-pentadecanaminium, inner salt (CAS®No. 71502-45-9), N-(2-hydroxy-3-sulfopropyl)-N,N-dimethyl-1-hexadecanaminium, inner salt (CAS®No. 7425-12-9), N-(2-hydroxy-3-sulfopropyl)-N,N-dimethyl-1-octadecanaminium, inner salt (CAS®No. 19223-56-4), 2-hydroxy-N,N-dimethyl-N-(3-((1-oxododecyl)amino)propyl)-3-sulfo-1-propanaminium, inner salt (CAS®No. 19223-55-3), 2-hydroxy-N,N-dimethyl-N-(3-((1-oxotetradecyl)amino)propyl)-3-sulfo-1-propanaminium, inner salt (CAS®No. 63663-10-5), 2-hydroxy-N,N-dimethyl-N-(3-((1-oxohexadecyl)amino)propyl)-3-sulfo-1-propanaminium, inner salt (CAS®No. 63663-11-6), 2-hydroxy-N,N-dimethyl-N-(3-((1-oxooctadecyl)amino)propyl)-3-sulfo-1-propanaminium, inner salt (CAS®No. 63663-12-7), N-(2-hydroxy-3-sulfopropyl)-N,N-dimethyl-1-tetradecanaminium, inner salt (CAS®No. 13177-42-9), and N-(2-hydroxy-3-sulfopropyl)-N,N-dimethyl-1-tetradecanaminium, inner salt (CAS®No. 71497-51-3), cocoamidopropyl hydroxysulfobetaine (CAS®No. 68139-30-0), alkylether hydroxypropylsulfobetaine (CAS®No. 108797-84-8), tallowamidopropyl hydroxypropylsulfobetaine, erucamidopropyl hydroxypropylsulfobetaine, and canolamidopropyl betaine.

10. The method of claim 9, wherein said SB-18-like detergent is selected from the group consisting of N,N-dimethyl-N-(2-sulfoethyl)-1-dodecanaminium, inner salt (CAS®No. 24020-67-5),
N,N-dimethyl-N-(2-sulfoethyl)-1-tetradecanaminium, inner salt (CAS®No. 58930-04-4),
N,N-dimethyl-N-(2-sulfoethyl)-1-hexadecanaminium, inner salt (CAS®No. 58930-05-5),
N,N-dimethyl-N-(3-sulfopropyl)-1-dodecanaminium, inner salt (CAS®No. 14933-08-5),
N,N-dimethyl-N-(3-sulfopropyl)-1-tetradecanaminium, inner salt (CAS®No. 14933-09-6),
N,N-dimethyl-N-(3-sulfopropyl)-1-pentadecanaminium, inner salt (CAS®No. 67030-70-0),
N,N-dimethyl-N-(3-sulfopropyl)-1-hexadecanaminium, inner salt (CAS®No. 2281-11-0),
N,N-dimethyl-N-(3-sulfopropyl)-1-hexadecanaminium, inner salt (CAS®No. 13177-41-8),
N,N-dimethyl-N-(3-((1-oxododecyl)amino)propyl)-3-sulfo-1-propanaminium, inner salt (CAS®No. 52562-28-4),
N,N-dimethyl-N-(3-((1-oxohexadecyl)amino)propyl)-3-sulfo-1-propanaminium, inner salt (CAS®No. 52562-29-5),
N,N-dimethyl-N-(4-sulfobutyl)-1-dodecanaminium, inner salt (CAS®No. 64463-49-6),
N,N-dimethyl-N-(4-sulfobutyl)-1-hexadecanaminium, inner salt (CAS®No. 58930-07-7),
N,N-dimethyl-N-(4-sulfobutyl)-1-octadecanaminium, inner salt (CAS®No. 22313-73-1), and
N,N-dimethyl-N-(3-((oxohexadecyl)amino)propyl)-4-sulfo-1-butanaminium, inner salt (CAS®No. 58930-08-8).

11. The method of claim 10, wherein said SB-18-like detergent is selected from the group consisting of N,N-dimethyl-N-(3-sulfopropyl)-1-hexadecanaminium, inner salt (CAS®No. 2281-11-0) and N,N-dimethyl-N-(3-sulfopropyl)-1-octadecanaminium, inner salt (CAS®No. 13177-41-8).

12. The method of claim 11, wherein said SB-18-like detergent is N,N-dimethyl-N-(3-sulfopropyl)-1-hexadecanaminium, inner salt (CAS®No. 2281-11-0).

13. The method of claim 11, wherein said SB-18-like detergent is N,N-dimethyl-N-(3-sulfopropyl)-1-octadecanaminium, inner salt (CAS®No. 13177-41-8).

14. The method of claim 7, wherein said CB-like detergent has the structure

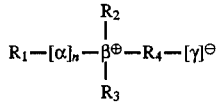

wherein $R_1$ is $C_8$–$C_{22}$;
α is —$CH_2$—, —CH(OH)—, —(CO)—NH—$CH_2CH_2CH_2$—, —O—, or —C(O)—;
n is 0 or 1;
β is —$N^\oplus$—, —$P^\oplus$—, or —$S^\oplus$—;
$R_2$ is —H, —$CH_3$, —$C_2H_5$, —$C_3H_7$, or —$C_4H_9$;
$R_3$ is —H, —$CH_3$, —$C_2H_5$, —$C_3H_7$, or —$C_4H_9$;
$R_4$ is —$CH_2$—, —$C_2H_4$—, —$C_3H_6$—, —$C_4H_8$—, —$C_5H_{10}$—, —$C_6H_{12}$—, —$CH_2$—$C_6H_4$—, —$C_mH_{2m}$—, —CH(OH)$CH_2CH_2$—, —$CH_2$CH(OH)$CH_2$—, or —$C_mH_{2m-1}$(OH)— where m is ≧1; and
γ—$COO^\ominus$.

15. The method of claim 14, wherein said CB-like detergent is selected from the group consisting of N-(carboxymethyl)-N,N-dimethyl-1-hexadecanaminium, inner salt (CAS®No. 693-33-4),
cococarboxymethylbetaine (CAS®No. 68424-94-2),
N-(carboxymethyl)-N,N-dimethyl-9-octadecen-1-aminium, inner salt (CAS®No. 871-37-4),
N-(carboxymethyl)-N,N-dimethyl-3-((1-oxooctadecyl)amino)-1-propanaminium, inner salt (CAS®No. 6179-44-8),
3-amino-N-(carboxymethyl)-N,N-dimethyl-1-propanaminium N-C8-C22 acyl derivatives, inner salt (CAS®No. 84082-44-0),
N-(carboxymethyl)-3-((12-hydroxy-1-oxo-9-octadecenyl)amino)-N,N-dimethyl-1-propanaminium, inner salt (CAS®No. 71850-81-2),
cocoamidopropyl carboxymethylbetaine (CAS®No. 61789-39-7 and CAS®No. 61789-40-0),
N-(2-carboxyethyl)-N,N-dimethyl-1-dodecanaminium, inner salt (CAS®No. 16527-85-8),
N-(2-carboxyethyl)-N,N-dimethyl-1-tridecanaminium, inner salt (CAS®No. 132621-79-5),
N-(2-carboxyethyl)-N,N-dimethyl-1-tetradecanaminium, inner salt (CAS®No. 69725-38-3),
N-(2-carboxyethyl)-N,N-dimethyl-1-hexadecanaminium, inner salt (CAS®No. 42416-43-3),
N-(2-carboxyethyl)-N,N-dimethyl-1-octadecanaminium, inner salt (CAS®No. 30612-73-8),
N-dodecyl-beta-alanine (CAS®No. 1462-54-0),
N-(3-carboxypropyl)-N,N-dimethyl-1-undecanaminium, inner salt (CAS®No. 150147-53-8),
N-(3-carboxypropyl)-N,N-dimethyl-1-dodecanaminium, inner salt (CAS®No. 15163-30-1),
N-(3-carboxypropyl)-N,N-dimethyl-1-tetradecanaminium, inner salt (CAS®No. 146959-90-2),
N-(3-carboxypropyl)-N,N-dimethyl-1-pentadecanaminium, inner salt (CAS®No. 146959-91-3),
N-(3-carboxypropyl)-N,N-dimethyl-1-hexadecanaminium, inner salt (CAS®No. 71695-32-4),
N-(3-carboxypropyl)-N,N-dimethyl-1-octadecanaminium, inner salt (CAS®No. 78195-27-4),
N-(4-carboxybutyl)-N,N-dimethyl-1-dodecanaminium, inner salt (CAS®No. 120139-51-7),
N-(5-carboxypentyl)-N,N-dimethyl-1-dodecanaminium, inner salt (CAS®No. 76392-97-7),
N-(5-carboxypentyl)-N,N-dimethyl-1-hexadecanaminium, inner salt (CAS®No. 73565-98-7),
N-(6-carboxyhexyl)-N,N-dimethyl-1-dodecanaminium, inner salt (CAS®No. 132621-80-8),
4-carboxy-N-dodecyl-N,N-dimethyl-benzenemethanaminium, inner salt (CAS®No. 71695-31-3),
2-carboxy-N-dodecyl-N,N-dimethyl-benzenemethanaminium, inner salt (CAS®No. 71695-34-6),
4-carboxy-N-hexadecyl-N,N-dimethyl-benzenemethanaminium, inner salt (CAS®No. 71695-33-5),
2-carboxy-N-hexadecyl-N,N-dimethyl-benzenemethanaminium, inner salt (CAS®No. 71695-35-7),
tallow glycinate (CAS®No. 70750-46-8),
soyamidopropyl carboxymethylbetaine, and babassuamidopropyl carboxymethylbetaine.

16. The method of claim 15, wherein said CB-like detergent is selected from the group consisting of N-(2-carboxyethyl)-N,N-dimethyl-1-dodecanaminium, inner salt (CAS®No. 16527-85-8),
N-(2-carboxyethyl)-N,N-dimethyl-1-tridecanaminium, inner salt (CAS®No. 132621-79-5),
N-(2-carboxyethyl)-N,N-dimethyl-1-tetradecanaminium, inner salt (CAS®No. 69725-38-3),
N-(2-carboxyethyl)-N,N-dimethyl-1-hexadecanaminium, inner salt (CAS®No. 42416-43-3),
N-(2-carboxyethyl)-N,N-dimethyl-1-octadecanaminium, inner salt (CAS®No. 30612-73-8),
N-(3-carboxypropyl)-N,N-dimethyl-1-undecanaminium, inner salt (CAS®No. 150147-53-8),
N-(3-carboxypropyl)-N,N-dimethyl-1-dodecanaminium, inner salt (CAS®No. 15163-30-1),
N-(3-carboxypropyl)-N,N-dimethyl-1-tetradecanaminium, inner salt (CAS®No. 146959-90-2),
N-(3-carboxypropyl)-N,N-dimethyl-1-pentadecanaminium, inner salt (CAS®No. 146959-91-3),
N-(3-carboxypropyl)-N,N-dimethyl-1-hexadecanaminium, inner salt (CAS®No. 71695-32-4),
N-(3-carboxypropyl)-N,N-dimethyl-1-octadecanaminium, inner salt (CAS®No. 78195-27-4), and
N-(4-carboxybutyl)-N,N-dimethyl-1-dodecanaminium, inner salt (CAS®No. 120139-51-7).

17. The method of claim 16, wherein said CB-like detergent is N-(3-carboxypropyl)-N,N-dimethyl-1-octadecanaminium, inner salt (CAS®No. 78195-27-4).

18. The method of claim 7, wherein said PB-like detergent has the structure

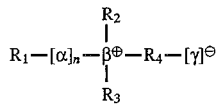

wherein $R_1$ is $C_8$–$C_{22}$;
α is —$CH_2$—, —CH(OH)—, —(CO)—NH—$CH_2CH_2CH_2$—, —O—, or —C(O)—;
n is 0 or 1;
β is —$N^\oplus$—, —$P^\oplus$—, or —$S^\oplus$—;
$R_2$ is —H, —$CH_3$, —$C_2H_5$, —$C_3H_7$, or —$C_4H_9$;
$R_3$ is —H, —$CH_3$, —$C_2H_5$, —$C_3H_7$, or —$C_4H_9$;
$R_4$ is —$CH_2$—, —$C_2H_4$—, —$C_3H_6$—, —$C_4H_8$—, —$C_5H_{10}$—, —$C_6H_{12}$—, —$CH_2$—$C_6H_4$—, —$C_mH_{2m}$—, —CH(OH)$CH_2CH_2$—, —$CH_2$CH(OH)$CH_2$—, or —$C_mH_{2m-1}$(OH)— where m is $\geq 1$; and
γ is —$PO_x^\ominus$ where x=1, 2, or 3.

19. The method of claim 18, wherein said PB-like detergent is selected from the group consisting of N,N-dimethyl-N-(2-(phosponooxy)ethyl)-1-decanaminium, inner salt (CAS®No. 134842-83-4),
N,N-dimethyl-N-(2-(phosphonooxy)ethyl)-1-undecanaminium, inner salt (CAS®No. 134842-84-5),
N,N-dimethyl-N-(2-(phosphonooxy)ethyl)-1-dodecanaminium, inner salt (CAS®No. 126712-86-5),
N,N-dimethyl-N-(2-(phosphonooxy)ethyl)-1-tetradecanaminium, inner salt (CAS®No. 126712-87-6),
N,N-dimethyl-N-(2-(phosphonooxy)ethyl)-1-hexadecanaminium, inner salt (CAS®No. 126712-88-7),
N,N-dimethyl-N-(2-(phosphonooxy)ethyl)-1-heptadecanaminium, inner salt (CAS®No. 145578-49-0),
N,N-dimethyl-N-(2-(phosphonooxy)ethyl)-1-octadecanaminium, inner salt (CAS®No. 126712-89-8),
N,N-dimethyl-N-(2-(phosphonooxy)ethyl)-octadecen-1-aminium, inner salt (CAS®No. 134590-60-6), N,N-dimethyl-N-(2-(phosphonooxy)ethyl)-9-octadecen-1-aminium, inner salt (CAS®No. 148716-30-7),
N,N-diethyl-N-(2-(phosphonooxy)ethyl)-1-hexadecanaminium, inner salt (CAS®No. 126712-90-1),
N-(2-(phosphonooxy)ethyl)-N,N-dipropyl-1-hexadecanaminium, inner salt (CAS®No. 126712-91-2),
N,N-dibutyl-N-(2-(phosphonooxy)ethyl)-1-hexadecanaminium, inner salt (CAS®No. 126712-92-3),
N-ethyl-N-(2-(phosphonooxy)ethyl)-N-propyl-1-hexadecanaminium, inner salt (CAS®No. 126712-93-4),
N-ethyl-N-methyl-N-(2-(phosphonooxy)ethyl)-1-hexadecanaminium, inner salt (CAS®No. 134842-85-6),
N,N-dimethyl-N-(3-(phosphonooxy)propyl)-1-hexadecanaminium, inner salt (CAS®No. 89367-17-9),
N,N-dimethyl-N-(4-(phosphonooxy)butyl)-1-hexadecanaminium, inner salt (CAS®No. 134842-86-7),
N,N-dimethyl-N-(6-(phosphonooxy)hexyl)-1-hexadecanaminium, inner salt (CAS®No. 134842-87-8),
2-hydroxy-N,N-dimethyl-N-(2-(phosphonooxy)ethyl)-1-dodecanaminium, inner salt (CAS®No. 124591-53-3),
2-hydroxy-N,N-dimethyl-N-(2-(phosphonooxy)ethyl)-1-tetradecanaminium, inner salt (CAS®No. 124591-54-4),
2-hydroxy-N,N-dimethyl-N-(2-(phosphonooxy) ethyl)-1-hexadecanaminium, inner salt (CAS®No. 124591-57-7),
N-butyl-N-ethyl-N-(2-(phosphonooxy)ethyl)-1-hexadecanaminium, inner salt (CAS®No. 126712-94-5),
2-hydroxy-N,N-dimethyl-N-(3-((1-oxododecyl)amino)propyl)-3-(phosphonooxy)-1-propanaminium, inner salt (CAS®No. 73602-79-6),
2-hydroxy-N,N-dimethyl-N-(3-((1-oxooctadecyl)amino)propyl)-3-(phosphonooxy)-1-propanaminium, inner salt (CAS®No. 144077-12-3),
3-(decyloxy)-2-hydroxy-N,N-dimethyl-N-(2-(phosphonooxy)ethyl)-1-propanaminium, inner salt (CAS®No. 128506-41-2),
3-(dodecyloxy)-2-hydroxy-N,N-dimethyl-N-(2-(phosphonooxy)ethyl)-1-propanaminium, inner salt (CAS®No. 128506-42-3), and
2-hydroxy-N,N-dimethyl-N-(2-(phosphonooxy)ethyl)-3-(tetradecyloxy)-1-propanaminium, inner salt (CAS®No. 128506-46-7).

20. The method of claim 19, wherein said PB-like detergent is selected from the group consisting of N,N-dimethyl-N-(2-(phosphonooxy)ethyl)-1-dodecanaminium, inner salt (CAS®No. 126712-86-5),
N,N-dimethyl-N-(2-(phosphonooxy)ethyl)-1-tetradecanaminium, inner salt (CAS®No. 126712-87-6),
N,N-dimethyl-N-(2-(phosphonooxy)ethyl)-1-hexadecanaminium, inner salt (CAS®No. 126712-88-7),
N,N-dimethyl-N-(2-(phosphonooxy)ethyl)-1-heptadecanaminium, inner salt (CAS®No. 145578-49-0),
N,N-dimethyl-N-(2-(phosphonooxy)ethyl)-1-octadecanaminium, inner salt (CAS®No. 126712-89-8),
N,N-dimethyl-N-(3-(phosphonooxy)propyl)-1-hexadecanaminium, inner salt (CAS®No. 89367-17-9), and
N,N-dimethyl-N-(4-(phosphonooxy)butyl)-1-hexadecanaminium, inner salt (CAS®No. 134842-86-7).

21. The method of any one of claims 1–6, wherein at least one species of said microorganism is a member of the Mycobacteria.

22. The method of claim 21, wherein said Mycobacteria is selected from one or more members of the group consisting of *M. tuberculosis* (MTB) complex, *M. avium* (MAC) complex, MAIS complex, *M. fortuitum* complex, photochromogens, nonphotochromogens, scotochromogens, *M. africanum*, *M. asiaticum*, *M. avium*, *M. bovis*, *M. bovis* (BCG), *M. butyricum*, *M. chelonae*, *M. duvalii*, *M.*

*flavescens, M. fortuitum, M. gastri, M. gordonae, M. haemophilum, M. intracellularae, M. kansasii, M. leprae, M. lepraemurium, M. linda, M. lufu, M. marinum, M. malmoense, M. microti, M. mucoscum, M. nonchromogenicum, M. paratuberculosis, M. peregrinum, M. phlei, M. rhodochrous, M. scrofulaceum, M. shimoidei, M. simiae, M. smegmatis, M. szulgai, M. terrae, M. thermoresistable, M. triviale, M. tuberculosis, M. ulcerans, M. vaccae, M. xenopi,* and serovars thereof.

23. The method of claim 2, wherein said Mycobacteria is selected from the group consisting of the *M. tuberculosis* (MTB) complex and the *M. avium* (MAC) complex.

24. The method of claim 23, wherein said Mycobacteria is a member of the *M. tuberculosis* (MTB) complex.

25. The method of claim 22, wherein said Mycobacteria is selected from the group consisting of *M. tuberculosis, M. avium, M. paratuberculosis, M. intracellulare, M. kansasii* and *M. marinum.*

26. A method for decreasing the buoyancy of a microorganism that contains mycolic-acid like structures the outer membrane of said microorganism, said method comprising degassing said microorganism.

27. The method of claim 26, wherein said method further comprises at least one wash step wherein said microorganism sample is plac N,N-dimethyl-N-(3-((1-oxohexadecyl)amino)propyl)-4-sulfo-benzenemethanaminium, inner salt (CAS®No. 65180-46-3), N,N-dimethyl-N-(3-((1-oxooctadecyl)amino)propyl)-4-sulfo-benzenemethanaminium, inner salt (CAS®No. 65180-47-4), N-(2-hydroxy-3-sulfopropyl)-N,N-dimethyl-1-decanaminium, inner salt (CAS®No. 34135-76-7), N-(2-hydroxy-3-sulfopropyl)-N,N-dimethyl-1-dodecanaminium, inner salt (CAS®No. 13197-76-7), N-(2-hydroxy-3-sulfopropyl)-N,N-dimethyl-2-tetradecanaminium, inner salt (CAS®No. 56505-82-9), N-(2-hydroxy-3-sulfopropyl)-N,N-dimethyl-1-pentadecanaminium, inner salt (CAS®No. 71502-45-9), N-(2-hydroxy-3-sulfopropyl)-N,N-dimethyl-1-hexadecanaminium, inner salt (CAS®No. 7425-12-9), N-(2-hydroxy-3-sulfopropyl)-N,N-dimethyl-1-octadecanaminium, inner salt (CAS®No. 19223-56-4), 2-hydroxy-N,N-dimethyl-N-(3-((1-oxododecyl)amino)propyl)-3-sulfo-1-propanaminium, inner salt (CAS®No. 19223-55-3), 2-hydroxy-N,N-dimethyl-N-(3-((1-oxotetradecyl)amino)propyl)-3-sulfo-1-propanaminium, inner salt (CAS®No. 63663-10-5), 2-hydroxy-N,N-dimethyl-N-(3-((1-oxohexadecyl)amino)propyl)-3-sulfo-1-propanaminium, inner salt (CAS®No. 63663-11-6), 2-hydroxy-N,N-dimethyl-N-(3-((1-oxooctadecyl) amino)propyl)-3-sulfo-1-propanaminium, inner salt (CAS®No. 63663-12-7), N-(2-hydroxy-3-sulfopropyl)-N,N-dimethyl-1-tetradecanaminium, inner salt (CAS®No. 13177-42-9), and N-(2-hydroxy-3-sulfopropyl)-N,N-dimethyl-1-tetradecanaminium, inner salt (CAS®No. 71497-51-3), cocoamidopropyl hydroxysulfobetaine (CAS®No. 68139-30-0), alkylether hydroxypropylsulfobetaine (CAS®No. 108797-84-8), tallowamidopropyl hydroxypropylsulfobetaine, erucamidopropyl hydroxypropylsulfobetaine, and canolamidopropyl betaine.

35. The method of claim 34, wherein said SB-18-like detergent is selected from the group consisting of SB-like detergents having the structure as defined by N,N-dimethyl-N-(2-sulfoethyl)-1-dodecanaminium, inner salt (CAS®No. 24020-67-5), N,N-dimethyl-N-(2-sulfoethyl)-1-tetradecanaminium, inner salt (CAS®No. 58930-04-4), N,N-dimethyl-N-(2-sulfoethyl)-1-hexadecanaminium, inner salt (CAS®No. 58930-05-5), N,N-dimethyl-N-(3-sulfopropyl)-1-dodecanaminium, inner salt (CAS®No. 14933-08-5), N,N-dimethyl-N-(3-sulfopropyl)-1-tetradecanaminium, inner salt (CAS®No. 14933-09-6), N,N-dimethyl-N-(3-sulfopropyl)-1-pentadecanaminium, inner salt (CAS®No. 67030-70-0), N,N-dimethyl-N-(3-sulfopropyl)-1-hexadecanaminium, inner salt (CAS®No. 2281-11-0), N,N-dimethyl-N-(3-sulfopropyl)-1-octadecanaminium, inner salt (CAS®No. 13177-41-8), N,N-dimethyl-N-(3-((1-oxododecyl)amino)propyl)-3-sulfo-1-propanaminium, inner salt (CAS®No. 52562-28-4), N,N-dimethyl-N-(3-((1-oxohexadecyl)amino)propyl)-3-sulfo-1-propanaminium, inner salt (CAS®No. 52562-29-5), N,N-dimethyl-N-(4-sulfobutyl)-1-dodecanaminium, inner salt (CAS®No. 64463-49-6), N,N-dimethyl-N-(4-sulfobutyl)-1-hexadecanaminium, inner salt (CAS®No. 58930-07-7), N,N-dimethyl-N-(4-sulfobutyl)-1-octadecanaminium, inner salt (CAS®No. 22313-73-1), and N,N-dimethyl-N-(3-((oxohexadecyl)amino)propyl)-4-sulfo-1-butanaminium, inner salt (CAS®No. 58930-08-8).

36. The method of claim 35, wherein said SB-18-like detergent is selected from the group consisting of SB-16(N,N-dimethyl-N-(3-sulfopropyl)-1-hexadecanaminium, inner salt (CAS®No. 2281-11-0)) and SB-18(N,N-dimethyl-N-(3-sulfopropyl)-1-octadecanaminium, inner salt (CAS®No. 13177-41-8)).

37. The method of claim 36, wherein said SB-18-like detergent is N,N-dimethyl-N-(3-sulfopropyl)-1-hexadecanaminium, inner salt (CAS®No. 2281-11-0).

38. The method of claim 36, wherein said SB-18-like detergent is N,N-dimethyl-N-(3-sulfopropyl)-1-octadecanaminium, inner salt (CAS®No. 13177-41-8).

39. The method of claim 31, wherein said CB-like detergent has the structure $$R_1-[\alpha]_n-\beta^{\oplus}-R_4-[\gamma]^{\ominus}$$
$$\phantom{R_1-[\alpha]_n-}\begin{array}{c}R_2\\|\\|\\R_3\end{array}$$

wherein $R_1$ is $C_8$–$C_{22}$;

$\alpha$ is —$CH_2$—, —$CH(OH)$—, —$(CO)$—$NH$—$CH_2CH_2CH_2$—, —$O$—, or —$C(O)$—;

n is 0 or 1;

$\beta$ is —$N^{\oplus}$—, —$P^{\oplus}$—, or —$S^{\oplus}$—;

$R_2$ is —H, —$CH_3$, —$C_2H_5$, —$C_3H_7$, or —$C_4H_9$;

$R_3$ is —H, —$CH_3$, —$C_2H_5$, —$C_{31}H_7$, or —$C_4H_9$;

$R_4$ is —$CH_2$—, —$C_2H_4$—, —$C_3H_6$—, —$C_4H_8$—, —$C_5H_{10}$—, —$C_6H_{12}$—, —$CH_2$—$C_6H_4$—, —$C_mH_{2m}$—, —$CH(OH)CH_2CH_2$—, —$CH_2CH(OH)CH_2$—, or —$C_mH_{2m-1}(OH)$— where m is $\geq 1$; and $\gamma$ is —$COO^{\oplus}$.

40. The method of claim 39, wherein said CB-like detergent is selected from the group consisting of N-(carboxymethyl)-N,N-dimethyl-1-hexadecanaminium, inner salt (CAS®No. 693-33-4), cococarboxymethylbetaine and (CAS®No. 68424-94-2), N-(carboxymethyl)-N,N-dimethyl-9-octadecen-1-aminium, inner salt (CAS®No. 871-37-4), N-(carboxymethyl)-N,N-dimethyl-3-((1-oxooctadecyl)amino)-1-propanaminium, inner salt (CAS®No. 6179-44-8), 3-amino-N(carboxymethyl)-N,N-dimethyl-1-propanaminium N-C8-C22 acyl derivatives, inner salt (CAS®No. 84082-44-0), N-(carboxymethyl)-3-((12-hydroxy-1-oxo-9-octadecenyl)amino)-N,N-dimethyl-1-propanaminium, inner salt (CAS®No. 71850-81-2), cocoamidopropyl carboxymethylbetaine (CAS®No. 61789-39-7 and CAS®No. 61789-40-0), N-(2-carboxyethyl)-N,N-dimethyl-1-dodecanaminium, inner salt (CAS®No. 16527-85-8), N-(2-carboxyethyl)-N,N-dimethyl-1-tridecanaminium, inner salt (CAS®No. 132621-79-5), N-(2-carboxyethyl)-N,N-dimethyl-1-tetradecanaminium, inner salt (CAS®No. 69725-38-3), N-(2-carboxyethyl)-N,N-dimethyl-1-hexadecanaminium, inner salt (CAS®No. 42416-43-3), N-(2-carboxyethyl)-N,N-dimethyl-1-octadecanaminium, inner salt (CAS®No. 30612-73-8), N-dodecyl-beta-alanine (CAS®No. 1462-54-0), N-(3-carboxypropyl)-N,N-dimethyl-1-undecanaminium, inner salt (CAS®No. 150147-53-8), N-(3-carboxypropyl)-N,N-dimethyl-1-dodecanaminium, inner salt (CAS®No. 15163-30-1), N-(3-carboxypropyl)-N,N-dimethyl-1-tetradecanaminium, inner salt (CAS®No. 146959-90-2), N-(3-carboxypropyl)-N,N-dimethyl-1-pentadecanaminium, inner salt (CAS®No. 146959-91-3), N-(3-carboxypropyl)-N,N-dimethyl-1-hexadecanaminium, inner salt (CAS®No. 1695-32-4), N-(3-carboxypropyl)-N,N-dimethyl-1-octadecanaminium, inner salt (CAS®No. 78195-27-4), N-(4-carboxybutyl)-N,N-dimethyl-1-dodecanaminium, inner salt (CAS®No. 120139-51-7), N-(5-carboxypentyl)-N,N-dimethyl-1-dodecanaminium, inner salt (CAS®No. 76392-97-7), N-(5-carboxypentyl)-N,N-dimethyl-1-hexadecanaminium, inner salt (CAS®No. 73565-98-7), N-(6-carboxyhexyl)-N,N-dimethyl-1-dodecanaminium, inner salt (CAS®No. 132621-80-8), 4-carboxy-N-dodecyl-N,N-dimethyl-benzenemethanaminium, inner salt (CAS®No. 71695-31-3), 2-carboxy-N-dodecyl-N,N-dimethyl-benzenemethanaminium, inner salt (CAS®No. 71695-34-6), 4-carboxy-N-hexadecyl-N,N-dimethyl-benzenemethanaminium, inner salt (CAS®No. 71695-33-5), 2-carboxy-N-hexadecyl-N,N-dimethyl-benzenemethanaminium, inner salt (CAS®No. 71695-35-7), tallow glycinate (CAS®No. 70750-46-8), soyamidopropyl carboxymethylbetaine, and babassuamidopropyl carboxymethylbetaine.

41. The method of claim 40, wherein said CB-like detergent is selected from the group consisting of N-(2-carboxyethyl)-N,N-dimethyl-1-dodecanaminium, inner salt (CAS®No. 16527-85-8), N-(2-carboxyethyl)-N,N-dimethyl-1-tridecanaminium, inner salt (CAS®No. 132621-79-5), N-(2-carboxyethyl)-N,N-dimethyl-1-tetradecanaminium, inner salt (CAS®No. 69725-38-3), N-(2-carboxyethyl)-N,N-dimethyl-1-hexadecanaminium, inner salt (CAS®No. 42416-43-3), N-(2-carboxyethyl)-N,N-dimethyl-1-octadecanaminium, inner salt (CAS®No. 30612-73-8), N-(3-carboxypropyl)-N,N-dimethyl-1-undecanaminium, inner salt (CAS®No. 150147-53-8), N-(3-carboxypropyl)-N,N-dimethyl-1-dodecanaminium, inner salt (CAS®No. 15163-30-1), N-(3-carboxypropyl)-N,N-dimethyl-1-tetradecanaminium, inner salt (CAS®No. 146959-90-2), N-(3-carboxypropyl)-N,N-dimethyl-1-pentadecanaminium, inner salt (CAS®No. 146959-91-3), N-(3-carboxypropyl)-N,N-dimethyl-1-hexadecanaminium, inner salt (CAS®No. 71695-32-4), N-(3-carboxypropyl)-N,N-dimethyl-1-octadecanaminium, inner salt (CAS®No. 78195-27-4), and N-(4-carboxybutyl)-N,N-dimethyl-1-dodecanaminium, inner salt (CAS®No. 120139-51-7).

42. The method of claim 41, wherein said CB-like detergent is N-(3-carboxypropyl)-N,N-dimethyl-1-octadecanaminium, inner salt (CAS®No. 78195-27-4).

43. The method of claim 31, wherein said PB-like detergent has the structure

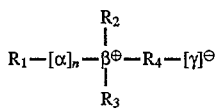

wherein $R_1$ is $C_8$–$C_{22}$;

α is —$CH_2$—, —$CH(OH)$—, —$(CO)$—$NH$—$CH_2CH_2CH_2$—, —$O$—, or —$C(O)$—;

n is 0 or 1;

β is —$N^\oplus$—, —$P^\oplus$—, or —$S^\oplus$—;

$R_2$ is —H, —$CH_3$, —$C_2H_5$, —$C_3H_7$, or —$C_4H_9$;

$R_3$ is —H, —$CH_3$, —$C_2H_5$, —$C_3H_7$, or —$C_4H_9$;

$R_4$ is —$CH_2$—, —$C_2H_4$—, —$C_3H_6$—, —$C_4H_8$—, —$C_5H_{10}$—, —$C_6H_{12}$—, —$CH_2$—$C_6H_4$—, —$C_mH_{2m}$—, —$CH(OH)CH_2CH_2$—, —$CH_2CH(OH)CH_2$—, or —$C_mH_{2m-1}(OH)$— where m is $\geq 1$; and γ is —$PO_x^\ominus$ where x=1, 2 or 3.

44. The method of claim 43, wherein said PB-like detergent is selected from the group consisting of N,N-dimethyl-N-(2-(phosphonooxy)ethyl)-1-decanaminium, inner salt (CAS®No. 134842-83-4), N,N-dimethyl-N-(2-(phosphonooxy)ethyl)-1-undecanaminium, inner salt (CAS®No. 134842-84-5), N,N-dimethyl-N-(2-(phosphonooxy)ethyl)-1-dodecanaminium, inner salt (CAS®No. 126712-86-5), N,N-dimethyl-N-(2-(phosphonooxy)ethyl)-1-tetradecanaminium, inner salt (CAS®No. 126712-87-6), N,N-dimethyl-N-(2-(phosphonooxy)ethyl)-1-hexadecanaminium, inner salt (CAS®No. 126712-88-7), N,N-dimethyl-N-(2-(phosphonooxy)ethyl)-1-heptadecanaminium, inner salt (CAS®No. 145578-49-0), N,N-dimethyl-N-(2-(phosphonooxy)ethyl)-1-octadecanaminium, inner salt (CAS®No. 126712-89-8), N,N-dimethyl-N-(2-(phosphonooxy)ethyl)-octadecen-1-aminium, inner salt (CAS®No. 134590-60-6), N,N-dimethyl-N-(2-(phosphonooxy)ethyl)-9-octadecen-1-aminium, inner salt (CAS®No. 148716-30-7), N,N-diethyl-N-(2-(phosphonooxy)ethyl)-1-hexadecanaminium, inner salt (CAS®No. 126712-90-1), N-(2-(phosphonooxy)ethyl)-N,N-dipropyl-1-hexadecanaminium, inner salt (CAS®No. 126712-91-2), N,N-dibutyl-N-(2-(phosphonooxy)ethyl)-1-hexadecanaminium, inner salt (CAS®No. 126712-92-3), N-ethyl-N-(2-(phosphonooxy)ethyl)-N-propyl-1-hexadecanaminium, inner salt (CAS®No. 126712-93-4), N-ethyl-N-methyl-N-(2-(phosphonooxy)ethyl)-1-hexadecanaminium, inner salt (CAS®No. 134842-85-6), N,N-dimethyl-N-(3-(phosphonooxy)propyl)-1-hexadecanaminium, inner salt (CAS®No. 89367-17-9), N,N-dimethyl-N-(4-(phosphonooxy)butyl)-1-hexadecanaminium, inner salt (CAS®No. 134842-86-7), N,N-dimethyl-N-(6-(phosphonooxy)hexyl)-1-hexadecanaminium, inner salt (CAS®No. 134842-87-8), 2-hydroxy-N,N-dimethyl-N-(2-(phosphonooxy)ethyl)-1-dodecanaminium, inner salt (CAS®No. 124591-53-3), 2-hydroxy-N,N-dimethyl-N-(2-(phosphonooxy)ethyl)-1-tetradecanaminium, inner salt (CAS®No. 124591-54-4), 2-hydroxy-N,N-dimethyl-N-(2-(phosphonooxy)ethyl)-1-hexadecanaminium, inner salt (CAS®No. 124591-57-7), N-butyl-N-ethyl-N-(2-(phosphonooxy)ethyl)-1-hexadecanaminium, inner salt (CAS®No. 126712-94-5), 2-hydroxy-N,N-dimethyl-N-(3-((1-oxododecyl)amino)propyl)-3-(phosphonooxy)-1-propanaminium, inner salt (CAS®No. 73602-79-6), 2-hydroxy-N,N-dimethyl-N-(3-((1-oxooctadecyl)amino)propyl)-3-(phosphonooxy)-1-propanaminium, inner salt (CAS®No. 144077-12-3), 3-(decyloxy)-2-hydroxy-N,N-dimethyl-N-(2-(phosphonooxy)ethyl)-1-propanaminium, inner salt (CAS®No. 128506-41-2), 3-(dodecyloxy)-2-hydroxy-N,N-dimethyl-N-(2-(phosphonooxy)ethyl)-1-propanaminium, inner salt (CAS®No. 128506-42-3), and 2-hydroxy-N,N-dimethyl-N-(2-(phosphonooxy)ethyl)-3-(tetradecyloxy)-1-propanaminium, inner salt (CAS®No. 128506-46-7).

45. The method of claim 44, wherein said PB-like detergent is selected from the group consisting of N,N-dimethyl-N-(2-(phosphonooxy)ethyl)-1-dodecanaminium, inner salt (CAS®No. 126712-86-5), N,N-dimethyl-N-(2-(phosphonooxy)ethyl)-1-tetradecanaminium, inner salt (CAS®No. 126712-87-6), N,N-dimethyl-N-(2-(phosphonooxy)ethyl)-1-hexadecanaminium, inner salt (CAS®No. 126712-88-7), N,N-dimethyl-N-(2-(phosphonooxy)ethyl)-1-heptadecanaminium, inner salt (CAS®No. 145578-49-0), N,N-dimethyl-N-(2-(phosphonooxy)ethyl)-1-octadecanaminium, inner salt (CAS®No. 126712-89-8), N,N-dimethyl-N-(3-(phosphonooxy)propyl)-1-hexadecanaminium, inner salt (CAS®No. 89367-17-9), and N,N-dimethyl-N-(4-(phosphonooxy)butyl)-1-hexadecanaminium, inner salt (CAS®No. 134842-86-7).

46. The method of any one of claims 27–30, 26 and 32, wherein at least one species of said microorganism is a member of the Mycobacteria.

47. The method of claim 46, wherein said Mycobacteria is selected from one or more members of the group consisting of *M. tuberculosis* (MTB) complex, *M. avium* (MAC) complex, MAIS complex, *M. fortuitum* complex, photochromogens, nonphotochromogens, scotochromogens, *M. africanum*, *M. asiaticum*, *M. avium*, *M. bovis*, *M. bovis* (BCG), *M. butyricum*, *M. chelonae*, *M. duvalii*, *M. flavescens*, *M. fortuitum*, *M. gastri*, *M. gordonae*, *M. haemophilum*, *M. intracellularae*, *M. kansasii*, *M. leprae*, *M. lepraemurium*, *M. linda*, *M. lufu*, *M. marinum*, *M. malmoense*, *M. microti*, *M. mucoscum*, *M. nonchromogenicum*, *M. paratuberculosis*, *M. peregrinum*, *M. phlei*, *M. rhodochrous*, *M. scrofulaceum*, *M. shimoidei*, *M. simiae*, *M. smegmatis*, *M. szulgai*, *M. terrae*, *M. thermoresistable*, *M. triviale*, *M. tuberculosis*, *M. ulcerans*, *M. vaccae*, *M. xenopi*, and serovars thereof.

48. The method of claim 47, wherein said Mycobacteria is selected from the group consisting of the *M. tuberculosis* (MTB) complex, and the *M. avium* (MAC) complex.

49. The method of claim 48, wherein said Mycobacteria is a member of the *M. tuberculosis* (MTB) complex.

50. The method of claim 47, wherein said Mycobacteria is selected from the group consisting of *M. tuberculosis*, *M. avium*, *M. paratuberculosis*, *M. intracellulare*, *M. kansasii* and *M. marinum*.

51. A kit for processing specimens for the detection of a microbacteria, said kit comprising an approximately-octadecyl detergent in close confinement and/or proximity with a detection means for said microbacteria.

52. The kit of claim 51, wherein said approximately-octadecyl detergent is selected from the group consisting of an SB-18-like detergent and a rod-like detergent.

53. The kit of claim 52, wherein said detergent is an SB-18-like detergent.

54. The kit of claim 53, wherein said SB-18-like detergent is selected from the group consisting of a CB-like, SB-like, HSB-like, PB-like, StB-like, PhB-like, So-like, Rev-B-like, AO-like, cAB-like and ImB-like detergent.

55. The kit of claim 54, wherein said SB-like and HSB-like detergent have the structure

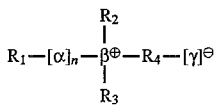

wherein $R_1$ is $C_{12}$–$C_{22}$;

$\alpha$ is —$CH_2$—, —$CH(OH)$—, —$(CO)$—$NH$—$CH_2CH_2CH_2$—, or —$C(O)$—;

n is 0 or 1;

$\beta$ is —$N^{\oplus}$—, —$P^{\oplus}$—, or —$S^{\oplus}$—;

$R_2$ is —H, —$CH_3$, —$C_2H_5$, —$C_3H_7$, or —$C_4H_9$;

$R_3$ is —H, —$CH_3$, —$C_2H_5$, —$C_3H_7$, or —$C_4H_9$;

$R_4$ is —$CH_2$—, —$C_2H_4$—, —$C_3H_6$—, —$C_4H_8$—, —$C_5H_{10}$—$C_6H_{12}$—, —$CH_2$—$C_6H_4$—, —$C_mH_{2m}$—, —$CH(OH)CH_2CH_2$—, —$CH_2CH(OH)CH_2$—, or —$C_mH_{2m-1}(OH)$—, where m is $\geq 1$; and $\gamma$ is —$SO_3^{\ominus}$.

56. The kit of claim 55, wherein said SB-like detergent is selected from the group consisting of N,N-dimethyl-N-(sulfomethyl)-1-dodecanaminium, inner salt (CAS®No. 52667-78-4), N,N-dimethyl-N-(sulfomethyl)-1-hexadecanaminium, inner salt (CAS®No. 69775-75-3), N,N-dimethyl-N-(sulfomethyl)-1-octadecanaminium, inner salt (CAS®No. 36051-36-2), N,N-dimethyl-N-(2-sulfoethyl)-1-dodecanaminium, inner salt (CAS®No. 24020-67-5), N,N-dimethyl-N-(2-sulfoethyl)-1-tetradecanaminium, inner salt (CAS®No. 58930-04-4), N,N-dimethyl-N-(2-sulfoethyl)-1-hexadecanaminium, inner salt (CAS®No. 58930-05-5), N,N-dimethyl-3-((1-oxohexadecyl)amino)-N-(2-sulfoethyl)-1-propanaminium, inner salt (CAS®No. 58930-06-6), N,N-dimethyl-N-(3-sulfopropyl)-1-octanaminium, inner salt (CAS®No. 15178-76-4), N,N-dimethyl-N-(3-sulfopropyl)-1-decanaminium, inner salt (CAS®No. 15163-36-7), N,N-dimethyl-N-(3-sulfopropyl)-1-dodecanaminium, inner salt (CAS®No. 14933-08-5), N,N-dimethyl-N-(3-sulfopropyl)-1-tetradecanaminium, inner salt (CAS®No. 14933-09-6), N,N-dimethyl-N-(3-sulfopropyl)-1-pentadecanaminium, inner salt (CAS®No. 67030-70-0), N,N-dimethyl-N-(3-sulfopropyl)-1-hexadecanaminium, inner salt (CAS®No. 2281-11-0), N,N-dimethyl-N-(3-sulfopropyl)-1-octadecanaminium, inner salt (CAS®No. 13177-41-8), dodecyldipropyl(3-sulfopropyl)-ammonium hydroxide, inner salt (CAS®No. 5163-34-5), N,N-dimethyl-N-(3-((1-oxododecyl)amino)propyl)-3-sulfo-1-propanaminium, inner salt (CAS®No. 52562-28-4), N,N-dimethyl-N-(3-((1-oxohexadecyl)amino)propyl)-3-sulfo-1-propanaminium, inner salt (CAS®No. 52562-29-5), N,N-dimethyl-N-(methyl-2-sulfoethyl)-1-dodecanaminium, inner salt (CAS®No. 59942-40-4), N,N-dimethyl-N-(methyl-2-sulfoethyl)-1-tetradecanaminium, inner salt (CAS®No. 59942-41-5), N,N-dimethyl-N-(methyl-2-sulfoethyl)-1-hexadecanaminium, inner salt (CAS®No. 59942-42-6), N,N-dimethyl-N-(3-((1-oxohexadecyl)amino)propyl)-2-sulfo-1-propanaminium, inner salt (CAS®No. 63663-13-8), N,N-dimethyl-N-(4-sulfobutyl)-1-dodecanaminium, inner salt (CAS®No. 64463-49-6), N,N-dimethyl-N-(4-sulfobutyl)-1-hexadecanaminium, inner salt (CAS®No. 58930-07-7), N,N-dimethyl-N-(4-sulfobutyl)-1-octadecanaminium, inner salt (CAS®No. 22313-73-1), N-(1,3-dimethyl-3-sulfobutyl)-N,N-dimethyl-1-dodecanaminium, inner salt (CAS®No. 35489-44-2), N,N-dimethyl-N-(3-((oxohexadecyl)amino)propyl)-4-sulfo-1-butanaminium, inner salt (CAS®No. 58930-08-8), N,N-dimethyl-N-(6-sulfohexyl)-1-hexadecanaminium, inner salt (CAS®No. 132621-81-9), N-dodecyl-N,N-dimethyl-4-sulfo-benzenemethanaminium, inner salt (CAS®No. 65180-40-7), N,N-dimethyl-4-sulfo-N-tetradecyl-benzenemethanaminium, inner salt (CAS®No. 65180-41-8), N-hexadecyl-N,N-dimethyl-4-sulfo-benzenemethanaminium, inner salt (CAS®No. 65180-42-9), N,N-dimethyl-N-octadecyl-4-sulfo-benzenemethanaminium, inner salt (CAS®No. 65180-43-0), N,N-dimethyl-N-(3-((1-oxododecyl)amino)propyl)-4-sulfo-benzenemethanaminium, inner salt (CAS®No. 65180-44-1), N,N-dimethyl-N-(3-((1-oxotetradecyl)amino)propyl)-4-sulfo-benzenemethanaminium, inner salt (CAS®No. 65180-45-2), N,N-dimethyl-N-(3-((1-oxohexadecyl)amino)propyl)-4-sulfo-benzenemethanaminium, inner salt (CAS®No. 65180-46-3), N,N-dimethyl-N-(3-((1-oxooctadecyl)amino)propyl)-4-sulfo-benzenemethanaminium, inner salt (CAS®No. 65180-47-4), N-(2-hydroxy-3-sulfopropyl)-N,N-dimethyl-1-decanaminium, inner salt (CAS®No. 34135-76-7), N-(2-hydroxy-3-sulfopropyl)-N,N-dimethyl-1-dodecanaminium, inner salt (CAS®No. 13197-76-7), N-(2-hydroxy-3-sulfopropyl)-N,N-dimethyl-2-tetradecanaminium, inner salt (CAS®No. 56505-82-9), N-(2-hydroxy-3-sulfopropyl)-N,N-dimethyl-1-pentadecanaminium, inner salt (CAS®No. 71502-45-9), N-(2-hydroxy-3-sulfopropyl)-N,N-dimethyl-1-hexadecanaminium, inner salt (CAS®No. 7425-12-9), N-(2-hydroxy-3-sulfopropyl)-N,N-dimethyl-1-octadecanaminium, inner salt (CAS®No. 19223-56-4), 2-hydroxy-N,N-dimethyl-N-(3-((1-oxododecyl)amino)propyl)-3-sulfo-1-propanaminium, inner salt (CAS®No. 19223-55-3), 2-hydroxy-N,N-dimethyl-N-(3-((1-oxotetradecyl)amino)propyl)-3-sulfo-1-propanaminium, inner salt (CAS®No. 63663-10-5), 2-hydroxy-N,N-dimethyl-N-(3-((1-oxohexadecyl)amino)propyl)-3-sulfo-1-propanaminium, inner salt (CAS®No. 63663-11-6), 2-hydroxy-N,N-dimethyl-N-(3-((1-oxooctadecyl)amino)propyl)-3-sulfo-1-propanaminium, inner salt (CAS®No. 63663-12-7), N-(2-hydroxy-3-sulfopropyl)-N,N-dimethyl-1-tetradecanaminium, inner salt (CAS®No. 13177-42-9), and N-(2-hydroxy-3-sulfopropyl)-N,N-dimethyl-1-tetradecanaminium, inner salt (CAS®No. 71497-51-3), cocoamidopropyl hydroxysulfobetaine (CAS®No. 68139-30-0), alkylether hydroxypropylsulfobetaine (CAS®No. 108797-84-8), tallowamidopropyl hydroxypropylsulfobetaine, erucamidopropyl hydroxypropylsulfobetaine, and canolamidopropyl betaine.

57. The kit of claim 56, wherein said SB-18-like detergent is selected from the group consisting of SB-like detergents having the structure as defined by N,N-dimethyl-N-(2-sulfoethyl)-1-dodecanaminium, inner salt (CAS®No. 24020-67-5), N,N-dimethyl-N-(2-sulfoethyl)-1-tetradecanaminium, inner salt (CAS®No. 58930-04-4), N,N-dimethyl-N-(2-sulfoethyl)-1-hexadecanaminium, inner salt (CAS®No. 58930-05-5), N,N-dimethyl-N-(3-sulfopropyl)-1-dodecanaminium, inner salt (CAS®No. 14933-08-5), N,N-dimethyl-N-(3-sulfopropyl)-1-tetradecanaminium, inner salt (CAS®No. 14933-09-6), N,N-dimethyl-N-(3-sulfopropyl)-1-pentadecanaminium, inner salt (CAS®No. 67030-70-0), N,N-dimethyl-N-(3-sulfopropyl)-1-hexadecanaminium, inner salt (CAS®No. 2281-11-0), N,N-dimethyl-N-(3-sulfopropyl)-1-octadecanaminium, inner salt (CAS®No. 13177-41-8), N,N-dimethyl-N-(3-((1-oxododecyl)amino)propyl)-3-sulfo-1-propanaminium, inner salt (CAS®No. 52562-28-4), N,N-dimethyl-N-(3-((1-oxohexadecyl)amino)propyl)-3-sulfo-1-propanaminium, inner salt (CAS®No. 52562-29-5), N,N-dimethyl-N-(4-sulfobutyl)-1-dodecanaminium, inner salt (CAS®No. 64463-49-6), N,N-dimethyl-N-(4-sulfobutyl)-1-hexadecanaminium, inner salt (CAS®No. 58930-07-7), N,N-dimethyl-N-(4-sulfobutyl)-1-octadecanaminium, inner salt (CAS®No. 22313-73-1), and N,N-dimethyl-N-(3-((oxohexadecyl)amino)propyl)-4-sulfo-1-butanaminium, inner salt (CAS®No. 58930-08-8).

58. The kit of claim 57, wherein said SB-18-like detergent is selected from the group consisting of N,N-dimethyl-N-(3-sulfopropyl)-1-hexadecanaminium, inner salt (CAS®No. 2281-11-0) and N,N-dimethyl-N-(3-sulfopropyl)-1-octadecanaminium, inner salt (CAS®No. 13177-41-8).

59. The kit of claim 58, wherein said SB-18-like detergent is N,N-dimethyl-N-(3-sulfopropyl)-1-hexadecanaminium, inner salt (CAS®No. 2281-11-0).

60. The kit of claim 58, wherein said SB-18-like detergent is N,N-dimethyl-N-(3-sulfopropyl)-1-octadecanaminium, inner salt (CAS®No. 13177-41-8).

61. The kit of claim 54, wherein said CB-like detergent has the structure $$R_1-[\alpha]_n-\beta^{\oplus}-R_4-[\gamma]^{\ominus}$$
$$|$$
$$R_3$$
(with $R_2$ above $\beta$)

wherein $R_1$ is $C_8$–$C_{22}$;

$\alpha$ is —$CH_2$—, —$CH(OH)$—, —$(CO)$—$NH$—$CH_2CH_2CH_2$—, —$O$—, or —$C(O)$—;

n is 0 or 1;

$\beta$ is —$N^{\oplus}$—, —$P^{\oplus}$—, or —$S^{\oplus}$—;

$R_2$ is —H, —$CH_3$, —$C_2H_5$, —$C_3H_7$, or —$C_4H_9$;

$R_3$ is —H, —$CH_3$, —$C_2H_5$, —$C_3H_7$, or —$C_4H_9$;

$R_4$ is —$CH_2$—, —$C_2H_4$—, —$C_3H_6$—, —$C_4H_8$—, —$C_5H_{10}$—$C_6H_{12}$—, —$CH_2$—$C_6H_4$—, —$C_mH_{2m}$—, —$CH(OH)CH_2CH_2$—, —$CH_2CH(OH)CH_2$—, or —$C_mH_{2m-1}(OH)$, where m is ≧1; and $\gamma$ is —$COO^{\ominus}$.

62. The kit of claim 61, wherein said CB-like detergent is selected from the group consisting of N-(carboxymethyl)-N,N-dimethyl-1-hexadecanaminium, inner salt (CAS®No. 693-33-4), cococarboxymethylbetaine (CAS®No. 68424-94-2), N-(carboxymethyl)-N,N-dimethyl-9-octadecen-1-aminium, inner salt (CAS®No. 871-37-4), N-(carboxymethyl)-N,N-dimethyl-3-((1-oxooctadecyl)amino)-1-propanaminium, inner salt (CAS®No. 6179-44-8), 3-amino-N(carboxymethyl)-N,N-dimethyl-1-propanaminium N-C8-C22 acyl derivatives, inner salt (CAS®No. 84082-44-0), N-(carboxymethyl)-3-((12-hydroxy-1-oxo-9-octadecenyl)amino)-N,N-dimethyl-1-propanaminium, inner salt (CAS®No. 71850-81-2), cocoamidopropyl carboxymethylbetaine (CAS®No. 61789-39-7 and CAS®No. 61789-40-0), N-(2-carboxyethyl)-N,N-dimethyl-1-dodecanaminium, inner salt (CAS®No. 16527-85-8), N-(2-carboxyethyl)-N,N-dimethyl-1-tridecanaminium, inner salt (CAS®No. 132621-79-5), N-(2-carboxyethyl)-N,N-dimethyl-1-tetradecanaminium, inner salt (CAS®No. 69725-38-3), N-(2-carboxyethyl)-N,N-dimethyl-1-hexadecanaminium, inner salt (CAS®No. 42416-43-3), N-(2-carboxyethyl)-N,N-dimethyl-1-octadecanaminium, inner salt (CAS®No. 30612-73-8), N-dodecyl-beta-alanine (CAS®No. 1462-54-0), N-(3-carboxypropyl)-N,N-dimethyl-1-undecanaminium, inner salt (CAS®No. 150147-53-8), N-(3-carboxypropyl)-N,N-dimethyl-1-dodecanaminium, inner salt (CAS®No. 15163-30-1), N-(3-carboxypropyl)-N,N-dimethyl-1-tetradecanaminium, inner salt (CAS®No. 146959-90-2), N-(3-carboxypropyl)-N,N-dimethyl-1-pentadecanaminium, inner salt (CAS®No. 146959-91-3), N-(3-carboxypropyl)-N,N-dimethyl-1-hexadecanaminium, inner salt (CAS®No. 71695-32-4), N-(3-carboxypropyl)-N,N-dimethyl-1-octadecanaminium, inner salt (CAS®No. 78195-27-4), N-(4-carboxybutyl)-N,N-dimethyl-1-dodecanaminium, inner salt (CAS®No. 120139-51-7), N-(5-carboxypentyl)-N,N-dimethyl-1-dodecanaminium, inner salt (CAS®No. 76392-97-7), N-(5-carboxypentyl)-N,N-dimethyl-1-hexadecanaminium, inner salt (CAS®No. 73565-98-7), N-(5-carboxyhexyl)-N,N-dimethyl-1-dodecanaminium, inner salt (CAS®No. 132621-80-8), 4-carboxy-N-dodecyl-N,N-dimethyl-benzenemethanaminium, inner salt (CAS®No. 71695-31-3), 2-carboxy-N-dodecyl-N,N-dimethyl-benzenemethanaminium, inner salt (CAS®No. 71695-34-6), 4-carboxy-N-hexadecyl-N,N-dimethyl-benzenemethanaminium, inner salt (CAS®No. 71695-33-5), 2-carboxy-N-hexadecyl-N,N-dimethyl-benzenemethanaminium, inner salt (CAS®No. 71695-35-7), tallow glycinate (CAS®No. 70750-46-8), soyamidopropyl carboxymethylbetaine, and babassuamidopropyl carboxymethylbetaine.

63. The kit of claim 62, wherein said CB-like detergent is selected from the group consisting of N-(2-carboxyethyl)-N,N-dimethyl-1-dodecanaminium, inner salt (CAS®No. 16527-85-8), N-(2-carboxyethyl)-N,N-dimethyl-1-tridecanaminium, inner salt (CAS®No. 132621-79-5), N-(2-carboxyethyl)-N,N-dimethyl-1-tetradecanaminium, inner salt (CAS®No. 69725-38-3), N-(2-carboxyethyl)-N,N-dimethyl-1-hexadecanaminium, inner salt (CAS®No. 42416-43-3), N-(2-carboxyethyl)-N,N-dimethyl-1-octadecanaminium, inner salt (CAS®No. 30612-73-8), N-(3-carboxypropyl)-N,N-dimethyl-1-undecanaminium, inner salt (CAS®No. 150147-53-8), N-(3-carboxypropyl)-N,N-dimethyl-1-dodecanaminium, inner salt (CAS®No. 15163-30-1), N-(3-carboxypropyl)-N,N-dimethyl-1-tetradecanaminium, inner salt (CAS®No. 146959-90-2), N-(3-carboxypropyl)-N,N-dimethyl-1-pentadecanaminium, inner salt (CAS®No. 146959-91-3), N-(3-carboxypropyl)-N,N-dimethyl-1-hexadecanaminium, inner salt (CAS®No. 71695-32-4), N-(3-carboxypropyl)-N,N-dimethyl-1-octadecanaminium, inner salt(CAS®No. 78195-27-4), and -(4-carboxybutyl)-N,N-dimethyl-1-dodecanaminium, inner salt (CAS®No. 120139-51-7).

64. The kit of claim 63, wherein said CB-like detergent is N-(3-carboxypropyl)-N,N-dimethyl-1-octadecanaminium, inner salt (CAS®No. 78195-27-4).

65. The kit of claim 54, wherein said PB-like detergent has the structure $$R_1-[\alpha]_n-\beta^{\oplus}-R_4-[\gamma]^{\ominus}$$
$$\text{with } R_2, R_3 \text{ on } \beta$$

wherein $R_1$ is $C_8$–$C_{22}$;

$\alpha$ is $-CH_2-$, $-CH(OH)-$, $-(CO)-NH-CH_2CH_2CH_2-$, $-O-$, or $-C(O)-$;

n is 0 or 1;

$\beta$ is $-N^{\oplus}-$, $-P^{\oplus}-$, or $-S^{\oplus}-$;

$R_2$ is $-H$, $-CH_3$, $-C_2H_5$, $-C_3H_7$, or $-C_4H_9$;

$R_3$ is $-H$, $-CH_3$, $-C_2H_5$, $-C_3H_7$, or $-C_4H_9$;

$R_4$ is $-CH_2-$, $-C_2H_4-$, $-C_3H_6-$, $-C_4H_8-$, $-C_5H_{10}-$, $-C_6H_{12}-$, $-CH_2-C_6H_4-$, $-C_mH_{2m}-$, $-CH(OH)CH_2CH_2-$, $-CH_2CH(OH)CH_2-$, or $-C_mH_{2m-1}(OH)-$ where m is $\geq 1$; and $\gamma$ is $-PO_x^{\ominus}$ where x is 1, 2 or 3.

66. The kit of claim 65, wherein said PB-like detergent is selected from the group consisting of N,N-dimethyl-N-(2-(phosphonooxy)ethyl)-1-decanaminium, inner salt (CAS®No. 134842-83-4), N,N-dimethyl-N-(2-(phosphonooxy)ethyl)-1-undecanaminium, inner salt (CAS®No. 134842-84-5), N,N-dimethyl-N-(2-(phosphonooxy)ethyl)-1-dodecanaminium, inner salt (CAS®No. 126712-86-5), N,N-dimethyl-N-(2-(phosphonooxy)ethyl)-1-tetradecanaminium, inner salt (CAS®No. 126712-87-6), N,N-dimethyl-N-(2-(phosphonooxy)ethyl)-1-hexadecanaminium, inner salt (CAS®No. 126712-88-7), N,N-dimethyl-N-(2-(phosphonooxy)ethyl)-1-heptadecanaminium, inner salt (CAS®No. 145578-49-0), N,N-dimethyl-N-(2-(phosphonooxy)ethyl)-1-octadecanaminium, inner salt (CAS®No. 126712-89-8), N,N-dimethyl-N-(2-(phosphonooxy)ethyl)-octadecen-1-aminium, inner salt (CAS®No. 134590-60-6), N,N-dimethyl-N-(2-(phosphonooxy)ethyl)-9-octadecen-1-aminium, inner salt (CAS®No. 148716-30-7), N,N-diethyl-N-(2-(phosphonooxy)ethyl)-1-hexadecanaminium, inner salt (CAS®No. 126712-90-1), N-(2-(phosphonooxy)ethyl)-N,N-dipropyl-1-hexadecanaminium, inner salt (CAS®No. 126712-91-2),
N,N-dibutyl-N-(2-(phosphonooxy)ethyl)-1-hexadecanaminium, inner salt (CAS®No. 126712-92-3),
N-ethyl-N-(2-(phosphonooxy)ethyl)-N-propyl-1-hexadecanaminium, inner salt (CAS®No. 126712-93-4),
N-ethyl-N-methyl-N-(2-(phosphonooxy)ethyl)-1-hexadecanaminium, inner salt (CAS®No. 134842-85-6),
N,N-dimethyl-N-(3-(phosphonooxy)propyl)-1-hexadecanaminium, inner salt (CAS®No. 89367-17-9),
N,N-dimethyl-N-(4-(phosphonooxy)butyl)-1-hexadecanaminium, inner salt (CAS®No. 134842-86-7),
N,N-dimethyl-N-(6-(phosphonooxy)hexyl)-1-hexadecanaminium, inner salt (CAS®No. 134842-87-8),
2-hydroxy-N,N-dimethyl-N-(2-(phosphonooxy)ethyl)-1-dodecanaminium, inner salt (CAS®No. 124591-53-3),
2-hydroxy-N,N-dimethyl-N-(2-(phosphonooxy)ethyl)-1-tetradecanaminium, inner salt (CAS®No. 124591-54-4),
2-hydroxy-N,N-dimethyl-N-(2-(phosphonooxy)ethyl)-1-hexadecanaminium, inner salt (CAS®No. 124591-57-7),
N-butyl-N-ethyl-N-(2-(phosphonooxy)ethyl)-1-hexadecanaminium, inner salt (CAS®No. 126712-94-5),
2-hydroxy-N,N-dimethyl-N-(3-((1-oxododecyl)amino)propyl)-3-(phosphonooxy)-1-propanaminium, inner salt (CAS®No. 73602-79-6),
2-hydroxy-N,N-dimethyl-N-(3-((1-oxooctadecyl)amino)propyl)-3-(phosphonooxy)-1-propanaminium, inner salt (CAS®No. 144077-12-3),
3-(decyloxy)-2-hydroxy-N,N-dimethyl-N-(2-(phosphonooxy)ethyl)-1-propanaminium, inner salt (CAS®No. 128506-41-2),
3-(dodecyloxy)-2-hydroxy-N,N-dimethyl-N-(2-(phosphonooxy) ethyl)-1-propanaminium, inner salt (CAS®No. 128506-42-3), and
2-hydroxy-N,N-dimethyl-N-(2-(phosphonooxy) ethyl)-3-(tetradecyloxy)-1-propanaminium, inner salt (CAS®No. 128506-46-7).

67. The kit of claim 66, wherein said PB-like detergent is selected from the group consisting of N,N-dimethyl-N-(2-(phosphonooxy)ethyl)-1-dodecanaminium, inner salt (CAS®No. 126712-86-5),
N,N-dimethyl-N-(2-(phosphonooxy)ethyl)-1-tetradecanaminium, inner salt (CAS®No. 126712-87-6),
N,N-dimethyl-N-(2-(phosphonooxy)ethyl)-1-hexadecanaminium, inner salt (CAS®No. 126712-88-7),
N,N-dimethyl-N-(2-(phosphonooxy)ethyl)-1-heptadecanaminium, inner salt (CAS®No. 145578-49-0),
N,N-dimethyl-N-(2-(phosphonooxy)ethyl)-1-octadecanaminium, inner salt (CAS®No. 126712-89-8),
N,N-dimethyl-N-(3-(phosphonooxy)propyl)-1-hexadecanaminium, inner salt (CAS®No. 89367-17-9), and
N,N-dimethyl-N-(4-(phosphonooxy)butyl)-1-hexadecanaminium, inner salt (CAS®No. 134842-86-7).

68. The kit of claim 51, wherein said microbacteria is selected from one or more members of the group consisting of *M. tuberculosis* (MTB) complex, *M. avium* (MAC) complex, MAIS complex, *M. fortuitum* complex, photochromogens, nonphotochromogens, scotochromogens, *M. africanum, M. asiaticum, M. avium, M. bovis, M. bovis* (BCG), *M. butyricum, M. chelonae, M. duvalii, M. flavescens, M. fortuitum, M. gastri, M. gordonae, M. haemophilum, M. intracellularae, M. kansasii, M. leprae, M. lepraemurium, M. linda, M. lufu, M. marinum, M. malmoense, M. microti, M. mucoscum, M. nonchromogenicum, M. paratuberculosis, M. peregrinum, M. phlei, M. rhodochrous, M. scrofulaceum, M. shimoidei, M. simiae, M. smegmatis, M. szulgai, M. terrae, M. thermoresistable, M. triviale, M. tuberculosis, M. ulcerans, M. vaccae, M. xenopi,* and serovars thereof.

69. The kit of claim 68, wherein said Mycobacteria is selected from the group consisting of the *M. tuberculosis* (MTB) complex, and the *M. avium* (MAC) complex.

70. The kit of claim 69, wherein said Mycobacteria is a member of the *M. tuberculosis* (MTB) complex.

71. The kit of claim 68, wherein said Mycobacteria is selected from the group consisting of *M. tuberculosis, M. avium, M. paratuberculosis, M. intracellulare, M. kansasii* and *M. marinum.*

72. The kit of claim 52, wherein said detergent is a rod-like detergent.

* * * * *